US007951802B2

(12) United States Patent
Graczyk et al.

(10) Patent No.: US 7,951,802 B2
(45) Date of Patent: May 31, 2011

(54) USE OF 7-AZAINDOLES IN THE INHIBITION OF C-JUN N-TERMINAL KINASE

(75) Inventors: Piotr Pawel Graczyk, London (GB);
Paschalis Dimopoulos, London (GB);
Christopher Neil Farthing, London (GB); Gurpreet Singh Bhatia, London (GB); Afzal Khan, London (GB)

(73) Assignee: Eisai R&D Management Co., Ltd., Tokyo (JP)

( * ) Notice: Subject to any disclaimer, the term of this patent is extended or adjusted under 35 U.S.C. 154(b) by 0 days.

(21) Appl. No.: 12/536,354

(22) Filed: Aug. 5, 2009

(65) Prior Publication Data

US 2010/0069358 A1 Mar. 18, 2010

Related U.S. Application Data

(63) Continuation of application No. PCT/EP2008/051427, filed on Feb. 5, 2008.

(30) Foreign Application Priority Data

Feb. 6, 2007 (GB) .................................. 0702259.3

(51) Int. Cl.
*A61K 31/535* (2006.01)
*A61K 31/497* (2006.01)
*A61K 31/44* (2006.01)
*C07D 413/14* (2006.01)
*C07D 401/14* (2006.01)
*C07D 471/04* (2006.01)

(52) U.S. Cl. ............. 514/232.5; 514/234.5; 514/253.04; 514/300; 544/121; 544/127; 544/238; 546/113

(58) Field of Classification Search .................. 546/113; 544/121, 127, 238; 514/232.5, 234.5, 253.04, 514/300
See application file for complete search history.

(56) References Cited

FOREIGN PATENT DOCUMENTS

WO WO 2004/078756 A1 * 9/2004

OTHER PUBLICATIONS

Amor, Sandra et al., "Identification of a Major Encephalitogenic Epitope of Proteolipid Protein (Residues 56-70) for the Induction of Experimental Allergic Encephalomyelitis in Biozzi AB/H and Nonobese Diabetic Mice," *The Journal of Immunology*, vol. 150(12):5666-5672 (1993).
Baker, D. et al., "Induction of chronic relapsing experimental allergic encephalomyelitis in Biozzi mice," *Journal of Neuroimmunology*, vol. 28:261-270 (1990).
Baldwin, Jake E. et al., "Parallel Synthesis of Novel Heteroaromatic Acromelic Acid Analogues from Kainic Acid," *J. Org. Chem.*, vol. 66:2586-2596 (2001).

Bansal, Ekta et al., "Synthesis of some new formazanyl-thiazolyl-indoles and formazanyl-oxazolyl-indoles as inflammation inhibitors," *Indian Journal of Chemistry*, vol. 39B:357-362 (2000).
Bhattacharya, Birendra K. et al., "Total synthesis of 2'-deoxy-2'-arafluoro-tubercidin,-toyocamycin,-sangivamycin and certain related nucleosides," *J. Chem. Soc. Perkin. Trans. I*, pp. 1543-1550 (1995).
Denmark, Scott E. et al., "Convergence of Mechanistic Pathways in the Palladium(0)-Catalyzed Cross-Coupling of Alkenylsilacyclobutanes and Alkenylsilanols," *Organic Letters*, vol. 2(16):2491-2494 (2000).
Di Fabio, Romano et al., "Novel Synthesis of Ethyl-3(Bromoacetyl)-4,6-Dichloro-1H-Indole-2-Carboxylate as Useful Intermediate in the Preparation of Potential Glycine Site Antagonists," *Synthetic Communications*, vol. 28(1):51-60 (1998).
Ehrentraut, Andreas et al., "A New Efficient Palladium Catalyst for Heck Reactions of Deactivated Aryl Chlorides," *Synlett*, vol. 11:1589-1592 (2000).
Escoubet, Stéphanie et al., "Thiyl Radical Mediated Racemization of Nonactivated Aliphatic Amines," *J. Org. Chem.*, vol. 71:7288-7292 (2006).
Graczyk, Piotr P., "Gini Coefficient: A New Way to Express Selectivity of Kinase Inhibitors against a Family of Kinases," *J. Med. Chem.*, vol. 50:5773-5779 (2007).
Gu, Xiao-Hui et al., "Syntheses and Biological Activities of Bis(3-indolyl)thiazoles, Analogues of Marine Bis(indole)alkaloid Nortopsentins," *Bioorganic & Medicinal Chemistry Letters*, vol. 9:569-572 (1999).
Hartung, Christian G. et al., "Highly Selective Palladium-Catalyzed Heck Reactions of Aryl Bromides with Cycloalkenes," *Organic Letters*, vol. 1(5):709-711 (1999).
Hatanaka, Yasuo et al., "Cross-Coupling of Organosilanes with Organic Halides Mediated by Palladium Catalyst and Tris(diethylamino)sulfonium Difluorotrimethylsilicate," *J. Org. Chem.*, vol. 53:918-920 (1988).
Hatanaka, Yasuo et al., "Highly Selective Cross-Coupling Reactions of Organosilicon Compounds Mediated by Fluoride Ion and a Palladium Catalyst," *Synlett*, pp. 845-853 (1991).
Hayashi, Hiroyuki et al., "Short Step Synthesis of a Natural Product, 6-Cyano-5-Methoxy-12-Methylindolo[2,3-a]Carbazole and Novel 6-Aminoindolo[2,3-a]-Thiazolo[5,4-c]Carbazoles," *Heterocycles*, vol. 51(6):1233-1235 (1999).
Heijmans, Nicole et al., "Encephalitogenic and tolerogenic potential of altered peptide ligands of MOG and PLP in Biozzi ABH mice," *Journal of Neuroimmunology*, vol. 167:23-33 (2005).
Hosoya, Takamitsu et al., "Rapid methylation on carbon frameworks useful for the synthesis of $^{11}CH_3$-incorporated PET tracers: Pd(0)-mediated rapid coupling of methyl iodide with an alkenyltributylstannane leading to a 1-methylalkene," *Org. Biomol. Chem.*, vol. 4:410-415 (2006).
Iakovou, K. et al., "Design, synthesis and biological evaluation of novel β-substituted indol-3-yl ethylamido melatoninergic analogues," *Journal of Pharmacy and Pharmacology*, vol. 54:147-156 (2001).

(Continued)

*Primary Examiner* — Rebecca L Anderson
(74) *Attorney, Agent, or Firm* — Nelson Mullins Riley & Scarborough LLP; Amy E. Mandragouras, Esq.; Pankaj N. Desai

(57) ABSTRACT

The present invention provides a compound of formula (I); or a pharmaceutically acceptable salt thereof in the inhibition of c-Jun N-terminal kinase (JNK) activity and particularly in the treatment of neurodegenerative disorders, inflammatory diseases and/or and autoimmune diseases. The invention also provides processes for the manufacture of compounds of formula (I) or a pharmaceutically acceptable salt thereof and compositions containing them.

11 Claims, 2 Drawing Sheets

OTHER PUBLICATIONS

Krawczyk, Steven H. et al., "Synthesis and Evaluation of Certain Thiosangivamycin Analogs as Potential Inhibitors of Cell Proliferation and Human Cytomegalovirus," *J. Med. Chem.*, vol. 38:4115-4119 (1995).

Lambert, Joseph B. et al., "Stabilization of Positive Charge by β Silicon," *J. Am. Chem. Soc.*, vol. 109:7838-7845 (1987).

Lin, Pen-Yuan et al., "A New Method for Converting Nitriles into Primary Thioamides by Sodium Trimethylsilanethiolate," *Synthesis*, pp. 1219-1220 (1992).

Littke, Adam F. et al., "Pd/P($t$-Bu)$_3$: A Mild and General Catalyst for Stille Reactions of Aryl Chlorides and Aryl Bromides," *J. Am. Chem. Soc.*, vol. 124:6343-6348 (2002).

Littke, Adam F. et al., "Versatile Catalysts for the Suzuki Cross-Coupling of Arylboronic Acids with Aryl and Vinyl Halides and Triflates under Mild Conditions," *J. Am. Chem. Soc.*, vol. 122:4020-4028 (2000).

Manaka, Akira et al., "Synthesis of Aromatic Thioamide from Nitrile Without Handling of Gaseous Hydrogen Sulfide," *Synthetic Communications*, vol. 35:761-764 (2005).

Mazzola, R.D. et al., "Improved Yields with Added Copper(I) Salts in Carbonylative Stille Couplings of Sterically Hindered Vinylstannanes," *J. Org. Chem.*, vol. 69:220-223 (2004).

Mitchell, Terence N., "Palladium-Catalysed Reactions of Organotin Compounds," *Synthesis*, pp. 803-815 (1992).

Miyake, Fumiko Y. et al., "A Facile Synthesis of Dragmacidin B and 2,5-Bis(6'-bromo-3'-indolyl)Piperazine," *Organic Letters*, vol. 2(20):3185-3187 (2000).

Nicolaou, K.C. et al., "Chemistry and Biology of Diazonamide A: First Total Synthesis and Confirmation of the True Structure," *J. Am. Chem. Soc.*, vol. 126:12888-12895 (2004).

Nicolaou, K.C. et al., "Chemistry and Biology of Diazonamide A: Second Total Synthesis and Biological Investigations," *J. Am. Chem. Soc.*, vol. 126:12897-12906 (2004).

Ognyanov, Vassil I. et al., "Design of Potent, Orally Available Antagonists of the Transient Receptor Potential Vanilloid 1. Structure-Activity Relationships of 2-Piperazin-1-yl-1$H$-benzimidazoles," *J. Med. Chem.*, vol. 49:3719-3742 (2006).

Paquette, Leo A. et al., "Total Synthesis of Dumsin. 1. Retrosynthetic Strategy and the Elaboration of Key Intermediates from (−)-Bornyl Acetate," *J. Org. Chem.*, vol. 68:6905-6918 (2003).

Pearson, William H. et al., "Total Synthesis of the Kopsia lapidilecta Alkaloid (±)-Lapidilectine B," *J. Org. Chem.*, vol. 69:9109-9122 (2004).

Qiao, Qi et al., "Stereochemical Control Factors in the Hantzsch Thiazole Synthesis: A Hammett Substitution Correlation Analysis," *Organic Letters*, vol. 3(23):3655-3658 (2001).

Saleh, Mohamed A., "Reaction of Glycosyl Isothiocynates with 3-Indolylaminomethyl-Ketone Hydrochloride," *Nucleosides, Nucleotides & Nucleic Acids*, vol. 21(4&5):401-409 (2002).

Schwarz, George, "2,4-Dimethylthiazole [Thiazole, 2,4-dimethyl-]," *Organic Syntheses, Coll.*, vol. 3:332 (1955): vol. 25:35 (1945).

Skundric, Dusanka S. et al., "Distinct immune regulation of the response to H-2$^b$ restricted epitope of MOG causes relapsing-remitting EAE in H-2$^{b/s}$ mice," *Journal of Neuroimmunology*, vol. 136:34-45 (2003).

Stille, John K., "The Palladium-Catalyzed Cross-Coupling Reactions of Organotin Reagents with Organic Electrophiles," *Chem. Int. Ed. Engl.*, vol. 25:508-524 (1986).

Suzuki, Akira, "Synthetic studies via the cross-coupling reaction of organoboron derivatives with organic halides," *Pure & Appl. Chem.*, vol. 63(3):419-422 (1991).

Suzuki, Hideharu et al., "Synthesis of Non-peptide Tryptamine Derivative (THS-12) Which Stimulates TPO Responsive Cell Growth (Synthetic Studies of Indoles and Related Compounds 51)," *Heterocycles*, vol. 56:519-524 (2002).

Tamao, Kohei et al., "Palladium-Catalyzed Cross-Coupling Reaction of Alkenylalkoxysilanes with Aryl and Alkenyl Halides in the Presence of a Fluoride Ion," *Tetrahedron Letters*, vol. 30(44):6051-6054 (1989).

Thompson, Scott K. et al., "Synthesis and Antiviral Activity of a Novel Class of HIV-1 Protease Inhibitors Containing a Heterocyclic $P_1'$-$P_2'$ Amide Bond Isostere," *Bioorganic & Medicinal Chemistry Letters*, vol. 4(20):2441-2446 (1994).

Tonsiengsom, Fay et al., "Reduction of 2,5-Bis(3'-indolyl)pyrazines to 2,5-Bis3'-indolyl)pyrazines: Synthesis of Bisindolylpiperazine Marine Alkaloids Dragmacidin A, B, and C," *Synthesis*, vol. 1:49-54 (2006).

Uozumi, Yasuhiro et al., "Heck Reaction in Water with Amphiphilic Resin-Supported Palladium-Phosphine Complexes," *Synlett*, vol. 12:2045-2047 (2002).

Zawistoski, Michael P., "Synthesis of 4-[3-(1$H$)-Indolyl]-2[$N$-guanidinomethyl]thiazole Dihydrochloride," *J. Heterocyclic Chem.*, vol. 27:519-521 (1990).

* cited by examiner

USE OF 7-AZAINDOLES IN THE INHIBITION OF C-JUN N-TERMINAL KINASE

RELATED APPLICATIONS

This application is a continuation of International Application Number PCT/EP2008/051427, filed on Feb. 5, 2008, which claims priority to GB 0702259.3, which was filed on Feb. 6, 2007. The entire contents of the aforementioned applications are hereby incorporated herein by reference.

FIELD OF THE INVENTION

The invention relates to 7-azaindole derivatives or pharmaceutically acceptable salts thereof, their use in the inhibition of c-Jun N-terminal kinase (JNK) activity, their use in medicine and particularly in the treatment of neurodegenerative disorders, inflammatory diseases, autoimmune diseases and/or organ failure. The invention also provides processes for the manufacture of said 7-azaindole derivatives and compositions containing them.

BACKGROUND OF THE INVENTION

The c-Jun N-terminal kinases (hereinafter referred to as "JNKs") are a family of serine/threonine protein kinases and members of the mitogen-activated protein kinase (MAPK) family. Three distinct genes (JNK1, JNK2 and JNK3) have been identified.

It is known that JNKs are related to neurodegenerative disorders such as multiple sclerosis and autoimmune diseases such as rheumatoid arthritis (WO2004/078756).

Furthermore, the above patent reference also discloses that 7-azaindole derivatives which have a ring on the C3 position and an aromatic group such as a phenyl group or a heterocyclic group such as a morpholino group on C5 position possess JNK inhibitory activity.

Also, it is known that certain 7-azaindole derivatives having substitution (for example a thiazolyl group) at the C3 position and substituton (for example a heterocyclic group) at the C5 position can show in vitro inhibitory activity against other kinases, namely TEC and JAK kinases (WO2006/004984).

However, there is no disclosure of 7-azaindole derivatives which have a thiazolyl group on the C3 position and a non-aromatic carbocyclic group on the C5 position.

It is desirable for a JNK inhibitor to have superior selectivity for JNK over other kinases. This is in order to reduce the risk of unexpected side-effects.

DESCRIPTION OF THE INVENTION

Under these circumstances, the present inventors have conducted intensive studies. As a result, they have found that 7-azaindole derivatives which have a thiazolyl group on C3 position and non-aromatic hydrocarbon cyclic group on C5 position (I) have a superior selectivity for JNK kinases over other kinases and have significant in vivo activity, thereby completing the present invention.

The first aspect of the invention therefore relates to a compound of formula (1); or a pharmaceutically acceptable salt thereof,

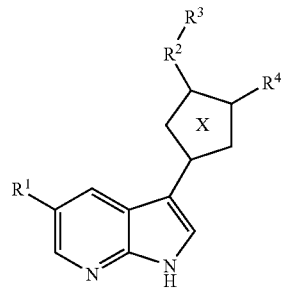
(I)

wherein Ring X represents a thiazole ring;
$R^1$ represents a 5-7 membered non-aromatic hydrocarbon cyclic group optionally and independently substituted with 1-4 substituent(s) selected from the group consisting of a halogen atom, an oxo group, an ethylenedioxy group, a $C_{1-6}$ alkyl group, a $C_{1-6}$ alkoxy group, a $C_{1-6}$ hydroxyalkyl group, —C(O)OH, a ($C_{1-6}$ alkyl)amino group, a di($C_{1-6}$ alkyl)amino group and —Ra—Rb;
wherein $R^a$ represents a single bond or —$CH_2$—;
wherein $R^b$ represents a 4-7 membered non-aromatic heterocyclic group, a $C_{6-10}$ aryl group or a 5-6 membered heteroaryl group, optionally and independently substituted with 1-4 substituent(s) selected from the group consisting of a halogen atom and a $C_{1-6}$ alkyl group;
wherein $R^2$ represents a single bond or a carbonyl group;
wherein $R^3$ represents hydrogen, a hydroxyl group, a $C_{1-6}$ alkyl group, a $C_{1-6}$ alkoxy group, a $C_{1-6}$ haloalkyl group, a di($C_{1-6}$ alkyl)amino group or a 4-7 membered non-aromatic heterocyclic group wherein at least one ring heteroatom is a nitrogen atom, optionally and independently substituted with 1-4 $C_{1-6}$ alkyl group(s); and
wherein $R^4$ represents hydrogen or a $C_{1-6}$ alkyl group.

In a preferred feature of the first aspect of the invention, the compound of formula (I) is a compound of formula (Ia)

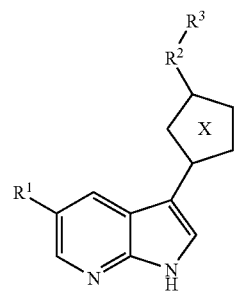
(Ia)

wherein Ring X represents a thiazole ring;
$R^1$ represents a 5-7 membered non-aromatic hydrocarbon cyclic group optionally and independently substituted with 1-4 substituent(s) selected from the group consisting of a halogen atom, an oxo group, an ethylenedioxy group, a $C_{1-6}$ alkyl group, a $C_{1-6}$ alkoxy group, a $C_{1-6}$ hydroxyalkyl group, —C(O)OH, a ($C_{1-6}$ alkyl)amino group, a di($C_{1-6}$ alkyl)amino group and —Ra—Rb;
wherein $R^a$ represents a single bond or —$CH_2$—;
wherein $R^b$ represents a 4-7 membered non-aromatic heterocyclic group, a $C_{6-10}$ aryl group or a 5-6 membered heteroaryl group, optionally and independently substituted with 1-4 substituent(s) selected from the group consisting of a halogen atom and a $C_{1-6}$ alkyl group;

wherein R² represents a single bond or a carbonyl group;

wherein R³ represents a hydroxyl group, a di(C₁₋₆ alkyl) amino group or a 4-7 membered non-aromatic heterocyclic group wherein at least one ring heteroatom is a nitrogen atom, optionally and independently substituted with 1-4 C₁₋₆ alkyl group(s).

Preferably, R¹ represents a 5-7 membered non-aromatic hydrocarbon cyclic group optionally and independently substituted with 1-4 substituent(s) selected from the group consisting of a halogen atom, an oxo group, an ethylenedioxy group, a C₁₋₆ alkyl group, a C₁₋₆ alkoxy group, a C₁₋₆ hydroxyalkyl group, —C(O)OH, and —Rᵃ-Rᵇ, wherein Rᵃ and Rᵇ are as defined above.

In a preferred embodiment, R¹ represents a cyclopentyl group, a cyclohexyl group, a cyclopentenyl group, a cyclohexenyl group or a cyclohexadienyl group, optionally and independently substituted with 1-4 substituent(s) selected from the group consisting of a halogen atom, an oxo group, an ethylenedioxy group, a C₁₋₆ alkyl group, a C₁₋₆ alkoxy group, a C₁₋₆ hydroxyalkyl group, —C(O)OH, a (C₁₋₆ alkyl)amino group, a di(C₁₋₆ alkyl)amino group and —Rᵃ-Rᵇ;

wherein Rᵃ represents a single bond or —CH₂—;

wherein Rᵇ represents a 4-7 membered non-aromatic heterocyclic group, a C₆₋₁₀ aryl group or a 5-6 membered heteroaryl group, optionally and independently substituted with 1-4 substituent(s) selected from the group consisting of halogen atom and C₁₋₆ alkyl group.

Preferably, R¹ represents a cyclopentyl group, a cyclohexyl group, a cyclopentenyl group, a cyclohexenyl group or a cyclohexadienyl group, optionally and independently substituted with 1-4 substituent(s) selected from the group consisting of an ethylenedioxy group, a C₁₋₆ alkyl group and a morpholino group.

In a preferred embodiment R² represents a single bond.

In an alternative preferred embodiment, R² represents a carbonyl group.

In a preferred embodiment, R³ represents hydrogen, a methyl group, a methyoxy group, an ethoxy group, a trifluoromethyl group, a dimethylamino group, a piperidyl group, a piperazinyl group or a morpholino group optionally and independently substituted with a C₁₋₆ alkyl group.

R⁴ preferably represents hydrogen or methyl.

In a second aspect, the invention relates to a compound selected from the following group or a pharmaceutically acceptable salt thereof;

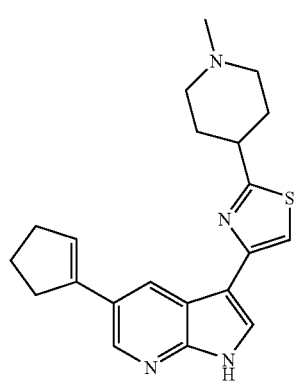

(I-1)

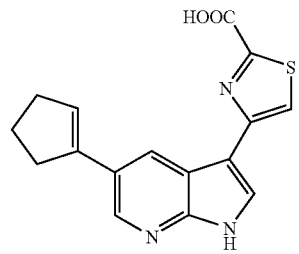

(I-2)

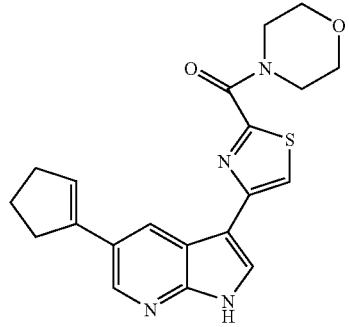

(I-3)

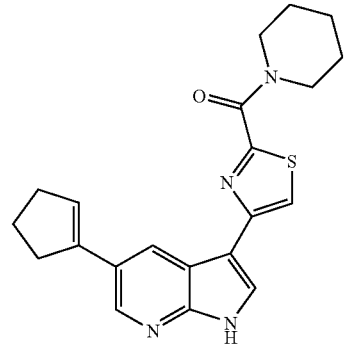

(I-4)

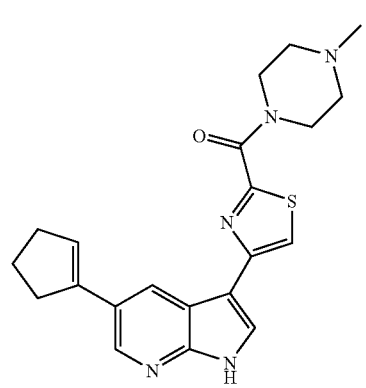

(I-5)

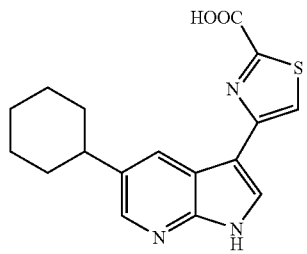

(I-6)

-continued
(I-7)
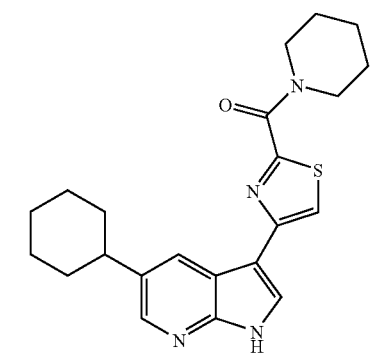
(I-8)
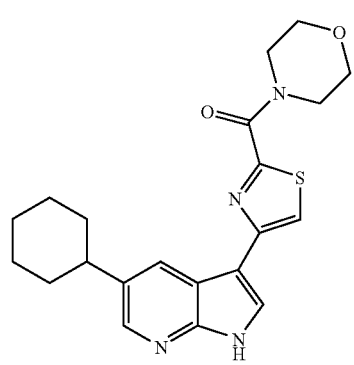
(I-9)
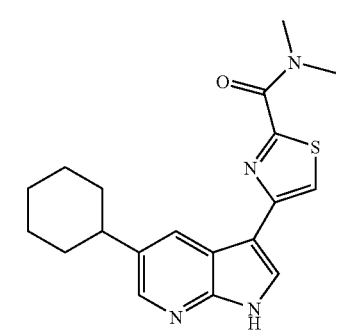
(I-10)
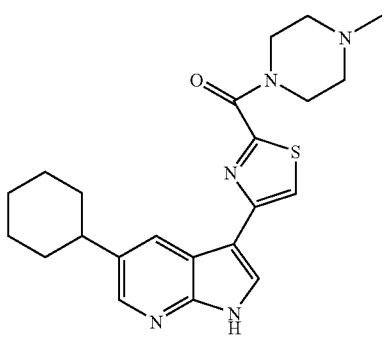
-continued
(I-11)
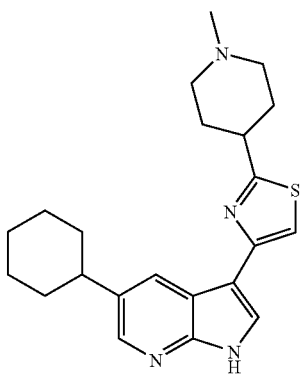
(I-12)
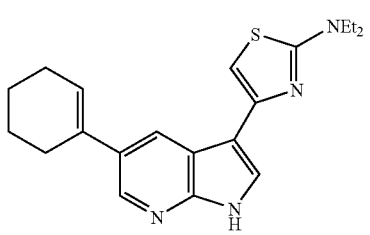
(I-13)
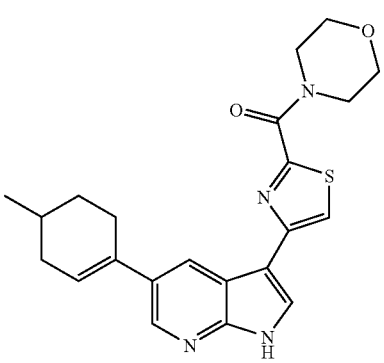
(I-14)
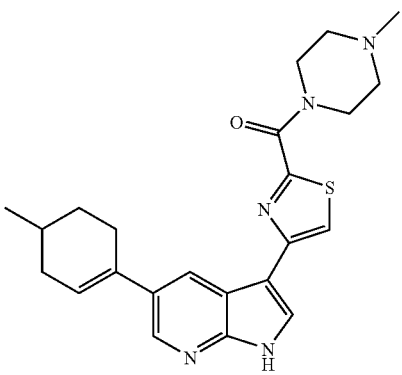
(I-15)
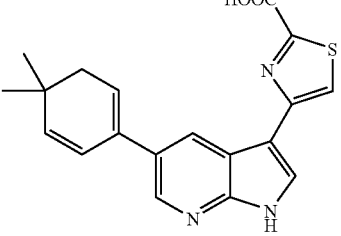

-continued
(I-16)
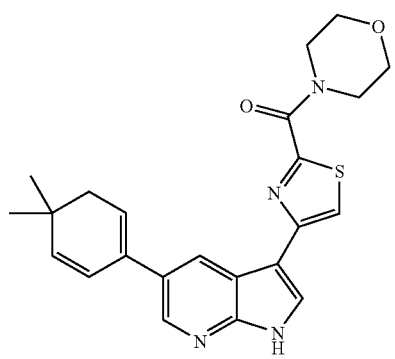
(I-17)
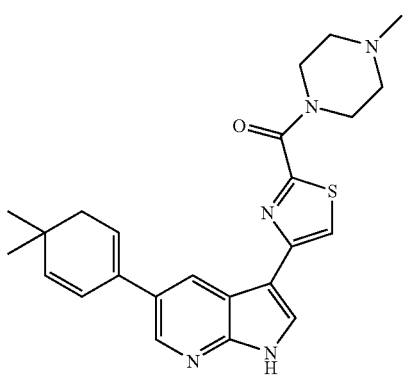
(I-18)
(I-19)
(I-20)
-continued
(I-21)
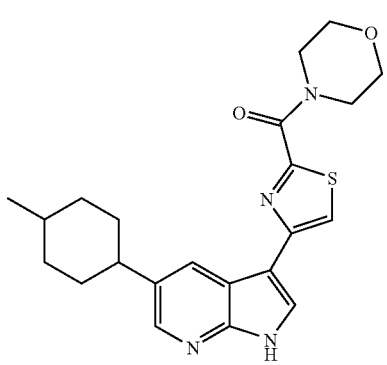
(I-22)
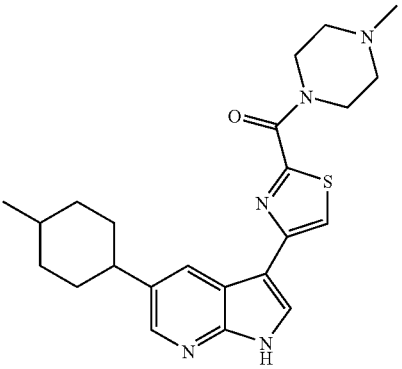
(I-23)
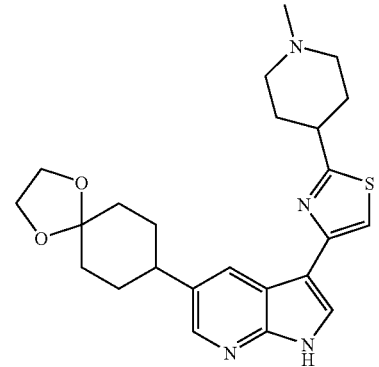
(I-24)
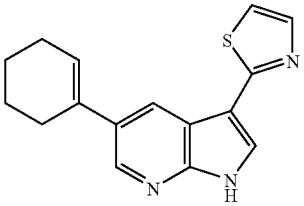
(I-25)
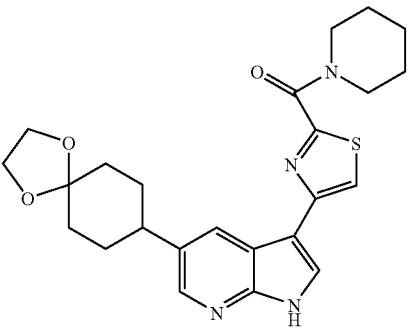

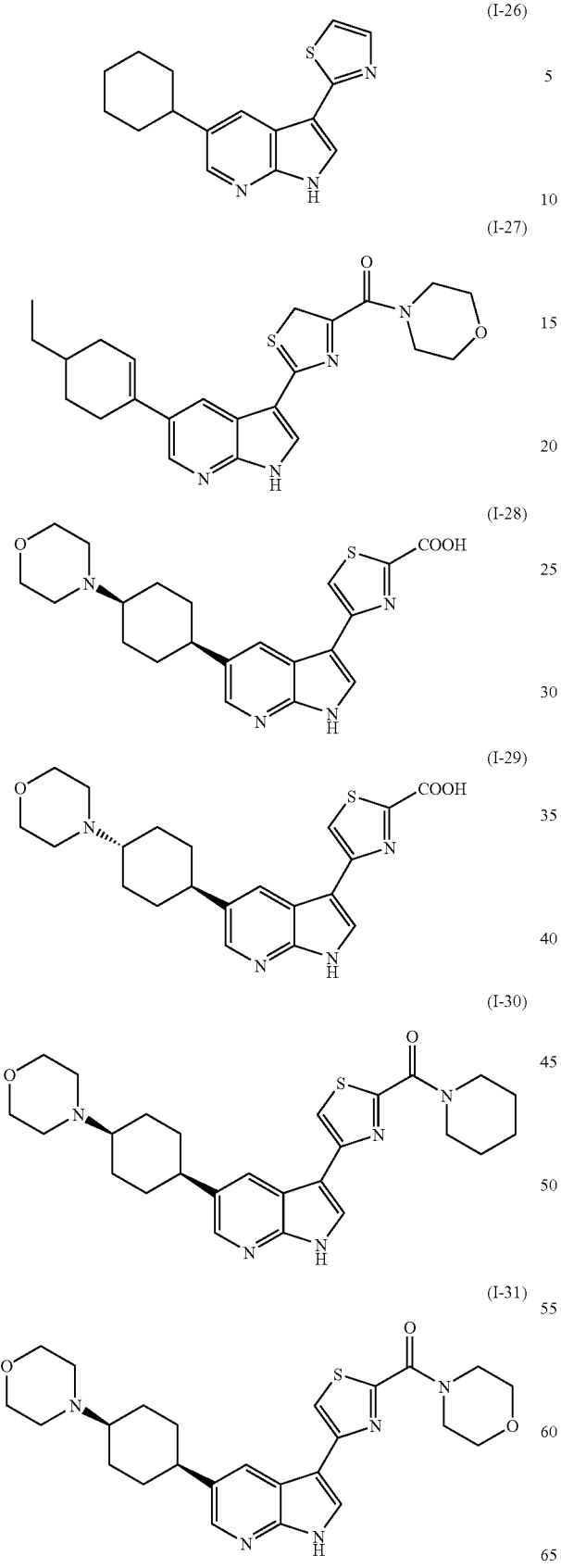

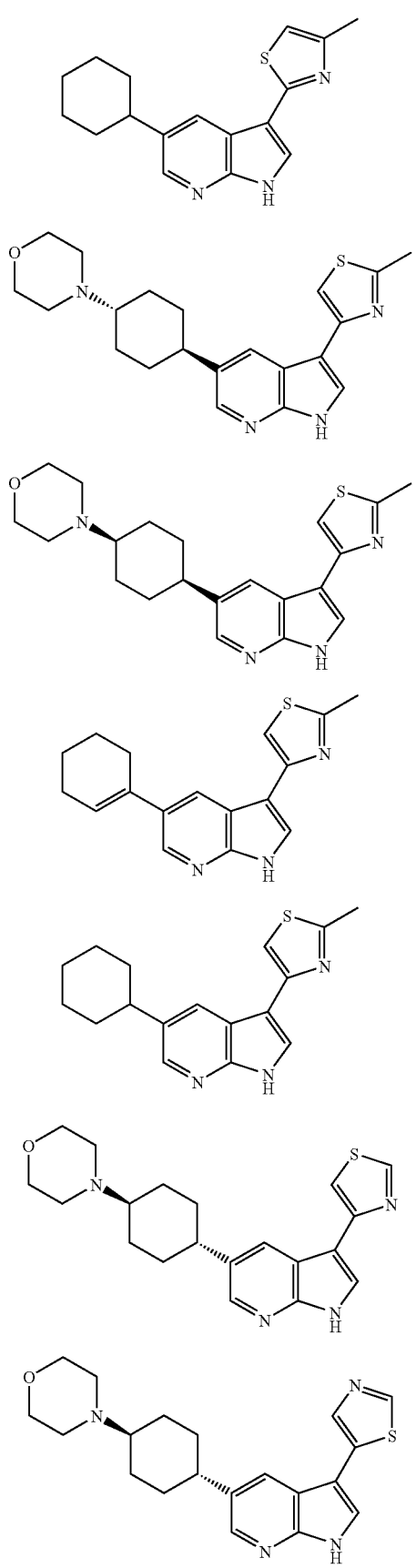
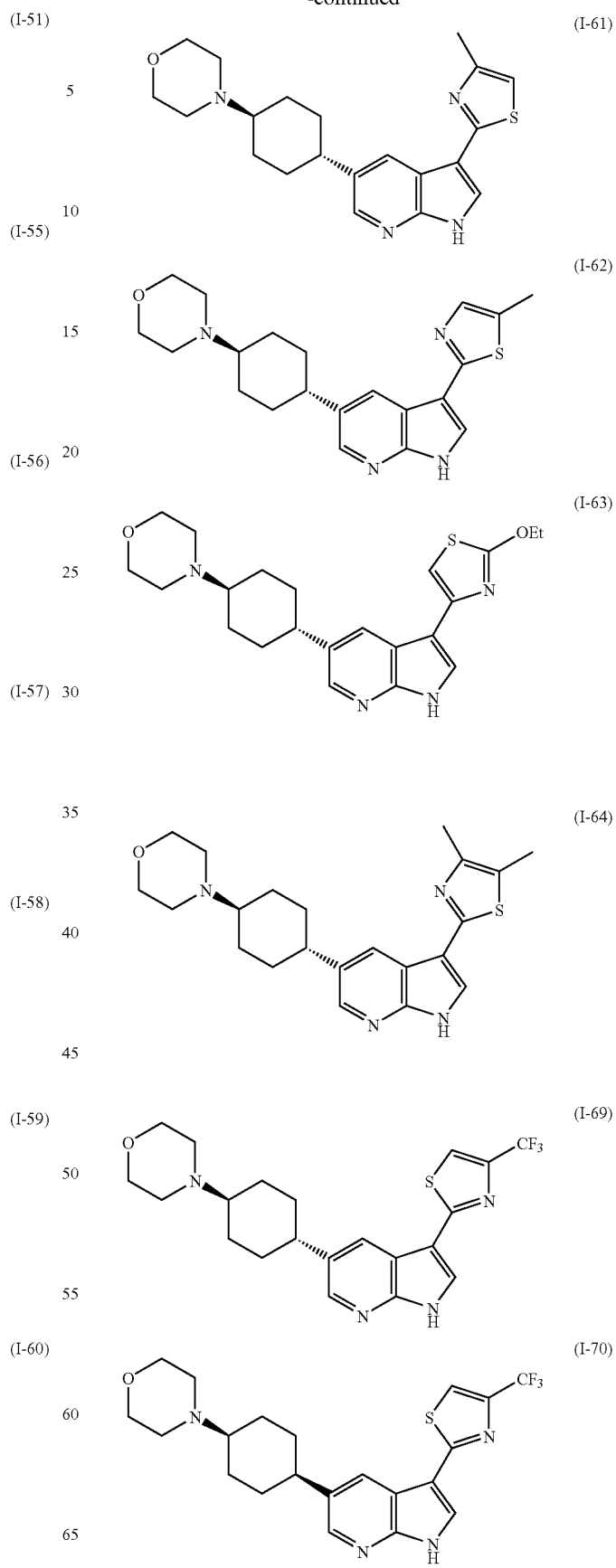

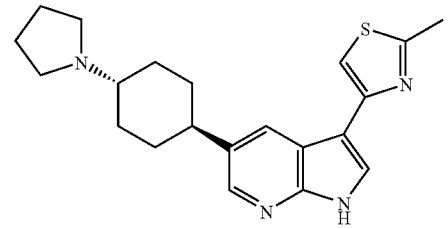
(I-74)
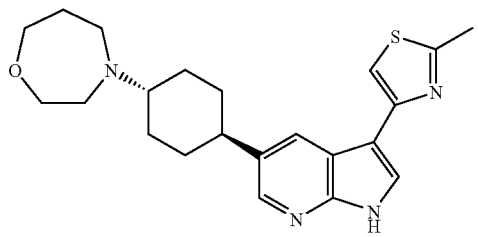
(I-75)
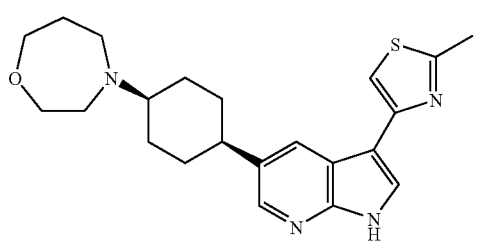
(I-76)
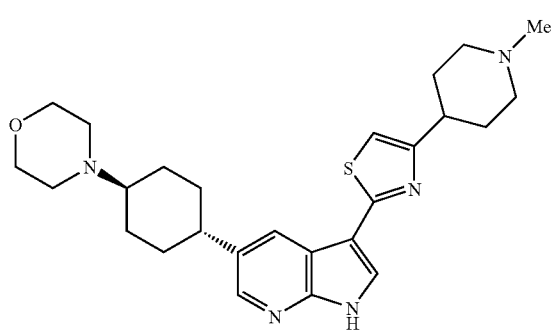
(I-78)
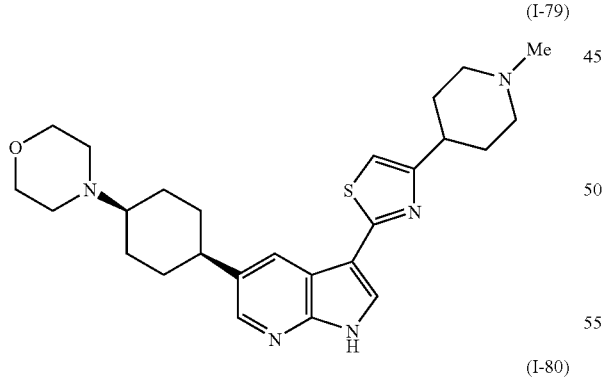
(I-79)
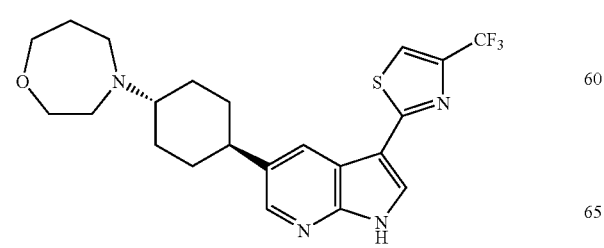
(I-80)
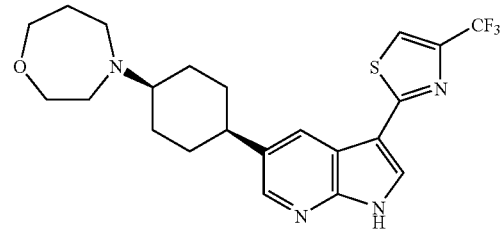
(I-81)
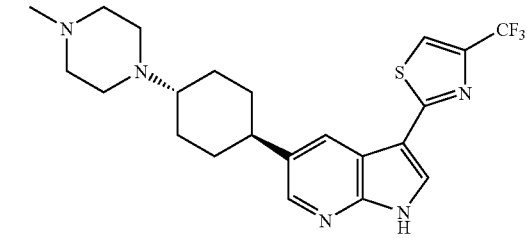
(I-82)
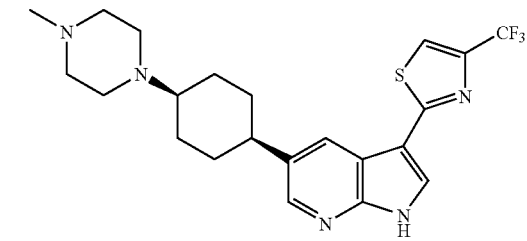
(I-83)
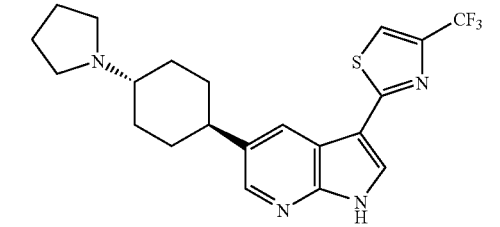
(I-84)
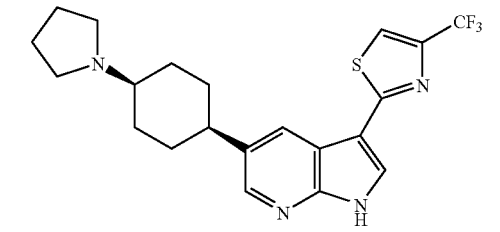
(I-85)
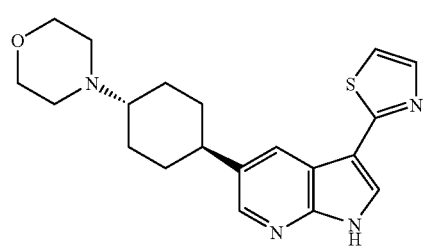
(I-89)

-continued
(I-90)
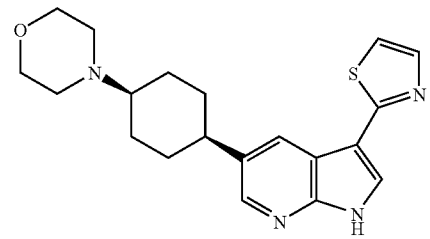
(I-91)
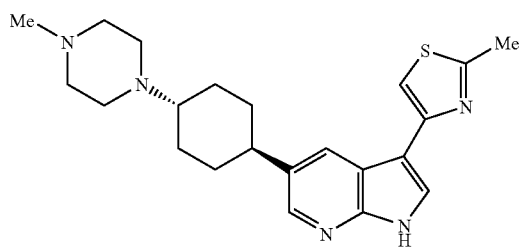
(I-92)
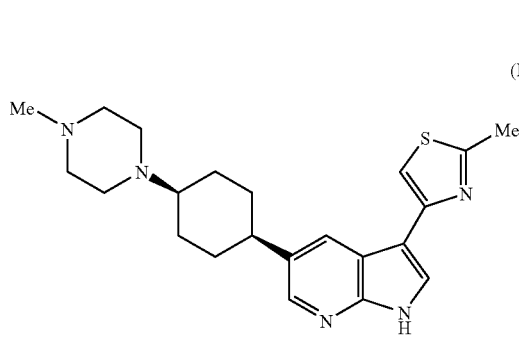
(I-94)
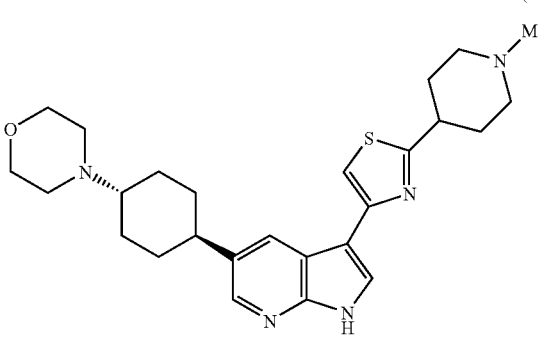
(I-96)
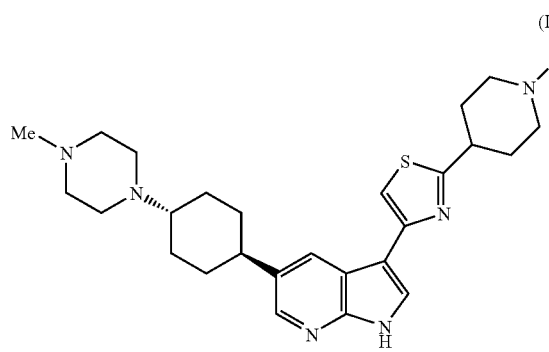
-continued
(I-98)
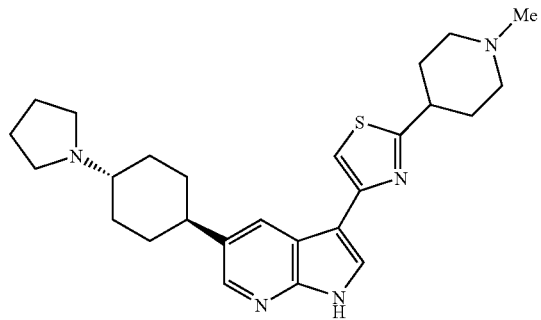
(I-100)
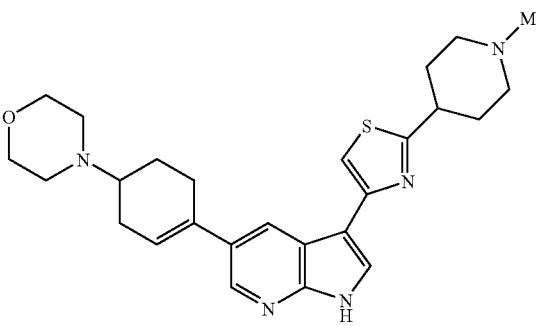
(I-101)
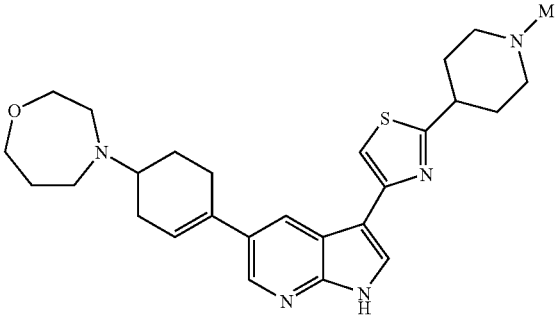
(I-102)
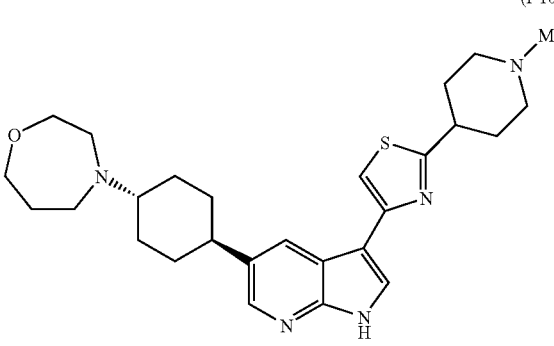

(I-107)
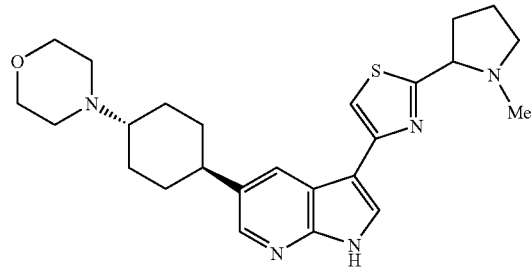
(I-108)
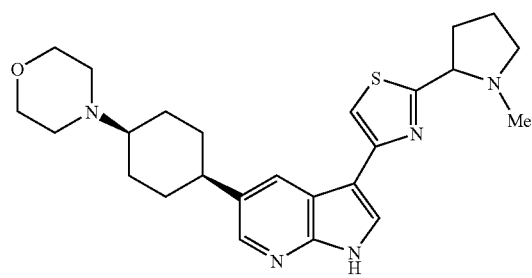
(I-109)
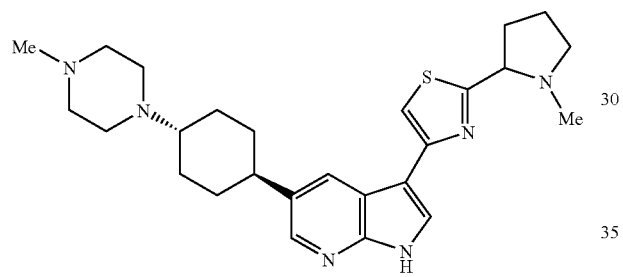
(I-110)
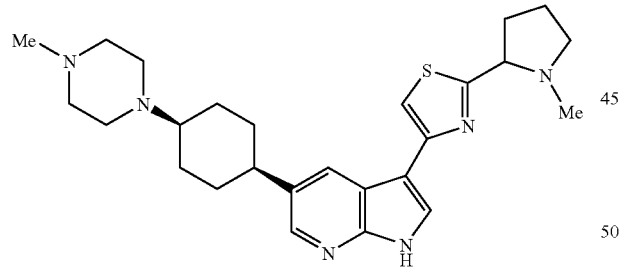
(I-111)
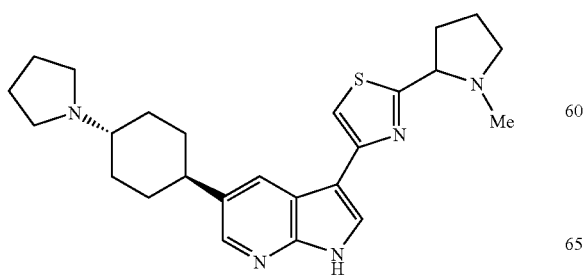
(I-113)
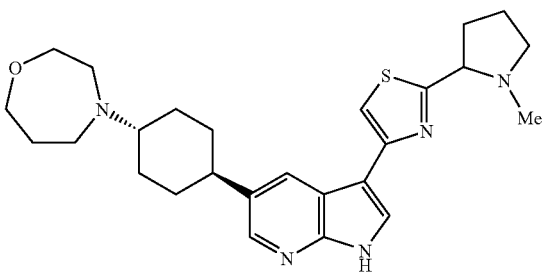
(I-114)
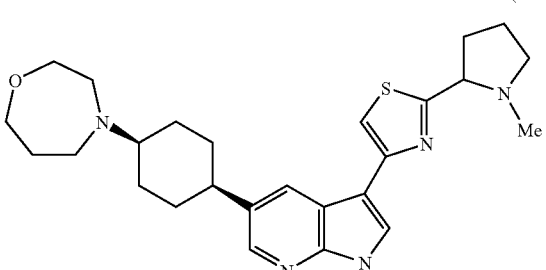
(I-116)
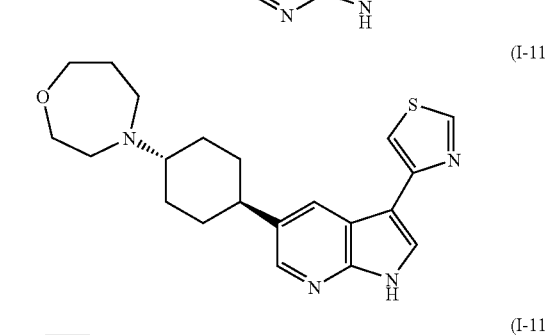
(I-117)
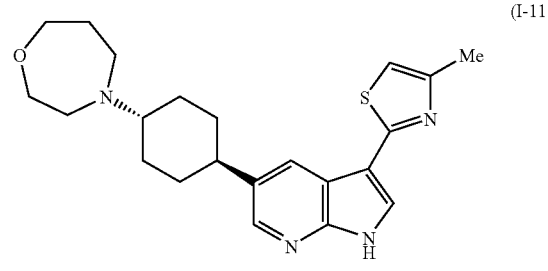
(I-118)
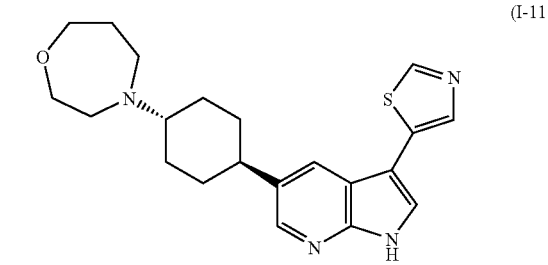
(I-119)
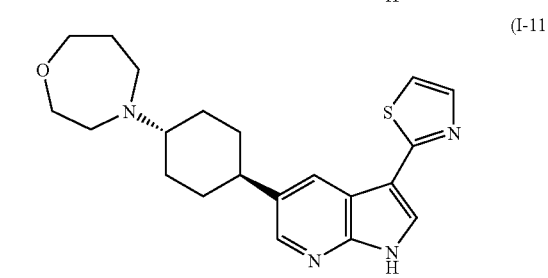

-continued

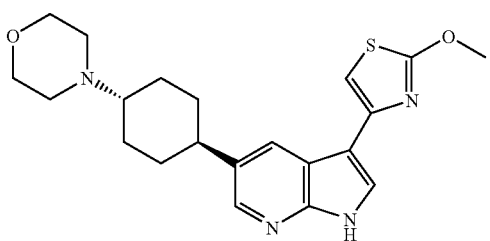
(I-120)

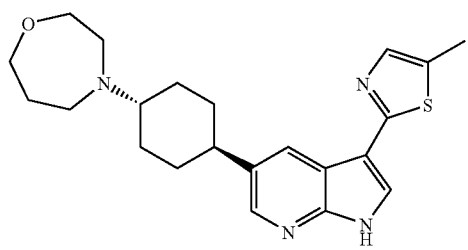
(I-121)

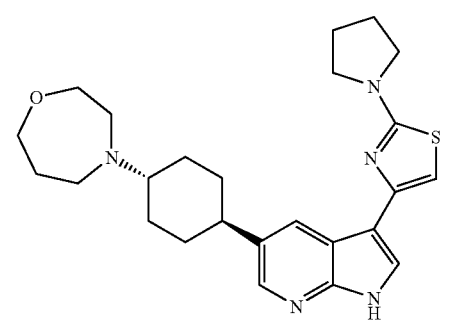
(I-122)

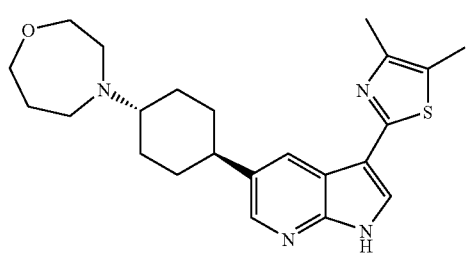
(I-123)

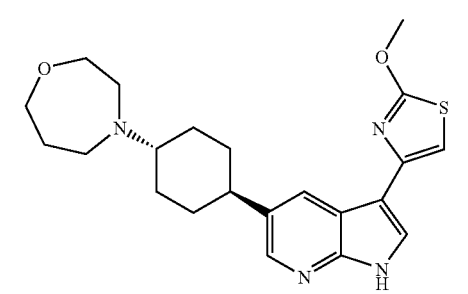
(I-124)

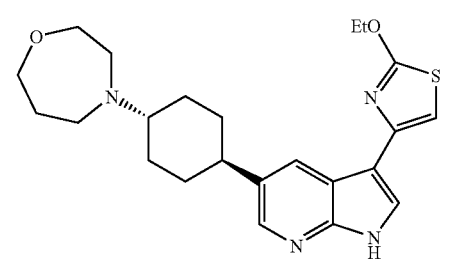
(I-125)

In a third aspect, the invention provides a pharmaceutical composition comprising a compound as defined herein.

In a fourth aspect, the invention provides a compound or a pharmaceutical composition as defined herein for use in medicine.

In a fifth aspect, the invention provides a compound or a pharmaceutical composition as defined herein for use in preventing and/or treating a neurodegenerative disorder, an inflammatory disease, an autoimmune disease and/or organ failure. Preferably, the neurodegenerative disorder is multiple sclerosis. Preferably, the inflammatory disease is multiple sclerosis. Preferably, the autoimmune disease is rheumatoid arthritis. Preferably the organ failure is heart failure, liver failure or diabetic nephropathy.

In a sixth aspect, the invention provides a method for preventing and/or treating a neurodegenerative disorder (for example multiple sclerosis), an inflammatory disease (for example multiple sclerosis), an autoimmune disease (for example rheumatoid arthritis) and/or organ failure (for example, heart failure, liver failure or diabetic nephropathy), which comprises administering to a mammalian animal an effective amount of a compound or pharmaceutically salt thereof or a composition as defined herein.

In a seventh aspect, the invention provides the use of a compound or pharmaceutically salt thereof as defined herein, for the manufacture of a medicament for the prevention and/or treatment of a neurodegenerative disorder (for example multiple sclerosis), an inflammatory disease (for example multiple sclerosis), an autoimmune disease (for example rheumatoid arthritis) and/or organ failure (for example, heart failure, liver failure or diabetic nephropathy).

The invention further provides a process for the manufacture of a compound of formula (I) and intermediates involved in the manufacture of a compound of formula (I). Processes for the manufacture of said compound and intermediates are described hereinafter in Reaction Schemes 1 to 8 and are illustrated in the accompanying examples.

BRIEF DESCRIPTION OF THE DRAWING(S)

DETAILED DESCRIPTION OF THE INVENTION

Figure 1:
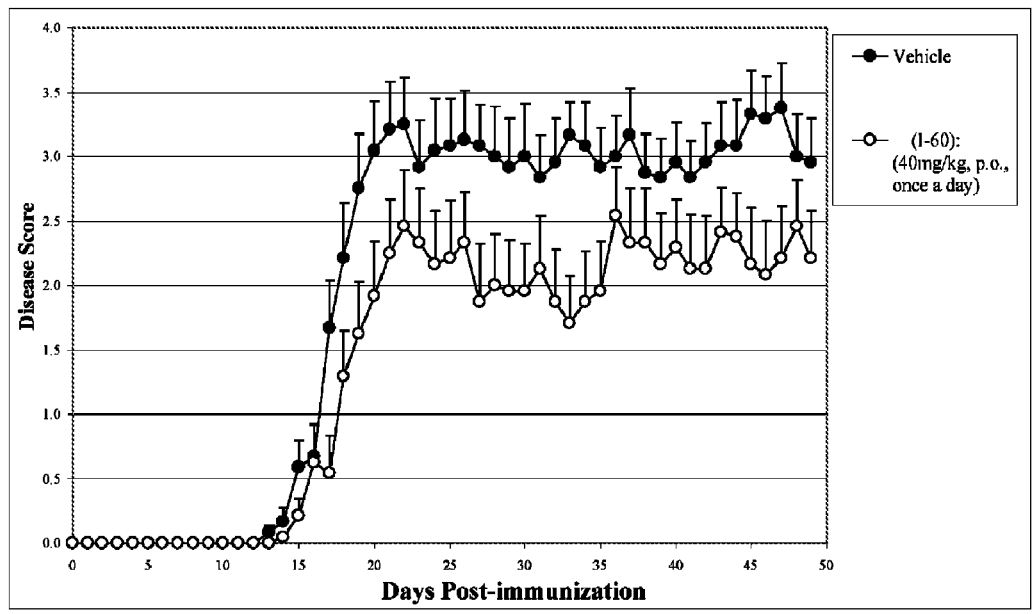
FIG. 1 shows the effect of (I-60) (40 mg/kg, p.o., once daily) on peak disease score in the EAE experiment in mice.

The meanings of symbols or terms used in the specification of the present application will be explained below, and the present invention will be described in detail.

The compounds of the present invention are provided for the prevention and or treatment of neurodegenerative disorders, inflammatory diseases and/or autoimmune diseases and/or organ failure.

Examples of "neurodegenerative disorders" used herein are: multiple sclerosis, dementia; Alzheimer's disease; Parkinson's disease; Amyotrophic Lateral Sclerosis; Huntington's disease; senile chorea; Sydenham's chorea; hypoglycemia; head and spinal cord trauma including traumatic head injury; acute and chronic pain; epilepsy and seizures; olivopontocerebellar dementia; neuronal cell death; hypoxia-related neurodegeneration; acute hypoxia; glutamate toxicity including glutamate neurotoxicity; cerebral ischemia;

dementia linked to meningitis and/or neurosis; cerebrovascular dementia; or dementia in an HIV-infected patient, preferably multiple sclerosis Examples of "autoimmune diseases" used herein are: rheumatoid arthritis, systemic lupus erythematosus, glumerulonephritis, scleroderma, chronic thyroiditis, Graves's disease, autoimmune gastritis, diabetes, autoimmune haemolytis anaemia, autoimmune neutropaenia, thrombocytopenia, atopic dermatitis, chronic active hepatitis, myasthenia gravis, multiple sclerosis, ulcerative colitis, Crohn's disease, psoriasis or graft vs host disease, preferably rheumatoid arthritis.

Examples of "inflammatory diseases" used herein are asthma, autoimmune diseases (including multiple sclerosis, systemic Lupus erythematosus), chronic inflammation, chronic prostatitis, glomerulonephritis, hypersensitivity, inflammatory bowel disease, pelvic inflammatory disease, reperfusion injury, rheumatoid arthritis, transplant rejection and vasculitis.

It will be appreciated that an inflammatory disease is a disease accompanied by a cascade of biochemical events including the local vascular system, the immune system and various cells within the injured tissues, e.g. brain, spinal cord, synovial joints, organ systems (heart, liver, kidney lung, gut) and soft tissue, (muscle, skin) etc. For the purposes of the present invention, inflammation can either be acute or chronic. The inflammatory diseases for the present invention include those which involve the immune system (i.e. as demonstrated in allergic reaction and some myopathies). The inflammatory diseases for the present invention further include non-immune diseases with aetiological orgins in inflammatory processes including cancer, atherosclerosis and ischameic heart disease.

The compounds of the present invention are further provided for the prevention and/or treatment of organ failure, particularly of the heart, liver or kidneys. Examples of "organ failure" used herein are chronic or acute cardiac failure, cardiac hypertrophy, dilated, hypertrophic or restrictive cardiomyopathy, acute myocardial infarction, post-myocardial infarction, acute or chronic myocarditis, diastolic dysfunction of the left ventricle, systolic dysfunction of the left ventricle; hypertension and nephropathy and nephritis as complications thereof, diabetic nephropathy, endothelial dysfunction, arteriosclerosis or post-angioplasty restenosis. The invention particularly relates to the prevention and/or treatment of diabetic nephropathy.

The compounds of the present invention are further provided for the prevention and/or treatment of chronic rheumatoid arthritis, osteoarthritis, gout, chronic obstructive pulmonary disease, asthma, bronchitis, cystic fibrosis, inflammatory bowel disease, irritable colon syndrome, mucous colitis, ulcerative colitis, Crohn's disease, gastritis, esophagitis, eczema, dermatitis, hepatitis, glomerulonephritis, ophthalmic diseases, diabetic retinopathy, diabetic macular edema, diabetic nephropathy, diabetic neuropathy, obesity, psoriasis, cancer, cerebral apoplexy, cerebrovascular disorder, an ischemic disorder of an organ selected from the heart, kidney, liver and brain, ischemia reperfusion injury, endotoxin shock or rejection in transplantation.

The term "halogen atom" used herein means a fluorine atom, a chlorine atom, a bromine atom, an iodine atom and the like, preferably a fluorine atom or a chlorine atom, and more preferably a fluorine atom.

The term "$C_{1-6}$ alkyl group" used herein means an alkyl group that is a straight or branched chain with 1 to 6 carbons. The alkyl group therefore has 1, 2, 3, 4, 5 or 6 carbon atoms. Specifically, examples of "$C_{1-6}$ alkyl group" include methyl group, ethyl group, n-propyl group, iso-propyl group, n-butyl group, iso-butyl group, sec-butyl group, tert-butyl group, n-pentyl group, 1,1-dimethylpropyl group, 1,2-dimethylpropyl group, 2,2-dimethylpropyl group, 1-ethylpropyl group, n-hexyl group, 1-ethyl-2-methylpropyl group, 1,1,2-trimethylpropyl group, 1-ethylbutyl group, 1-methylbutyl group, 2-methylbutyl group, 1,1-dimethylbutyl group, 1,2-dimethylbutyl group, 2,2-dimethylbutyl group, 1,3-dimethylbutyl group, 2,3-dimethylbutyl group, 2-ethylbutyl group, 2-methylpentyl group, 3-methylpentyl group and the like.

The term "$C_{1-6}$ alkoxy group" used herein means an oxy group that is bonded to the previously defined "$C_{1-6}$ alkyl group". Specifically, examples of "$C_{1-6}$ alkoxy group" include methoxy group, ethoxy group, n-propoxy group, iso-propoxy group, n-butoxy group, iso-butoxy group, sec-butoxy group, tert-butoxy group, n-pentyloxy group, iso-pentyloxy group, sec-pentyloxy group, n-hexyloxy group, iso-hexyloxy group, 1,1-dimethylpropoxy group, 1,2-1 dimethylpropoxy group, 2,2-dimethylpropoxy group, 2-methylbutoxy group, 1-ethyl-2-methylpropoxy group, 1,1,2-trimethylpropoxy group, 1,1-dimethylbutoxy group, 1,2-dimethylbutoxy group, 2,2-dimethylbutoxy group, 2,3-dimethylbutoxy group, 1,3-dimethylbutoxy group, 2-ethylbutoxy group, 2-methylpentyloxy group, 3-methylpentyloxy group and the like.

The term "($C_{1-6}$ alkyl)amino group" used herein means an amino group which is substituted with a $C_{1-6}$ alkyl group as described above.

The term "di($C_{1-6}$ alkyl)amino group" used herein means an amino group which is substituted with two $C_{1-6}$ alkyl group as described above.

The term "5-7 membered non-aromatic hydrocarbon cyclic group" used herein means 5-7 membered cycloalkyl group, 5-7 membered cycloalkenyl group and 5-7 membered cycloalkadienyl group. The non-aromatic hydrocarbon cyclic group therefore has 5, 6 or 7 ring members. Specifically, examples of "5-7 membered non-aromatic hydrocarbon cyclic group" include cyclopentyl group, cyclohexyl group, cycloheptyl group, cyclopentenyl group, cyclohexenyl group, cycloheptenyl group, cyclopentadienyl group, cyclohexadienyl group and cycloheptadienyl group.

The term "4-7 membered non-aromatic heterocyclic group" used herein means heterocyclic group, which has no aromaticity and the number of atoms forming the ring is 4, 5, 6 or 7, containing one or more species of heteroatom selected from the group consisting of a nitrogen atom, a sulphur atom and an oxygen atom. Specifically, examples of "4-7 membered non-aromatic heterocyclic group" include azetidinyl group, pyrrolidinyl group, imidazolidinyl group, pyrazolidinyl group, piperidinyl group, piperazinyl group, morpholinyl group, tetrahydropyranyl group, dioxanyl group, diazepanyl, oxazepanyl group and the like.

The term "$C_{6-10}$ aryl group" used herein means an aryl group constituted by 6, 7, 8, 9, or 10 carbon atoms and includes condensed ring groups such as monocyclic ring group, or bicyclic ring group and the like. Specifically, examples of "$C_{6-10}$ aryl group" include phenyl group, indenyl group, naphthyl group or azulenyl group and the like. It should be noted that condensed rings such as indan and tetrahydro naphthalene are also included in the aryl group.

The term "5-6 membered heteroaryl group" used herein means a monocyclic heteroaryl group, in which the number of atoms forming the ring is 5 to 6, containing one or more species of heteroatom selected from the group consisting of a nitrogen atom, a sulphur atom and an oxygen atom. Specifically, examples of "5-6 membered heteroaryl group" include 1) pyrrolyl group, pyridyl group, pyridazinyl group, pyrimidinyl group, pyrazinyl group, triazolyl group, tetrazolyl group, pyrazolyl group, imidazolyl group and the like as a nitrogen-containing heteroaryl group; 2) thienyl group and the like as a sulphur-containing heteroaryl group; 3) furyl group, pyranyl group and the like as an oxygen-containing heteroaryl group; and 4) thiazolyl group, isothiazolyl group, isoxazolyl group, furazanyl group, oxazolyl group, oxadiazolyl group, pyrazolooxazolyl group, imidazothiazolyl group, furopyrrolyl group or pyridooxazinyl group and the like as a heteroaryl group containing two or more different species of heteroatoms.

Subsequently, a substituent in the compounds according to the present invention represented by the formula (I) will be explained.

$R^1$ represents a 5-7 membered non-aromatic hydrocarbon cyclic group optionally and independently substituted with 1-4 substituent(s) selected from the group consisting of a halogen atom, an oxo group, an ethylenedioxy group, a $C_{1-6}$ alkyl group, a $C_{1-6}$ alkoxy group, a $C_{1-6}$ hydroxyalkyl group, —C(O)OH, a ($C_{1-6}$ alkyl)amino group, a di($C_{1-6}$ alkyl)amino group and —Ra—Rb;

wherein $R^a$ represents a single bond or —CH$_2$—;

wherein $R^b$ represents a 4-7 membered non-aromatic heterocyclic group, a $C_{6-10}$ aryl group or a 5-6 membered heteroaryl group, optionally and independently substituted with 1-4 substituent(s) selected from the group consisting of a halogen atom and a $C_{1-6}$ alkyl group.

Preferably $R^1$ represents a cyclopentyl group, a cyclohexyl group, a cyclopentenyl group, a cyclohexenyl group or a cyclohexadienyl group.

Preferably, $R^1$ represents a cyclohexyl group or a cyclohexenyl group, more preferably $R^1$ represents a cyclohexyl group.

Preferably $R^1$ is optionally and independently substituted with 1-4 substituent(s) selected from the group consisting of a halogen atom, an oxo group, an ethylenedioxy group, a $C_{1-6}$ alkyl group, a $C_{1-6}$ alkoxy group, a $C_{1-6}$ hydroxyalkyl group, —C(O)OH, a ($C_{1-6}$ alkyl)amino group, a di($C_{1-6}$ alkyl)amino group and —$R^a$-$R^b$;

wherein $R^a$ represents a single bond or —CH$_2$—;

wherein $R^b$ represents a 4-7 membered non-aromatic heterocyclic group, a $C_{6-10}$ aryl group or a 5-6 membered heteroaryl group, optionally and independently substituted with 1-4 substituent(s) selected from the group consisting of halogen atom and $C_{1-6}$ alkyl group.

$R^1$ is preferably optionally and independently substituted with 1-4 substituent(s) selected from the group consisting of a halogen atom, an oxo group, an ethylenedioxy group, a $C_{1-6}$ alkyl group, a $C_{1-6}$ alkoxy group, a $C_{1-6}$ hydroxyalkyl group, —C(O)OH, and —$R^a$-$R^b$; wherein $R^a$ and $R^b$ are as defined above.

Preferably, $R^1$ is optionally and independently substituted with 1-4 substituent(s) selected from the group consisting of a fluorine atom, an oxo group, an ethylenedioxy group, a methyl group, an ethyl group, a t-butyl group, a methoxy group, a methylamino group, a dimethylamino group, a diethylamino group, an azetidinyl group, a piperidyl group, a fluoropiperidyl group, a pyrrolidinyl group, a methylpiperazinyl group, an isopropylpiperazinyl group, a methyldiazepanyl group, a morpholino group, an oxazepanyl group.

Preferably $R^1$ represents a 5-7 membered non-aromatic hydrocarbon cyclic group optionally and independently substituted with 1-4 substituent(s) selected from the group consisting of a halogen atom, an oxo group, an ethylenedioxy group, a $C_{1-6}$ alkyl group, a $C_{1-6}$ alkoxy group, a $C_{1-6}$ hydroxyalkyl group, —C(O)OH, a ($C_{1-6}$ alkyl)amino group, a di($C_{1-6}$ alkyl)amino group and —Ra—Rb;

wherein $R^a$ represents a single bond or —CH$_2$—;

wherein $R^b$ represents a 4-7 membered non-aromatic heterocyclic group, a $C_{6-10}$ aryl group or a 5-6 membered heteroaryl group, optionally and independently substituted with 1-4 substituent(s) selected from the group consisting of a halogen atom and a $C_{1-6}$ alkyl group.

Preferably, $R^1$ represents a 5-7 membered non-aromatic hydrocarbon cyclic group optionally and independently substituted with 1-4 substituent(s) selected from the group consisting of a halogen atom, an oxo group, an ethylenedioxy group, a $C_{1-6}$ alkyl group, a $C_{1-6}$ alkoxy group, a $C_{1-6}$ hydroxyalkyl group, —C(O)OH, and —$R^a$-$R^b$;wherein $R^a$ and $R^b$ are as defined above.

Preferably $R^1$ represents a cyclopentyl group, a cyclohexyl group, a cyclopentenyl group, a cyclohexenyl group or a cyclohexadienyl group, optionally and independently substituted with 1-4 substituent(s) selected from the group consisting of a halogen atom, an oxo group, an ethylenedioxy group, a $C_{1-6}$ alkyl group, a $C_{1-6}$ alkoxy group, a $C_{1-6}$ hydroxyalkyl group, —C(O)OH, a ($C_{1-6}$ alkyl)amino group, a di($C_{1-6}$ alkyl) amino group and —$R^a$-$R^b$; wherein $R^a$ represents a single bond or —CH$_2$—;

wherein $R^b$ represents a 4-7 membered non-aromatic heterocyclic group, a $C_{6-10}$ aryl group or a 5-6 membered heteroaryl group, optionally and independently substituted with 1-4 substituent(s) selected from the group consisting of halogen atom and $C_{1-6}$ alkyl group.

Preferably $R^1$ represents a cyclopentyl group, a cyclohexyl group, a cyclopentenyl group, a cyclohexenyl group or a cyclohexadienyl group, optionally and independently substituted with 1-4 substituent(s) selected from the group consisting of an ethylenedioxy group, a $C_{1-6}$ alkyl group and a morpholino group.

Preferably, $R^1$ represents a cyclohexyl group or a cyclohexenyl group optionally and independently substituted with 1-4 substituent(s) selected from the group consisting of a fluorine atom, an oxo group, an ethylenedioxy group, a methyl group, an ethyl group, a t-butyl group, a methoxy group, a methylamino group, a dimethylamino group, a diethylamino group, an azetidinyl group, a piperidyl group, a fluoropiperidyl group, a pyrrolidinyl group, a methylpiperazinyl group, an isopropylpiperazinyl group, a methyldiazepanyl group, a morpholino group, an oxazepanyl group.

More preferably, $R^1$ represents a cyclohexyl group optionally and independently substituted with 1-4 substituent(s) selected from the group consisting of a fluorine atom, an oxo group, an ethylenedioxy group, a methyl group, an ethyl group, a t-butyl group, a methoxy group, a methylamino group, a dimethylamino group, a diethylamino group, an azetidinyl group, a piperidyl group, a fluoropiperidyl group, a pyrrolidinyl group, a methylpiperazinyl group, an isopropylpiperazinyl group, a methyldiazepanyl group, a morpholino group, an oxazepanyl group.

Most preferably, $R^1$ represents a cyclohexyl group optionally and independently substituted with a substituent selected from a methylpiperazinyl group, a morpholino group and an oxazepanyl group.

$R^2$ represents a single bond or a carbonyl group. Preferably, $R^2$ represents a single bond.

$R^3$ represents hydrogen, a hydroxyl group, a $C_{1-6}$ alkyl group, a $C_{1-6}$ alkoxy group, a $C_{1-6}$ haloalkyl group, a di($C_{1-6}$ alkyl)amino group or a 4-7 membered non-aromatic heterocyclic group wherein at least one ring heteroatom is a nitrogen atom, optionally and independently substituted with 1-4 $C_{1-6}$ alkyl group(s).

Preferably $R^3$ represents a hydroxyl group, a di($C_{1-6}$ alkyl) amino group or a 4-7 membered non-aromatic heterocyclic group wherein at least one ring heteroatom is a nitrogen atom, optionally and independently substituted with 1-4 $C_{1-6}$ alkyl group(s).

Preferably, $R^3$ represents hydrogen, a methyl group, a methyoxy group, an ethoxy group, a trifluoromethyl group, a dimethylamino group, a piperidyl group, a piperazinyl group or a morpholino group optionally and independently substituted with a $C_{1-6}$ alkyl group.

Preferably, $R^3$ represents a dimethylamino group, piperidyl group, piperazinyl group or morpholino group optionally and independently substituted with $C_{1-6}$ alkyl group.

$R^4$ represents hydrogen or a $C_{1-6}$ alkyl group, preferably $R^4$ is hydrogen or methyl.

JNK inhibitory compounds of formula (I) as defined above have significant in vivo activity.

Specifically, preferable compounds according to the present invention are following:

(I-1)
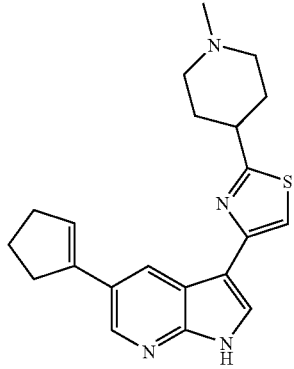

(I-2)
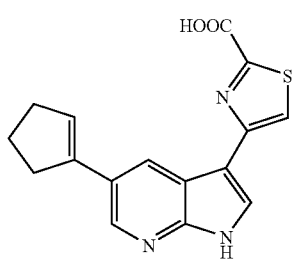

(I-3)
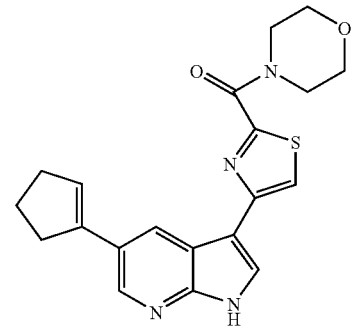

(I-4)
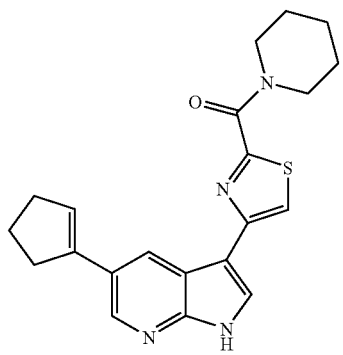

(I-5)
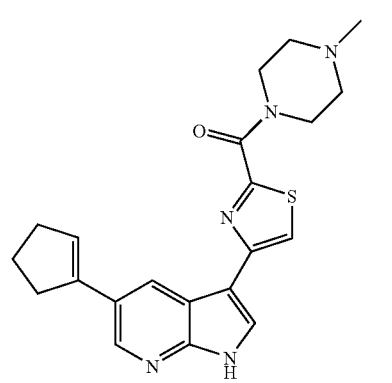

(I-6)
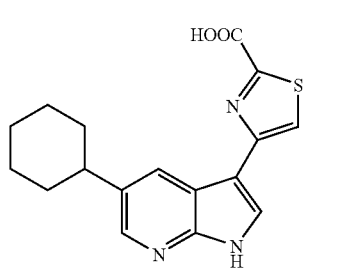

(I-7)
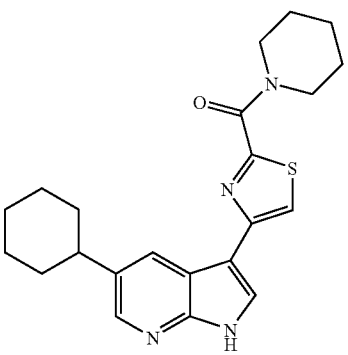

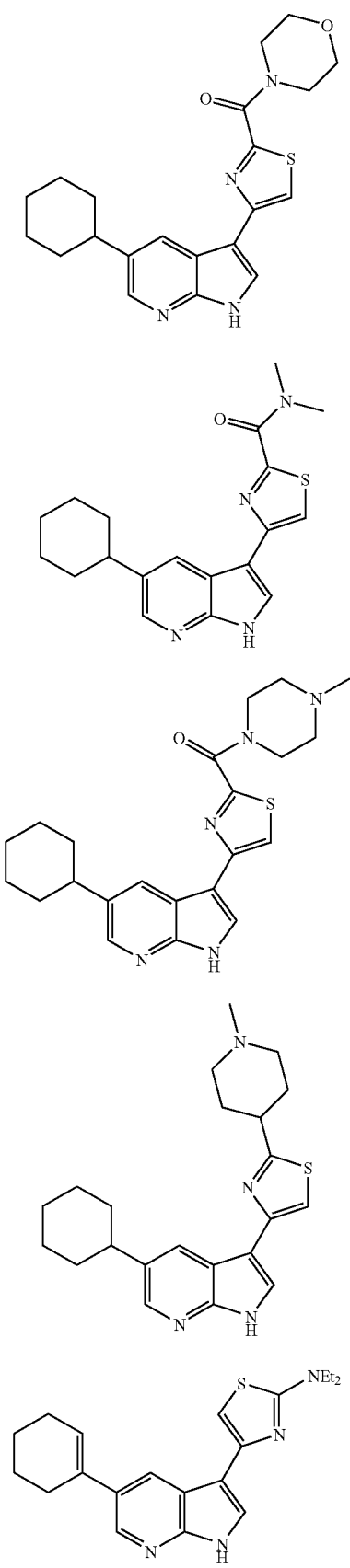
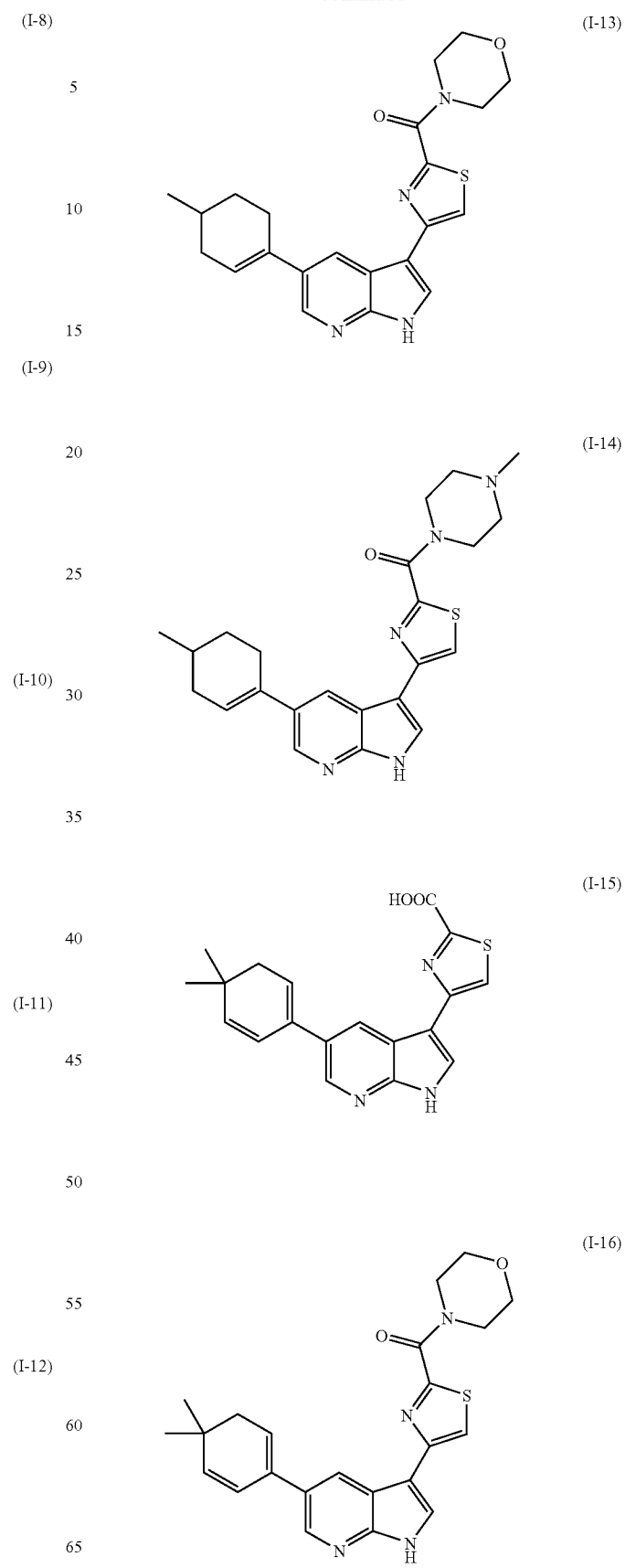

-continued
(I-17)
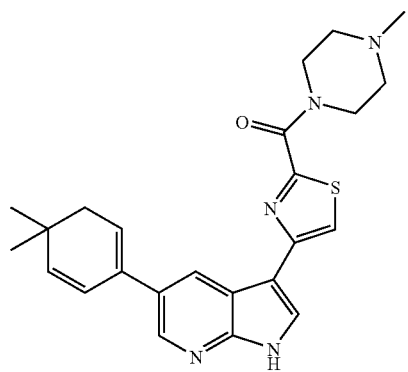
(I-18)
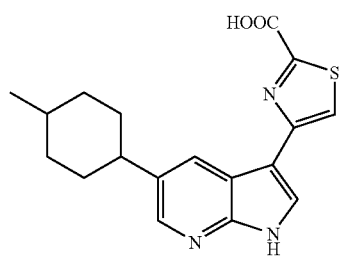
(I-19)
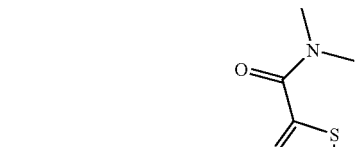
(I-20)
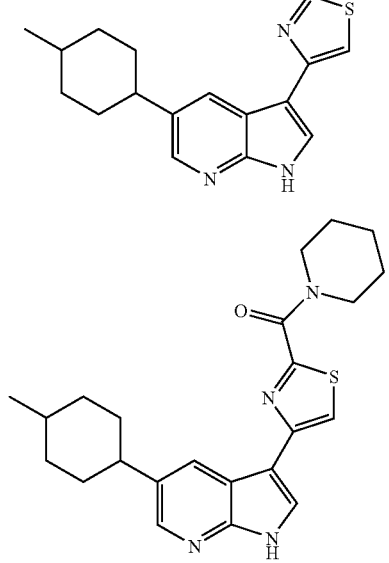
(I-21)
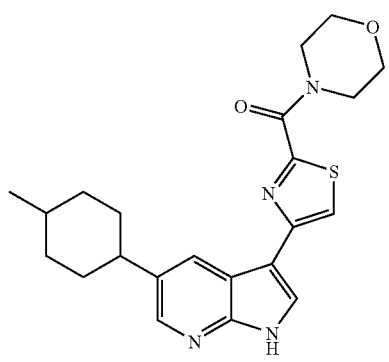
-continued
(I-22)
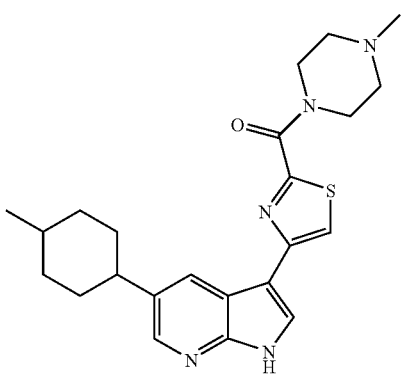
(I-23)
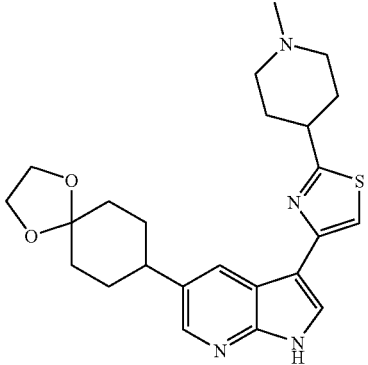
(I-24)
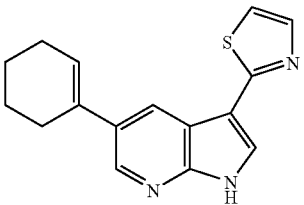
(I-25)
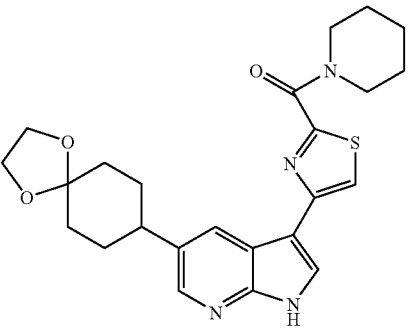
(I-26)
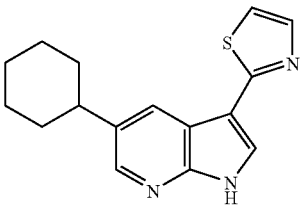

-continued
(I-27)
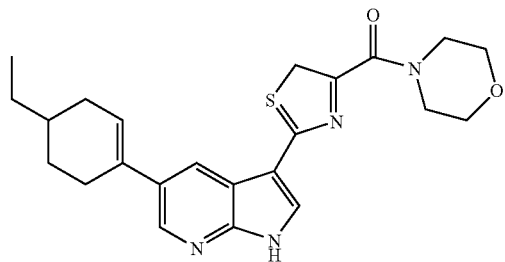
(I-28)
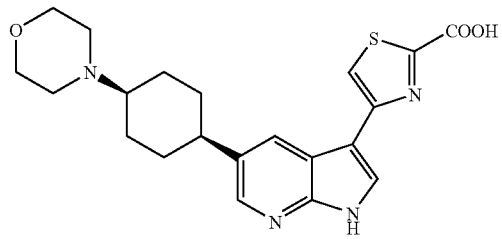
(I-29)
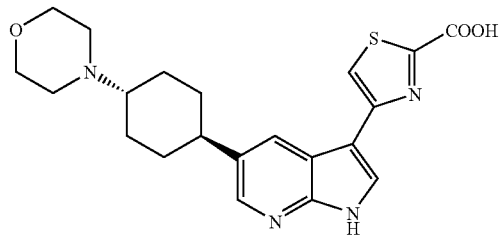
(I-30)
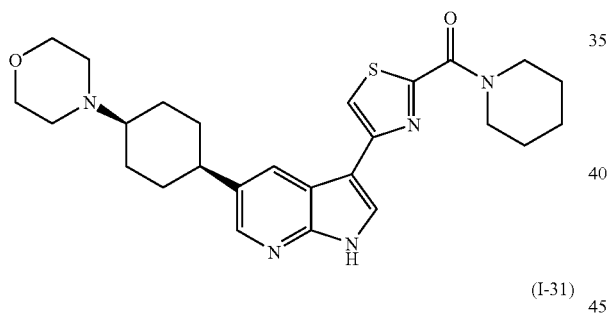
(I-31)
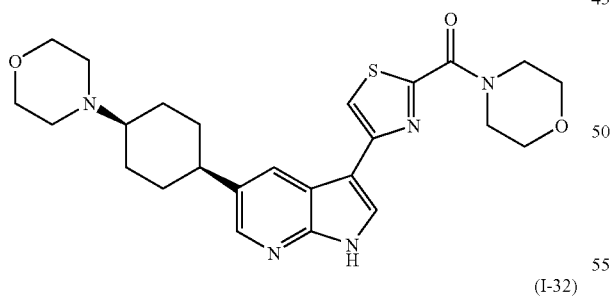
(I-32)
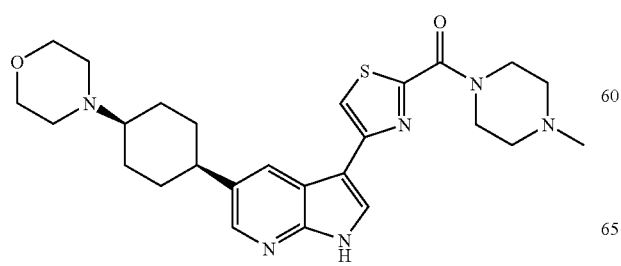
-continued
(I-33)
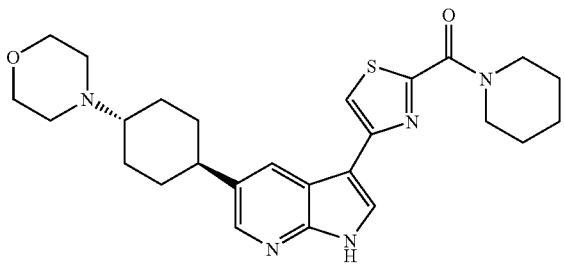
(I-34)
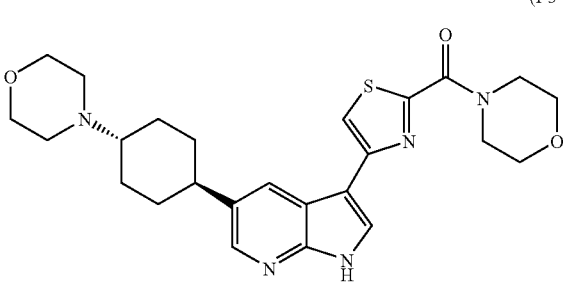
(I-48)
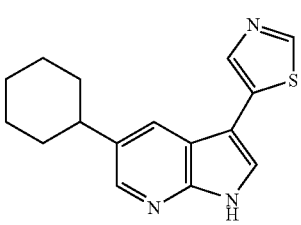
(I-49)
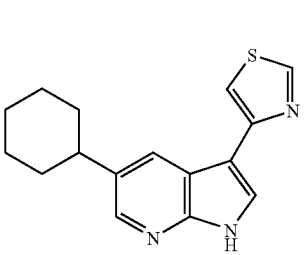
(I-50)
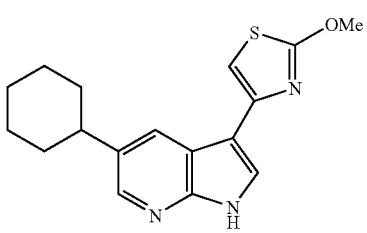
(I-51)
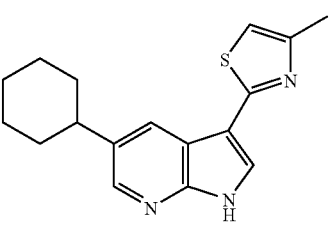

-continued
(I-55)
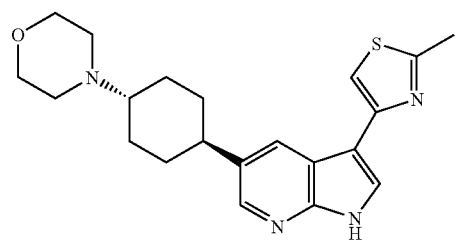
(I-56)
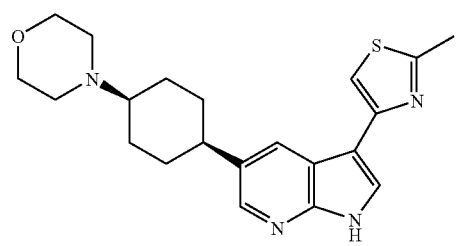
(I-57)
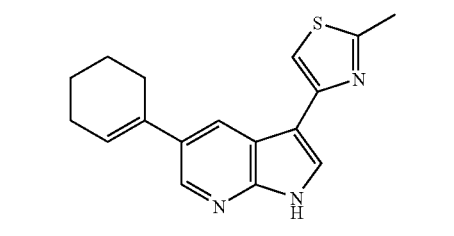
(I-58)
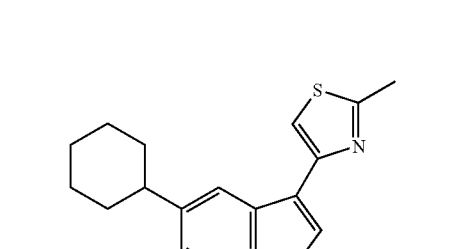
(I-59)
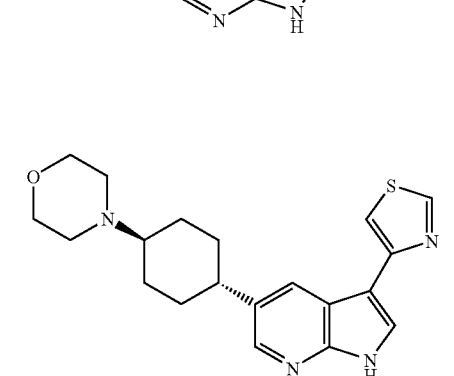
(I-60)
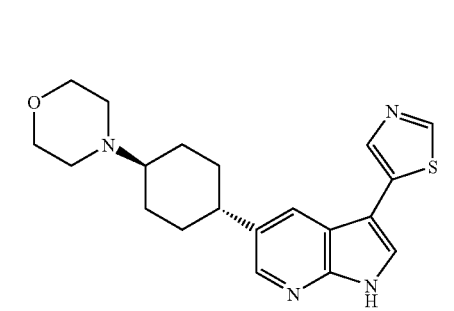
-continued
(I-61)
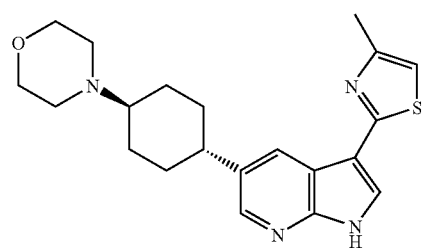
(I-62)
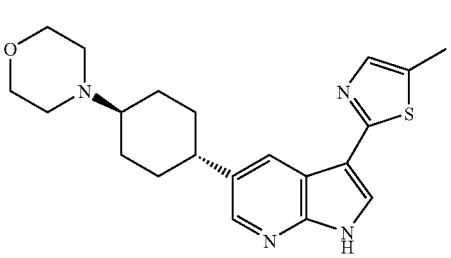
(I-63)
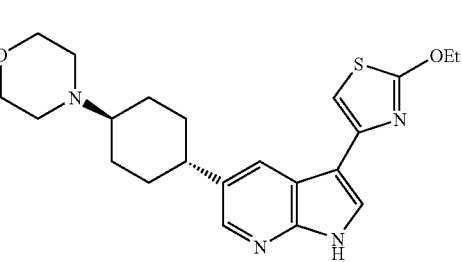
(I-64)
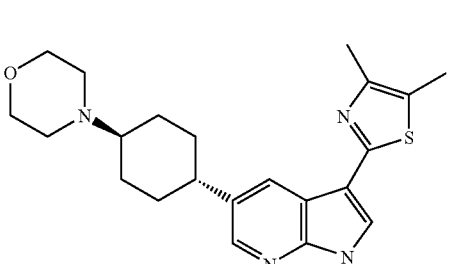
(I-69)
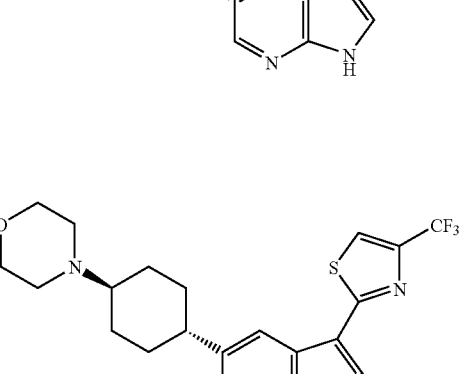
(I-70)
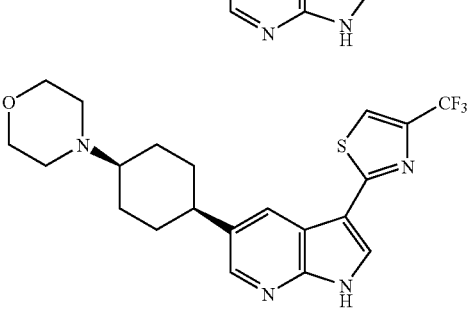

(I-74)
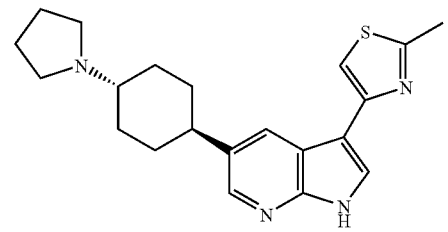
(I-75)
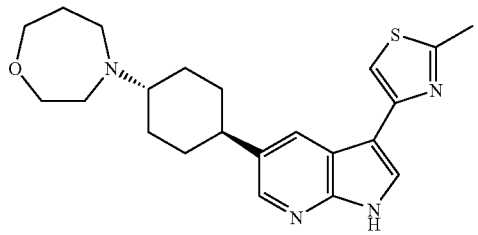
(I-76)
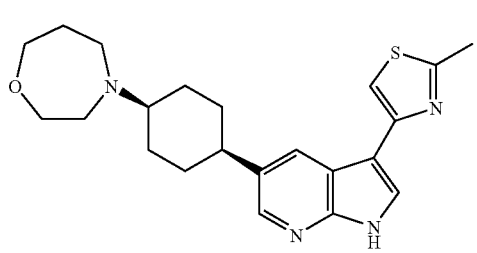
(I-78)
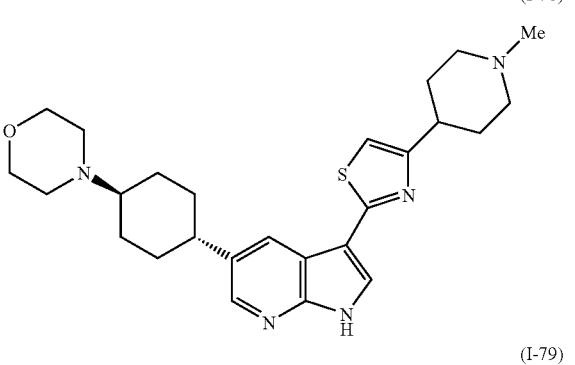
(I-79)
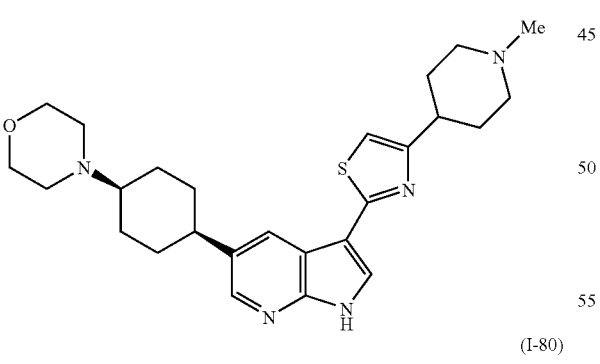
(I-80)
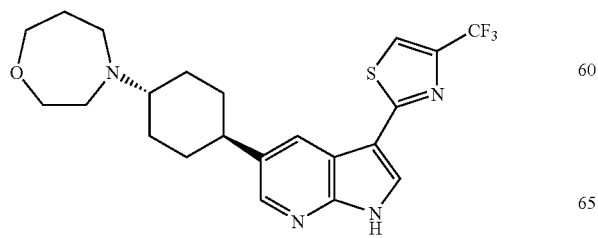
(I-81)
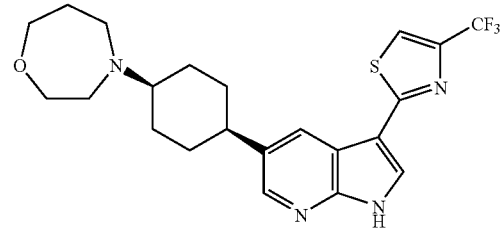
(I-82)
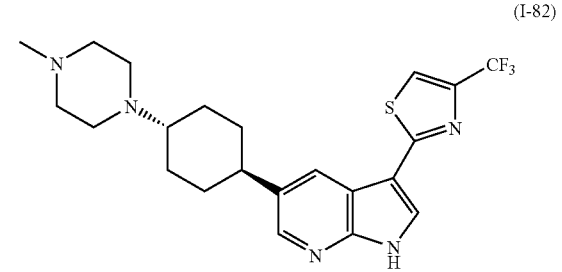
(I-83)
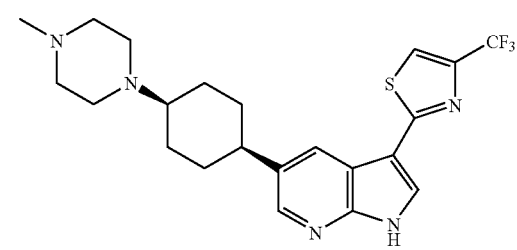
(I-84)
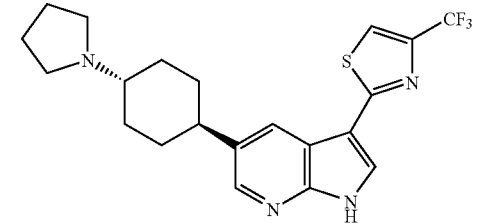
(I-85)
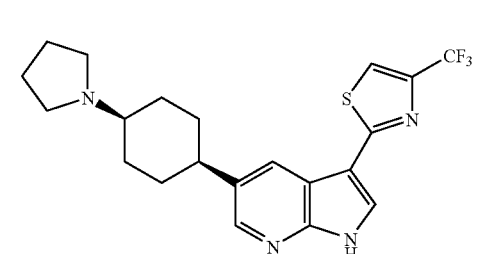
(I-89)
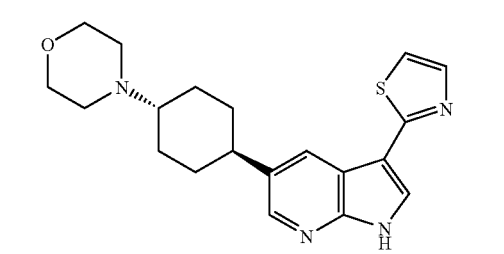

(I-90) 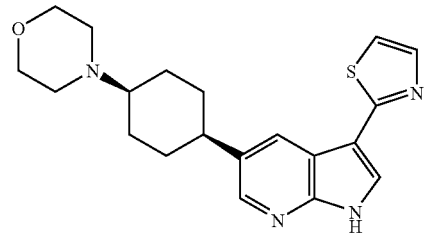
(I-91) 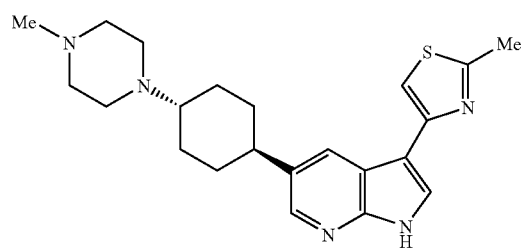
(I-92) 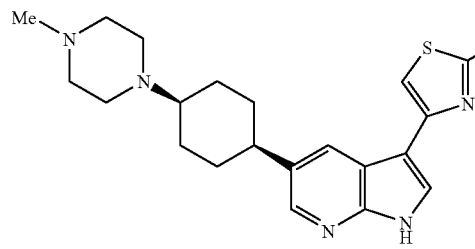
(I-94) 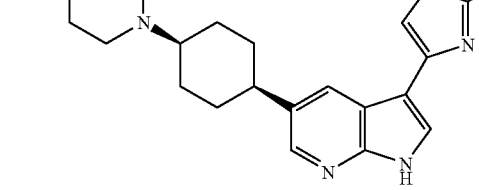
(I-96) 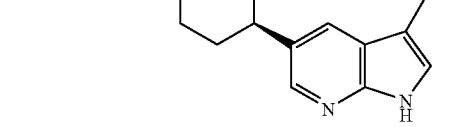
(I-98) 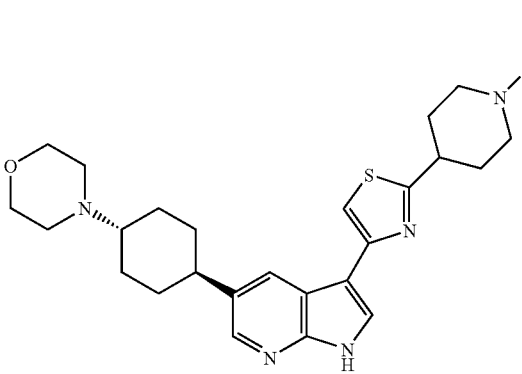
(I-100) 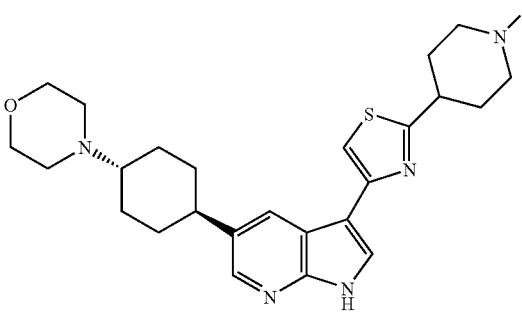
(I-101) 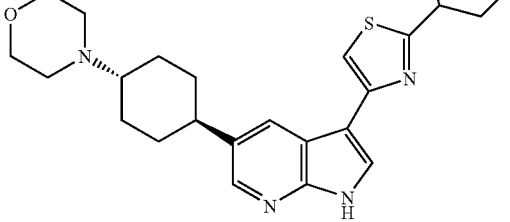
(I-102) 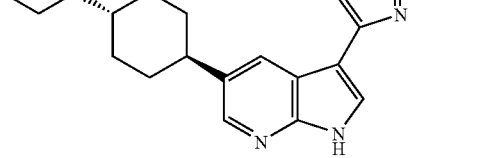

(I-107)
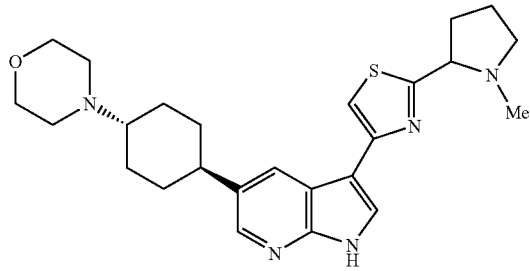
(I-108)
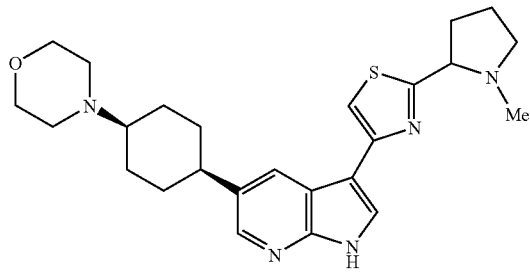
(I-109)
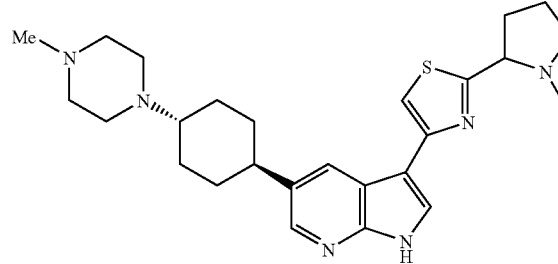
(I-110)
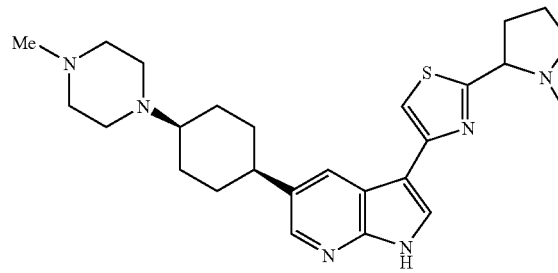
(I-111)
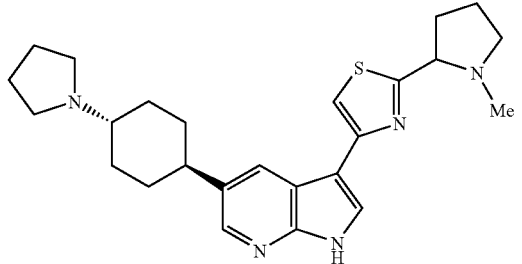
(I-113)
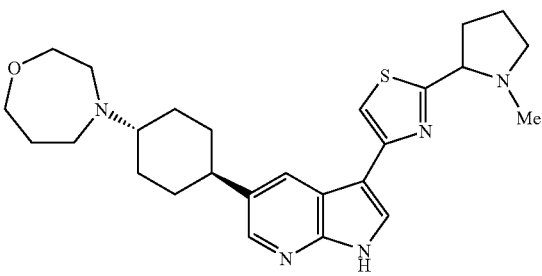
(I-114)
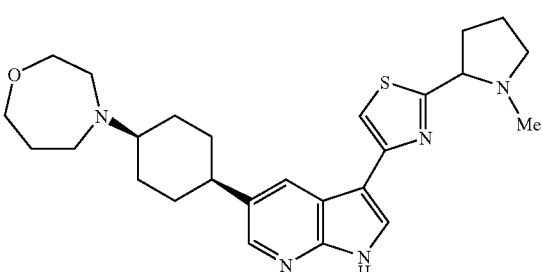
(I-116)
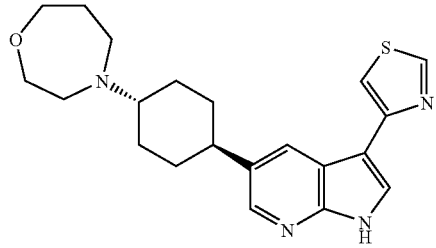
(I-117)
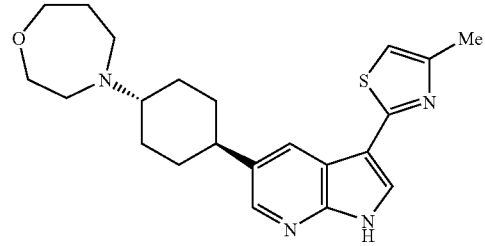
(I-118)
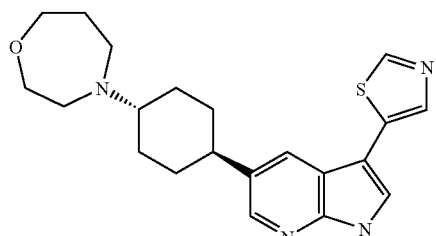
(I-119)
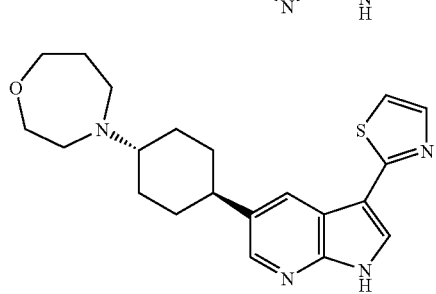

(I-120)
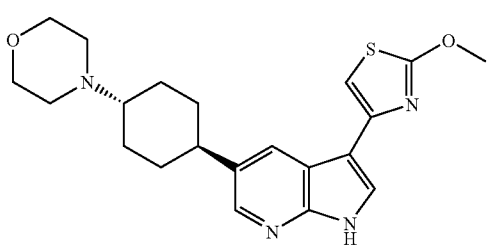

(I-121)
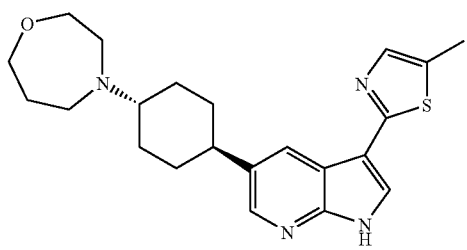

(I-122)
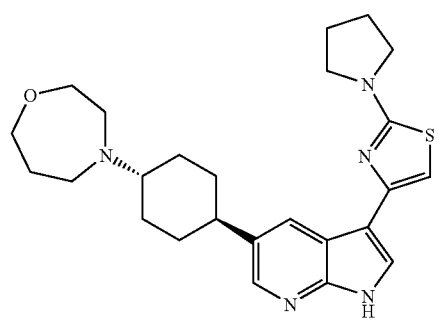

(I-123)
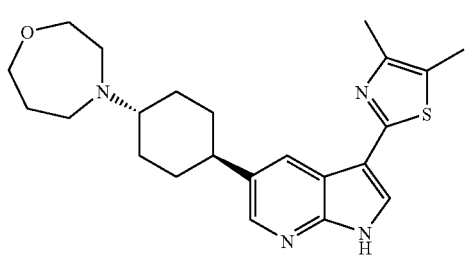

(I-124)
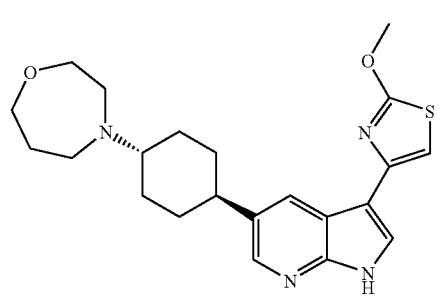

(I-125)
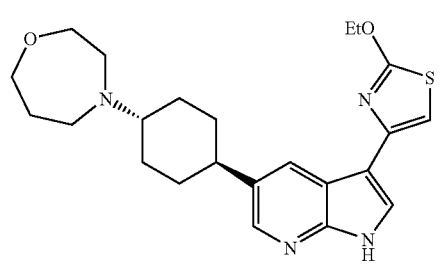

The structural formula of the compound may be described to represent a given isomer for the sake of convenience; however, all isomers of the compound that may occur structurally such as an geometric isomer, an optical isomer, a stereoisomer and a tautomer are included in the present invention, and there is no limitation to the formula described for the sake of convenience, regardless of whether it is an isolated isomer (for instance, an enantiomer), or a mixture of isomers (for instance, a racemic mixture).

When the compound according to the present invention is obtained in free form, it can be converted into a salt or a hydrate thereof by a conventional method.

Herein, there is no limitation on the "salt" according to the present invention as long as it forms a salt with the compound according to the present invention, and is pharmacologically acceptable. The preferred examples of the salt include hydrohalogenates (for instance, hydrochloride salt, hydrobromide salt, hydroiodide salt and the like), inorganic acid salts (for instance, sulphate salt, nitrate salt, perchlorate salt, phosphate salt, carbonate salt, bicarbonate salt and the like), organic carboxylic acid salts (for instance, acetate salt, maleate salt, tartrate salt, fumarate salt, citrate salt and the like), organic sulfonic acid salts (for instance, methanesulfonate salt, ethane sulfonate salt, benzenesulfonate salt, toluenesulfonate salt, camphorsulfonate salt and the like), amino acid salt (for instance, aspartate salt, glutamate salt and the like), quaternary ammonium salts, alkaline metal salts (for instance, sodium salt, potassium salt and the like), alkaline earth metal salts (magnesium salt, calcium salt and the like) and the like. In addition, hydrochloride salt, sulphate salt, methanesulfonate salt, acetate salt and the like are preferable as a "pharmacologically acceptable salt" of compounds according to the present invention.

Furthermore, when the compound according to the present invention may comprise various isomers (for instance, the geometric isomer, the optical isomer, the rotational isomer, the tautomer and the like), it can also be purified into a single isomer by means of a conventional separation method, for instance, recrystallization, optical resolution such as diastereomeric salt method, enzyme fractionation method, various chromatographic methods (for instance, thin layer chromatography, column chromatography, glass chromatography and the like). However, a single isomer herein includes not only the isomer having 100% purity, but also the isomer containing non-target isomers still remaining after undergoing conventional purification operation. In addition, when using the compound according to the present invention as a raw material for medicinal drug, the single isomer mentioned above may be used, in addition, a mixture of isomers in any proportions may be used.

Crystal polymorphism may exist for the compound according to the present invention, salts thereof, or hydrates thereof, however, all the polymorphic crystals thereof are included in the present invention. Crystal polymorphism may exist for a single isomer or a mixture, and both are included in the present invention.

In addition, a compound still demonstrating the desired pharmacological activity after the compound according to the present invention has been subjected to metabolism such as oxidation and hydrolysis in vivo is also included in the present invention.

Furthermore, a compound in which when subjected to metabolism such as oxidation, reduction and hydrolysis in vivo, generates the compound according to the present invention, a so-called prodrug, is also included in the present invention.

The compound according to the present invention can be provided as a pharmaceutical composition. The pharmaceutical composition may additionally comprise a pharmaceutically acceptable excipient for example a pharmaceutically acceptable carrier and/or a pharmaceutically acceptable diluent. Suitable carrier and/or diluents are well known in the art and include pharmaceutical grade starch, mannitol, lactose, magnesium stearate, sodium saccharin, talcum, cellulose, glucose, sucrose (or other sugar), magnesium carbonate, gelatin oil, alcohol, detergents, emulsifiers or water (preferably sterile). The composition may be a mixed preparation of a composition or may be a combined preparation for simultaneous separate or sequential use (including administration).

The compound according to the present invention, a salt thereof or a hydrate thereof can be formulated by a conventional method. Examples of the preferred dosage forms include a tablet, a powder, a subtle granule, a granule, a coated tablet, a capsule, a syrup, a troche, a inhalant, a suppository, a injectable, an ointment, an ophthalmic ointment, an eye drop, a nasal drop, an ear drop, a cataplasm, a lotion and the like. For formulation, a diluent, a binder, a disintegration agent, a lubricant, a colorant and a flavoring agent used in general, and as necessary, additives such as a stabilizer, an emulsifier, an absorption enhancer, a surfactant, a pH adjuster, an antiseptic agent, and an antioxidant can be used. In addition, formulation is also possible by combining ingredients that are used in general as raw materials of pharmaceutical formulation, by the conventional method. Examples of these ingredients include (1) soybean oil, animal oil such as beef tallow and synthethic glyceride; (2) hydrocarbon such as liquid paraffin, squalane and solid paraffin; (3) an ester oil such as octyldodecylmyristate and isopropylmyristate; (4) higher alcohol such as cetostearylalcohol and behenyl alcohol; (5) a silicon resin; (6) a silicon oil; (7) a surfactant such as polyoxyethylene fatty acid ester, sorbitan fatty acid ester, glycerin fatty acid ester, polyoxyethylene sorbitan fatty acid ester, polyoxyethylene hardened castor oil and polyoxyethylene polyoxypropylene block co-polymer; (8) a water-soluble polymer such as hydroxyethyl cellulose, polyacrylic acid, carboxyvinyl polymer, polyethyleneglycol, polyvinylpyrrolidone and methyl cellulose; (9) lower alcohol such as ethanol and isopropanol; (10) multivalent alcohol such as glycerin, propylene glucol, dipropylene glycol and sorbitol; (11) a sugar such as glucose and cane sugar; (12) an inorganic powder such as anhydrous silicic acid, magnesium aluminium silicate and aluminium silicate; and (13) purified water and the like.

Among the aforementioned additives, use can be made of 1) lactose, corn starch, sucrose, glucose, mannitol, sorbit, crystalline cellulose, silicon dioxide and the like as a diluting agent; 2) polyvinyl alcohol, polyvinyl ether, methyl cellulose, ethyl cellulose, gum arabic, traganth, gelatine, shellac, hydroxypropyl cellulose, hydroxypropylmethyl cellulose, polyvinylpyrrolidone, polypropyleneglycol.polyoxyethylene block co-polymer, meglumine, calcium citrate, dextrin, pectin and the like as a binder; 3) a starch, agar, gelatine powder, crystalline cellulose, calcium carbonate, sodium bicarbonate, calcium citrate, dextrin, pectin, calcium carboxymethylcellulose and the like as a disintegration agent; 4) magnesium stearate, talc, polyethyleneglycol, silica, hardened plant oil and the like as a lubricant; 5) a colorant, as long as addition thereof to a pharmaceutical drug is authorized, as a colorant; 6) a cocoa powder, menthol, fragrance, a peppermint oil, a cinnamon powder as a flavoring agent; and 7) an antioxidants whose addition to a pharmaceutical drug is authorized such as ascorbic acid and α-tocophenol as an antioxidant. The compounds of the invention will normally be administered in a daily dosage regimen (for an adult patient) of, for example, an oral dose of between 1 mg and 2000 mg, preferably between 30 mg and 1000 mg, e.g. between 10 and 250 mg or an intravenous, subcutaneous, or intramuscular dose of between 0.1 mg and 100 mg, preferably between 0.1 mg and 50 mg, e.g. between 1 and 25 mg of the compound of the formula (I) or a physiologically acceptable salt thereof calculated as the free base, the compound being administered 1 to 4 times per day. Suitably the compounds will be administered for a period of continuous therapy, for example for a week or more.

General Procedure

The method for preparation of compound represented by formula (I) will be described below.

Compound (I) can be obtained by the methods represented by the following Reaction Schemes 1 to 8 or methods equivalent thereto.

Each reference symbol in the compounds shown in the following Reaction Schemes 1 to 8 has the same meaning as defined above. The compounds shown in the reaction schemes include salts formed from the compounds and examples of the salts include the same ones as the salts of compound (I), and the like.

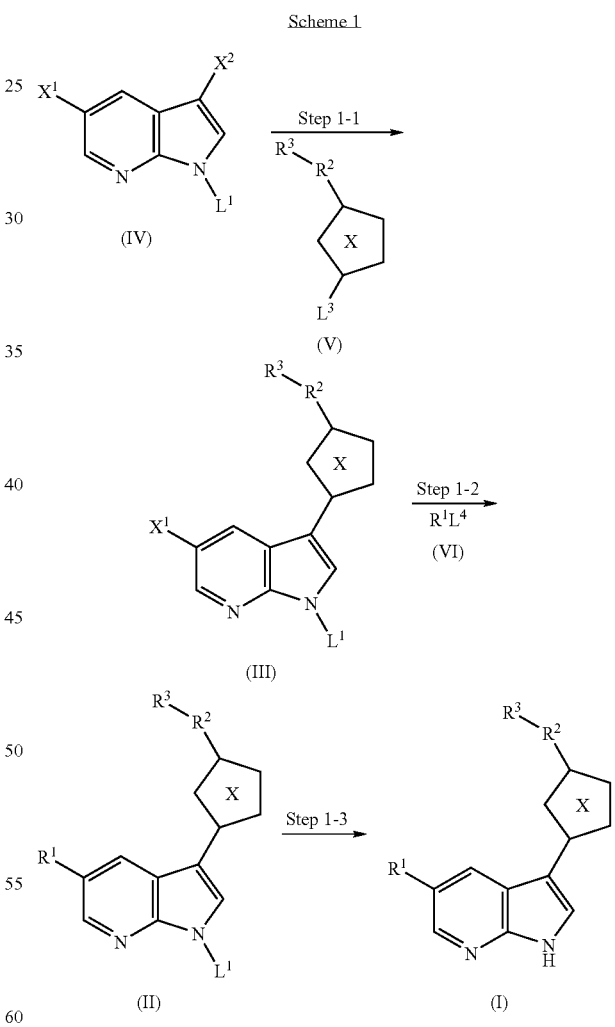

wherein $R^1$, $R^2$ and $R^3$ have the same meanings as described above; and $X^1$ and $X^2$ represent independently halogen atom, $L^1$ represents amino-protecting group such as phenylsulfonyl group or dimethylamino group, $L^3$ and $L^4$ represent independently trialkyl tin group, $B(OR^{32})_2$ or $SiR^{33}_2$ wherein each of $R^{32}$ independently represent hydrogen or $C_{1-6}$ alkyl or two $R^{32}$ together form a 5-7 membered ring with the boron and oxygen atoms, wherein the ring is optionally substituted with 1-4 $C_{1-6}$ alkyl group(s), and each of $R^{33}$ represents fluoro atom, hydroxyl group or $C_{1-6}$ alkyl group.

Step 1-1

Compound (III) can be produced by coupling compound (IV) with compound (V) in the presence of a metal catalyst as disclosed in WO2004/078756 and WO2006/015123. Coupling reaction includes known coupling reactions; Stille reaction, Suzuki coupling, Hiyama reaction and the like. Stille reaction can be carried out according to Stille (*Angew. Chem., Int. Ed, Engl.* 1986, 25, 508); Mitchell (*Synthesis*, 1992, 803) or Littke et al. (*J. Am. Chem. Soc.* 2002, 124, 6343). Suzuki coupling can be carried out according to Suzuki (*Pure Appl. Chem.* 1991, 63, 419) or Littke et al. (*J. Am. Chem. Soc.* 2000, 122, 4020). Hiyama reaction can be carried out according to Hatanaka et al. (*J. Org. Chem.* 1988, 53, 918), Hatanaka et al. (*Synlett*, 1991, 845), Tamao et al. (*Tetrahedron Lett.* 1989, 30, 6051), or Denmark et al. (*Org. Lett.* 2000, 2, 565, ibid. 2491).

Compound (IV) may be commercially available or may be prepared from commercially available product by methods known to those skilled in the art.

Compound (V) may be commercially available or may be prepared from commercially available product by methods known to those skilled in the art.

Step 1-2

Compound (II) can be produced by coupling compound (III) with compound (VI) in the presence of a metal catalyst like in step 1-1.

Compound (VI) may be commercially available or may be prepared from commercially available product by methods known to those skilled in the art. For example, stannane described as (VIa) can be produced from the relevant ketone using several methods well-known in the art (*J. Org. Chem.* 2004, 69, 9109). For instance, ketone can be converted first to enol triflate as shown below

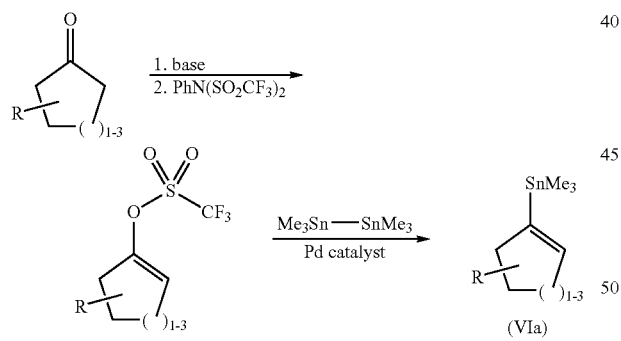

wherein R represents a halogen atom, an oxo group, an ethylenedioxy group, a $C_{1-6}$ alkyl group, a $C_{1-6}$ alkoxy group, a $C_{1-6}$ hydroxyalkyl group, —C(O)OH, a ($C_{1-6}$ alkyl)amino group, a di($C_{1-6}$ alkyl)amino group or —$R^a$-$R^b$; wherein $R^a$ represents a single bond or —$CH_2$—; wherein $R^b$ represents a 4-7 membered non-aromatic heterocyclic group, a $C_{6-10}$ aryl group or a 5-7 membered heteroaryl group, optionally and independently substituted with 1-4 substituent(s) selected from the group consisting of halogen atom or $C_{1-6}$ alkyl group;

As base either NaH (*Org. Biomol. Chem.* 2006, 4(3), 410), $(CH_3Si)_2NLi$, $(CH_3Si)_2NK$ (*J. Org. Chem.* 2003, 68, 6905) or i-$Pr_2NLi$ can be used. Suitable palladium catalysts for the second step include tetrakis(triphenylphoshine)palladium (0) $Pd(PPh_3)_4$. An alternative method (*J. Org. Chem.* 2004, 69, 220) involves the relevant vinyllithium derivative as an intermediate and starts from commercially available ketone (VII).

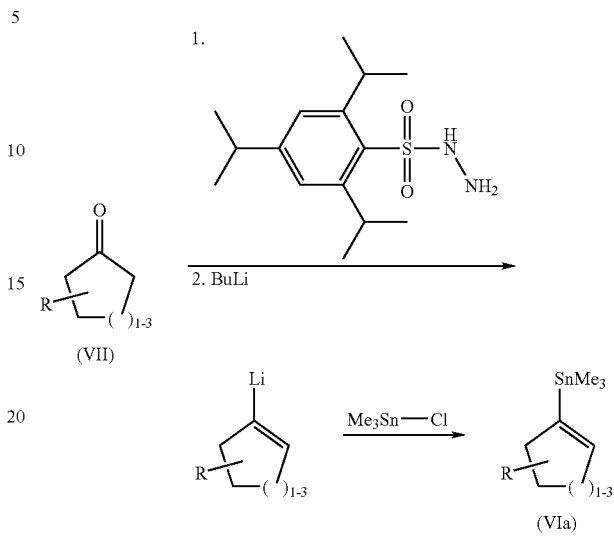

Boronic ester described as (VIb) can also be produced from the relevant ketone (VII) using the methodology well-known in the art (*J. Med. Chem.* 2006, 49, 3719-3742 or WO2005/005422) as shown below:

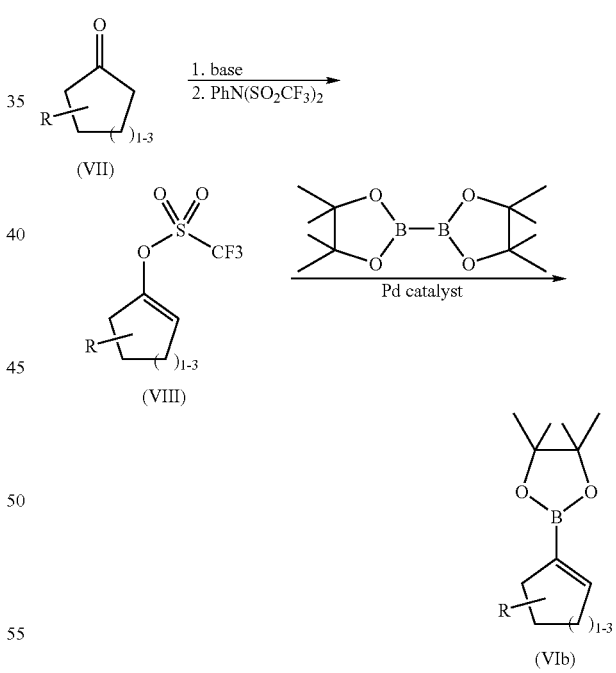

As base either $(CH_3Si)_2NLi$ or i-$Pr_2NLi$ can be used. Suitable palladium catalysts for the reaction of the triflate (VIII) with bis(pinacolato)diboron include palladium (II) chloride complex with 1,1'-bis(diphenylphosphino)ferrocene $PdCl_2$.dppf or palladium (II) chloride complex with triphenylphosphine, $PdCl_2(PPh_3)_2$.

Chemistry analogous to that used for the preparation of stannanes described as (VIa) can be used to convert ketones (VII) into the relevant silanes described as (VIc) (*J. Am. Chem. Soc.* 1987, 109, 7838).

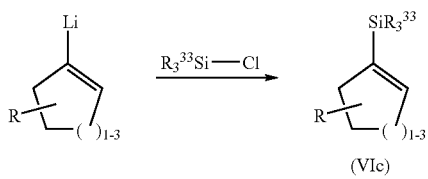

(VIc)

Compound (II) can also be prepared by the Heck reaction as shown below.

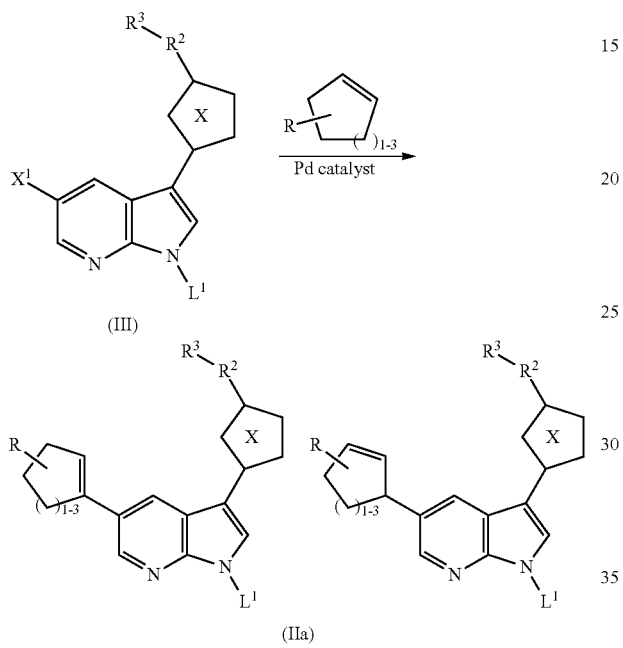

(IIa)

Various regioisomers of (IIa) can be formed depending on the reaction conditions. The reaction may involve $X^1$=I (Synlett 2002, 12, 2045), $X^1$=Br (*Org. Lett.* 1999, 1, 709), $X^1$=Cl (Synlett 2000, 11, 1589) and a variety of palladium catalysts including elemental Pd, chloro[4-(diphenylphosphino-κP)benzamide](η3-2-propenyl)palladium, tris(dibenzylideneacetone)dipalladium, palladium diacetate, etc. The reaction may be run in the presence of phosphine such as butylbis(tricyclo[3.3.1.13,7]dec-1-yl)phosphine, tricyclohexylphosphine, or triphenylphosphine.

Step 1-3

The conditions for the removal of the $L^1$ group will depend on the property of the $L^1$ group. For example, when $L^1$ is phenylsulfonyl group, the compound of formula (I) can be produced by the treatment of the compound of formula (II) under basic conditions, for instance using sodium hydroxide in water/ethanol. Specifically, following working examples will be specified.

If desired, a modification of $R^1$, $R^2$ or $R^3$ might be conducted either prior or subsequent to each step. For example, compound (IIa) which contains unsaturated ring can be reduced into compound (IIb) which contains saturated ring. The reduction can be accomplished by using hydrogen gas over catalyst such as palladium, palladium hydroxide, platinum, or rhodium.

In particular, the reduction of cyclohexenyl derivative (IIa) may produce a mixture of cis- and trans-(IIb) as shown below.

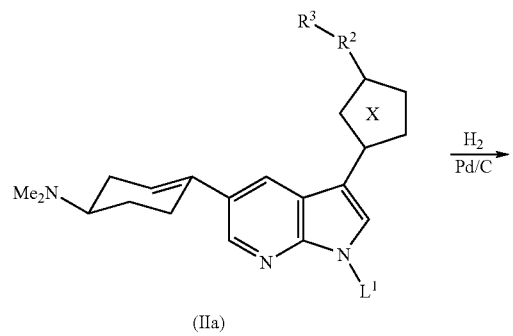

(IIa)

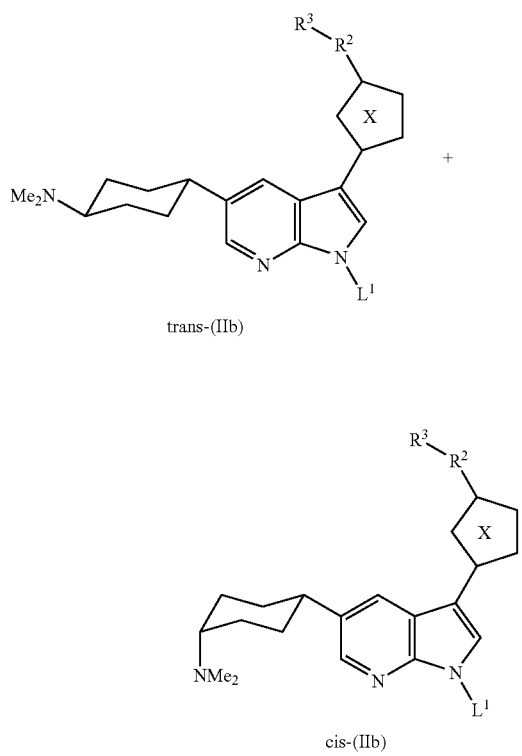

trans-(IIb)

+ cis-(IIb)

Such mixture, if needed, can be separated using chromatographic methods well known in the art. Alternatively, the cis isomers such as cis-(IIb) can be converted into the more thermodynamically stable trans-isomers such as trans-(IIb) using a free-radical method developed by Bertrand et al. (*J. Org. Chem.* 2006, 71, 7288).

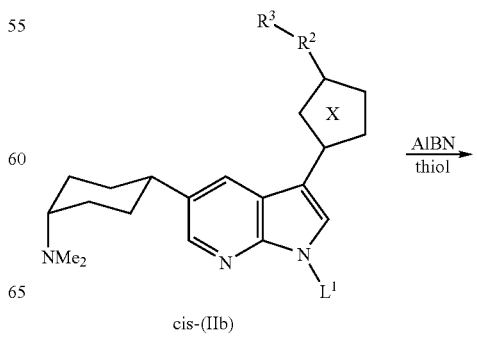

cis-(IIb)

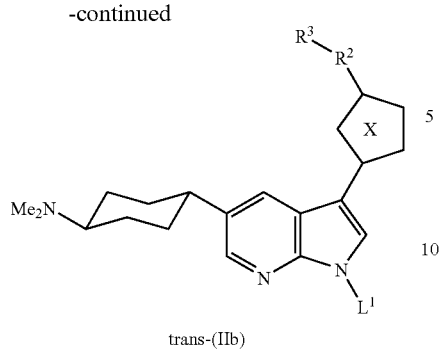

trans-(IIb)

Compound (II) may undergo one or more further reactions to provide a different compound (II). For example, a compound may undergo hydrolysis, reductive amination, reduction, oxidation, elimination, substitution and/or addition reaction. In particular, with regard to reductive amination, following working examples will be specified.

Furthermore, if desired, the sequence between step 1-1 and step 1-2 can be alternated as described below. Alternatively, compound of formula (II) can be prepared by a) reaction of a compound of formula (IX) with stannane (Va) in the presence of a palladium catalyst or
b) reaction of a compound of formula (IX) with boronic acid or ester (Vb) in a presence of a suitable palladium catalyst or
c) reaction of a compound of formula (IX) with silane (Vc) in the presence of a palladium catalyst

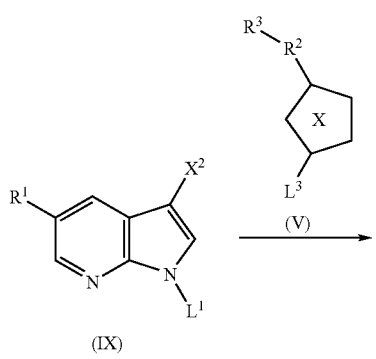

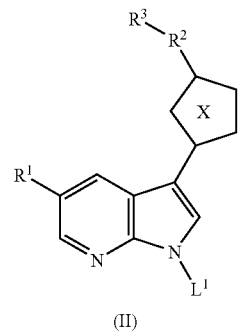

(II)

wherein all symbols in the scheme has the same meanings as described above;

Suitable catalysts for the purpose of this invention include $(PPh_3)_2PdCl_2$ or $(PPh_3)_4Pd$, $Pd(OAc)_2$, $[PdCl(\eta^3\text{-}C_3H_5)]_2$, $Pd_2(dba)_3$ (wherein dba=dibenzylidenacetone), $Pd/P(t\text{-}Bu)_3$ It will be appreciated that the reaction set out as option a) is a Stille reaction, which can be carried out according to Stille (*Angew. Chem., Int. ed, Engl.* 1986, 25, 508); Mitchell (*Synthesis,* 1992, 803) or Littke et al. (*J. Am. Chem. Soc.* 2002, 124, 6343), The reaction set out as option b) is a Suzuki reaction which can be carried out according to Suzuki (*Pure Appl. Chem.* 1991, 63, 419) or Littke et al. (*J. Am. Chem. Soc.* 2000, 122, 4020).

It will be appreciated that the reaction set out as option c) is a Hiyama reaction which can be carried out according to Hatanaka et al. (*J. Org. Chem.* 1988, 53, 918), Hatanaka et al. (*Synlett,* 1991, 845), Tamao et al. (*Tetrahedron Lett.* 1989, 30, 6051), or Denmark et al. (*Org. Lett.* 2000, 2, 565, ibid. 2491).

Alternatively, the thiazole group can be introduced at the C(3) position of the compound stepwise. Scheme 2 shows the ways the thiazol-2-yl group can be formed to provide compound (III). The key intermediate for this purpose is thioamide (XIII) synthesized as shown in Scheme 2a.

Scheme 2 a)

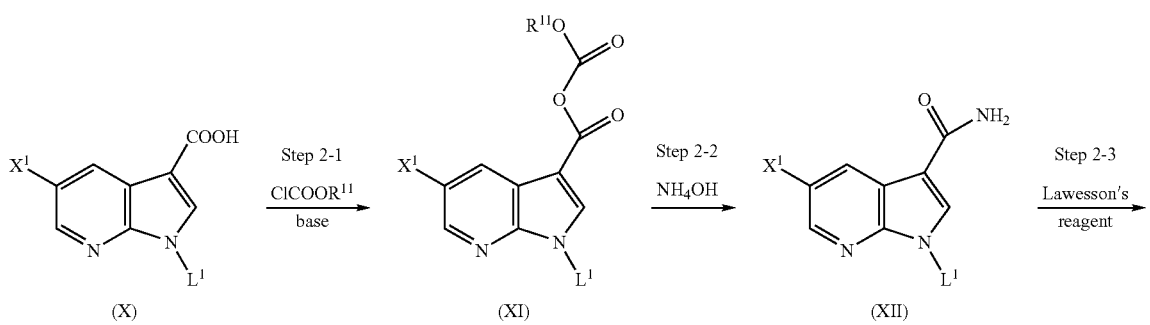

-continued

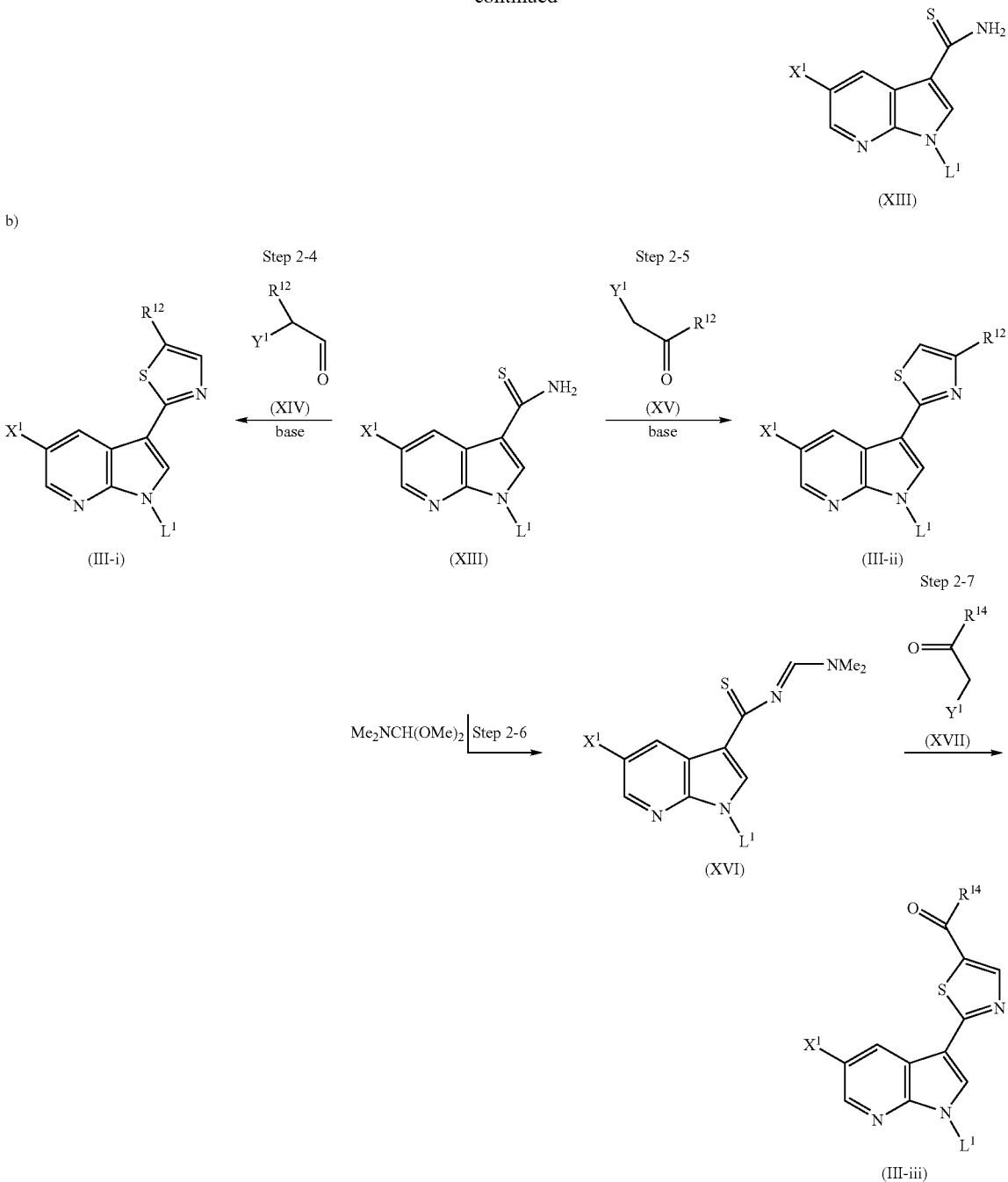

Step 2-1
Mixed anhydride ($R^{11}$=alkyl) is obtained from the relevant carboxylic acid (X) using standard procedure known to those skilled in the art. Preparation of the relevant acids and amides was disclosed in WO2003082868.

Step 2-2
Amide (XII) can readily be synthesized from the relevant mixed anhydride (XI) using standard method by acting on compound (XI) with ammonia or ammonium hydroxide.

Step 2-3
Thioamide (XIII) can be readily prepared from amide (XII) using methods known in the art, such as acting on (XII) with the Lawesson's reagent.

Step 2-4
In order to prepare thiazole (III-i), amide (XIII) is reacted with aldehyde (XIV) as shown by Thompson et al. *Bioorg. Med. Chem. Lett.* 1994, 4, 2441.

Step 2-5
Thiazole (III-ii) is available by condensation of thioamide (XIII) with α-haloketone (XV) (Schwarz *Org. Synth.* 1955, III, 332; Gu et al. *Bioorg. Med. Chem. Lett.* 1999, 9, 569).

Step 2-6
Amidine (XVI) can be prepared from thioamide (XIII) by reaction with dimethylformamide dimethylacetal $Me_2CH(OMe)_2$ (Thompson et al. *Bioorg. Med. Chem. Lett.* 1994, 4, 2441).

Step 2-7

Alkylcarbonyl groups $R^{14}C(O)-$ can be installed α to the sulphur atom by reacting amidine (XVI) with α-haloketone $R^{14}C(O)CH_2Y^1$ (XVII) using the method well-known in the art (Thompson et al. *Bioorg. Med. Chem. Lett.* 1994, 4, 2441).

Alternatively, thioamide (XIII) can be formed from nitrile (XVIII), preparation of which was disclosed in WO2004101565 (Scheme 3).

Scheme 3

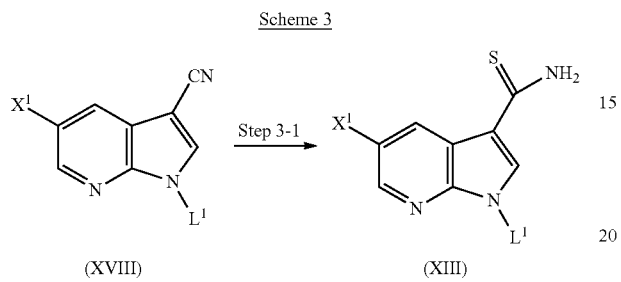

Step 3-1

Conversion of nitrile (XVIII) into thioamide (XIII) can be achieved under a variety of conditions. For instance, thioamide (XIII) is formed using:

- $H_2S$ under basic conditions (Bhattacharya et al. *J. Chem. Soc., Perkin Trans.* I 1995, 1543; Krawczyk et al. *J. Med. Chem.* 1995, 38, 4115)
- thioacetamide under acidic conditions (Gu et al. *Bioorg. Med. Chem. Lett.* 1999, 9, 569)
- sodium hydrogen sulfide and magnesium chloride in dimethylformamide (DMF) (Manaka and Sato *Synth. Commun.* 2005, 35, 761)
- $(Me_3Si)_2S$/MeONa system (Lin et al. *Synthesis* 1992, 1219; Qiao et al. *Org. Lett.* 2001, 3, 3655)

Creation of the thiazolyl group at C(3) of the unprotected 7-azaindole system allows compound (III) to be made by protection of compound (XXIII) as shown below

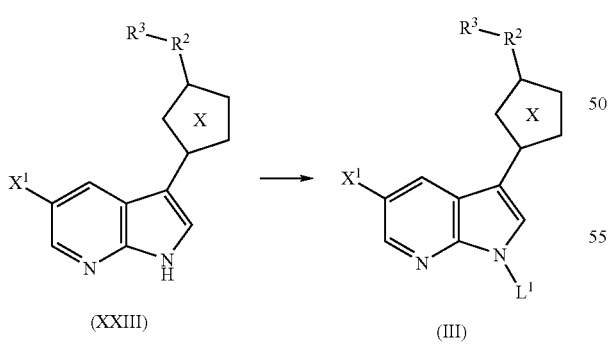

and presented in more detail in Scheme 4. Compound (III), then can be converted into (II) and (I) as presented above in Scheme 1.

Scheme 4

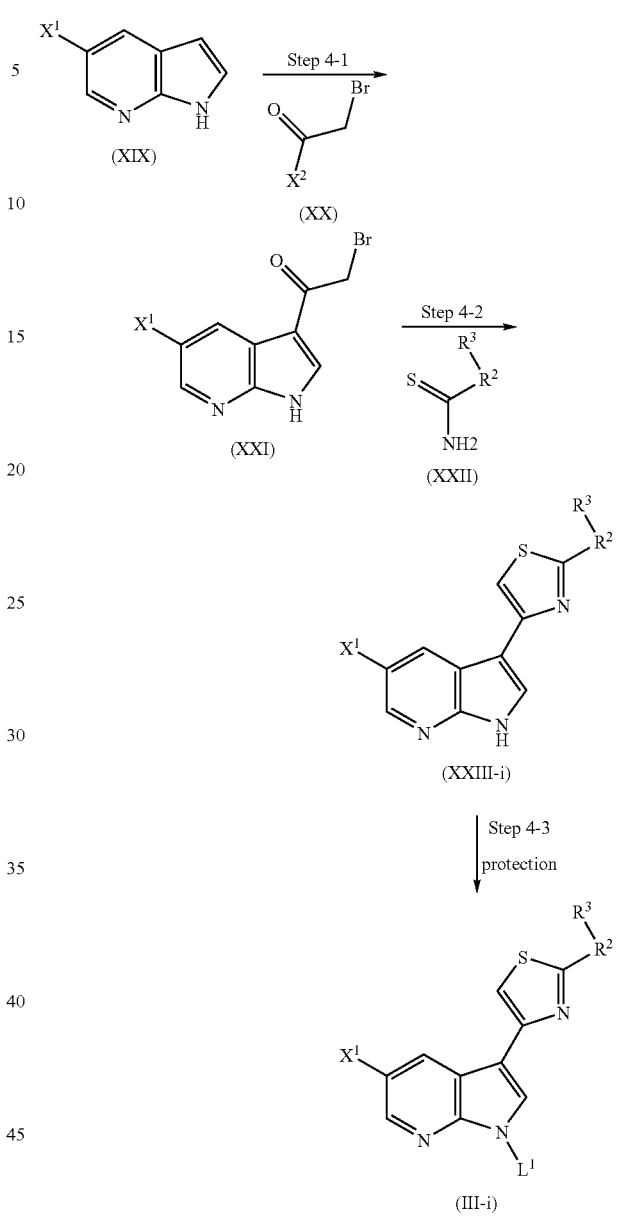

Step 4-1

Haloketone (XXI) can be synthesized from commercially available (XIX) using the method disclosed in WO2006015123.

Step 4-2

Thiazole derivative (XXIII-i) is formed by reaction between haloketone (XXI) and thioamide (XXII). Reaction works for $R^2$-$R^3$=$NH_2$ (Hayashi et al. *Heterocycles* 1999, 51, 1233; Bansal et al. *Indian J. Chem., Sect. B: Org. Chem. Incl. Med. Chem.* 2000, 39, 357), $R^2$-$R^3$=NH-Aryl (Di Fabio and Pentassuglia *Synth. Commun.* 1998, 28, 51), $R^2$-$R^3$= (substituted)alkyl (Zawistoski *J. Heterocycl. Chem.* 1990, 27, 519) and $R^2$-$R^3$=aryl (Baldwin et al. *J. Org. Chem.* 2001, 66, 2588).

Step 4-3

Compound (III-i) is made by protecting compound (XXIII) with a suitable protecting group using the methods well-known in the art. Preferred protecting groups include the phenylsulfonyl, toluenesulfonyl, and SEM.

Compound (XXIII) can be directly converted into (I) as shown below and using the conditions indicated for Step 1-2, however such conversion is usually accompanied by lower overall yield.

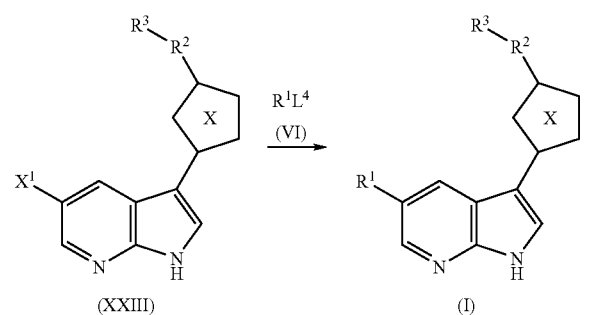

By applying the methodology developed by Saleh (*Nucleosides, Nucleotides Nucleic Acids* 2002, 21, 401) for the indole analogues, thiazol-5-yl derivatives can be prepared as shown in Scheme 5.

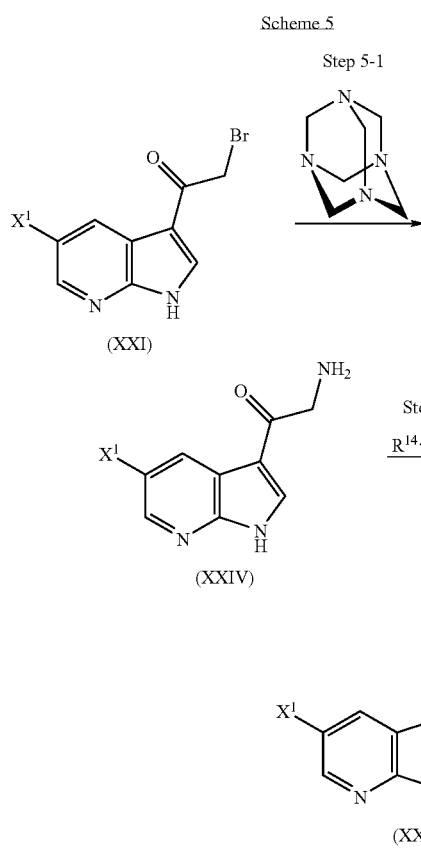

Step 5-1

Compound (XXIV) is synthesized from the relevant bromoketone (XXI) by reacting it with hexamethylenetetramine followed by acidic workup as described in *Heterocycles* 2002, 56(1-2), 519 and *J. Pharm. Pharmacol.* 2002, 54, 147. Alternative methods to obtain indole analogues of (XXIV) are also known (*Synthesis* 2006, 1, 49; *J. Am. Chem. Soc.* 2004, 126, 12888; *Org. Lett.* 2000, 2, 3185; ibid 2000, 2, 2121).

Step 5-2

Compound (XXIII-ii) is formed in the reaction between α-aminoketone (XXIV) and isothiocyanate $R^{14}NCS$ ($R^{14}$=alkyl, heterocyclyl) as taught by Saleh (*Nucleosides, Nucleotides Nucleic Acids* 2002, 21, 401).

Alternatively, aminoketone (XIV) can be reacted with $R^3$—$R^2$—$C(S)SCH_2COOH$ as shown in Scheme 6.

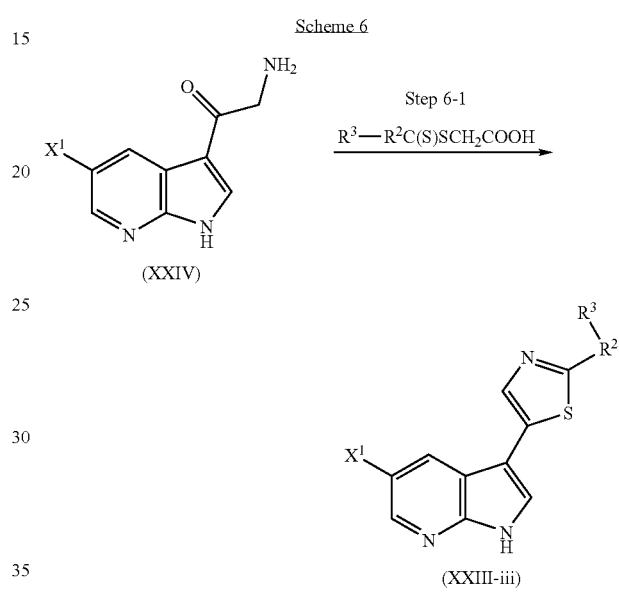

Step 6-1

This transformation can be performed following the method described in *J. Am. Chem. Soc.* 2004, 126, 12897.

If desired, the sequence among each step can be alternated.

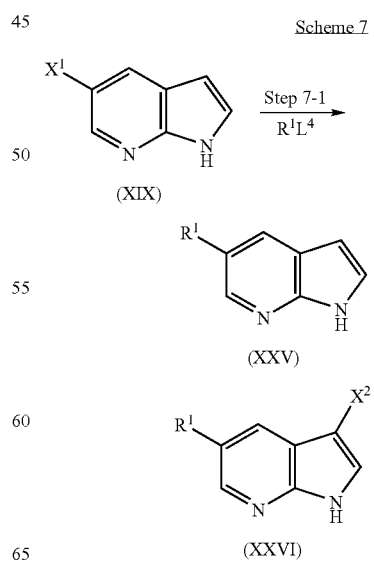

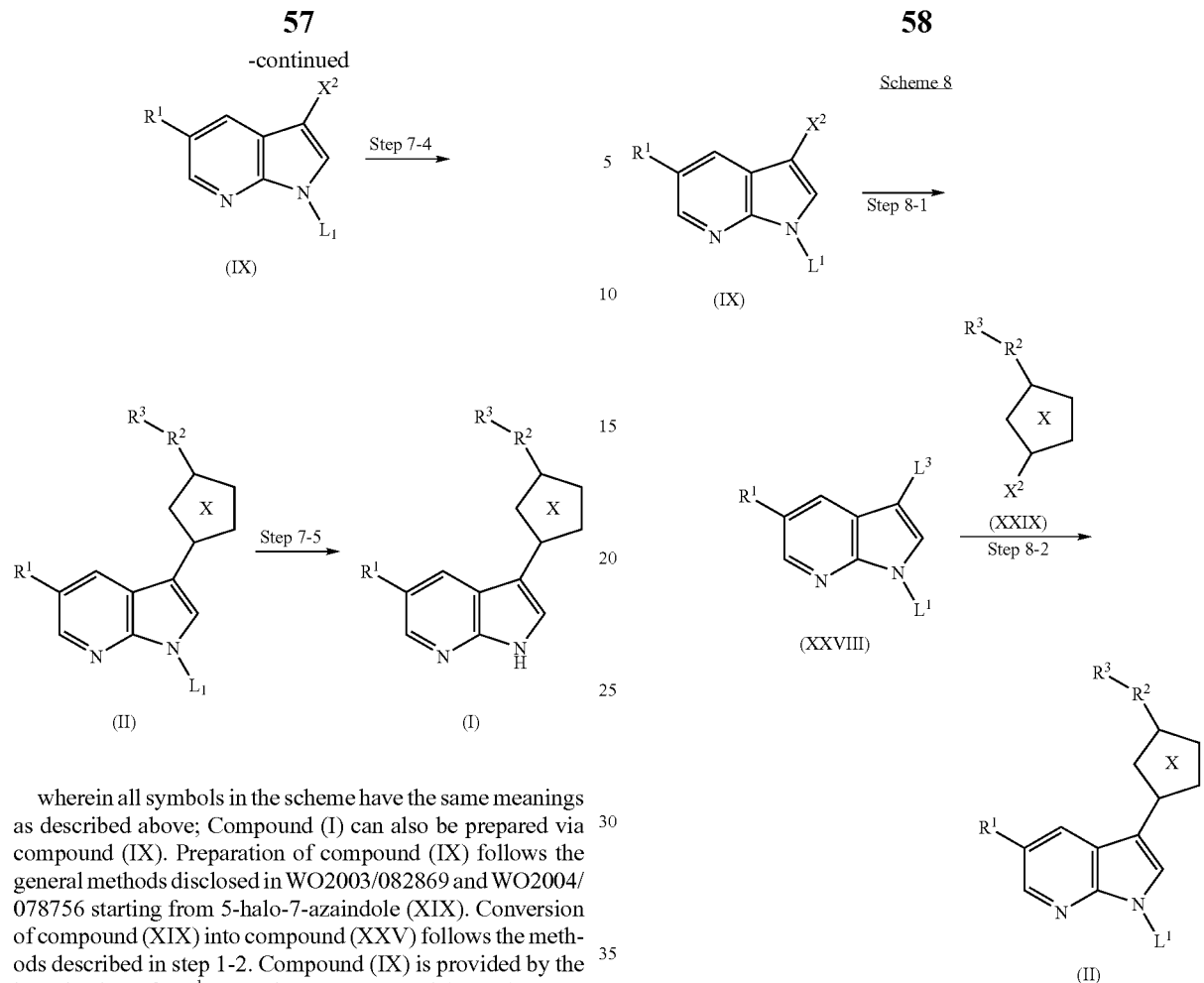

wherein all symbols in the scheme have the same meanings as described above; Compound (I) can also be prepared via compound (IX). Preparation of compound (IX) follows the general methods disclosed in WO2003/082869 and WO2004/078756 starting from 5-halo-7-azaindole (XIX). Conversion of compound (XIX) into compound (XXV) follows the methods described in step 1-2. Compound (IX) is provided by the introduction of a $L^1$ group into a compound (XXVI). However, a skilled person will appreciate that the actual synthetic sequence to prepare compound (IX) will depend on the type of protecting group $L^1$ used. In particular where $L^1$ is a silyl group, introduction of $L^1$ may occur prior to the introduction of $X^2$ as shown below:

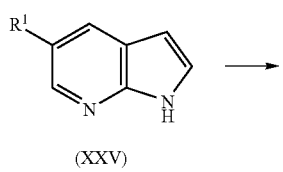

The synthetic scheme leading from compound (IX) to compound (II) can be modified by reversing the reactive functionalities as shown in Scheme 8.

wherein all symbols in the scheme have the same meanings as described above:

Step 8-1

Synthesis of (XXVIII) can be performed using methods known in the art. For instance, preparation of $R^1$=substituted phenyl, $L^1$=t-butyldimethylsilyl, $L^3$=SnBu$_3$ and $R^1$=substituted phenyl, $L^1$=phenylsulfonyl, $L^3$=—B(OCMe$_2$)$_2$ has been disclosed in WO2004078756.

Step 8-2

Coupling reaction between halide (XXVIII) and stannane (XXIX-a) or borane (XXIX-b) or silane (XXIX-c) is performed under the conditions discussed in Scheme 1.

Scheme 9

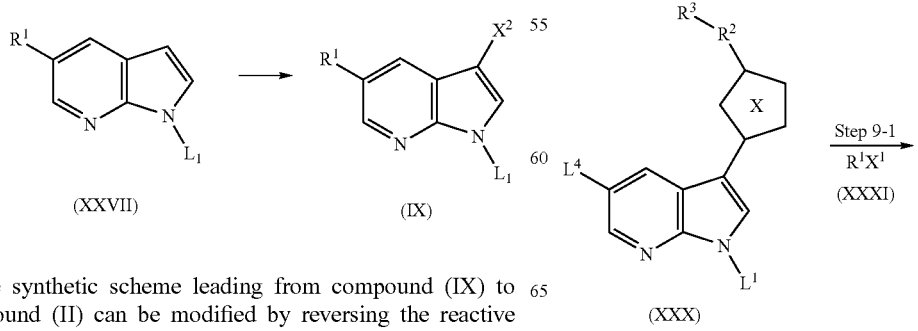

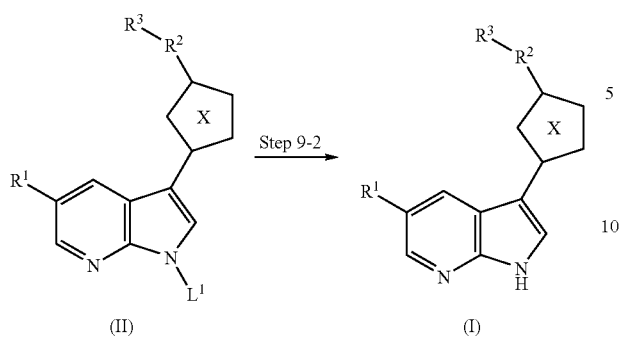

wherein all symbols in the scheme have the same meanings as described above:

Step 9-1

Compound (II) can be prepared by reacting compound (XXX) with compound (XXXI).

Method for installation of the stannane (—SnBu$_3$) and silane (—SiMe$_3$) moieties at C(5) of the 7-azaindole system was disclosed in WO2004/078757. Boronates and boronic acids analogous to (IX) were also disclosed in WO2006/015123 and WO2005/028475.

Step 9-2

This step can be conducted according to step 1-3.

EXAMPLES

The present invention will be described in more detail with reference to examples, which however shall not be construed as limiting the scope of the invention thereto.

Synthetic Methods for Synthesis of Compounds of the Invention

General Procedure A for the Deprotection of 7-azaindoles

Procedure A

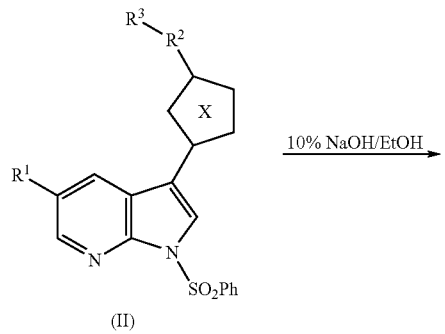

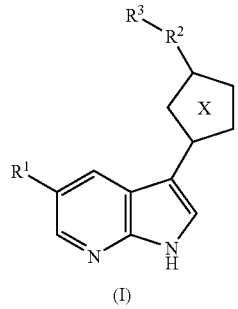

The 7-azaindole (II) (1 mmol) was dissolved in EtOH (10 mL). 10% NaOH (5 mL) was added and the reaction was heated to 80° C.—reflux for 30-40 mins. It was allowed to cool down and a saturated solution of NaHCO$_3$ (10 mL) was added. It was then extracted with ethyl acetate (3×20 mL) and the combined organic extracts were dried over MgSO$_4$ and concentrated. The crude product was purified by silicagel chromatography (SGC) using appropriate solvent as eluent or by preparative TLC (PTLC) using appropriate solvent as the eluent or by LCMS (column LUNA 10µ C18(2) 00G-4253-V0 250×50 mm) using water-acetonitrile (0.1% AcOH) as eluent (in gradient; flow 80 mL/min).

For compounds (II) containing ester functionality, the crude reaction mixture was concentrated under reduced pressure to remove EtOH, and neutralized by dropwise addition of glacial acetic acid, which led to precipitation of compound (I). The precipitate was filtered off, dried in vacuum and used in further transformations without additional purifications.

Procedure B

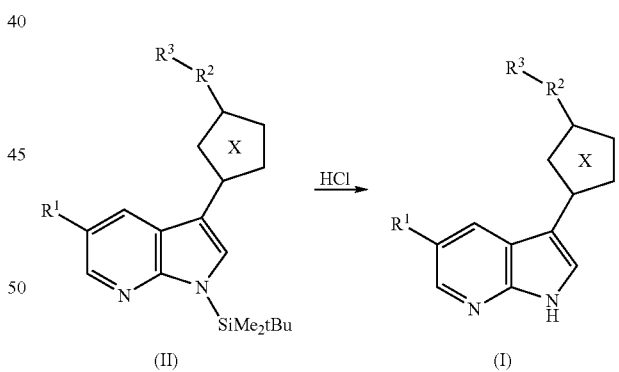

Concentrated aqueous HCl (1 mL) was added to a solution of silyl-protected azaindole (II) (0.28-0.9 mmol) in methanol (10 mL) and the reaction mixture was stirred at room temperature for 15-30 min. The mixture was then added to saturated aqueous NaHCO$_3$ (50 mL) and extracted with AcOEt (2×40 mL). The combined organic portions were dried (MgSO$_4$), concentrated, and purified by trituration with Et$_2$O (5 mL) to afford 7-azaindole (I) as a white powder (50-95%).

General Procedure for the Formation of amides using 7-azaindoles Containing a carboxylic acid Functionality

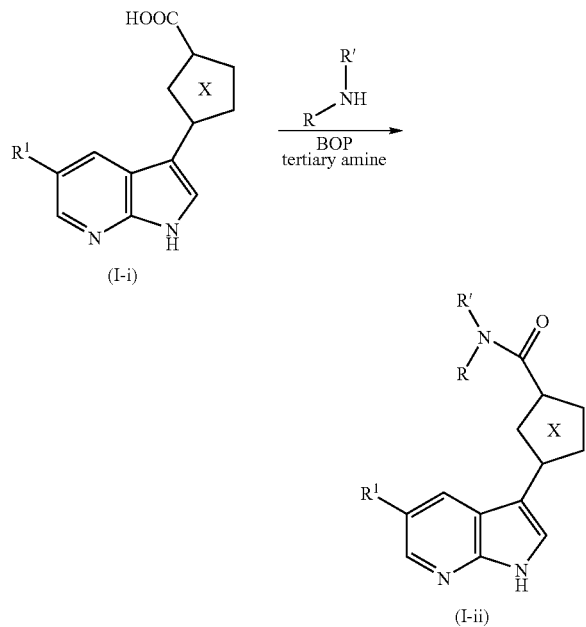

wherein $R^1$ has the same meaning as described above; R and R' independently represents hydrogen atom, C1-6 alkyl group or R and R', together with the nitrogen atom they are bonded to, form a 4-8 membered ring optionally substituted with halogen atom or C1-6 alkyl group:

To a solution of crude acid (I-i) (0.10 mmol) in DMF (1-2 mL) was added amine R'RNH or its hydrochloride (0.74 mmol), tertiary amine such as triethylamine or diisopropylethylamine (0.26 mmol; 0.52 mmol if using R'RNH hydrochloride), and (benzotriazol-1-yloxy)tris(dimethylamino)phosphonium hexafluorophosphate (BOP; 130 mg, 0.30 mmol). The reaction mixture was stirred for 2 h-3 days, diluted with AcOEt (65 mL) and washed with saturated aqueous NaHCO$_3$ (2×30 mL). The organic layer was dried over MgSO$_4$, concentrated, and the residue was purified by LCMS (column LUNA 10μ C18(2) 00G-4253-V0 250×50 mm) using water-acetonitrile (0.1% AcOH) as eluent (in gradient; flow 80 mL/min) to give amide (I-ii) as solid. Alternatively, no workup is performed and the crude reaction mixture is directly purified by LCMS using the above conditions. Yield 10-60%.

General Procedure for the Hydrogenation of 7-azaindoles Containing a Partially Unsaturated Ring at C(5)

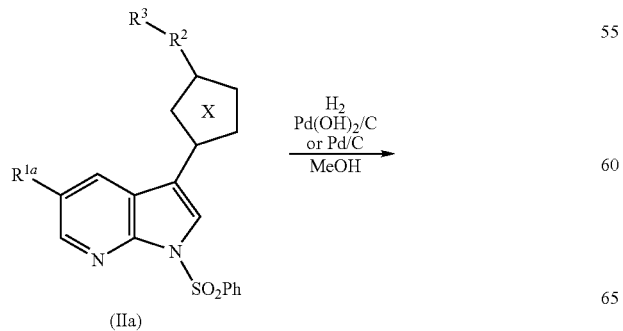

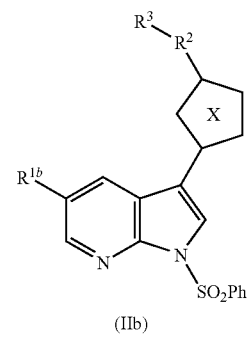

wherein $R^2$ has the same meanings as described above, $R^{1a}$ represents 5-7 membered unsaturated hydrocarbon ring, $R^{1b}$ represents 5-7 membered saturated hydrocarbon ring;

Compound (II-a) (1 mmol) was dissolved in appropriate solvent (MeOH or a mixture of MeOH and CH$_2$Cl$_2$ or ethyl acetate to improve solubility) (10-30 mL). Pd(OH)$_2$ (0.1-0.3 mmol) (20% on C, wet, Degussa type) or Pd/C (0.25-0.50 mmol) (10% on C, wet Degussa type E101) was added in one portion. The reaction was stirred under hydrogen for 1-7 days. The reaction mixture was filtered through a small pad of Celite and washed with copious amount of MeOH. The solvent was removed to give the product (IIb) which was taken forward crude.

General Procedure for the Reductive Amination Involving amines and 7-azaindoles Containing keto Functionality Procedure A

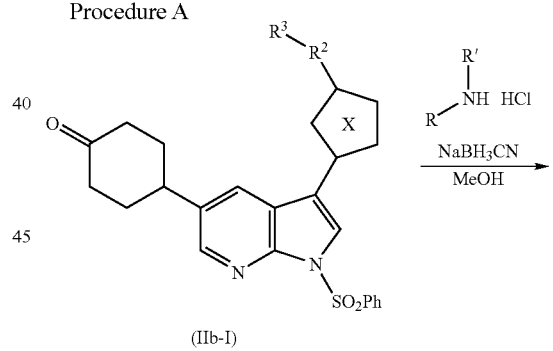

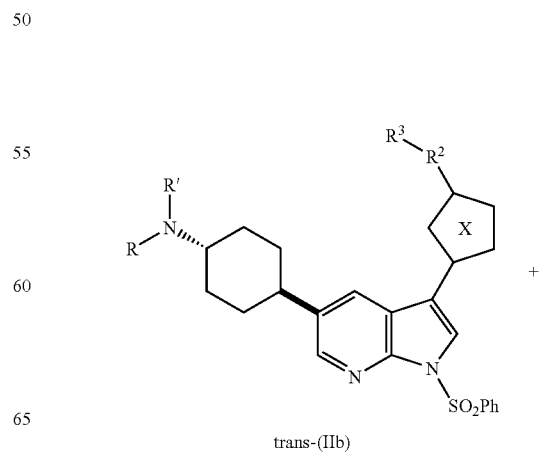

-continued

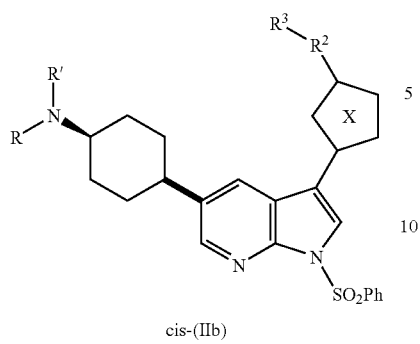

cis-(IIb)

wherein R², R³, R and R' have the same meaning as described above. Ketone (IIb-i) (1 mmol) was added at room temperature (RT) over 5 min to a solution of secondary amine R'RNH hydrochloride (6 mmol) in dry MeOH (10 ml) under nitrogen and the mixture was then stirred for 5 min at RT. When using free amine, its hydrochloride was prepared in situ by adding dropwise 1.25 M solution of HCl in MeOH (2 mmol) and stirring at RT for 5 min. Solid NaBH$_3$CN (2 mmol) was added as solid in one portion at room temperature or as a solution in MeOH (4 mL) at −20° C. The reaction was then stirred at RT overnight. Saturated solution of NaHCO$_3$ (30 ml) was added and the reaction mixture was extracted with ethyl acetate (4×35 ml). The combined organic extracts were dried over MgSO$_4$ and concentrated. The crude product was purified by silicagel chromatography (SGC) using appropriate solvent as eluent or by preparative TLC (PTLC) using appropriate solvent as the eluent or by LCMS (column LUNA 10μ C18(2) 00G-4253-V0 250×50 mm) using water-acetonitrile (0.1% AcOH) as eluent (in gradient; flow 80 mL/min) to afford trans-(IIb) and cis-(IIb).

Procedure B

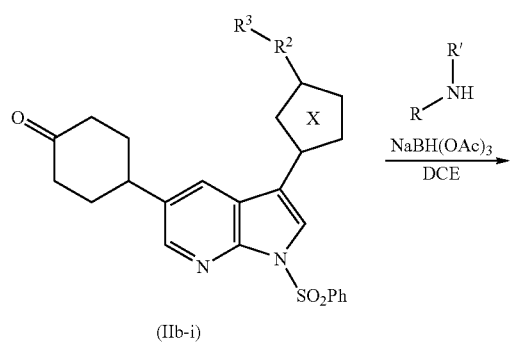

(IIb-i)

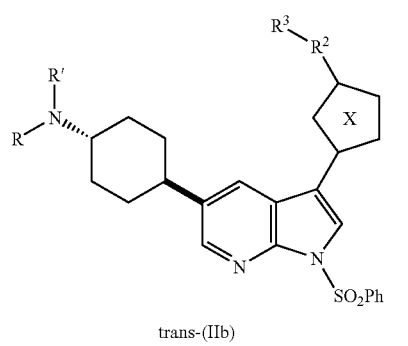

trans-(IIb)

+

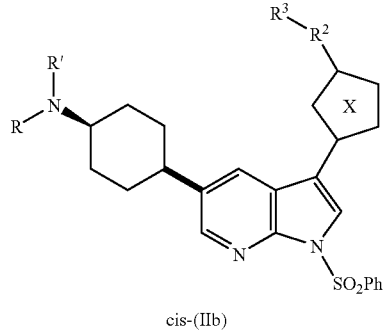

cis-(IIb)

Acetic acid (1 mmol) was added to a solution of ketone (IIb-i) (0.5 mmol) and amine RR'NH (1.5 mmol) in 1,2-dichloroethane (4.4 mL) and the reaction mixture stirred at RT for 10 min. Sodium triacetoxyborohydride (210 mg, 1 mmol) was then added and the reaction mixture allowed to stir overnight. The solution was then poured onto saturated aqueous NaHCO$_3$ (37 mL), and extracted with AcOEt (3×60 mL). The combined organic extracts were dried over MgSO$_4$, concentrated and purified by silicagel chromatography (SGC) using appropriate solvent as eluent or by preparative TLC (PTLC) using appropriate solvent as the eluent or by LCMS (column LUNA 10μ C18(2) 00G-4253-V0 250×50 mm) using water-acetonitrile (0.1% AcOH) as eluent (in gradient; flow 80 mL/min) to afford trans-(IIb) and cis-(IIb).

General Procedures for the Suzuki Reaction

Procedure A

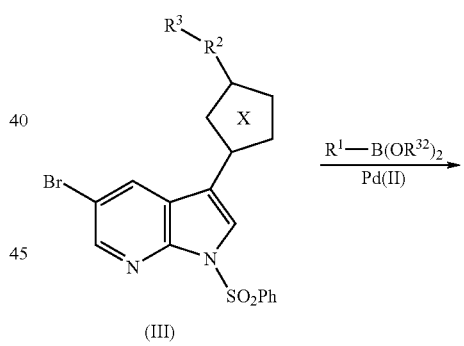

(III)

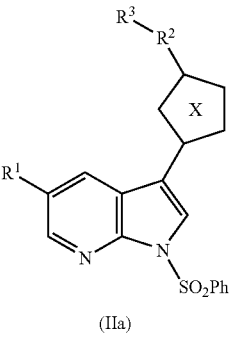

(IIa)

wherein each symbol has the same meanings as described above;

Bromide (III) (1 mmol), boronic acid or boronic acid pinacol ester R¹—B(OR³²)$_2$ (2 mmol), LiCl (3 mmol), and Pd(PPh$_3$)$_2$Cl$_2$ (0.1 mmol), were dissolved in EtOH (20 mL)

and toluene (20 mL). Then 1.0 M Na₂CO₃ solution (20-25 mL) was added and the reaction was heated to 105-110° C. for 8 hours. The reaction mixture was allowed to cool down. It was poured into water (30 mL) and was extracted with ethyl acetate (3×40 mL). The combined organic extracts were dried over MgSO₄ and concentrated. Product (IIa) was isolated by means of silicagel chromatography (SGC) using hexane/ethyl acetate as the eluent (gradient elution 0%-100% ethyl acetate) or by preparative TLC (PTLC) using appropriate solvent system as the eluent.

Essentially Identical Protocol can be Used for Conversion of (XXIII) into (Ia).

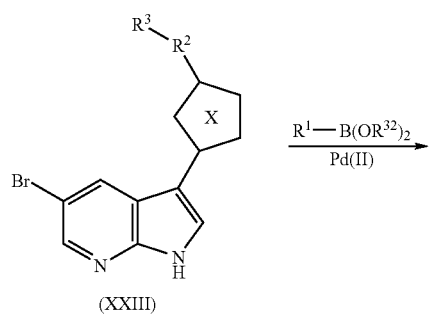

Crude extract of product (Ia) is then purified by LCMS (column LUNA 10μ C18(2) 00G4253-V0 250×50 mm) using water-acetonitrile (0.1% AcOH) as eluent (in gradient; flow 80 mL/min).

Procedure B

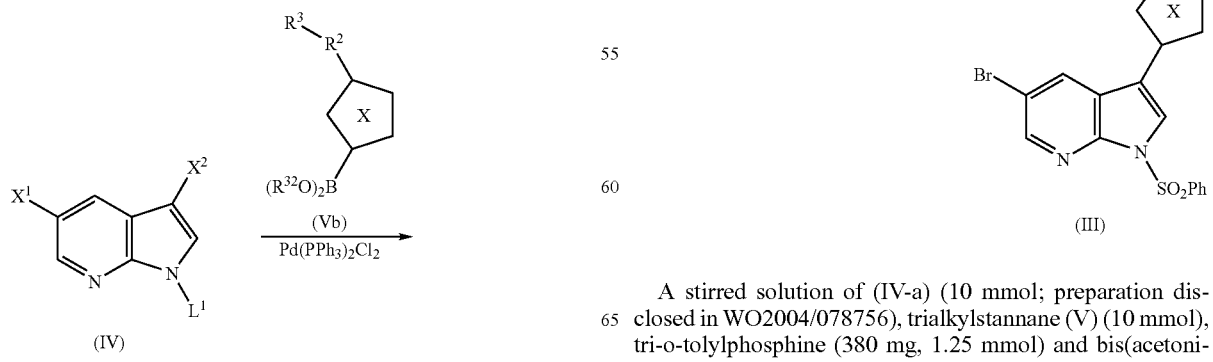

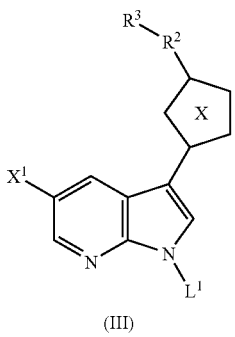

wherein each symbol has the same meanings as described above:

A mixture of halide (IV) [10 mmol; preparation of (IV-a) (X¹=Br, X²=I, L¹=SO₂Ph) disclosed in WO2004/078756], boronic acid or boronic acid pinacol ester (Vb) (11 mmol), LiCl (30 mmol), Pd(PPh₃)₂Cl₂ (0.5 mmol) and 1.0 M Na₂CO₃ solution (25 mL) in EtOH (25 mL) and toluene (25 mL) was heated at 100° C. for 3 h. The reaction mixture was cooled down to RT, diluted with water (35 mL) and extracted with ethyl acetate (4×40 mL). The combined organic extracts were dried (MgSO₄) and concentrated. The product (III) was isolated by crystallization and/or by silicagel chromatography (SGC) using an appropriate solvent system as eluent. Yield 33-80%.

General Procedure for the Stille Reaction

Procedure A Involving (IV-a)

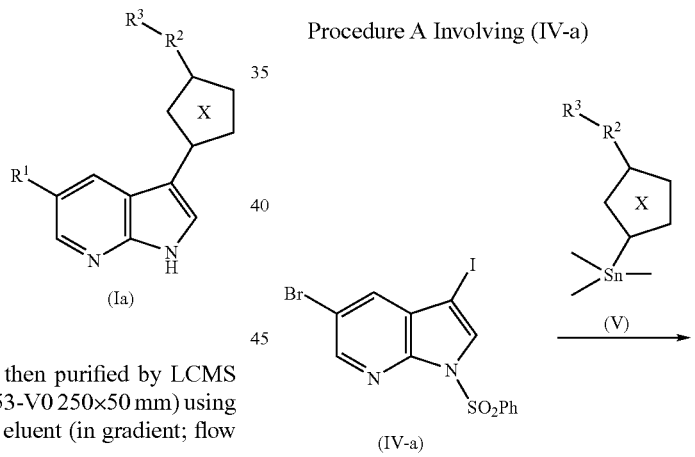

A stirred solution of (IV-a) (10 mmol; preparation disclosed in WO2004/078756), trialkylstannane (V) (10 mmol), tri-o-tolylphosphine (380 mg, 1.25 mmol) and bis(acetonitrile)dichloropalladium (II) (160 mg, 0.62 mmol) in toluene (32 mL) was refluxed for 6 h (bath temperature 110° C.). The reaction mixture was then cooled, diluted with AcOEt (210 mL) and washed with saturated aqueous NaHCO₃ (2×50 mL). The organic layer was dried (MgSO₄) and concentrated. The residue was purified by silicagel chromatography (SGC) using an appropriate solvent system as eluent. Yield 44%.

Procedure B Involving (IX)

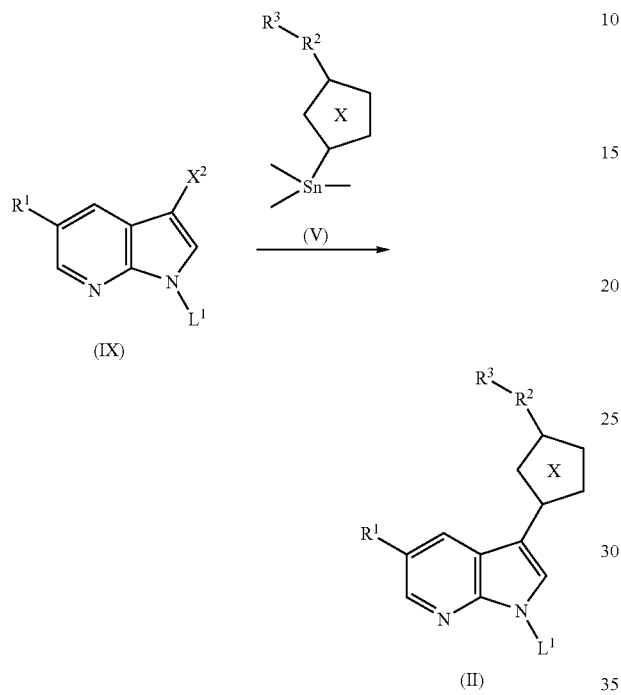

To a stirred solution of (IX) (0.5 mmol) in toluene (2.3 mL) was added dichlorobis(acetonitrile)palladium (II) (12 mg, 0.05 mmol), tri-o-tolylphosphine (28 mg, 0.09 mmol) and the relevant stannane (V) (0.6 mmol). The reaction was heated to reflux (bath temperature 110° C.) and the reaction monitored by TLC. When starting material was no longer present (2-6 hrs), the reaction mixture was poured onto saturated aqueous NaHCO₃ (60 mL) and extracted with AcOEt (2×60 mL). The combined organic solutions were dried (MgSO₄) and concentrated to give an oil which was purified using SGC and CH₂Cl₂:hexane:AcOEt as eluent (gradient from CH₂Cl₂:hexane:AcOEt=1:1:0 to 9:9:2, v/v) to afford the protected 3-thiazolyl 7-azaindole (II). Yield 25-80%.

General Procedure for Protection of (XXIII)

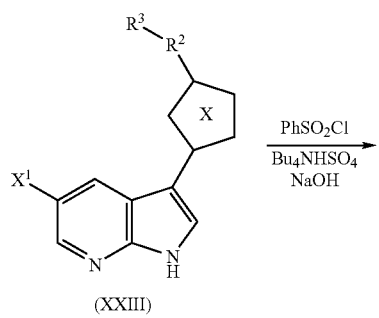

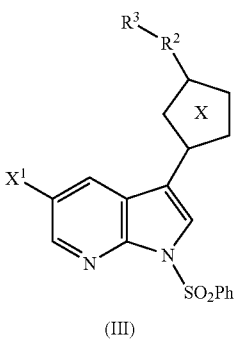

To a stirred solution of (XXIII) (10 mmol) in CH₂Cl₂ (53 mL) was added n-Bu₄NHSO₄ (71 mg-500 mg, 0.21 mmol-1.47 mmol) and 50% aqueous NaOH (1.4 mL). PhSO₂Cl (1.8 mL, 14 mmol) was then added dropwise, and the reaction stirred at RT for 1.5 h. The mixture was then diluted with EtOAc (290 mL) and acetone (14 mL), washed with brine (2×70 mL) and concentrated to give crude (III). This product can be purified by SGC using appropriate solvent system as eluent or recrystallized from CH₂Cl₂/hexane to afford pure (III). Additional product was obtained from the mother liquors by purification by SGC. Total yield of (III) 40-60%. The same procedure can be applied for protection of (XXVI) to afford (IX).

General Procedure for the Synthesis of Enol Triflates

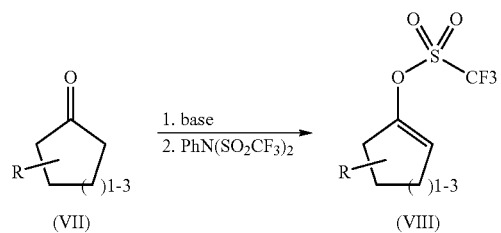

wherein R has the same meaning as described above;

To a solution of ketone (VII) (10 mmol) in THF (35 mL), cooled to −78° C., was added 1.0 M solution of LiHMDS in THF (12 mL, 12 mmol) dropwise. The stirring continued at −78° C. for 1 h. N-phenylbis(trifluoromethanesulfonimide) (3.93 g, 11 mmol) was added in one portion and the stirring continued at −78° C. for 1 h then at RT for 19.5 h. The solvent was evaporated and the crude product purified by column chromatography on alumina (Neutral, Grade I) using hexane:ethyl acetate=7:1 (v/v) as the eluent. Alternatively, the product can be isolated by SGC using ethyl acetate:hexane:

Et$_3$N=39:60:1 (v/v/v) as eluent (gradient elution starting with 19:80:1) to give triflate (VIII). Yield 62-84%.

General Procedure for the Synthesis of Boronic Pinacol Esters

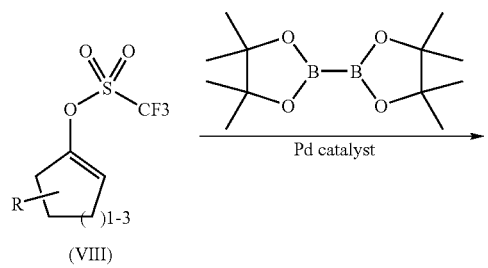

(VIII)

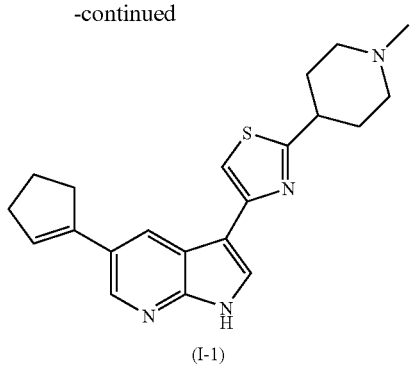

(VI-b)

wherein R has the same meaning as described above;

A mixture of triflate (VIII) (10 mmol), bis(pinacolatodiboron) (3.80 g, 15 mmol), potassium acetate (2.94 g, 30 mmol) and dichloro[1,1'-bis(diphenylphosphino)ferrocene]palladium (II) dichloromethane adduct (0.41 g, 0.5 mmol) in DMF (43 mL) was stirred at 85° C. for 6-17 h to give a homogeneous black solution. Reaction mixture was concentrated and diluted with ethyl acetate. The solid was filtered off and the filtrate concentrated. The residue was purified by SGC using ethyl acetate:hexane=1:1 (v/v) as eluent (gradient elution) to give compound (VI-b). Yield 47-67%.

5-Cyclopent-1-enyl-3-[2-(1-methyl-piperidin-4-yl)-thiazol-4-yl]-1H-pyrrolo[2,3-b]pyridine (I-1)

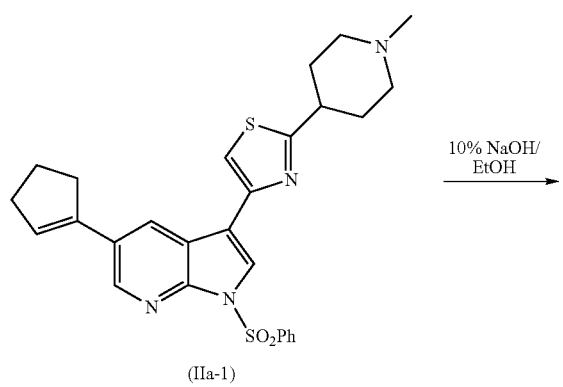

(IIa-1)

10% NaOH/EtOH →

(I-1)

Compound (IIa-1) (213 mg, 0.42 mmol) in EtOH (4 mL) and 10% aqueous NaOH (2 mL), was deprotected as described in the general procedure A for the deprotection of 7-azaindoles by refluxing for 30 min. The crude product (I-1) (xx mg, xx %), a pale yellow solid, was sufficiently pure. $^1$H NMR (400 MHz, CDCl$_3$) δ 1.94-2.28 (m, 8H), 2.37 (s, 3H), 2.57-2.65 (m, 2H), 2.83-2.90 (m, 2H), 3.02 (br d, J=11.6 Hz, 2H), 3.10 (tt, J=3.9, 11.6 Hz, 1H), 6.70 (pentet, J=2.1 Hz, 1H), 7.28 (s, 1H), 7.85 (d, J=2.3 Hz, 1H), 8.39 (d, J=1.9 Hz, 1H), 8.55 (d, J=1.9 Hz, 1H), 10.27 (s, 1H). MS (CI) m/z 365 (MH$^+$).

4-(5-cyclopentenyl-1H-pyrrolo[2,3-b]pyridin-3-yl)thiazole-2-carboxylic acid (I-2)

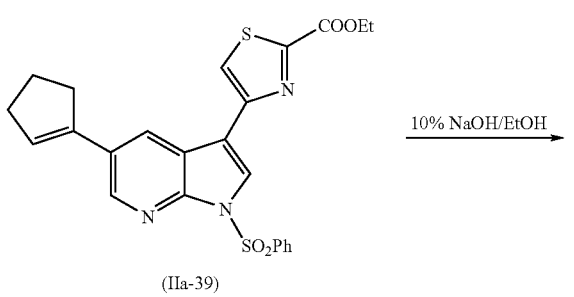

(IIa-39)

10% NaOH/EtOH →

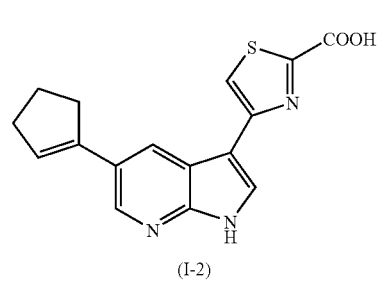

(I-2)

Compound (IIa-39) (372 mg, 0.22 mmol) in EtOH (4 mL) and 10% aqueous NaOH (2 mL), was deprotected as described in the general procedure A for the deprotection of 7-azaindoles by refluxing for 1 h. The reaction mixture was concentrated to ~2 mL, and neutralised by the dropwise addition of AcOH. The precipitate was filtered off to afford crude (I-2) (256 mg, crude yield >100%) as a yellow powder. $^1$H NMR (400 MHz, DMSO-d$_6$) δ 2.23 (pentet, J=7.5 Hz, 2H), 2.71-2.79 (m, 2H), 2.99-3.07 (m, 2H), 6.58-6.62 (m, 1H), 8.04 (s, 1H), 8.23 (s, 1H), 8.66 (d, J=2.0 Hz, 1H), 8.67 (d, J=2.0 Hz, 1H).

[4-(5-Cyclopent-1-enyl-1H-pyrrolo[2,3-b]pyridin-3-yl)-thiazol-2-yl]-morpholin-4-yl-methanone (I-3)

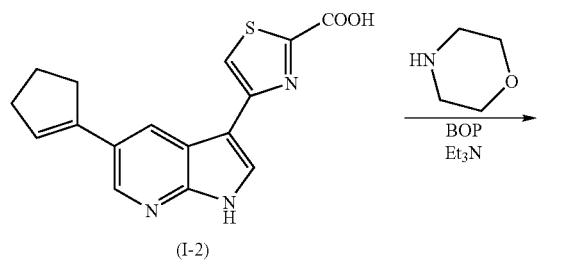

Compound (I-2) (25 mg, up to 75 μmol), triethylamine (20 mg, 0.20 mmol), morpboline (50 mg, 0.57 mmol) and BOP (100 mg, 0.23 mmol) in DMF (1 mL) were converted into (I-3) following the general procedure for the formation of amides. The crude product obtained by extractive workup (36 mg) was purified by LCMS (column LUNA 10μ C18(2) 00G-4253-V0 250×50 mm) using water-acetonitrile (0.1% AcOH) as eluent (in gradient; flow 80 mL/min) to give (I-3) (18 mg, 47 μmol, 59%) as a white powder. ¹H NMR (400 MHz, CDCl₃) δ 2.21 (pentet, J=7.5 Hz, 2H), 2.59-2.66 (m, 2H), 2.81-2.88 (m, 2H), 3.85-3.95 (m, 6H), 4.66-4.74 (m, 2H), 6.26-6.29 (m, 1H), 7.59 (s, 1H), 7.80 (s, 1H), 8.37 (d, J=1.8 Hz, 1H), 8.58 (d, J=1.8 Hz, 1H), 10.02 (br s, 1H). MS (CI) m/z 381 (MH⁺).

[4-(5-Cyclopent-1-enyl-1H-pyrrolo[2,3-b]pyridin-3-yl)-thiazol-2-yl]-piperidin-1-yl-methanone (I-4)

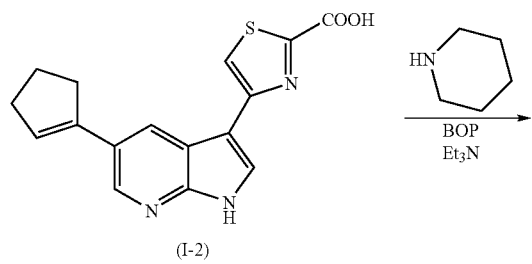

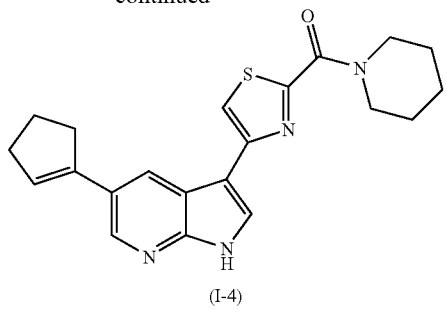

Compound (I-2) (100 mg, up to 0.30 mmol), triethylamine (50 mg, 0.49 mmol), piperidine (80 mg, 0.94 mmol) and BOP (150 mg, 0.34 mmol) in DMF (2 mL) were converted into (I-4) by stirring for 18 h and following the general procedure for the formation of amides. The crude reaction mixture was purified by LCMS (column LUNA 10μ C18(2) 00G-4253-V0 250×50 mm) using water-acetonitrile (0.1% AcOH) as eluent (in gradient; flow 80 mL/min) to give (1-4) (57 mg, 0.15 mmol, 50%) as a white powder. ¹H NMR (400 MHz, CDCl₃) δ 1.73-1.84 (m, 6H), 2.12 (pentet, J=7.5 Hz, 2H), 2.59-2.66 (m, 2H), 2.81-2.89 (m, 2H), 3.76-3.86 (m, 2H), 4.40-4.52 (m, 2H), 6.27 (pentet, J=2.2 Hz, 1H), 7.55 (s, 1H), 7.82 (d, J=2.4 Hz, 1H), 8.14 (d, J=1.9 Hz, 1H), 8.59 (d, J=1.9 Hz, 1H), 10.14 (s, 1H). MS (CI) m/z 379 (MH⁺).

[4-(5-Cyclopent-1-enyl-1H-pyrrolo[2,3-b]pyridin-3-yl)-thiazol-2-yl]-(4-methyl-piperazin-1-yl)-methanone (I-5)

Compound (I-2) (100 mg, up to 0.30 mmol), triethylamine (50 mg, 0.49 mmol), N-methylpiperazine (80 mg, 0.80 mmol) and BOP (150 mg, 0.34 mmol) in DMF (2 mL) were converted into (I-5) by stirring for 18 h and following the general procedure for the formation of amides. The crude reaction mixture was purified by LCMS (column LUNA 10μ C18(2) 00G-4253-V0 250×50 mm) using water-acetonitrile (0.1% AcOH) as eluent (in gradient; flow 80 mL/min) to give (I-5) (52 mg, 0.13 mmol, 44%) as a yellow powder. ¹H NMR (400

MHz, D-6 DMSO) δ 2.02 (pentet, J=7.5 Hz, 2H), 2.42-2.57 (m, 7H), 2.76-2.83 (m, 2H), 2.92-3.00 (m, 2H), 3.68-3.75 (m, 2H), 4.41-4.49 (m, 2H), 6.35 (pentet, J=2.2 Hz, 1H), 8.08 (d, J=2.6 Hz, 1H), 8.19 (s, 1H), 8.40 (d, J=1.9 Hz, 1H), 8.52 (d, J=1.9 Hz, 1H), 12.03 (s, 1H). MS (CI) m/z 394 (MH$^+$).

4-(5-cyclohexyl-1H-pyrrolo[2,3-b]pyridin-3-yl)thiazole-2-carboxylic acid (I-6)

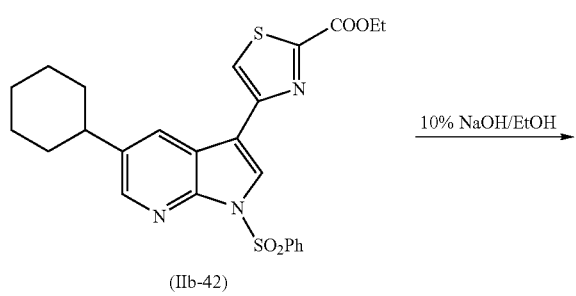

Crude compound (IIb-42) (600 mg, up to 1.12 mmol) in EtOH (7 mL) and 10% aqueous NaOH (3.5 mL), was deprotected as described in the general procedure A for the deprotection of 7-azaindoles by refluxing for 1 h. The reaction mixture was concentrated to ~4 mL, and neutralised by the dropwise addition of AcOH. The precipitate was filtered off to afford crude (I-6) (370 mg, crude yield 100%) as a powder. $^1$H NMR (400 MHz, D-6 DMSO) δ 1.23-1.50 (m, 4H), 1.52-1.65 (m, 2H), 1.69-1.89 (m, 4H), 2.65-2.69 (m, 1H), 7.72 (s, 1H), 7.93(s, 1H), 8.15 (d, J=2.1 Hz, 1H), 8.29 (d, J=2.1 Hz, 1H), 11.68(br s, 1H).

[4-(5-Cyclohexyl-1H-pyrrolo[2,3-b]pyridin-3-yl)-thiazol-2-yl]-piperidin-1-yl-methanone (I-7)

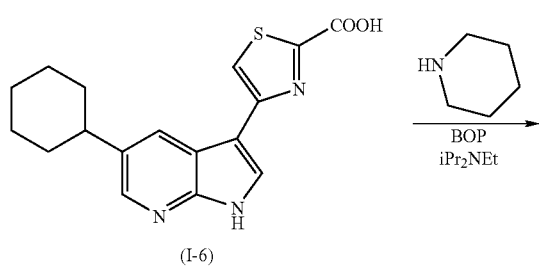

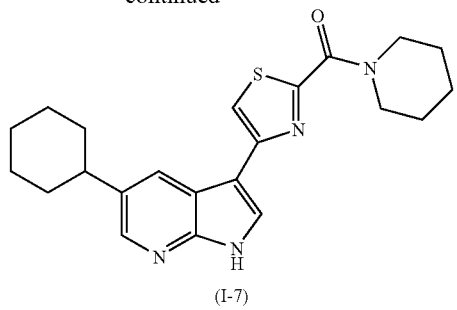

Compound (I-6) (75 mg, up to 0.23 mmol), diisopropylethylamine (80 mg, 0.62 mmol), piperidine (85 mg, 1.00 mmol) and BOP (150 mg, 0.34 mmol) in DMF (1 mL) were converted into (I-7) by stirring for 24 h and following the general procedure for the formation of amides. The crude reaction mixture was purified by LCMS (column LUNA 10μ C18(2) 00G-4253-V0 250×50 mm) using water-acetonitrile (0.1% AcOH) as eluent (in gradient; flow 80 mL/min) to give (I-7) (19 mg, 49 μmol, 21%) as a white powder. $^1$H NMR (400 MHz, CDCl$_3$) δ 1.26-1.40 (m, 1H), 1.42-1.61 (m, 4H), 1.80-2.05 (m, 6H), 2.67-2.77 (m, 1H), 3.83-3.95 (m, 6H), 4.64-4.75 (m, 2H), 7.54 (s, 1H), 7.82 (s, J=1H), 8.28 (d, J=2.0 Hz, 1H), 8.30 (d, J=2.0 Hz, 1H), 10.33 (br s, 1H). MS (CI) m/z 395 (MH$^+$).

[4-(5-Cyclohexyl-1H-pyrrolo[2,3-b]pyridin-3-yl)-thiazol-2-yl]-morpholin-4-yl-methanone (I-8)

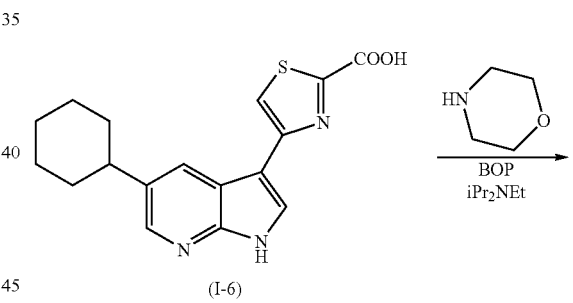

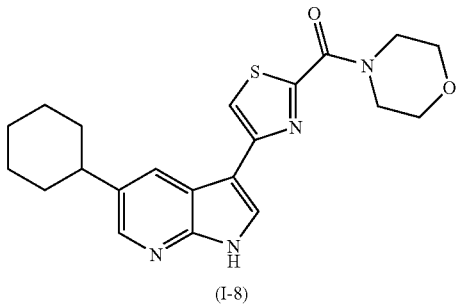

Compound (I-6) (75 mg, up to 0.23 mmol), diisopropylethylamine (80 mg, 0.62 mmol), morpholine (87 mg, 1.00 mmol) and BOP (150 mg, 0.34 mmol) in DMF (1 mL) were converted into (I-8) by stirring for 24 h and following the general procedure for the formation of amides. The crude reaction mixture was purified by LCMS (column LUNA 10μ C18(2) 00G-4253-V0 250×50 mm) using water-acetonitrile (0.1% AcOH) as eluent (in gradient; flow 80 mL/min) to give (I-8) (46 mg, 116 μmol, 50%) as a white powder. $^1$H NMR (400 MHz, CDCl$_3$) δ 1.25-1.39 (m, 1H), 1.42-1.63 (m, 4H), 1.72-1.88 (m, 7), 1.89-2.04 (m, 4H), 2.67-2.76 (m, 1H), 3.78-3.86 (m, 2H), 4.43-4.51 (m, 2H), 7.55 (s, 1H), 7.82 (s, J=1H), 8.23 (d, J=2.0 Hz, 1H), 8.31 (d, J=2.0 Hz, 1H), 10.57 (br s, 1H). MS (CI) m/z 397 (MH$^+$).

4-[5-cyclohexyl-1H-pyrrolo[2,3-b]pyridin-3-yl]-thiazole-2-carboxylic acid dimethylamide (I-9)

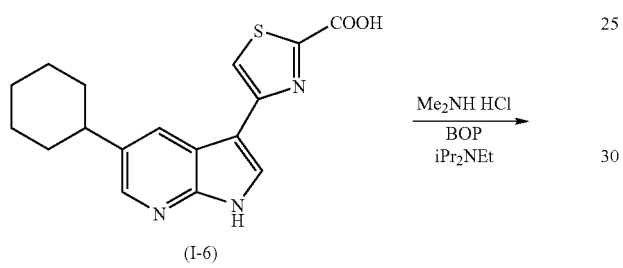

Compound (I-6) (75 mg, up to 0.23 mmol), diisopropylethylamine (160 mg, 1.24 mmol), dimethylamine hydrochloride (82 mg, 1.00 mmol) and BOP (150 mg, 0.34 mmol) in DMF (1 mL) were converted into (I-8) by stirring for 24 h and following the general procedure for the formation of amides. The crude reaction mixture was purified by LCMS (column LUNA 10μ C18(2) 00G-4253-V0 250×50 mm) using water-acetonitrile (0.1% AcOH) as eluent (in gradient; flow 80 mL/min) to give (I-9) (31 mg, 87 μmol, 38%) as a white powder. $^1$H NMR (400 MHz, CDCl$_3$) δ 1.29-1.39 (m, 1H), 1.42-1.60 (m, 4H), 1.79-1.87 (m, 1H), 1.89-1.96 (m, 2H), 1.97-2.04 (m, 2H), 2.66-2.76 (m, 1H), 3.25 (s, 3H), 3.80 (s, 3H), 7.56 (s, 1H), 7.79 (d, J=1.9 Hz, 1H), 8.26 (d, J=2.1 Hz, 1H), 8.27 (d, J=2.1 Hz, 1H), 9.22 (br s, 1H). MS (CI) m/z 355 (MH$^+$).

[4-(5-Cyclohexyl-1H-pyrrolo[2,3-b]pyridin-3-yl)-thiazol-2-yl]-(4-methyl-piperazin-1-yl)-methanone (I-10)

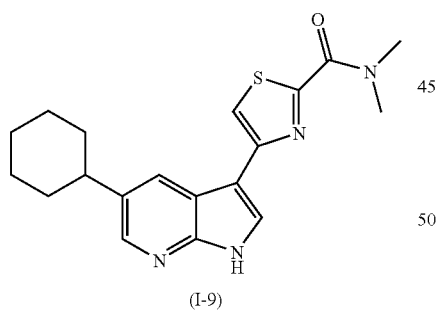

Compound (I-6) (75 mg, up to 0.23 mmol), diisopropylethylamine (80 mg, 0.62 mmol), N-methyl piperidine (100 mg, 1.00 mmol) and BOP (150 mg, 0.34 mmol) in DMF (1 mL) were converted into (I-8) by stirring for 24 h and following the general procedure for the formation of amides. The crude reaction mixture was purified by LCMS (column LUNA 10μ C18(2) 00G-4253-V0 250×50 mm) using water-acetonitrile (0.1% AcOH) as eluent (in gradient; flow 80 mL/min) to give (I-10) (17 mg, 42 μmol, 18%) as a white powder. $^1$H NMR (400 MHz, CDCl$_3$) δ 1.20-1.31 (m, 1H), 1.33-1.54 (m, 4H), 1.71-1.80 (m, 1H), 1.81-1.96 (m, 4H), 2.31 (s, 3H), 2.47-2.59 (m, 4H), 2.59-2.69 (m, 1H), 3.79-3.88 (m, 2H), 4.51-4.61 (m, 2H), 7.47 (s, 1H), 7.72 (s, 1H), 8.19 (d, J=1.9 Hz, 1H), 8.35 (d, J=1.9 Hz, 1H). MS (CI) m/z 410 (MH$^+$).

5-Cyclohexyl-3-[2-(1-methyl-piperidin-4-yl)-thiazol-4-yl]-1H-pyrrolo[2,3-b]pyridine (I-11)

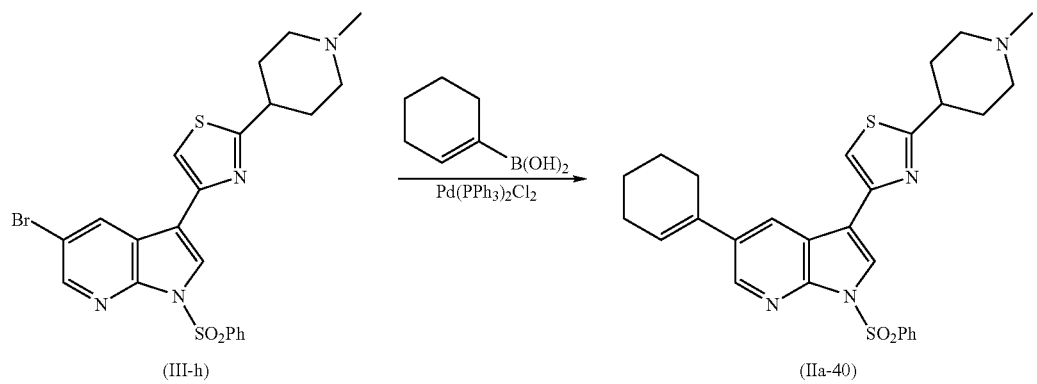

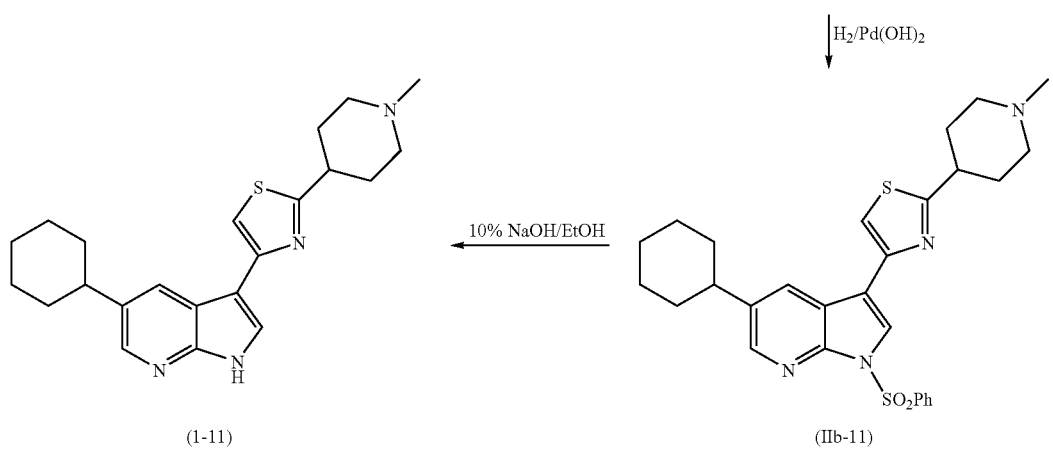

Bromide (III-h) (291 mg, 0.56 mmol), cyclohex-1-enyl boronic acid (90 mg, 0.71 mmol), lithium chloride (70 mg, 1.65 mmol), and Pd(PPh$_3$)$_2$Cl$_2$ (30 mg, 43 µmol), in EtOH (2 ml), toluene (2 ml) and 1.0 M Na$_2$CO$_3$ solution (1.0 ml) were reacted for 1 h using the general procedure A for the Suzuki reaction. The biphasic mixture was then cooled, diluted with AcOEt (100 mL), and washed with NaHCO$_3$ (3×25 mL). The organic layer was then dried over MgSO$_4$ and concentrated to afford crude (IIa-40) (218 mg). This product was hydrogenated using the general procedure for hydrogenation of 7-azaindoles using 20% Pd(OH)$_2$/C (Degussa type, 40 mg) in MeOH (5 mL) over a period of 2 days. The reaction mixture was then filtered through Celite, and concentrated to afford crude reduction product (IIb-11) (115 mg) as oil. Crude compound (IIb-11) (115 mg) in EtOH (2 mL) and 10% aqueous NaOH (1 mL), was deprotected as described in the general procedure A for the deprotection of 7-azaindoles by refluxing for 1 h. The crude product (I-11) was then purified by LCMS (column LUNA 10µ C18(2) 00G-4253-V0 250×50 mm) using water-acetonitrile (0.1% AcOH) as eluent (in gradient; flow 80 mL/min) to give (I-11) (4 mg, 11 µmol, 2%) as a white solid. $^1$H NMR (400 MHz, CDCl$_3$) δ 1.29-1.39 (m, 1H), 1.41-1.61 (m, 4H), 1.78-1.86 (m, 1H), 1.87-2.01 (m, 4H), 2.09-2.20 (m, 2H), 2.28-2.36 (m, 2H), 2.43-2.56 (m, 5H), 2.65-2.75 (m, 1H), 3.16-3.27 (m, 3H), 7.27 (s, 1H), 7.80 (m, 1H), 8.15 (d, J=1.8 Hz, 1H), 8.24 (d, J=1.8 Hz, 1H), 10.51 (s, 1H). MS (CI) m/z 381 (MH$^+$).

4-(5-cyclohexenyl-1H-pyrrolo[2,3-b]pyridin-3-yl)-N,N-diethylthiazol-2-amine (I-12)

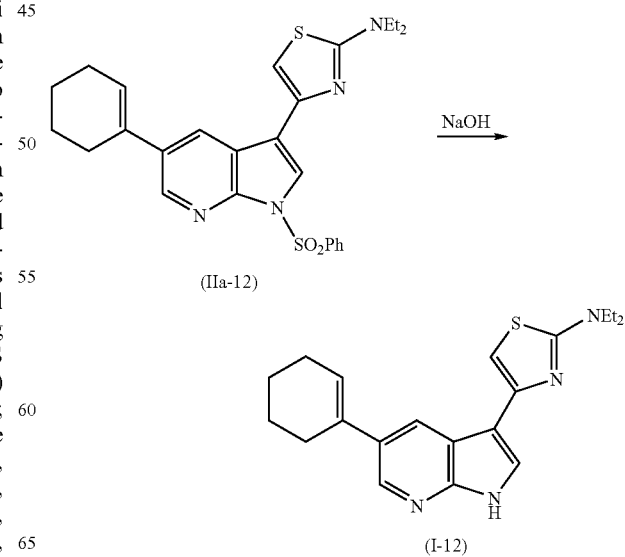

Compound (IIa-12) (17 mg, 35 µmol) in EtOH (1 mL) and 10% aqueous NaOH (0.5 mL), was deprotected as described in the general procedure A for the deprotection of 7-azaindoles by refluxing for 1.5 h. The crude product (I-12) was obtained as an off-white solid (11.3 mg, 32 µmol, 92%). $^1$H NMR (400 MHz, CDCl$_3$) δ 1.23 (t, J=7.1 Hz, 6H), 1.60-1.67 (m, 2H), 1.73-1.81 (m, 2H), 2.15-2.22 (m, 2H), 2.41-2.48 (m, 2H), 3.50 (q, J=7.1 Hz, 4H), 6.06-6.10 (m, 1H), 6.49 (s, 1H), 7.65 (d, J=2.5 Hz, 1H), 8.28 (d, J=2.1 Hz, 1H), 8.33 (d, J=2.1 Hz, 1H), 9.19 (s, 1H).

{4-[5-(4-Methyl-cyclohex-1-enyl)-1H-pyrrolo[2,3-b]pyridin-3-yl]-thiazol-2-yl}-morpholin-4-yl-methanone (I-13)

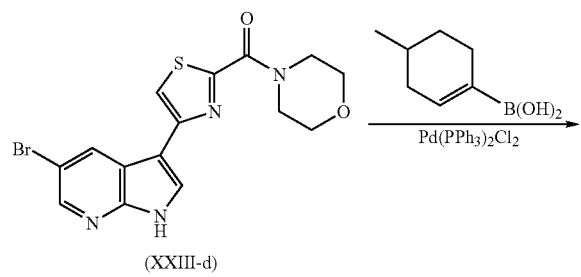

Crude bromide (XXIII-d) (110 mg, up to 0.28 mmol), 4-methyl-cyclohexen-1-yl boronic acid (45 mg, 0.32 mmol), lithium chloride (40 mg, 0.95 mmol), and Pd(PPh$_3$)$_2$Cl$_2$ (25 mg, 36 µmol), in EtOH (1. ml), toluene (1 ml) and 1.0 M Na$_2$CO$_3$ solution (0.5 ml) were reacted for 2 h under reflux using the general procedure A for the Suzuki reaction. Crude product (109 mg) was purified by LCMS (column LUNA 10µ C18(2) 00G-4253-V0 250×50 mm) using water-acetonitrile (0.1% AcOH) as eluent (in gradient; flow 80 mL/min) to give (I-13) (12 mg, 29 µmol, 10%) as a white powder. $^1$H NMR (400 MHz, CDCl$_3$) δ 0.92 (d, J=6.5 Hz, 3H), 1.25-1.37 (m, 1H), 1.52-1.85 (m, 3H), 2.17-2.27 (m, 1H), 2.38-2.45 (m, 2H), 3.67-3.79 (m, 6H), 4.48-4.59 (m, 2H), 5.96-6.01 (m, 1H), 7.44 (s, 1H), 7.64 (s, 1H), 8.18 (d, J=2.0 Hz, 1H), 8.31 (s, 1H), 9.68 (br s, 1H). MS (CI) n/z 409 (MH$^+$).

{4-[5-(4-Methyl-cyclohex-1-enyl)-1H-pyrrolo[2,3-b]pyridin-3-yl]-thiazol-2-yl}-(4-methyl-piperazin-1-yl)-methanone (I-14)

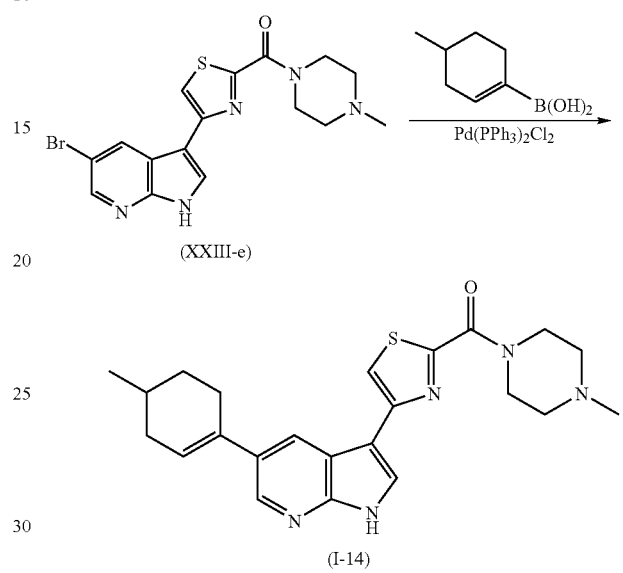

Crude bromide (XXIII-e) (110 mg, up to 0.27 mmol), 4-methyl-cyclohexen-1-yl boronic acid (45 mg, 0.32 mmol), lithium chloride (40 mg, 0.95 mmol), and Pd(PPh$_3$)$_2$Cl$_2$ (25 mg, 36 µmol), in EtOH (1 ml), toluene (1 ml) and 1.0 M Na$_2$CO$_3$ solution (0.5 ml) were reacted for 2 h under reflux using the general procedure A for the Suzuki reaction. Crude product (89 mg) was purified by LCMS (column LUNA 10µ C18(2) 00G-4253-V0 250×50 mm) using water-acetonitrile (0.1% AcOH) as eluent (in gradient; flow 80 mL/min) to give (I-14) (42 mg, 99 µmol, 37%) as a white powder. $^1$H NMR (400 MHz, CDCl$_3$) δ 1.07 (d, J=6.4 Hz, 3H), 1.39-1.53 (m, 1H), 1.75-1.99 (m, 3H), 2.33-2.37 (m, 1H), 2.40 (s, 3H), 2.48-2.68 (m, 6H), 3.88-3.96 (m, 2H), 4.80-4.88 (m, 2H), 6.11-6.16 (m, 1H), 7.57 (s, 1H), 7.78 (s, 1H), 8.39 (d, J=1.9 Hz, 1H), 8.40 (d, J=1.9 Hz, 1H), 10.38 (br s, 1H). MS (CI) m/z 422 (MH$^+$).

4-(5-(4,4-dimethylcyclohexa-1,5-dienyl)-1H-pyrrolo[2,3-b]pyridin-3-yl)thiazole-2-carboxylic acid (I-15)

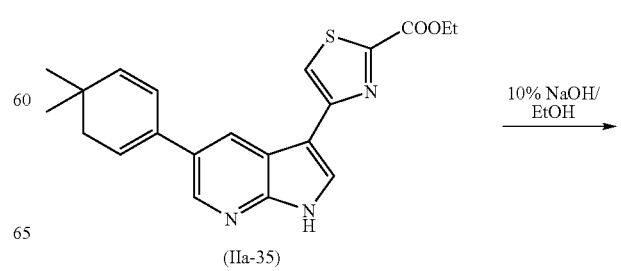

-continued

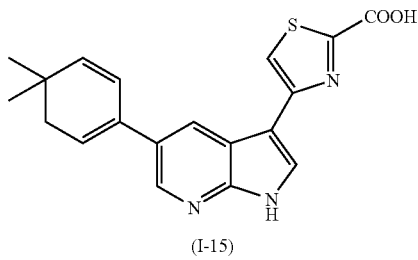

(I-15)

Compound (IIa-35) (112 mg, 0.22 mmol) in EtOH (2 mL) and 10% aqueous NaOH (1 mL), was deprotected as described in the general procedure A for the deprotection of 7-azaindoles by refluxing for 1 h. The reaction mixture was concentrated to ~5 mL, and neutralised by the dropwise addition of AcOH. The precipitate was filtered off to afford crude (I-15) (61 mg, 0.18 mmol, 83%) as a brown powder. $^1$H NMR (400 MHz, DMSO-$d_6$) δ 1.06 (s, 6H), 2.30 (d, J=4.7 Hz, 2H), 5.80 (dd, J=0.6, 9.8 Hz, 1H), 6.16 (t, J=4.7 Hz, 1H), 6.36 (dd, J=1.6, 9.7 Hz, 1H), 8.01 (s, 1H), 8.10 (s, 1H), 8.37 (d, J=2.1 Hz, 1H), 8.44 (d, J=2.1 Hz, 1H), 11.94 (br s, 1H).

{4-[5-(4,4-Dimethyl-cyclohexa-1,5-dienyl)-1H-pyrrolo[2,3-b]pyridin-3-yl]-thiazol-2-yl}-morpholin-4-yl-methanone (I-16)

Compound (I-15) (30 mg, 88 μmol), diisopropylethylamine (20 mg, 0.15 mmol), morpholine (30 mg, 0.34 mmol), and BOP (75 mg, 0.17 mmol) in DMF (1 mL) were converted into (I-16) by stirring for 3 days and following the general procedure for the formation of amides. The crude reaction mixture was purified by LCMS (column LUNA 10μ C18(2) 00G-4253-V0 250×50 mm) using water-acetonitrile (0.1% AcOH) as eluent (in gradient; flow 80 mL/min) to give (I-16) (14.5 mg, 34 μmol, 39%) as a white powder. $^1$H NMR (400 MHz, CDCl$_3$) δ 1.13 (s, 6H), 2.36 (d, J=4.6 Hz, 2H), 3.85-3.91 (m, 6H), 4.64-4.71 (m, 2H), 5.83 (d, J=9.8 Hz, 1H), 6.06 (t, J=4.6 Hz, 1H), 6.24 (d, J=9.8 Hz, 1H), 7.60 (s, 1H), 7.77 (d, J=2.6 Hz, 1H), 8.34 (d, J=1.9 Hz, 1H), 8.47 (d, J=2.0 Hz, 1H), 8.97 (br s, 1H). MS (CI) m/z 421 (MH$^+$).

{4-[5-(4,4-Dimethyl-cyclohexa-1,5-dienyl)-1H-pyrrolo[2,3-b]pyridin-3-yl]-thiazol-2-yl}-(4-methyl-piperazin-1-yl)-methanone (I-17)

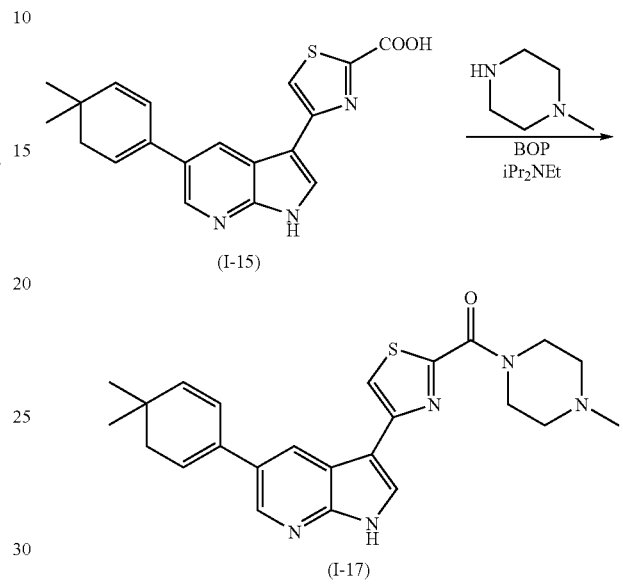

Compound (I-15) (30 mg, 88 μmol), diisopropylethylamine (20 mg, 0.15 mmol), N-methylpiperazine (30 mg, 0.30 mmol), and BOP (75 mg, 0.17 mmol) in DMF (1 mL) were converted into (I-16) by stirring for 3 days and following the general procedure for the formation of amides. The crude reaction mixture was purified by LCMS (column LUNA 10μ C18(2) 00G-4253-V0 250×50 mm) using water-acetonitrile (0.1% AcOH) as eluent (in gradient; flow 80 mL/min) to give (I-17) (13.9 mg, 32 μmol, 36%) as a white powder. $^1$H NMR (400 MHz, CDCl$_3$) δ 1.03 (s, 6H), 2.28 (d, J=4.7 Hz, 2H), 2.41 (s, 3H), 2.61-2.74 (m, 4H), 3.81-3.91 (m, 2H), 4.56-4.67 (m, 2H), 5.72 (dd, J=0.8, 9.8 Hz, 1H), 5.95 (t, J=4.5 Hz, 1H), 6.14 (dd, J=1.6, 9.8 Hz, 1H), 7.51 (s, 1H), 7.71 (s, 1H), 8.27 (s, 2H). MS (CI) m/z 434 (MH$^+$).

4-(5-(4-methylcyclohexyl)-1H-pyrrolo[2,3-b]pyridin-3-yl)thiazole-2-carboxylic acid (I-18)

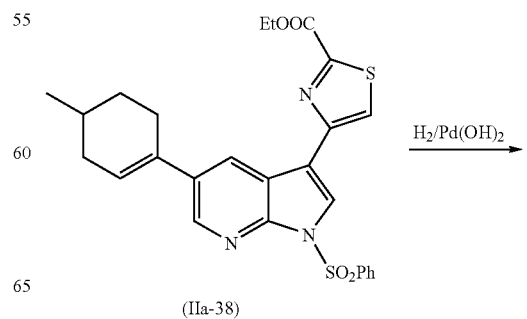

83

-continued

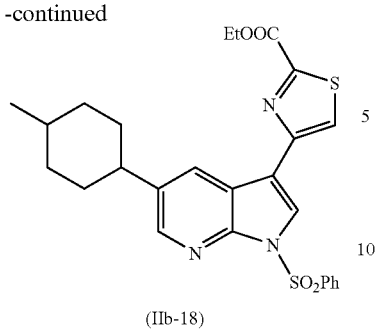

(IIb-18)

↓ 10% NaOH/EtOH

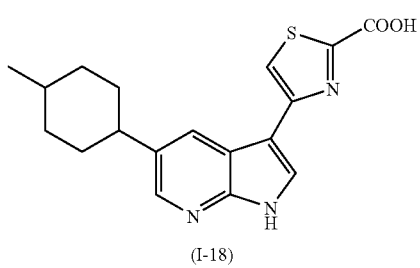

(I-18)

Compound (IIa-38) (540 mg, 0.99 mmol) was hydrogenated using the general procedure for hydrogenation of 7-azaindoles using 20% Pd(OH)$_2$/C (Degussa type, 100 mg) in MeOH (25 mL) over a period of 3 days. The reaction mixture was then filtered through Celite, and concentrated to afford crude reduction product (IIb-18) (524 mg, crude yield 96%) as an oil. Crude compound (IIb-18) (524 mg) in EtOH (10 mL) and 10% aqueous NaOH (5 mL), was deprotected as described in the general procedure A for the deprotection of 7-azaindoles by refluxing for 1 h. The reaction mixture was concentrated to ~5 mL, and neutralised by the dropwise addition of AcOH. The precipitate was filtered off to afford a crude mixture of diastereomeric acids (I-18) (xx mg, xx %), which was used without additional purification.

4-[5-(4-Methyl-cyclohexyl)-1H-pyrrolo[2,3-b]pyridin-3-yl]-thiazole-2-carboxylic acid dimethylamide
(I-19)

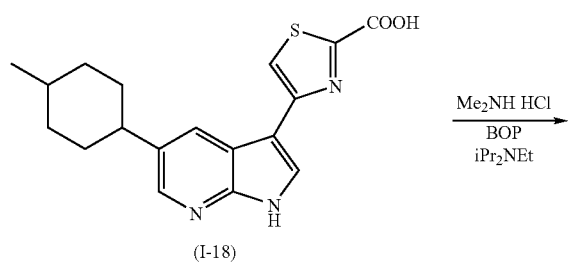

(I-18) → Me$_2$NH HCl / BOP / iPr$_2$NEt

84

-continued

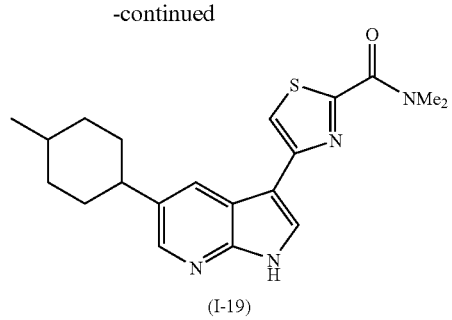

(I-19)

Compound (I-18) (48 mg, 0.14 mmol), diisopropylethylamine (100 mg, 0.77 mmol), dimethylamine hydrochloride (40 mg, 0.49 mmol), and BOP (150 mg, 0.29 mmol) in DMF (1.5 mL) were converted into (I-19) by stirring for 2 h and following the general procedure for the formation of amides. The crude reaction mixture was purified by LCMS (column LUNA 10μ C18(2) 00G-4253-V0 250×50 mm) using water-acetonitrile (0.1% AcOH) as eluent (in gradient; flow 80 mL/min) to give (I-19) (34 mg, 92 μmol, 66%) as a white powder. $^1$H NMR (400 MHz, CDCl$_3$) δ 1.00 (d, J=6.7 Hz, 1.2H), 1.09 (d, J=7.1 Hz, 1.8H), 1.11-1.23 (m, 1H), 1.49-2.08 (m, 8H), 2.62-2.71 (m, 0.4H), 2.72-2.81 (m, 0.6H), 3.25 (s, 3H), 3.80 (s, 1.2H), 3.81 (s, 1.8H), 7.56 (s, 1H), 7.82 (s, 1H), 8.24 (d, J=1.9 Hz, 0.4H), 8.27 (d, J=1.9 Hz, 0.6H), 8.32 (d, J=1.9 Hz, 0.4H), 8.37 (d, J=1.9 Hz, 0.6H), 10.43 (br s, 1H). MS (CI) m/z 369 (MH$^+$).

{4-[5-(4-Methyl-cyclohexyl)-1H-pyrrolo[2,3-b]pyridin-3-yl]-thiazol-2-yl}-piperidin-1-yl-methanone
(I-20)

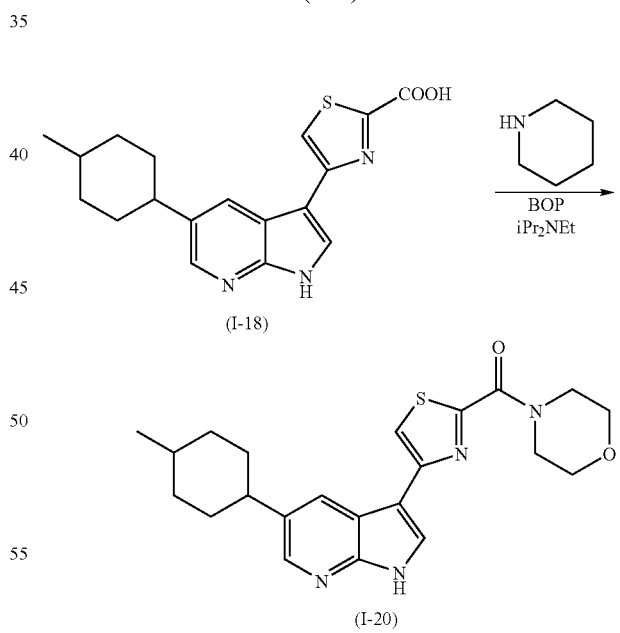

Compound (I-18) (65 mg, 0.23 mmol), diisopropylethylamine (100 mg, 0.77 mmol), piperidine (50 mg, 0.59 mmol), and BOP (200 mg, 0.38 mmol) in DMF (1.5 mL) were converted into (I-20) by stirring for 3 h and following the general procedure for the formation of amides. The crude reaction mixture was purified by LCMS (column LUNA 10μ C18(2) 00G-4253-V0 250×50 mm) using water-acetonitrile (0.1% AcOH) as eluent (in gradient; flow 80 mL/min) to give (I-20)

(33 mg, 81 µmol, 35%) as a white powder. $^1$H NMR (400 MHz, CDCl$_3$) δ 1.00 (d, J=6.6 Hz, 1.2H), 1.10 (d, J=7.2 Hz, 1.8H), 1.12-1.23 (m, 1H), 1.43-2.10 (m, 14H), 2.61-2.71 (m, 0.4H), 2.71-2.81 (m, 0.6H), 3.74-3.89 (m, 2H), 4.39-4.54 (m, 2H), 7.54 (s, 1H), 7.79 (s, 1H), 8.26 (d, J=1.8 Hz, 0.4H), 8.28 (d, J=1.8 Hz, 0.6H), 8.29 (d, J=2.0 Hz, 0.4H), 8.32 (d, J=2.0 Hz, 0.6H), 9.85 (br s, 1H). MS (CI) m/z 409 (MH$^+$).

{4-[5-(4-Methyl-cyclohexyl)-1H-pyrrolo[2,3-b]pyridin-3-yl]-thiazol-2-yl}-morpholin-4-yl-methanone (I-21)

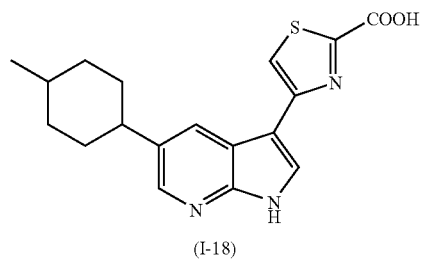
(I-18)

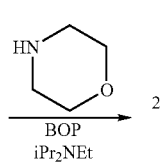

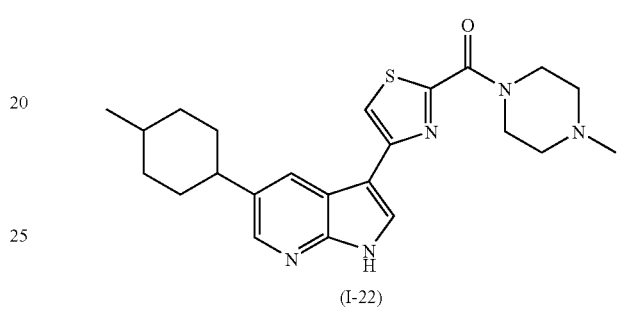
(I-21)

Compound (I-18) (65 mg, 0.23 mmol), diisopropylethylamine (100 mg, 0.77 mmol), morpholine (50 mg, 0.57 mmol), and BOP (200 mg, 0.38 mmol) in DMF (1.5 mL) were converted into (I-20) by stirring for 3 h and following the general procedure for the formation of amides. The crude reaction mixture was purified by LCMS (column LUNA 10µ C18(2) 00G-4253-V0 250×50 mm) using water-acetonitrile (0.1% AcOH) as eluent (in gradient; flow 80 mL/min) to give (I-21) (38 mg, 93 µmol, 40%) as a white powder. $^1$H NMR (400 MHz, CDCl$_3$) δ 1.00 (d, J=6.6 Hz, 1.2H), 1.10 (d, J=7.2 Hz, 1.8H), 1.13-1.24 (m, 1H), 1.48-2.11 (m, 8H), 2.62-2.72 (m, 0.4H), 2.73-2.82 (m, 0.6H), 3.80-3.97 (m, 6H), 4.63-4.76 (m, 2H), 7.59 (s, 1H), 7.81 (s, 1H), 8.23 (d, J=1.9 Hz, 0.4H), 8.26 (d, J=1.9 Hz, 0.6H), 8.29 (d, J=2.0 Hz, 0.4H), 8.33 (d, J=2.0 Hz, 0.6H), 10.26 (br s, 1H). MS (CI) m/z 411 (MH$^+$).

{4-[5-(4-Methyl-cyclohexyl)-1H-pyrrolo[2,3-b]pyridin-3-yl]-thiazol-2-yl}-(4-methyl-piperazin-1-yl)-methanone (I-22)

(I-18)

(I-22)

Compound (I-18) (65 mg, 0.23 mmol), diisopropylethylamine (100 mg, 0.77 mmol), N-methylpiperazine (50 mg, 0.50 mmol), and BOP (200 mg, 0.38 mmol) in DMF (1.5 mL) were converted into (I-20) by stirring for 3 h and following the general procedure for the formation of amides. The crude reaction mixture was purified by LCMS (column LUNA 10µ C18(2) 00G-4253-V0 250×50 mm) using water-acetonitrile (0.1% AcOH) as eluent (in gradient; flow 80 mL/min) to give (I-22) as a white powder (36 mg, 85 µmol, 37%). $^1$H NMR (400 MHz, CDCl$_3$) δ 0.90 (d, J=6.4 Hz, 1.2H), 1.00 (d, J=7.2 Hz, 1.8H), 1.03-1.14 (m, 1H), 1.42-2.00 (m, 8H), 2.32 (s, 1.8H), 2.32 (s, 1.8H), 2.46-2.62 (m, 5.4H), 2.63-2.72 (m, 0.6H), 3.76-3.91 (m, 2H), 4.49-4.65 (m, 2H), 7.47 (s, 1H), 7.70 (s, 1H), 8.13-8.25 (m, 2H), 10.19 (br s, 1H). MS (CI) m/z 424 (MH$^+$).

5-(1,4-Dioxa-spiro[4.5]dec-8-yl)-3-[2-(1-methyl-piperidin-4-yl)-thiazol-4-yl]-1H-pyrrolo[2,3-b]pyridine (I-23)

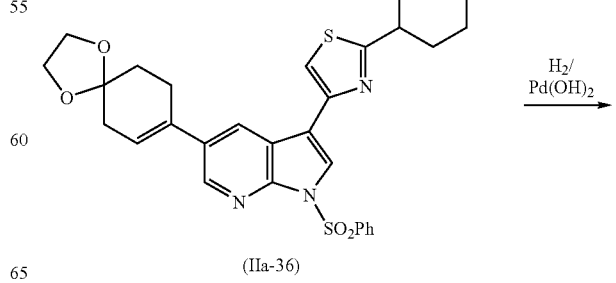
(IIa-36)

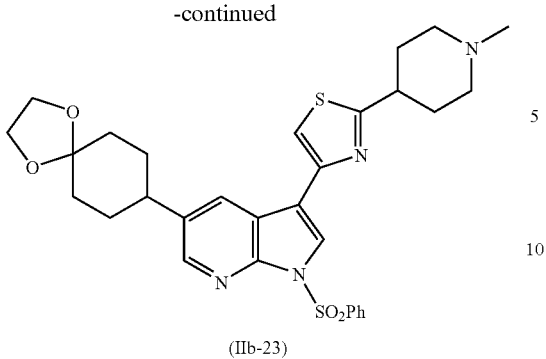

(IIb-23)

↓ 10% NaOH/EtOH

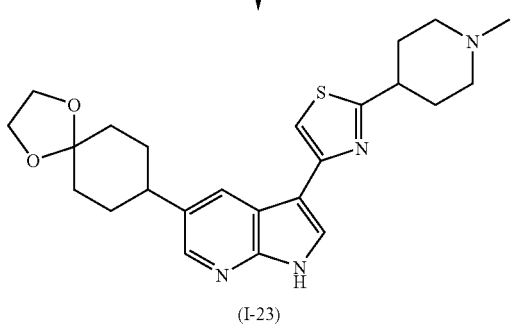

(I-23)

Compound (IIa-36) (148 mg, 0.26 mmol) was hydrogenated using the general procedure for hydrogenation of 7-azaindoles using 20% Pd(OH)$_2$/C (Degussa type, 40 mg) in MeOH (5 mL)-CH$_2$Cl$_2$ (5 mL) over a period of 20 h. The reaction mixture was then filtered through Celite, and concentrated to afford crude reduction product (IIb-23) (131 mg) as an oil. Crude compound (IIb-23) (131 mg) in EtOH (2 mL) and 10% aqueous NaOH (1 mL), was deprotected as described in the general procedure A for the deprotection of 7-azaindoles by refluxing for 1 h. The crude product (I-23) (92 mg) was then purified by LCMS (column LUNA 10µ C18(2) 00G-4253-V0 250×50 mm) using water-acetonitrile (0.1% AcOH) as eluent (in gradient; flow 80 mL/min) to give (I-23) (13.5 mg, 30 µmol, 14%) as a white powder. $^1$H NMR (400 MHz, CDCl$_3$) δ 1.76-1.83 (m, 2H), 1.89-2.03 (m, 6H), 2.26-2.35 (m, 2H), 2.38-2.50 (m, 5H), 2.72-2.82 (m, 1H), 3.13-3.25 (m, 5H), 4.04 (s, 4H), 7.27 (s, 1H), 7.80 (s, 1H), 8.19 (d, J=1.9 Hz, 1H), 8.26 (d, J=1.9 Hz, 1H), 10.18 (s, 1H). MS (CI) m/z 453 (MH$^+$).

2-(5-cyclohexenyl-1H-pyrrolo[2,3-b]pyridin-3-yl)thiazole (I-24)

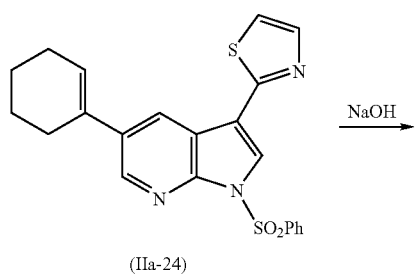

(IIa-24) → NaOH

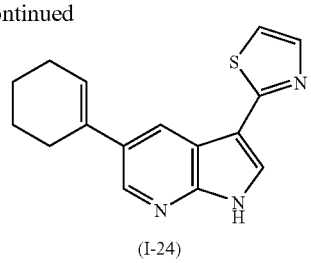

(I-24)

Compound (IIa-24) (25 mg, 59 µmol) in EtOH (1 mL) and 10% aqueous NaOH (0.5 mL), was deprotected as described in the general procedure A for the deprotection of 7-azaindoles by refluxing for 90 min. The crude product (I-24) (15 mg, 39 µmol, 66%) was obtained as an off-white powder, which did not require further purification. $^1$H NMR (400 MHz, CDCl$_3$) δ 1.61-1.68 (m, 2H), 1.75-1.82 (m, 2H), 2.17-2.23 (m, 2H), 2.44-2.50 (m, 2H), 6.09-6.13 (m, 1H), 7.17 (d, J=3.3 Hz, 1H), 7.78 (d, J=3.3 Hz, 1H), 7.88 (s, 1H), 8.40 (d, J=2.1 Hz, 1H), 8.49 (d, J=2.1 Hz, 1H), 10.65 (br s, 1H).

{4-[5-(1,4-Dioxa-spiro[4.5]dec-8-yl)-1H-pyrrolo[2,3-b]pyridin-3-yl]-thiazol-2-yl}-piperidin-1-yl-methanone (I-25)

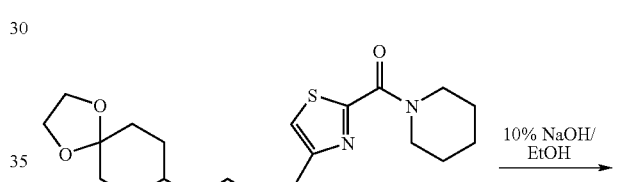

(IIb-25) → 10% NaOH/EtOH

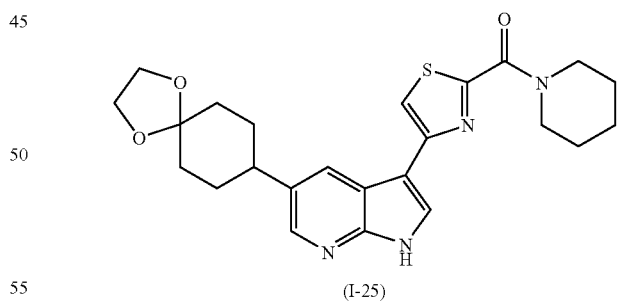

(I-25)

Compound (IIb-25) (103 mg, 0.17 mmol) in EtOH (2 mL) and 10% aqueous NaOH (1 mL), was deprotected as described in the general procedure A for the deprotection of 7-azaindoles by refluxing for 1 h. The crude product (I-25) (61 mg) was then purified by LCMS (column LUNA 10µ C18(2) 00G4253-V0 250×50 mm) using water-acetonitrile (0.1% AcOH) as eluent (in gradient; flow 80 mL/min) to give (I-25) (3 mg, 6.6 µmol, 4%) as a white solid. $^1$H NMR (400 MHz, CDCl$_3$) δ 1.72-2.04 (m, 14H), 2.73-2.83 (m, 1H), 3.78-3.87 (m, 2H), 4.03 (s, 4H), 4.46-4.55 (m, 2H), 7.55 (s, 1H), 7.80 (d, J=2.5 Hz, 1H), 8.31 (d, J=1.9 Hz, 1H), 8.33 (d, J=1.9 Hz, 1H), 9.80 (s, 1H). MS (CI) m/z 453 (MH+).

2-(5-cyclohexyl-1H-pyrrolo[2,3-b]pyridin-3-yl)thiazole (I-26)

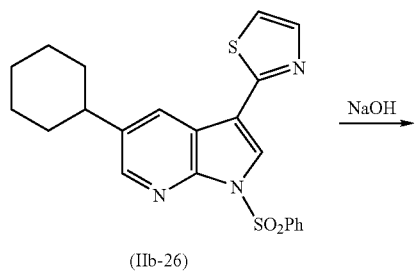

Compound (IIb-26) (55 mg, 0.13 mmol) in EtOH (2 mL) and 10% aqueous NaOH (1 mL), was deprotected as described in the general procedure A for the deprotection of 7-azaindoles by refluxing for 90 min. The crude product (I-26) was obtained as an off-white powder (34.5 mg, 0.12 mmol, 94%). $^1$H NMR (400 MHz, CDCl$_3$) δ 1.16-1.60 (m, 5H), 1.68-1.95 (m, 5H), 2.66 (tt, J=3.4, 12.0 Hz, 1H), 7.17 (d, J=3.3 Hz, 1H), 7.78 (d, J=3.3 Hz, 1H), 7.87 (s, 3H), 8.23 (d, J=2.0 Hz, 1H), 8.37 (d, J=2.0 Hz, 1H), 10.35 (br s, 1H).

{4-[5-(4-Ethyl-cyclohex-1-enyl)-1H-pyrrolo[2,3-b]pyridin-3-yl]-thiazol-2-yl}-morpholin-4-yl-methanone (I-27)

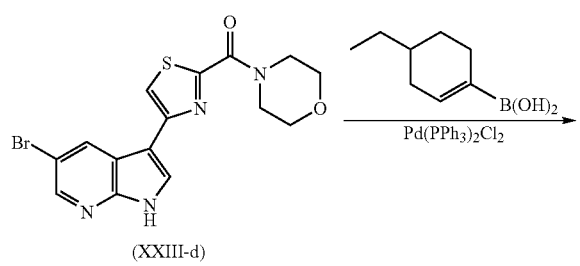

Crude bromide (XXIII-d) (150 mg, up to 0.38 mmol), 4-ethyl-cyclohexen-1-yl boronic acid (117 mg, 0.76 mmol), lithium chloride (48 mg, 1.14 mmol), and Pd(PPh$_3$)$_2$Cl$_2$ (26.7 mg, 38 µmol), in EtOH (1 ml), toluene (1 ml) and 1.0 M Na$_2$CO$_3$ solution (1.0 ml) were reacted for 6 h under reflux using the general procedure A for the Suzuki reaction. Crude product (109 mg) was purified by PTLC using AcOEt as eluent to give (I-27) (32 mg, 20%) as a white solid. $^1$H NMR (400 MHz, CDCl$_3$) δ 0.99 (t, J=7.4 Hz, 3H), 1.35-1.49 (m, 3H), 1.52-1.64 (m, 1H), 1.84-1.95 (m, 1H), 1.97-2.05 (m, 1H), 2.35-2.45 (m, 1H), 2.53-2.61 (m, 2H), 3.83-3.95 (m, 6H), 4.65-4.73 (m, 2H), 6.12-6.18 (m, 1H), 7.57 (s, 1H), 7.82 (s, 1H), 8.34 (d, J=1.8 Hz, 1H), 8.49 (d, J=1.8 Hz, 1H), 11.26 (br s, 1H).

4-(5-((1s,4s)-4-morpholinocyclohexyl)-1H-pyrrolo[2,3-b]pyridin-3-yl)thiazole-2-carboxylic acid (I-28)

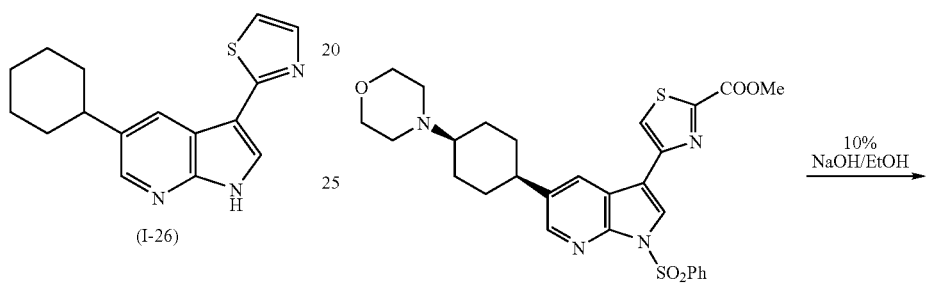

Crude compound (IIb-46) (138 mg, 0.24 mmol) in EtOH (6 mL) and 10% aqueous NaOH (3 mL), was deprotected as described in the general procedure A for the deprotection of 7-azaindoles by heating to 80° C. for 2 h 15 min. The reaction mixture was concentrated to ~3 mL, and neutralised by the dropwise addition of AcOH. A yellow semisolid was formed. The supernatant was removed and the yellow solid was dried overnight in vaccum to produce the crude product (I-28) (99 mg, 99%), which was used without additional purification.

4-(5-((1r,4r)-4-morpholinocyclohexyl)-1H-pyrrolo[2,3-b]pyridin-3-yl)thiazole-2-carboxylic acid (I-29)

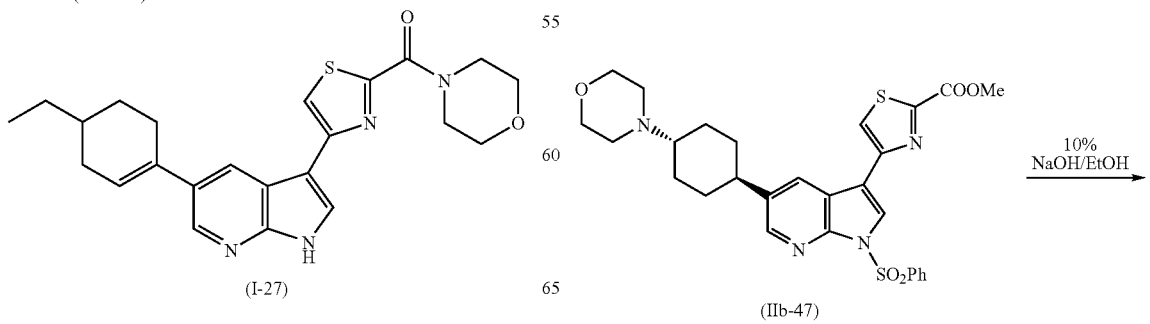

-continued

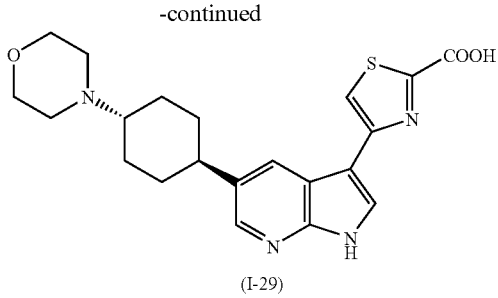

(I-29)

Crude compound (II-47) (148 mg, 0.26 mmol) in EtOH (6 mL) and 10% aqueous NaOH (3 mL), was deprotected as described in the general procedure A for the deprotection of 7-azaindoles by heating to 80° C. for 3 h. The reaction mixture was concentrated to ~3 mL, and neutralised by the dropwise addition of AcOH. Solvents were evaporated to give a yellow solid. Water (1 mL) was added to the solid and the mixture was stirred for 5 minutes. The solid was filtered off to give (I-29) (55 mg, 51%), which was used without additional purification.

(4-(5-((1r,4r)-4-morpholinocyclohexyl)-1H-pyrrolo[2,3-b]pyridin-3-yl)thiazol-2-yl)(piperidin-1-yl)methanone (I-30)

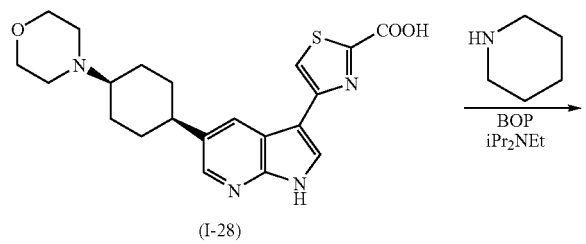

(I-28)

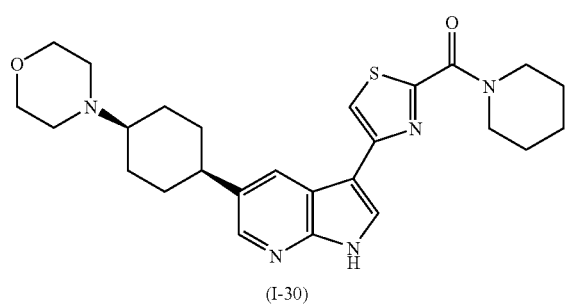

(I-30)

Compound (I-28) (33 mg, 0.08 mmol), diisopropylethylamine (0.14 mL, 0.80 mmol), piperidine (14 mg, 0.16 mmol), and BOP (70 mg, 0.16 mmol) in DMF (1 mL) were converted into (I-30) by stirring overnight and following the general procedure for the formation of amides. The crude reaction mixture was purified by LCMS (column LUNA 10μ C18(2) 00G-4253-V0 250×50 mm) using water-acetonitrile (0.1% AcOH) as eluent (in gradient; flow 80 mL/min) to give the compound (I-30) as a white solid (7 mg, 18%; retention time 16.3-16.7 min); MS (CI) m/z 480.2 (MH$^+$).

morpholino(4-(5-((1s,4s)-4-morpholinocyclohexyl)-1H-pyrrolo[2,3-b]pyridin-3-yl)thiazol-2-yl)methanone (I-31)

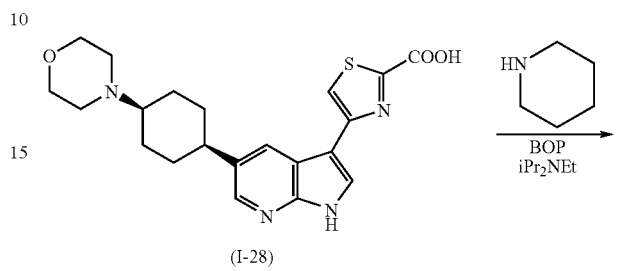

(I-28)

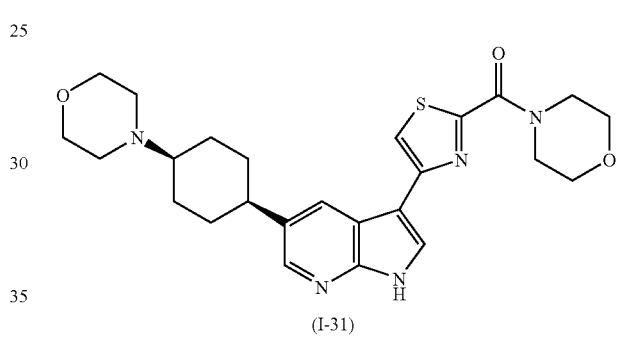

(I-31)

Compound (I-28) (33 mg, 0.08 mmol), diisopropylethylamine (0.14 mL, 0.80 mmol), morpholine (14 mg, 0.16 mmol), and BOP (70 mg, 0.16 mmol) in DMF (1 mL) were converted into (I-31) by stirring overnight and following the general procedure for the formation of amides. The crude reaction mixture was purified by LCMS (column LUNA 10μ C18(2) 00G-4253-V0 250×50 mm) using water-acetonitrile (0.1% AcOH) as eluent (in gradient; flow 80 mL/min) to give the compound (I-31) (2 mg, 5%; retention time 15.5-16.5 min) as a white solid; MS (CI) m/z 482.2 (MH$^+$).

(4-methylpiperazin-1-yl)(4-(5-((1s,4s)-4-morpholinocyclohexyl)-1H-pyrrolo[2,3-b]pyridin-3-yl)thiazol-2-yl)methanone (I-32)

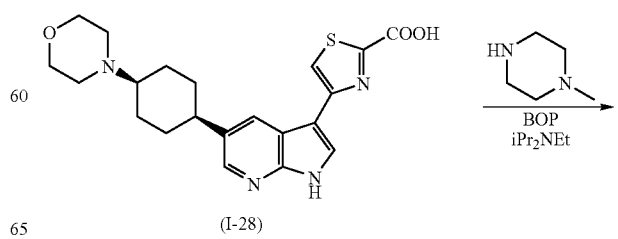

(I-28)

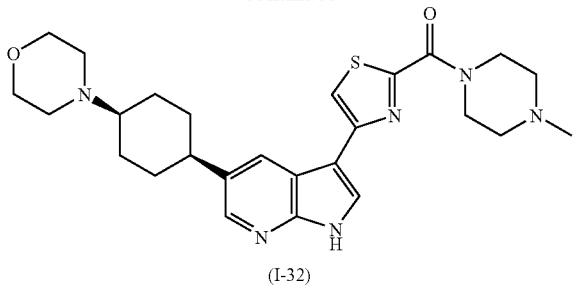

(I-32)

Compound (I-28) (33 mg, 0.08 mmol), diisopropylethylamine (0.14 mL, 0.80 mmol), N-methyl piperazine (16 mg, 0.16 mmol), and BOP (70 mg, 0.16 mmol) in DMF (1 mL) were converted into (I-31) by stirring overnight and following the general procedure for the formation of amides. The crude reaction mixture was purified by LCMS (column LUNA 10μ C18(2) 00G-4253-V0 250×50 mm) using water-acetonitrile (0.1% AcOH) as eluent (in gradient; flow 80 mL/min) to give the compound (I-32) (7 mg, 18%; retention time 12.6-13.1 min) as a colourless oil; $^1$H NMR (400 MHz, CDCl$_3$) δ 1.56-1.66 (m, 2H), 1.67-1.76 (m, 2H), 197-2.01 (m, 2H), 2.02-2.06 (m, 4H), 2.25-2.34 (m, 2H), 2.36 (s, 3H), 2.50-2.55 (m, 4H), 2.59 (t, J=5.0 Hz, 4H), 3.76 (t, J=4.8 Hz, 4H), 3.85-3.90 (m, 2H), 4.55-4.61 (m, 2H), 7.56 (s, 1H), 7.76 (s, 1H), 7.98 (br s, NH, 1H), 8.21 (d, J=2.0 Hz, 1H), 8.25 (d, J=1.8 Hz, 1H), MS (CI) m/z 495.2 (MH$^+$).

(4-(5-((1r,4r)-4-morpholinocyclohexyl)-1H-pyrrolo[2,3-b]pyridin-3-yl)thiazol-2-yl)(piperidin-1-yl)methanone (I-33)

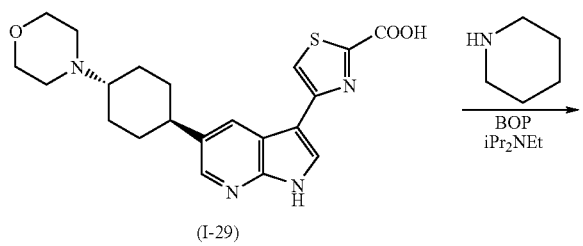

(I-29)

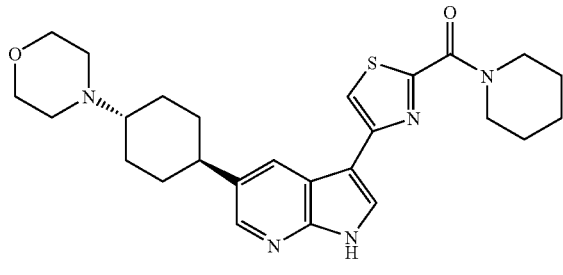

(I-33)

Compound (I-29) (27 mg, 0.066 mmol), diisopropylethylamine (0.12 mL, 0.66 mmol), piperidine (34 mg, 0.40 mmol), and BOP (59 mg, 0.13 mmol) in DMF (1 mL) were converted into (I-33) by stirring overnight and following the general procedure for the formation of amides. The crude reaction mixture was purified by LCMS (column LUNA 10μ C18(2) 00G-4253-V0 250×50 mm) using water-acetonitrile (0.1% AcOH) as eluent (in gradient; flow 80 mL/min) to give the compound (I-33) (5.8 mg, 18%; retention time 17.2-17.8 min) as a yellow solid; $^1$H NMR (400 MHz, CH$_3$CN) δ 1.69-1.81 (m, 10H), 2.13-2.19 (m, 2H), 2.25-2.30 (m, 2H), 2.78-2.88 (m, 1H), 3.16-3.36 (m, 3H), 3.45 (d, J=12.3 Hz, 2H), 3.71-3.79 (m, 2H), 3.82 (d, J=12 Hz, 2H), 4.11 (dd, J=3.0 and 13.0 Hz, 2H), 4.36-4.42 (m, 2H), 7.82 (s, 1H), 7.95 (s, 1H), 8.26 (s, 1H), 8.45 (d, J=1.5 Hz, 1H), 10.1 (br s, NH, 1H); MS (CI) m/z 480.2 (MH$^+$).

morpholino(4-(5-((1r,4r)-4-morpholinocyclohexyl)-1H-pyrrolo[2,3-b]pyridin-3-yl)thiazol-2-yl)methanone (I-34)

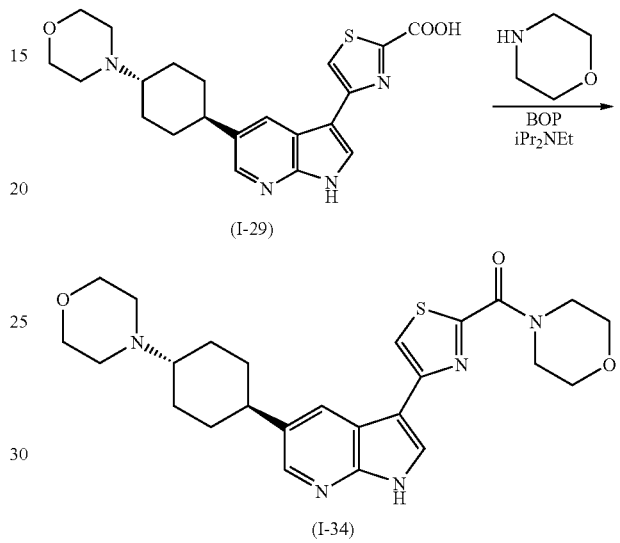

Compound (I-29) (27 mg, 0.066 mmol), diisopropylethylamine (0.12 mL, 0.66 mmol), morpholine (35 mg, 0.40 mmol), and BOP (59 mg, 0.13 mmol) in DMF (1 mL) were converted into (I-34) by stirring overnight and following the general procedure for the formation of amides. The crude reaction mixture was purified by LCMS (column LUNA 10μ C18(2) 00G-4253-V0 250×50 mm) using water-acetonitrile (0.1% AcOH) as eluent (in gradient; flow 80 mL/min) to give the compound (I-34) (9 mg, 28%; retention time 14.2-15.0 min) as a yellow solid; $^1$H NMR (400 MHz, CDCl$_3$) δ 1.41-1.52 (m, 2H), 1.53-1.65 (m, 2H), 2.02-2.15 (m, 4H), 2.41-2.50 (m, 1H), 2.62-2.68 (m, 1H), 2.70 (t, J=4.4 Hz, 4H), 2.95-2.97 (m, 4H), 3.77 (t, J=4.4 Hz, 4H), 3.79-3.82 (m, 4H), 7.54 (s, 1H), 7.73 (s, 1H), 8.12 (s, 1H), 8.14 (d, J=1.9 Hz, 1H), MS (CI) m/z 482.2 (MH$^+$).

5-(5-cyclohexyl-1H-pyrrolo[2,3-b]pyridin-3-yl)thiazole (I-48)

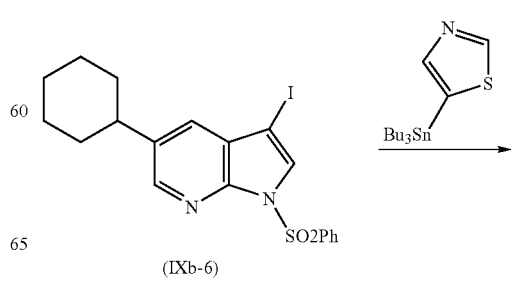

(IXb-6)

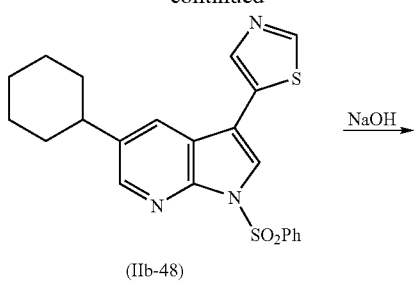

(IIb-48)

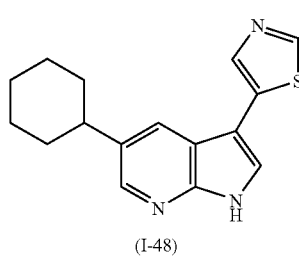

(I-48)

Iodide (IXb-6) and 5-(tributylstannyl)thiazole were reacted using the general procedure B for the Stille reaction (yield 25%) followed by deprotection according to the general procedure A for the deprotection of 7-azaindoles (yield 70%). The crude product was purified by LCMS (column LUNA 10μ C18(2) 00G-4253-V0 250×50 mm) using water-acetonitrile (0.1% AcOH) as eluent (in gradient; flow 80 mL/min) to give (I-48). $^1$H NMR (400 MHz, CDCl$_3$) δ 1.28-1.66 (m, 5H), 1.78-2.04 (m, 5H), 2.73 (tt, J=3.5, 11.8 Hz, 1H), 7.45 (d, J=2.0 Hz, 1H), 7.89 (d, J=2.1 Hz, 1H), 8.25 (d, J=1.9 Hz, 1H), 8.30 (d, J=1.9 Hz, 1H), 8.95 (d, J=2.0 Hz, 1H), 10.00 (br s, 1H).

4-(5-cyclohexyl-1H-pyrrolo[2,3-b]pyridin-3-yl)thiazole (I-49)

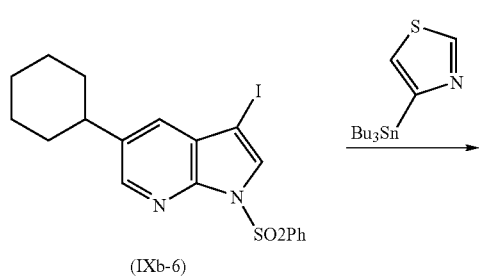

(IXb-6)

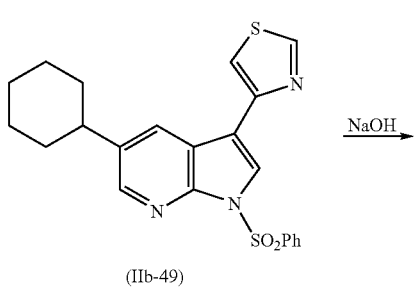

(IIb-49)

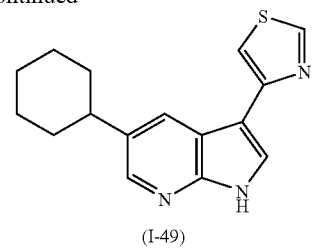

(I-49)

Iodide (IXb-6) and 4-(tributylstannyl)thiazole were reacted using the general procedure B for the Stille reaction (yield 25%) followed by deprotection according to the general procedure A for the deprotection of 7-azaindoles (yield 58%). The crude product was purified by LCMS (column LUNA 10μ C18(2) 00G-4253-V0 250×50 mm) using water-acetonitrile (0.1% AcOH) as eluent (in gradient; flow 80 mL/min) to give (I-49). $^1$H NMR (400 MHz, CDCl$_3$) δ 1.28-1.63 (m, 5H), 1.79-2.04 (m, 5H), 2.72 (tt, J=3.4, 11.8 Hz, 1H), 7.60 (d, J=2.2 Hz, 1H), 8.03 (d, J=1.9 Hz, 1H), 8.11 (s, 1H), 8.32 (d, J=1.9 Hz, 1H), 8.78 (s, 1H), 10.19 (br s, 1H).

4-(5-cyclohexyl-1H-pyrrolo[2,3-b]pyridin-3-yl)-2-methoxythiazole (I-50)

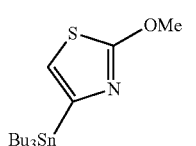

(IXb-6)

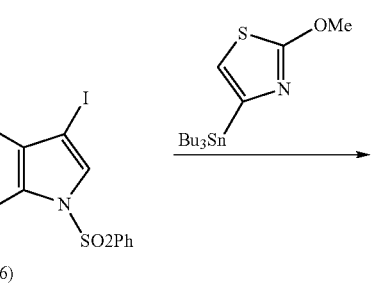

(IIb-50)

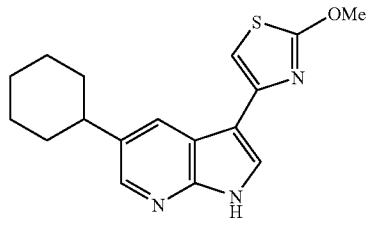

(I-50)

Iodide (IXb-6) and 2-methoxy-4-(tributylstannyl)thiazole were reacted using the general procedure B for the Stille reaction (yield 62%) followed by deprotection according to the general procedure A for the deprotection of 7-azaindoles (yield 87%). The crude product was purified by LCMS (column LUNA 10μ C18(2) 00G-4253-V0 250×50 mm) using water-acetonitrile (0.1% AcOH) as eluent (in gradient; flow 80 mL/min) to give (I-50). $^1$H NMR (400 MHz, CDCl$_3$) δ 1.16-1.55 (m, 5H), 1.67-1.94 (m, 5H), 2.62 (tt, J=3.4, 11.8 Hz, 1H), 4.11 (s, 3H), 6.67 (s, 1H), 7.70 (d, J=2.2 Hz, 1H), 8.08 (d, J=1.9 Hz, 1H), 8.17 (d, J=1.9 Hz, 1H), 8.78 (s, 1H), 9.96 (br s, 1H).

2-(5-cyclohexyl-1H-pyrrolo[2,3-b]pyridin-3-yl)-4-methylthiazole (I-51)

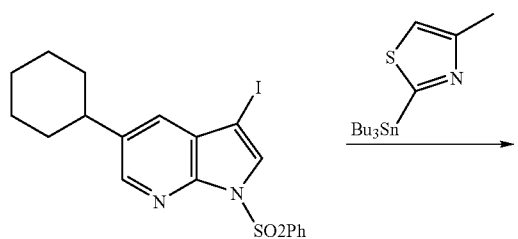

(IXb-6)

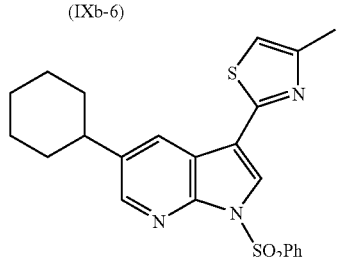

(IIb-51)

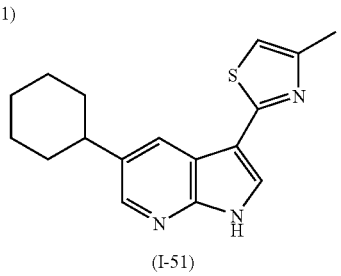

(I-51)

Iodide (IXb-6) and 4-methyl-2-(tributylstannyl)thiazole were reacted using the general procedure B for the Stille reaction (yield 63%) followed by deprotection according to the general procedure A for the deprotection of 7-azaindoles (yield 49%). The crude product was purified by LCMS (column LUNA 10μ C18(2) 00G-4253-V0 250×50 mm) using water-acetonitrile (0.1% AcOH) as eluent (in gradient; flow 80 mL/min) to give (I-51). $^1$H NMR (400 MHz, CDCl$_3$) δ 1.16-1.51 (m, 5H), 1.63-1.89 (m, 5H), 2.41 (s, 3H), 2.59 (tt, J=3.3, 11.9 Hz, 1H), 6.66 (d, J=1.0 Hz, 1H), 7.81 (d, J=1.1 Hz, 1H), 8.15 (d, J=2.0 Hz, 1H), 8.24 (d, J=2.0 Hz, 1H), 10.52 (br s, 1H).

2-(5-cyclohexyl-1H-pyrrolo[2,3-b]pyridin-3-yl)-5-methylthiazole (I-52)

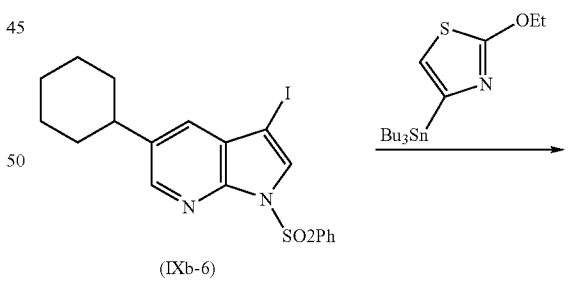

(IXb-6)

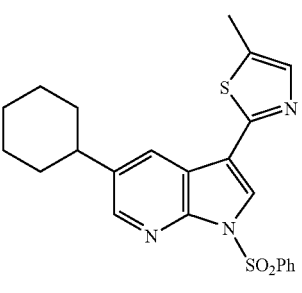

(IIb-52)

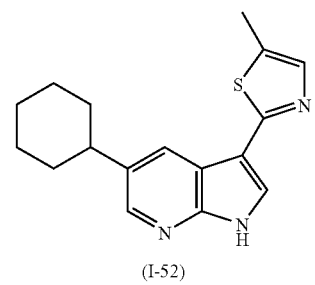

(I-52)

Iodide (IXb-6) and 5-methyl-2-(tributylstannyl)thiazole were reacted using the general procedure B for the Stille reaction (yield 32%) followed by deprotection according to the general procedure A for the deprotection of 7-azaindoles (yield 61%). The crude product was purified by LCMS (column LUNA 10μ C18(2) 00G-4253-V0 250×50 mm) using water-acetonitrile (0.1% AcOH) as eluent (in gradient; flow 80 mL/min) to give (I-52). $^1$H NMR (400 MHz, CDCl$_3$) δ 1.24-1.65 (m, 5H), 1.77-2.02 (m, 5H), 2.54 (s, 3H), 2.72 (tt, J=3.2, 11.7 Hz, 1H), 7.49 (d, J=1.2 Hz, 1H), 7.83 (s, 1H), 8.19 (d, J=2.0 Hz, 1H), 8.45 (d, J=2.0 Hz, 1H), 10.94 (br s, 1H).

4-(5-cyclohexyl-1H-pyrrolo[2,3-b]pyridin-3-yl)-2-ethoxythiazole (I-53)

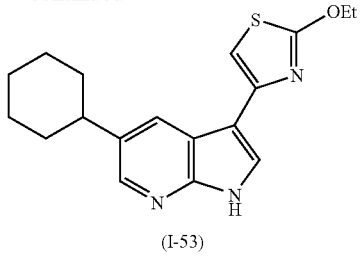

(I-53)

Iodide (IXb-6) and 2-ethoxy-4-(tributylstannyl)thiazole were reacted using the general procedure B for the Stille reaction (yield 63%) followed by deprotection according to the general procedure A for the deprotection of 7-azaindoles (yield 93%). The crude product was purified by LCMS (column LUNA 10μ C18(2) 00G-4253-V0 250×50 mm) using water-acetonitrile (0.1% AcOH) as eluent (in gradient; flow 80 mL/min) to give (I-53). $^1$H NMR (400 MHz, CDCl$_3$) δ 1.16-1.53 (m, 8H), 1.69-1.94 (m, 5H), 2.61 (tt, J=3.3, 11.8 Hz, 1H), 4.49 (q, J=7.1 Hz, 2H), 6.66 (s, 1H), 7.68 (d, J=2.4 Hz, 1H), 8.07 (d, J=1.9 Hz, 1H), 8.17 (d, J=1.9 Hz, 1H), 9.66 (br s, 1H).

4-((1r,4r)-4-(3-(2-methylthiazol-4-yl)-1H-pyrrolo[2,3-b]pyridin-5-yl)cyclohexyl)morpholine (I-55)

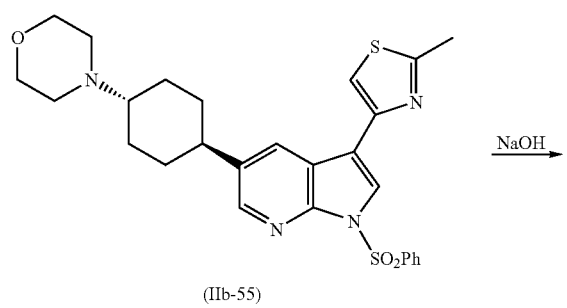

Compound (IIb-55) (491 mg, 0.94 mmol) in EtOH (4 mL) and 10% aqueous NaOH (2 mL), was deprotected as described in the general procedure A for the deprotection of 7-azaindoles by refluxing for 90 min. The crude product was obtained as a yellow powder (350 mg), which was purified by trituration with Et$_2$O (5 mL) to afford (I-55) as a white powder (251 mg, 0.66 mmol, 70%). $^1$H NMR (400 MHz, CDCl$_3$) δ 1.41-1.73 (m, 4H), 2.06-2.18 (m, 4H), 2.39 (tt, J=3.3, 11.5 Hz, 1H), 2.60-2.76 (m, 5H), 2.83 (s, 3H), 3.79 (t, J=4.6 Hz, 4H), 7.22 (s, 1H), 7.82 (d, J=2.6 Hz, 1H), 8.16 (d, J=1.9 Hz, 1H), 8.26 (d, J=2.1 Hz, 1H), 9.07 (br s, 1H).

4-((1s,4s)-4-(3-(2-methylthiazol-4-yl)-1H-pyrrolo[2,3-b]pyridin-5-yl)cyclohexyl)morpholine (I-56)

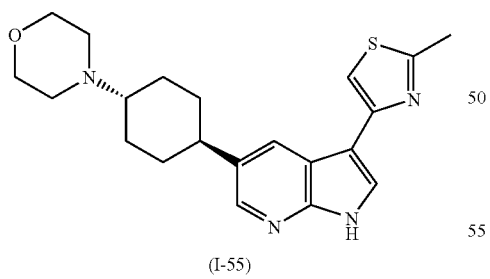

Compound (IIb-56) (411 mg, 0.79 mmol) in EtOH (4 mL) and 10% aqueous NaOH (2 mL), was deprotected as described in the general procedure A for the deprotection of 7-azaindoles by refluxing for 90 min. The product (I-56) was obtained as an off-white powder (218 mg, 0.57 mmol, 72%). $^1$H NMR (400 MHz, CDCl$_3$) δ 1.54-1.76 (m, 4H), 2.00-2.13 (m, 4H), 2.29-2.34 (m, 1H), 2.47-2.59 (m, 5H), 2.81-2.92 (m, 4H), 3.80 (t, J=4.6 Hz, 2H), 7.22 (s, 1H), 7.82 (d, J=2.6 Hz, 1H), 8.23 (d, J=2.0 Hz, 1H), 8.31 (d, J=2.0 Hz, 1H), 9.01 (br s, 1H).

4-(5-cyclohexenyl-1H-pyrrolo[2,3-b]pyridin-3-yl)-2-methylthiazole (I-57)

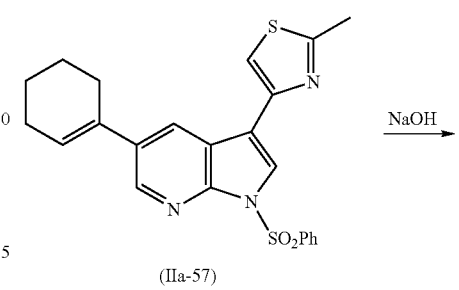

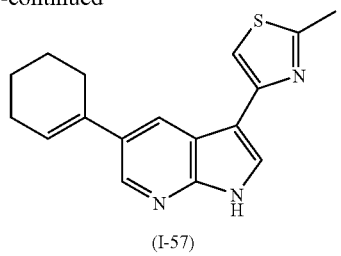

(I-57)

Compound (IIa-57) (44 mg, 0.10 mmol) in EtOH (1 mL) and 10% aqueous NaOH (0.5 mL), was deprotected as described in the general procedure A for the deprotection of 7-azaindoles by refluxing for 90 min. The crude product (23 mg) was purified by trituration with $Et_2O$ (2 mL) to afford (I-57) (18 mg, 0.05 mmol, 17%) as an off-white powder. $^1$H NMR (400 MHz, $CDCl_3$) δ 1.60-1.68 (m, 2H), 1.74-1.82 (m, 2H), 2.16-2.22 (m, 2H), 2.42-2.48 (m, 2H), 2.73 (s, 3H), 6.04-6.09 (m, 1H), 7.15 (s, 1H), 7.74 (d, J=2.5 Hz, 1H), 8.20 (d, J=2.0 Hz, 1H), 8.35 (d, J=2.0 Hz, 1H), 9.19 (br s, 1H).

4-(5-cyclohexyl-1H-pyrrolo[2,3-b]pyridin-3-yl)-2-methylthiazole (I-58)

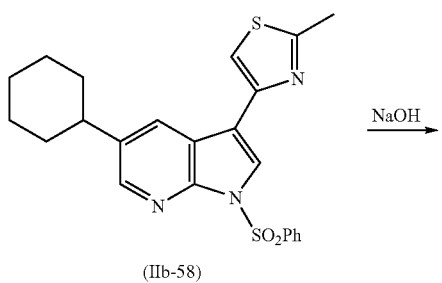

Compound (IIb-58) (133 mg, 0.30 mmol) in EtOH (2 mL) and 10% aqueous NaOH (1.0 mL), was deprotected as described in the general procedure A for the deprotection of 7-azaindoles by refluxing for 90 min. The crude product was purified by preparative LCMS (column LUNA 10μ C18(2) 00G-4253-V0 250×50 mm) using water-acetonitrile (0.1% AcOH) as eluent (in gradient; flow 80 mL/min) to give (I-58) (16 mg, 0.05 mmol, 17%) as an off-white powder. $^1$H NMR (400 MHz, $CDCl_3$) δ 1.30-1.63 (m, 5H), 1.78-2.03 (m, 5H), 2.66-2.76 (m, 1H), 2.83 (s, 3H), 7.23 (s, 1H), 7.83 (d, J=2.4 Hz, 1H), 8.17 (d, J=1.9 Hz, 1H), 8.26 (d, J=2.0 Hz, 1H), 9.28 (br s, 1H).

4-((1r,4r)-4-(3-(thiazol-4-yl)-1H-pyrrolo[2,3-b]pyridin-5-yl)cyclohexyl)morpholine (I-59)

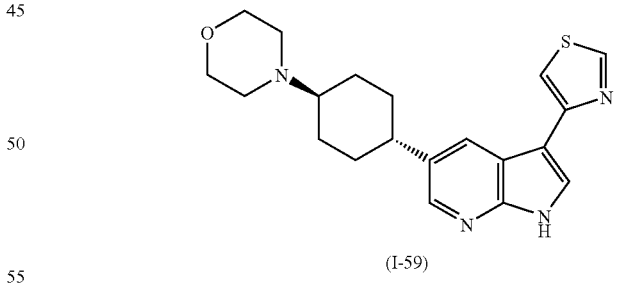

Iodide (IXb-29) and 4-tributylstannyl thiazole were reacted using the general procedure B for the Stille reaction (yield 57%) followed by deprotection according to the general procedure B for the deprotection of 7-azaindoles (yield 69%). $^1$H NMR (400 MHz, DMSO-$d_6$) δ 1.33-1.46 (m, 2H), 1.57-1.71 (m, 2H), 1.89-2.02 (m, 4H), 2.30-2.41 (m, 1H), 2.50-2.59 (m, 1H), 3.59 (t, J=4.4 Hz, 4H), 7.95 (d, J=1.9 Hz, 1H), 7.97 (d, J=2.6 Hz, 1H), 8.18 (d, J=1.9 Hz, 1H), 8.33 (d, J=1.8 Hz, 1H), 9.20 (d, J=1.8 Hz, 1H), 11.79 (d, J=1.8 Hz, 1H). Remaining aliphatic peaks hidden under solvent peak at ~2.5 ppm.

4-((1r,4r)-4-(3-(thiazol-5-yl)-1H-pyrrolo[2,3-b]pyridin-5-yl)cyclohexyl)morpholine (I-60)

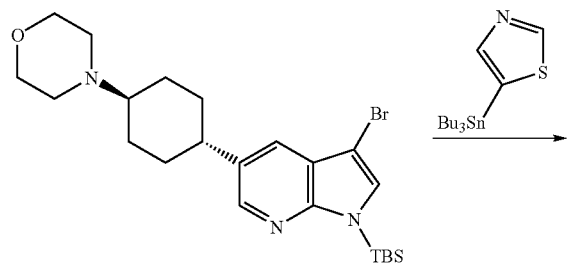

(IXb-29)

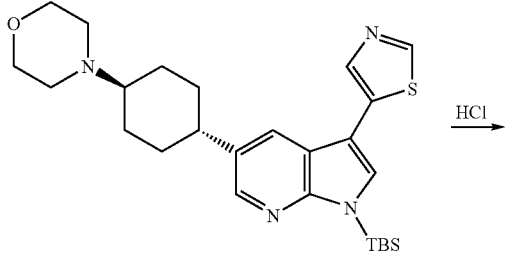

(IIb-60)

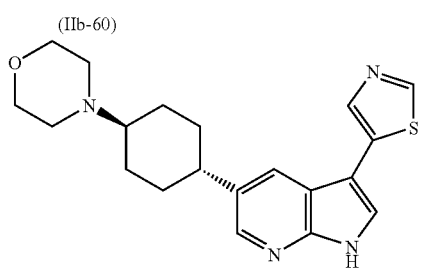

(I-60)

Iodide (IXb-29) and 5-tributylstannyl thiazole were reacted using the general procedure B for the Stille reaction (yield 44%) followed by deprotection according to the general procedure B for the deprotection of 7-azaindoles (yield 86%). $^{1}$H NMR (400 MHz, CDCl$_3$) δ 1.40-1.54 (m, 2H), 1.56-1.71 (m, 2H), 2.05-2.18 (m, 4H), 2.34-2.43 (m, 1H), 2.61-2.75 (m, 5H), 3.78 (t, J=4.4 Hz, 4H), 7.56 (d, J=1.7 Hz, 1H), 7.99-8.01 (m, 1H), 8.06-8.10 (m, 1H), 8.22-8.32 (m, 1H), 8.76-8.79 (m, 1H).

4-((1r,4r)-4-(3-(4-methylthiazol-2-yl)-1H-pyrrolo[2,3-b]pyridin-5-yl)cyclohexyl)morpholine (I-61)

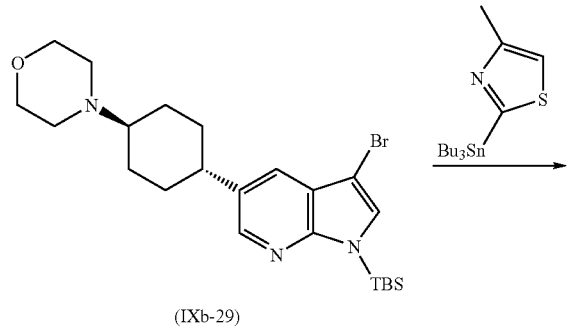

(IXb-29)

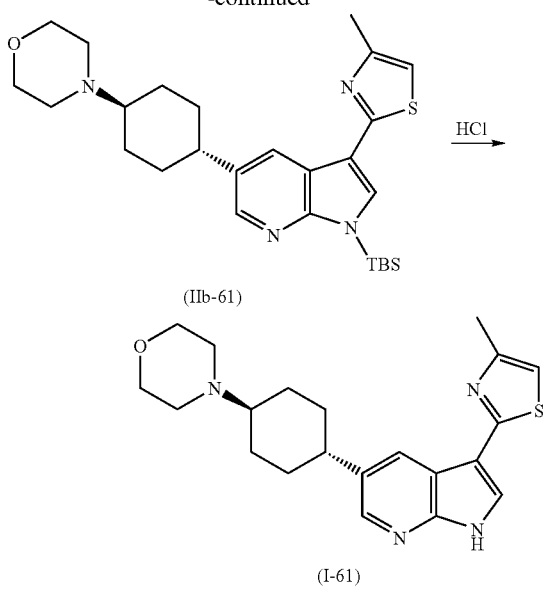

Iodide (IXb-29) and 4-methyl-2-tributylstannyl thiazole were reacted using the general procedure B for the Stille reaction (yield 39%) followed by deprotection according to the general procedure B for the deprotection of 7-azaindoles (yield 75%). $^{1}$H NMR (400 MHz, CDCl$_3$) δ 1.40-1.54 (m, 2H), 1.56-1.71 (m, 2H), 2.05-2.18 (m, 4H), 2.34-2.43 (m, 1H), 2.61-2.75 (m, 5H), 3.78 (t, J=4.4 Hz, 4H), 7.56 (d, J=1.7 Hz, 1H), 7.99-8.01 (m, 1H), 8.06-8.10 (m, 1H), 8.22-8.32 (m, 1H), 8.76-8.79 (m, 1H).

4-((1r,4r)-4-(3-(5-methylthiazol-2-yl)-1H-pyrrolo[2,3-b]pyridin-5-yl)cyclohexyl)morpholine (I-62)

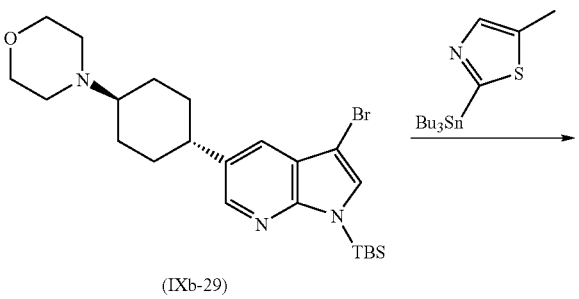

(IIb-62)

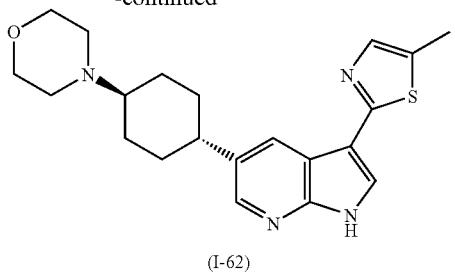

(I-62)

Iodide (IXb-29) and 5-methyl-2-tributylstannyl thiazole were reacted using the general procedure B for the Stille reaction (yield 9%) followed by deprotection according to the general procedure B for the deprotection of 7-azaindoles (yield 75%). $^1$H NMR (400 MHz, CDCl$_3$) δ 1.40-1.52 (m, 2H), 1.61-1.74 (m, 2H), 2.05-2.17 (m, 4H), 2.36-2.43 (m, 1H), 2.54 (d, J=1.1 Hz, 3H), 2.61-2.75 (m, 5H), 3.78 (t, J=4.6 Hz, 4H), 7.49 (q, J=1.1 Hz, 1H), 7.80 (d, J=2.8 Hz, 1H), 8.28 (d, J=2.0 Hz, 1H), 8.39 (d, J=2.0 Hz, 1H), 8.79 (br s, 1H).

4-((1r,4r)-4-(3-(2-ethoxythiazol-4-yl)-1H-pyrrolo[2,3-b]pyridin-5-yl)cyclohexyl)morpholine (I-63)

5H), 3.76-3.84 (m, 4H), 4.58 (q, J=7.1 Hz, 2H), 6.75 (s, 1H), 8.15 (d, J=1.8 Hz, 1H), 8.25 (d, J=1.8 Hz, 1H), 9.36 (br s, 1H).

4-((1r,4r)-4-(3-(4,5-dimethylthiazol-2-yl)-1H-pyrrolo[2,3-b]pyridin-5-yl)cyclohexyl)morpholine (I-64)

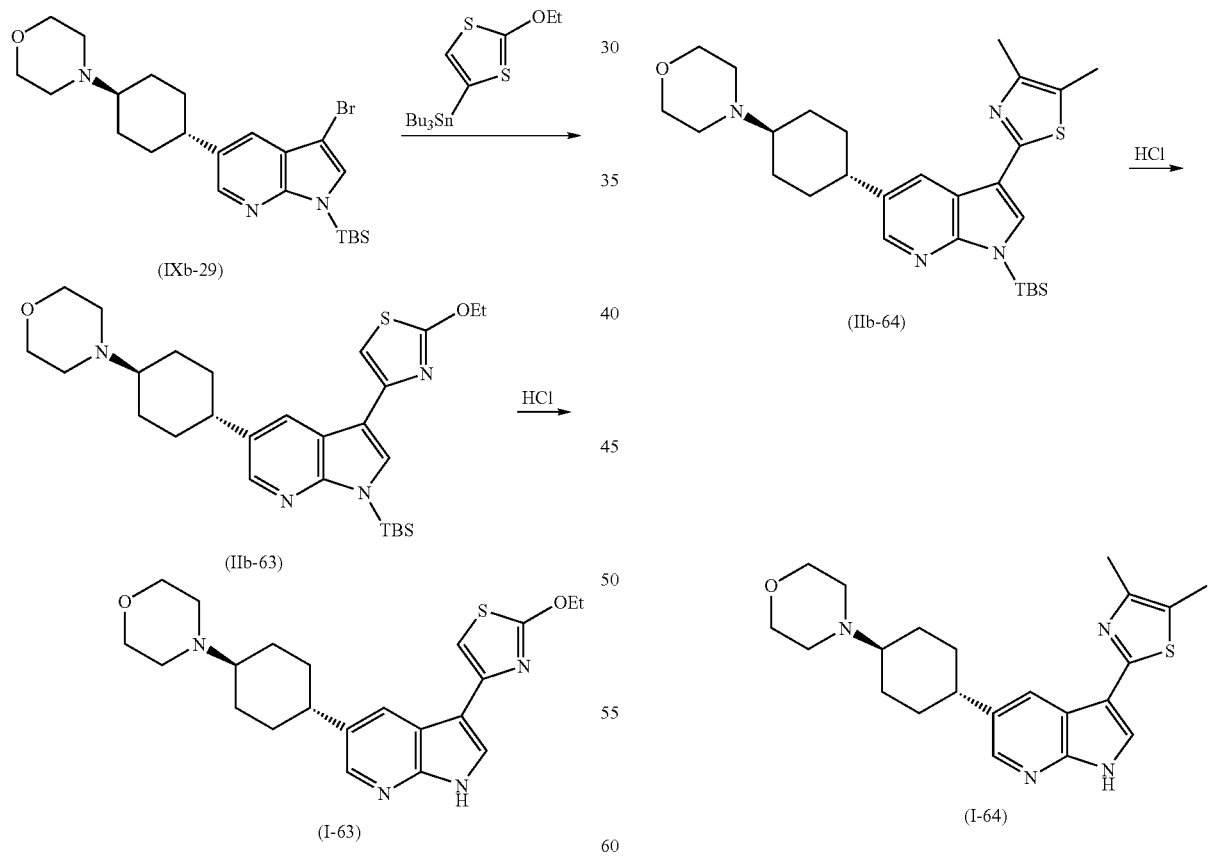

Iodide (IXb-29) and 2-ethoxy-4-tributylstannyl thiazole were reacted using the general procedure B for the Stille reaction (yield 80%) followed by deprotection according to the general procedure B for the deprotection of 7-azaindoles (yield 85%). $^1$H NMR (400 MHz, CDCl$_3$) δ 1.42-1.74 (m, 7H), 2.07-2.20 (m, 4H), 2.33-2.44 (m, 1H), 2.59-2.74 (m, Iodide (IXb-29) and 4,5-dimethyl-2-tributylstannyl thiazole were reacted using the general procedure B for the Stille reaction (yield 43%) followed by deprotection according to the general procedure B for the deprotection of 7-azaindoles (yield 50%). $^1$H NMR (400 MHz, CDCl$_3$) δ 1.41-1.55 (m, 2H), 1.60-1.74 (m, 2H), 2.06-2.19 (m, 4H), 2.35-2.47 (m, 7H), 2.61-2.77 (m, 5H), 3.75-3.85 (m, 4H), 7.85 (s, 1H), 8.28 (s, 1H), 8.34 (s, 1H), 9.49 (br s, 1H).

4-((1r,4r)-4-(3-(4-(trifluoromethyl)thiazol-2-yl)-1H-pyrrolo[2,3-b]pyridin-5-yl)cyclohexyl)morpholine (I-69)

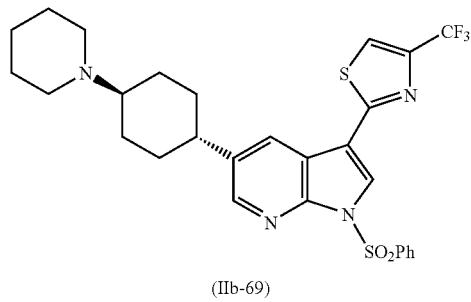

(IIb-69)

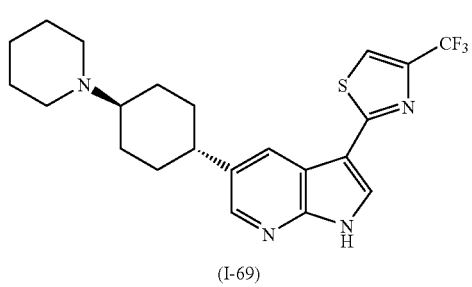

(I-69)

Compound (IIb-69) (78 mg, 0.14 mmol) in EtOH (3 mL) and 10% aqueous NaOH (1.5 mL), was deprotected as described in the general procedure A for the deprotection of 7-azaindoles by refluxing for 90 min. The crude product was purified by trituration with Et$_2$O (2 mL) to afford (I-69) (37 mg, 0.08 mmol, 63%) as a white powder. $^1$H NMR (400 MHz, CDCl$_3$) δ 1.43-1.75 (m, 4H), 2.08-2.21 (m, 4H), 2.37-2.48 (m, 1H), 2.64-2.80 (m, 5H), 3.79 (t, J=4.5 Hz, 4H), 7.67 (s, 1H), 8.00 (d, J=2.6 Hz, 1H), 8.33 (d, J=1.9 Hz, 1H), 8.40 (d, J=1.9 Hz, 1H), 9.87 (br s, 1H).

4-((1s,4s)-4-(3-(4-(trifluoromethyl)thiazol-2-yl)-1H-pyrrolo[2,3-b]pyridin-5-yl)cyclohexyl)morpholine (I-70)

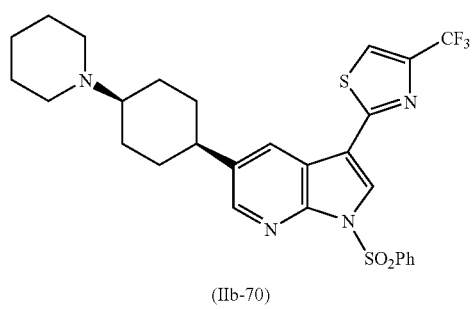

(IIb-70)

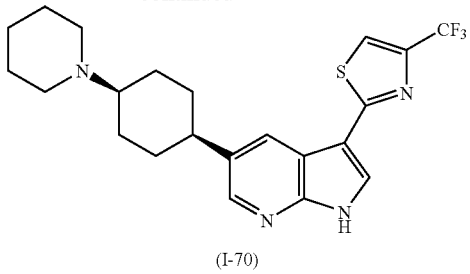

(I-70)

Compound (IIb-70) (58 mg, 0.14 mmol) in EtOH (3 mL) and 10% aqueous NaOH (1.5 mL), was deprotected as described in the general procedure A for the deprotection of 7-azaindoles by refluxing for 90 min. The crude product was purified by trituration with Et$_2$O (2 mL) to afford (I-70) (30 mg, 0.07 mmol, 68%) as a white powder. $^1$H NMR (400 MHz, CDCl$_3$) δ 1.55-1.77 (m, 4H), 2.00-2.15 (m, 4H), 2.29-2.35 (m, 1H), 2.47-2.61 (m, 4H), 2.85-2.95 (m, 1H), 3.81 (t, J=4.5 Hz, 4H), 7.66 (s, 1H), 7.96-8.00 (m, 1H), 8.36 (d, J=1.9 Hz, 1H), 8.52 (d, J=1.9 Hz, 1H), 10.20 (br s, 1H).

2-methyl-4-(5-((1r,4r)-4-(pyrrolidin-1-yl)cyclohexyl)-1H-pyrrolo[2,3-b]pyridin-3-yl)thiazole (I-74)

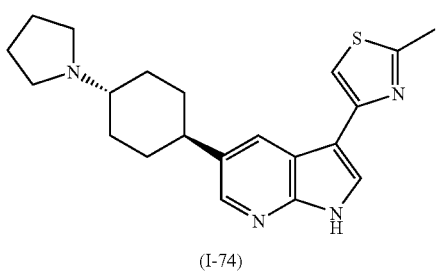

(IIb-74)

(I-74)

Compound (IIb-74) (177 mg, 0.35 mmol) in EtOH (4 mL) and 10% aqueous NaOH (2 mL), was deprotected as described in the general procedure A for the deprotection of 7-azaindoles by refluxing for 90 min. The crude product (109 mg) was purified by trituration with Et$_2$O (5 mL) to afford (I-74) (81 mg, 0.22 mmol, 63%) as a pale yellow powder. $^1$H NMR (400 MHz, CDCl$_3$) δ 1.46-1.59 (m, 2H), 1.61-1.74 (m, 2H), 1.82-1.90 (m, 4H), 2.02-2.10 (m, 2H), 2.14-2.27 (m, 3H), 2.65-2.78 (m, 5H), 2.83 (s, 3H), 7.23 (s, 1H), 7.84 (d, J=2.5 Hz, 1H), 8.17 (d, J=2.0 Hz, 1H), 8.28 (d, J=2.0 Hz, 1H), 9.46 (br s, 1H).

4-((1r,4r)-4-(3-(2-methylthiazol-4-yl)-1H-pyrrolo[2,3-b]pyridin-5-yl)cyclohexyl)-1,4-oxazepane (I-75)

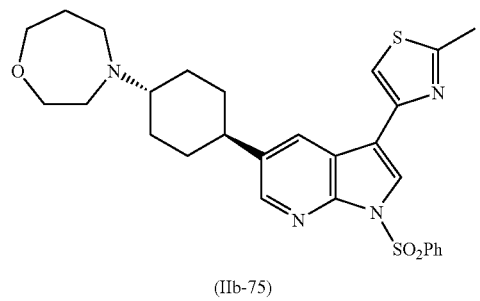

(IIb-75)

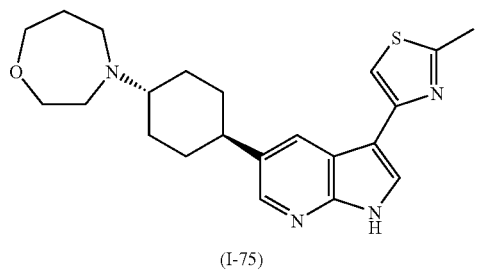

(I-75)

Compound (IIb-75) (343 mg, 0.64 mmol) in EtOH (4 mL) and 10% aqueous NaOH (2 mL), was deprotected as described in the general procedure A for the deprotection of 7-azaindoles by refluxing for 90 min. The crude product (187 mg) was purified by trituration with Et$_2$O (5 mL) to afford (I-75) (149 mg, 0.37 mmol, 59%) as a pale yellow powder. $^1$H NMR (400 MHz, CDCl$_3$) δ 1.46-1.67 (m, 4H), 1.91 (pentet, J=6.8 Hz, 2H), 1.99-2.14 (m, 4H), 2.63-2.76 (m, 1H), 2.83 (s, 3H), 2.84-2.91 (m, 4H), 3.75-3.80 (m, 2H), 3.85 (t, J=5.9 Hz, 2H), 7.22 (s, 1H), 7.82 (d, J=2.5 Hz, 1H), 8.16 (d, J=1.9 Hz, 1H), 8.26 (d, J=1.9 Hz, 1H), 9.14 (br s, 1H).

4-((1s,4s)-4-(3-(2-methylthiazol-4-yl)-1H-pyrrolo[2,3-b]pyridin-5-yl)cyclohexyl)-1,4-oxazepane (I-76)

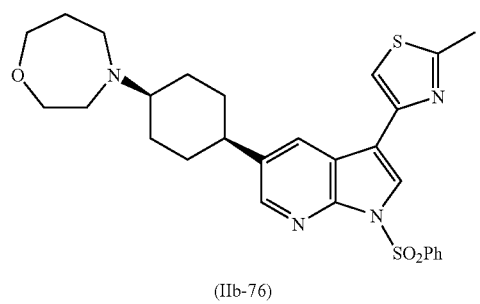

(IIb-76)

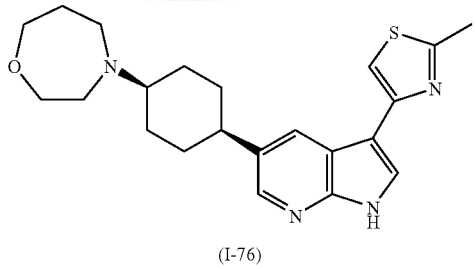

(I-76)

Compound (IIb-76) (223 mg, 0.42 mmol) in EtOH (4 mL) and 10% aqueous NaOH (2 mL), was deprotected as described in the general procedure A for the deprotection of 7-azaindoles by refluxing for 90 min. The crude product (125 mg) was purified by trituration with Et$_2$O (5 mL) to afford (I-76) (93 mg, 0.23 mmol, 56%) as a pale yellow powder. $^1$H NMR (400 MHz, CDCl$_3$) δ 1.59-1.71 (m, 2H), 1.71-1.81 (m, 2H), 1.89 (pentet, J=5.8 Hz, 2H), 1.93-2.04 (m, 2H), 2.06-2.18 (m, 2H), 2.83 (s, 3H), 2.84-2.99 (m, 6H), 3.79 (t, J=5.0 Hz, 2H), 3.84 (t, J=5.8 Hz, 2H), 7.22 (s, 1H), 7.82 (d, J=2.6 Hz, 1H), 8.25 (d, J=1.9 Hz, 1H), 8.33 (d, J=1.9 Hz, 1H), 9.03 (br s, 1H).

4-((1r,4r)-4-(3-(4-(1-methylpiperidin-4-yl)thiazol-2-yl)-1H-pyrrolo[2,3-b]pyridin-5-yl)cyclohexyl)morpholine (I-78)

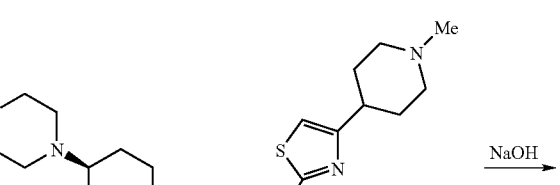

(IIb-78)

(I-78)

Compound (IIb-78) (276 mg, ~80% pure, 0.36 mmol) in EtOH (3 mL) and 10% aqueous NaOH (1.5 mL), was deprotected as described in the general procedure A for the deprotection of 7-azaindoles by refluxing for 90 min. The crude product (97 mg) was purified by LCMS (column LUNA 10μ C18(2) 00G-4253-V0 250×50 mm) using water-acetonitrile (0.1% AcOH) as eluent (in gradient; flow 80 mL/min) to afford (I-78) (46 mg, 0.10 mmol, 27%) as a white powder. $^1$H NMR (400 MHz, CDCl$_3$) δ 1.49-1.73 (m, 4H), 2.10-2.24 (m, 6H), 2.30-2.39 (m, 2H), 2.52-2.62 (m, 1H), 2.65-2.81 (m, 10H), 3.00-3.09 (m, 1H), 3.42-3.52 (m, 2H), 3.83 (t, J=4.6 Hz, 4H), 6.88 (s, 1H), 7.89 (s, 1H), 8.21 (d, J=1.9 Hz, 1H), 8.39 (d, J=1.9 Hz, 1H), 10.78 (br s, 1H).

4-((1s,4s)-4-(3-(4-(1-methylpiperidin-4-yl)thiazol-2-yl)-1H-pyrrolo[2,3-b]pyridin-5-yl)cyclohexyl)morpholine (I-79)

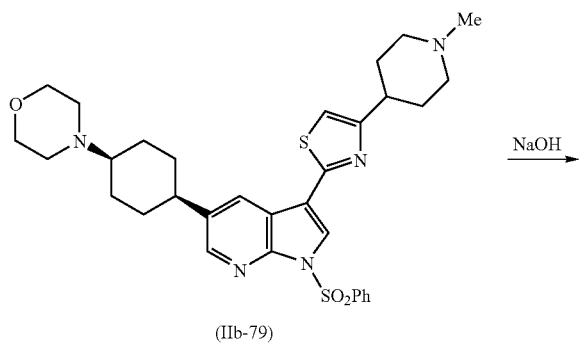

Compound (IIb-79) (149 mg, ~80% pure, 0.20 mmol) in EtOH (3 mL) and 10% aqueous NaOH (1.5 mL), was deprotected as described in the general procedure A for the deprotection of 7-azaindoles by refluxing for 90 min. The crude product (96 mg) was purified by trituration with Et$_2$O (2 mL) to afford (I-79) (45 mg, 0.07 mmol, 49%) as a white powder. $^1$H NMR (400 MHz, CDCl$_3$) δ 1.56-1.76 (m, 4H), 1.86-2.00 (m, 2H), 2.02-2.26 (m, 8H), 2.29-2.35 (m, 1H), 2.38 (s, 3H), 2.49-2.59 (m, 4H), 2.81-2.95 (m, 2H), 3.00-3.09 (m, 2H), 3.80 (t, J=4.6 Hz, 4H), 6.83 (s, 1H), 7.89 (s, 1H), 8.34 (d, J=1.9 Hz, 1H), 8.47 (d, J=1.9 Hz, 1H), 9.54 (br s, 1H).

4-((1r,4r)-4-(3-(4-(trifluoromethyl)thiazol-2-yl)-1H-pyrrolo[2,3-b]pyridin-5-yl)cyclohexyl)-1,4-oxazepane (I-80)

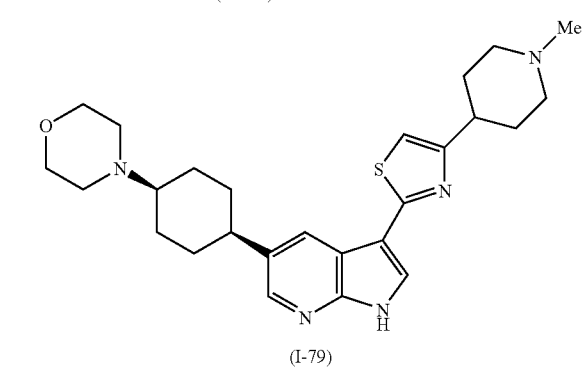

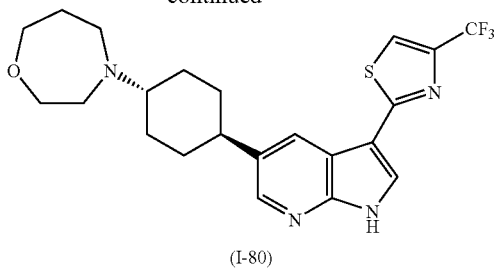

Compound (IIb-80) (97 mg, 0.16 mmol) in EtOH (2 mL) and 10% aqueous NaOH (1 mL), was deprotected as described in the general procedure A for the deprotection of 7-azaindoles by refluxing for 90 min. The crude product (69 mg) was purified by trituration with Et$_2$O (2 mL) to afford (I-80) (48 mg, 0.11 mmol, 64%) as a pale yellow powder. $^1$H NMR (400 MHz, CDCl$_3$) δ 1.56-1.75 (m, 4H), 1.87-1.99 (m, 2H), 2.02-2.15 (m, 4H), 2.67-2.78 (m, 2H), 2.83-2.97 (m, 4H), 3.76-3.83 (m, 2H), 3.85 (t, J=5.9 Hz, 2H), 7.67 (q, J=0.9 Hz, 1H), 7.97 (s, 1H), 8.32 (d, J=2.0 Hz, 1H), 8.38 (d, J=2.0 Hz, 1H), 9.19 (br s, 1H).

4-((1s,4s)-4-(3-(4-(trifluoromethyl)thiazol-2-yl)-1H-pyrrolo[2,3-b]pyridin-5-yl)cyclohexyl)-1,4-oxazepane (I-81)

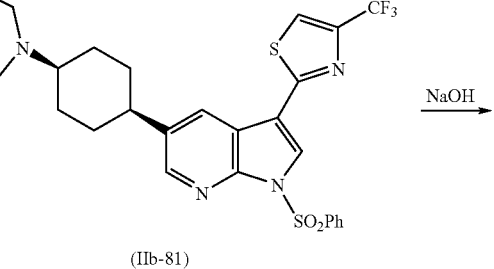

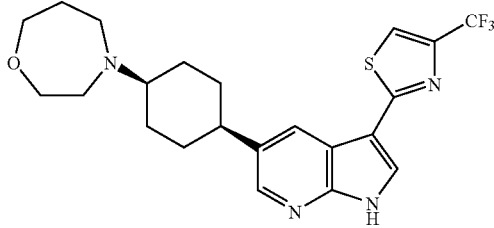

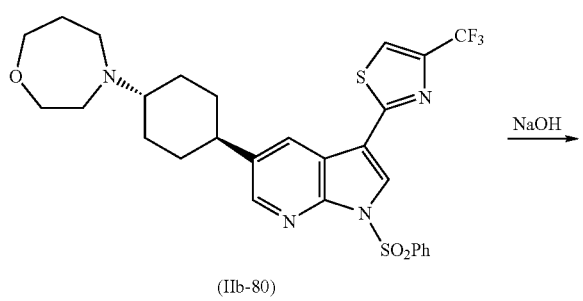

Compound (IIb-81) (74 mg, 0.13 mmol) in EtOH (2 mL) and 10% aqueous NaOH (1 mL), was deprotected as described in the general procedure A for the deprotection of 7-azaindoles by refluxing for 90 min. The crude product (55 mg) was purified by trituration with Et$_2$O (2 mL) to afford (I-81) (35 mg, 0.08 mmol, 62%) as a pale yellow powder. $^1$H NMR (400 MHz, CDCl$_3$) δ 1.61-1.73 (m, 2H), 1.73-1.83 (m, 2H), 1.90 (pentet, J=5.8 Hz, 2H), 1.95-2.06 (m, 2H), 2.08-2.20 (m, 2H), 2.81-3.02 (m, 6H), 3.80 (t, J=4.9 Hz, 2H), 3.84

(t, J=5.8 Hz, 2H), 7.66 (s, 1H), 8.02 (s, 1H), 8.39 (d, J=2.0 Hz, 1H), 8.53 (d, J=2.0 Hz, 1H), 10.27 (br s, 1H).

2-(5-((1r,4r)-4-(4-methylpiperazin-1-yl)cyclohexyl)-1H-pyrrolo[2,3-b]pyridin-3-yl)-4-(trifluoromethyl)thiazole (I-82)

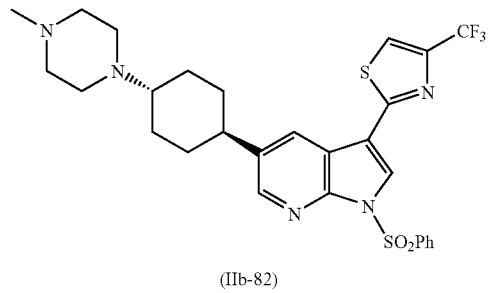

(IIb-82)

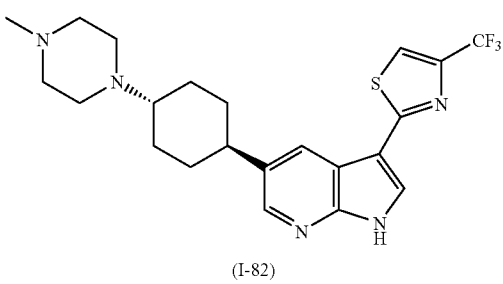

(I-82)

Compound (IIb-82) (93 mg, 0.16 mmol) in EtOH (2 mL) and 10% aqueous NaOH (1 mL), was deprotected as described in the general procedure A for the deprotection of 7-azaindoles by refluxing for 90 min. The crude product (43 mg) was purified by trituration with Et$_2$O (2 mL) to afford (I-82) (34 mg, 0.08 mmol, 48%) as a pale yellow powder. $^1$H NMR (400 MHz, CDCl$_3$) δ 1.45-1.58 (m, 2H), 1.60-1.75 (m, 2H), 2.05-2.18 (m, 4H), 2.34 (s, 3H), 2.40-2.78 (m, 10H), 7.66 (q, J=0.8 Hz, 1H), 8.02 (s, 1H), 8.33 (d, J=2.0 Hz, 1H), 8.40 (d, J=2.0 Hz, 1H), 10.31 (br s, 1H).

2-(5-((1s,4s)-4-(4-methylpiperazin-1-yl)cyclohexyl)-1H-pyrrolo[2,3-b]pyridin-3-yl)-4-(trifluoromethyl)thiazole (I-83)

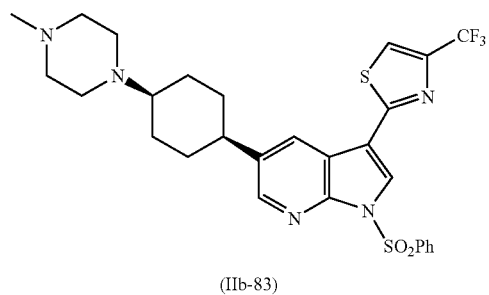

(IIb-83)

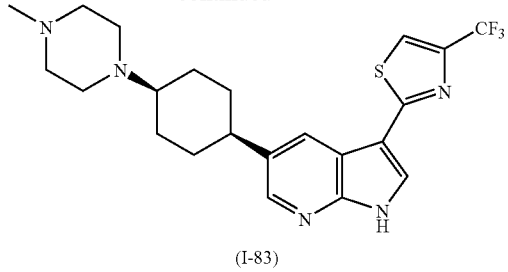

(I-83)

Compound (IIb-83) (40 mg, 0.068 mmol) in EtOH (2 mL) and 10% aqueous NaOH (1 mL), was deprotected as described in the general procedure A for the deprotection of 7-azaindoles by refluxing for 90 min. The crude product (30 mg) was purified by trituration with hexane (2 mL) to afford (I-83) (28 mg, 0.06 mmol, 92%) as a pale yellow powder. $^1$H NMR (400 MHz, CDCl$_3$) δ 1.52-1.82 (m, 7H), 2.03-2.14 (m, 4H), 2.34 (s, 3H), (m, 4H), 2.40-2.77 (m, 5H), 2.87-2.96 (m, 1H), 7.66 (q, J=0.9 Hz, 1H), 7.99 (s, 1H), 8.37 (d, J=2.0 Hz, 1H), 8.52 (d, J=2.0 Hz, 1H), 9.89 (br s, 1H).

2-(5-((1r,4r)-4-(pyrrolidin-1-yl)cyclohexyl)-1H-pyrrolo[2,3-b]pyridin-3-yl)-4-(trifluoromethyl)thiazole (I-84)

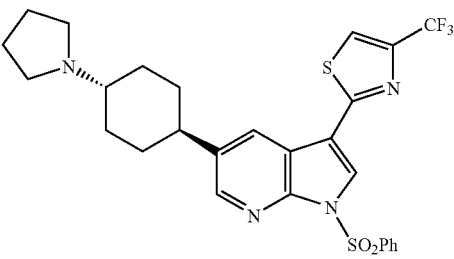

(IIb-84)

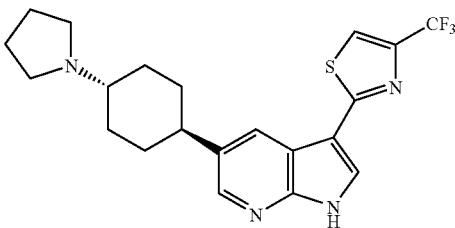

(I-84)

Compound (IIb-84) (23 mg, 0.04 mmol) in EtOH (2 mL) and 10% aqueous NaOH (1 mL), was deprotected as described in the general procedure A for the deprotection of 7-azaindoles by refluxing for 90 min. The crude product (20 mg) was purified by LCMS (column LUNA 10μ C18(2) 00G-4253-V0 250×50 mm) using water-acetonitrile (0.1% AcOH) as eluent (in gradient; flow 80 mL/min) to afford (I-84) (12 mg, 0.03 mmol, 71%) as a white powder. $^1$H NMR (400 MHz, CDCl$_3$) δ 1.59-1.82 (m, 4H), 1.94-2.00 (m, 4H), 2.04-2.12 (m, 2H), 2.21-2.28 (m, 2H), 2.57-2.68 (m, 1H), 2.73-2.83 (m, 1H), 2.98-3.06 (m, 4H), 7.65 (q, J=0.9 Hz, 1H), 8.02 (s, 1H), 8.28 (d, J=1.9 Hz, 1H), 8.40 (d, J=1.9 Hz, 1H), 11.64 (br s, 1H).

2-(5-((1s,4s)-4-(pyrrolidin-1-yl)cyclohexyl)-1H-pyrrolo[2,3-b]pyridin-3-yl)-4-(trifluoromethyl)thiazole (I-85)

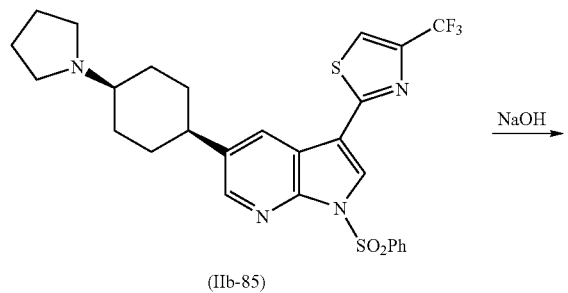

Compound (IIb-85) (54 mg, 0.10 mmol) in EtOH (2 mL) and 10% aqueous NaOH (1 mL), was deprotected as described in the general procedure A for the deprotection of 7-azaindoles by refluxing for 90 min. The crude product (55 mg) was purified by LCMS (column LUNA 10μ C18(2) 00G-4253-V0 250 ×50 mm) using water-acetonitrile (0.1% AcOH) as eluent (in gradient; flow 80 mL/min) to afford (I-85) (22 mg, 0.05 mmol, 54%) as a white powder. $^1$H NMR (400 MHz, CDCl$_3$) δ 1.60-1.73 (m, 4H), 1.75-1.84 (m, 4H), 1.91-2.01 (m, 2H), 2.06-2.18 (m, 2H), 2.38-2.44 (m, 1H), 2.63-2.73 (m, 4H), 2.82 (tt, J=3.9, 10.2 Hz, 1H), 7.55 (q, J=0.8 Hz, 1H), 7.93 (s, 1H), 8.31 (d, J=1.9 Hz, 1H), 8.39 (d, J=1.9 Hz, 1H), 11.44 (br s, 1H).

4-((1r,4r)-4-(3-(thiazol-2-yl)-1H-pyrrolo[2,3-b]pyridin-5-yl)cyclohexyl)morpholine (I-89)

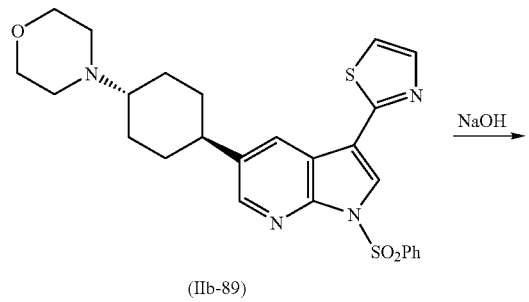

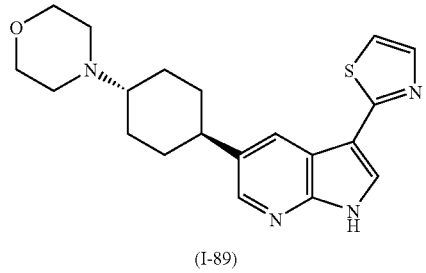

Compound (IIb-89) (44 mg, 0.09 mmol) in EtOH (2 mL) and 10% aqueous NaOH (1 mL), was deprotected as described in the general procedure A for the deprotection of 7-azaindoles by refluxing for 90 min. The crude product (I-89) (28 mg, 0.07 mmol, 86%), pale yellow powder, did not require further purification. $^1$H NMR (400 MHz, CDCl$_3$) δ 1.42-1.55 (m, 2H), 1.64-1.77 (m, 2H), 2.06-2.19 (m, 4H), 2.36-2.47 (m, 1H), 2.62-2.79 (m, 5H), 3.79 (t, J=4.5 Hz, 2H), 7.26 (d, J=3.3 Hz, 1H), 7.87 (d J=3.3 Hz, 1H), 7.94 (s, 1H), 8.31 (br s, 1H), 8.47 (br s, 1H), 10.03 (br s, 1H).

4-((1s,4s)-4-(3-(thiazol-2-yl)-1H-pyrrolo[2,3-b]pyridin-5-yl)cyclohexyl)morpholine (I-90)

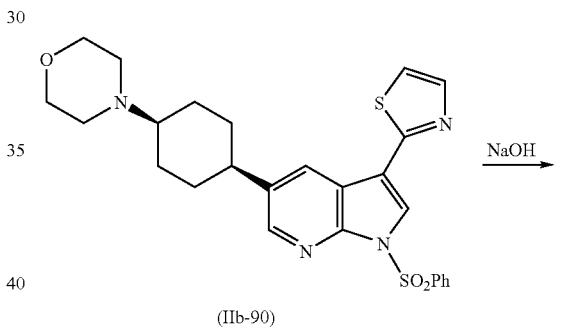

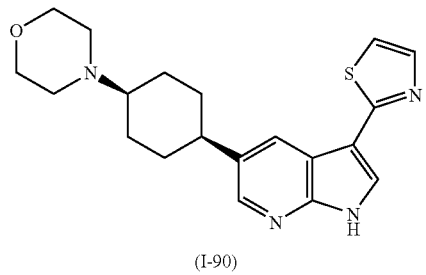

Compound (IIb-90) (86 mg, 0.17 mmol) in EtOH (2 mL) and 10% aqueous NaOH (1 mL), was deprotected as described in the general procedure A for the deprotection of 7-azaindoles by refluxing for 90 min. The crude product (I-90) (58 mg, 0.16 mmol, 94%), a pale yellow powder, did not require further purification. $^1$H NMR (400 MHz, CDCl$_3$) δ 1.56-1.67 (m, 2H), 1.69-1.78 (m, 2H), 2.03-2.16 (m, 4H), 2.29-2.35 (m, 1H), 2.49-2.59 (m, 4H), 2.87-2.96 (m, 1H), 3.81 (t, J=4.6 Hz, 2H), 7.28 (d, J=3.3 Hz, 1H), 7.88 (d. J=3.3 Hz, 1H), 7.97 (s, 1H), 8.37 (br s, 1H), 8.51 (br s, 1H), 10.36 (br s, 1H).

2-methyl-4-(5-((1r,4r)-4-(4-methylpiperazin-1-yl)cyclohexyl)-1H-pyrrolo[2,3-b]pyridin-3-yl)thiazole (I-91)

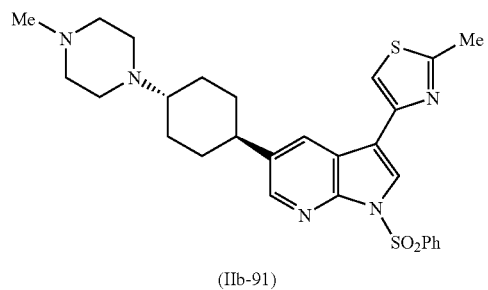

Compound (IIb-91) (192 mg, 0.36 mmol) in EtOH (2 mL) and 10% aqueous NaOH (1 mL), was deprotected as described in the general procedure A for the deprotection of 7-azaindoles by refluxing for 1 h. The crude product (I-91) (130 mg, 92%), a white solid, did not require further purification. $^1$H NMR (400 MHz, CDCl$_3$+few drops of CD$_3$OD). δ 1.38-1.50 (q, J=12.4 Hz, 2H), 1.54-1.66 (q, J=11.6 Hz, 2H), 2.06 (d, J=14.8 Hz, 4H), 2.29 (s, 3H), 2.36-2.75 (m, 10H), 2.77 (s, 3H), 7.17 (s, 1H), 7.78 (s, 1H), 8.11, (s, 1H), 8.12 (s, 1H).

2-methyl-4-(5-((1s,4s)-4-(4-methylpiperazin-1-yl)cyclohexyl)-1H-pyrrolo[2,3-b]pyridin-3-yl)thiazole (I-92)

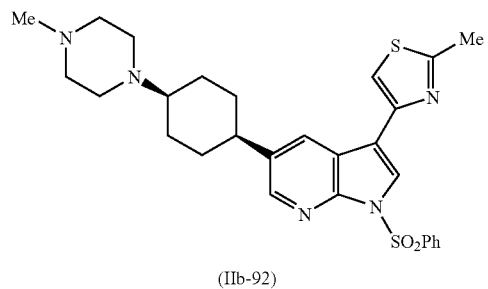

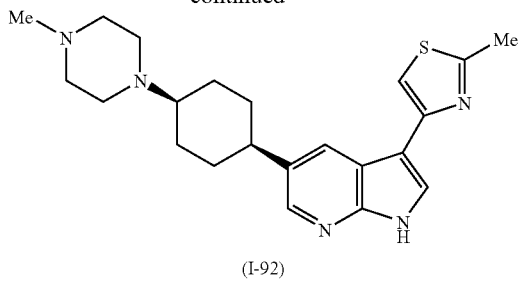

Compound (IIb-92) (178 mg, 0.33 mmol) in EtOH (2 mL) and 10% aqueous NaOH (0.6 mL), was deprotected as described in the general procedure A for the deprotection of 7-azaindoles by refluxing for 1 h. The crude product (I-92) (111 mg, 84%), a white solid, did not require further purification. $^1$H NMR (400 MHz, CDCl$_3$+few drops of CD$_3$OD) δ 1.54-1.73 (m, 4H), 1.92-2.07 (m, 4H), 2.31 (s, 3H), 2.44-2.71 (m, 5H), 2.76 (s, 3H), 2.80-2.89 (m, 1H), 2.94-3.02 (m, 4H), 7.19 (s, 1H), 7.78 (s, 1H), 8.18, (d, J=1.9 Hz, 1H), 8.19 (d, J=1.9 Hz, 1H).

4-((1r,4r)-4-(3-(2-(1-methylpiperidin-4-yl)thiazol-4-yl)-1H-pyrrolo[2,3-b]pyridin-5-yl)cyclohexyl)morpholine (I-94)

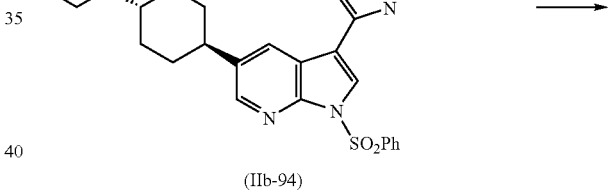

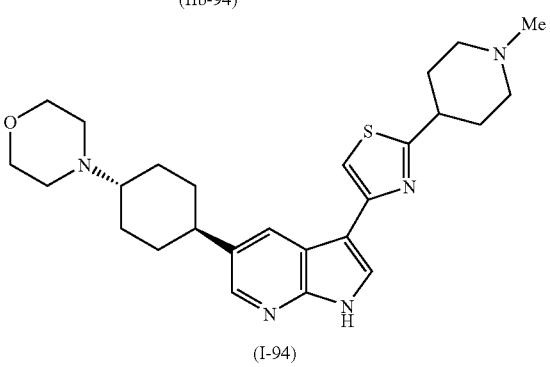

Compound (IIb-94) (48 mg, 0.079 mmol) in EtOH (2 mL) and 10% aqueous NaOH (0.6 mL), was deprotected as described in the general procedure A for the deprotection of 7-azaindoles by refluxing for 20 min. The crude product was purified by PTLC using CHCl$_3$:MeOH:NH$_4$OH=83:15:2 (v/v/v) as the eluent to give (I-94) as a white solid (19 mg, 51%). $^1$H NMR (400 MHz, CDCl$_3$) δ 1.41-1.52 (dq, J=2.6, 12.2 Hz, 2H), 1.58-1.70 (dq, J=2.2, 12.6 Hz, 2H), 1.94-2.26 (m, 12H), 2.36 (s, 3H), 2.65 (t, J=4.5 Hz, 4H), 2.97-3.04 (m, 2H), 3.04-3.13 (tt, J=3.6, 11.4 Hz, 1H), 3.74 (t, J=4.6 Hz, 4H), 7.22 (s, 1H), 7.83 (s, 1H), 8.18 (d, J=1.9 Hz, 1H). 8.25 (d, J=1.9 Hz, 1H), 10.32 (br s, NH, 1H).

4-(5-((1r,4r)-4-(4-methylpiperazin-1-yl)cyclohexyl)-1H-pyrrolo[2,3-b]pyridin-3-yl)-2-(1-methylpiperidin-4-yl)thiazole (I-96)

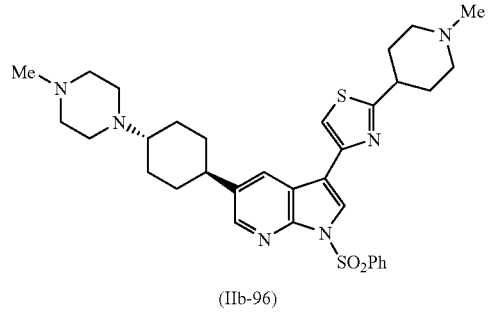
(IIb-96)

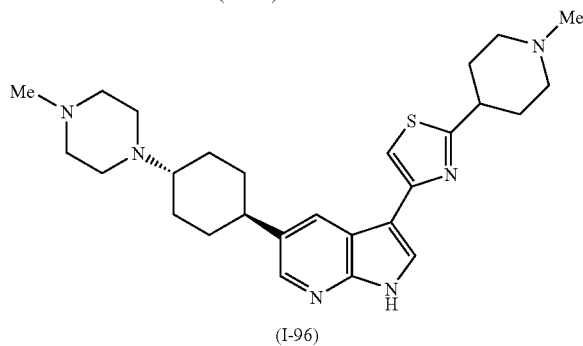
(I-96)

Compound (IIb-96) (44 mg, 0.071 mmol) in EtOH (2 mL) and 10% aqueous NaOH (0.57 mL), was deprotected as described in the general procedure A for the deprotection of 7-azaindoles by refluxing for 20 min. The crude product was purified by PTLC using CHCl₃:MeOH:NH₄OH=83:15:2 (v/v/v) as the eluent to give (I-96) (19.5 mg, 57%) as a white solid. ¹H NMR (400 MHz, CDCl₃) δ 1.43-1.55 (dq, J=2.1, 12.1 Hz, 2H), 1.57-1.70 (dq, J=1.9, 12.6 Hz, 2H), 1.91-2.25 (m, 12H), 2.32 (s, 3H), 2.35 (s, 3H), 2.39-2.48 (tt, J=3.3, 12.2 Hz, 1H), 2.46-2.59 (m, 3H), 2.61-2.76 (m, 4H), 2.95-3.03 (m, 2H), 3.04-3.12 (tt, J=3.8, 11.5 Hz, 1H), 7.23 (s, 1H), 7.83 (d, J=2.0 Hz, 1H), 8.17 (d, J=2.0 Hz, 1H). 8.24 (d, J=2.0 Hz, 1H), 10.33 (br s, NH, 1H).

2-(1-methylpiperidin-4-yl)-4-(5-((1r,4r)-4-(pyrrolidin-1-yl)cyclohexyl)-1H-pyrrolo[2,3-b]pyridin-3-yl)thiazole (I-98)

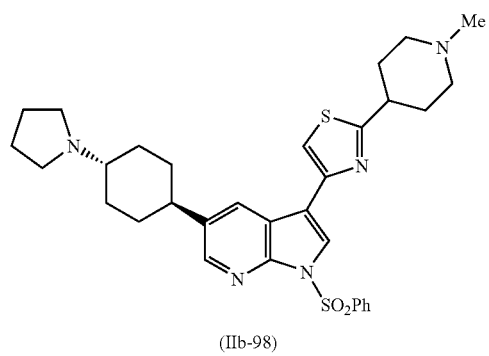
(IIb-98)

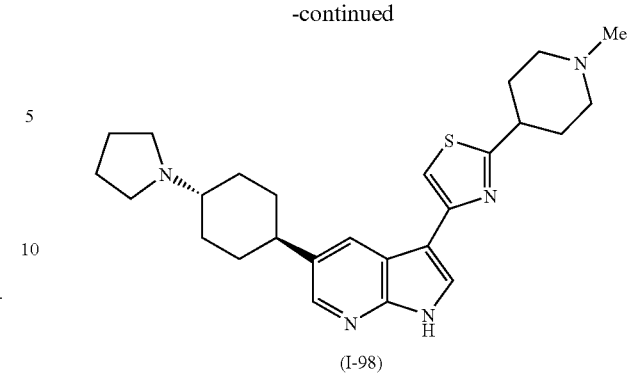
(I-98)

Compound (IIb-98) (57 mg, 0.097 mmol) in EtOH (2 mL) and 10% aqueous NaOH (0.39 mL), was deprotected as described in the general procedure A for the deprotection of 7-azaindoles by refluxing for 20 min. The crude product was purified by PTLC using CHCl₃:MeOH:NH₄OH=83:15:2 (v/v/v) as the eluent to give (I-98) (21 mg, 48%) as a white solid. ¹H NMR (400 MHz, CDCl₃) δ 1.45-1.57 (dq, J=2.0, 12.1 Hz, 2H), 1.59-1.71 (dq, J=2.2, 12.2 Hz, 2H), 1.79-1.87 (m, 4H), 1.91-2.08 (m, 4H), 2.10-2.24 (m, 7H), 2.35 (s, 3H), 2.65-2.75 (m, 5H), 2.95-3.02 (m, 2H), 3.04-3.12 (tt, J=3.8, 11.5 Hz, 1H), 7.23 (s, 1H), 7.84 (d, J=1.6 Hz, 1H), 8.17 (d, J=1.9 Hz, 1H). 8.26 (d, J=2.0 Hz, 1H), 10.65 (br s, NH, 1H).

4-(4-(3-(2-(1-methylpiperidin-4-yl)thiazol-4-yl)-1H-pyrrolo[2,3-b]pyridin-5-yl)cyclohex-3-enyl)morpholine (I-100)

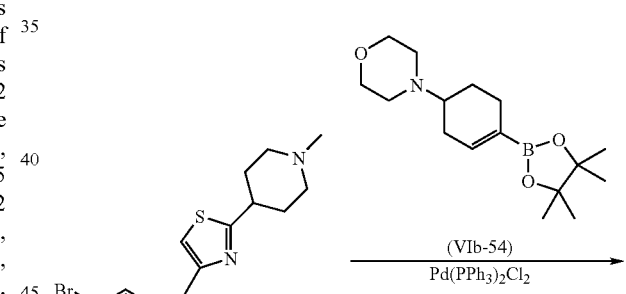
(III-h)

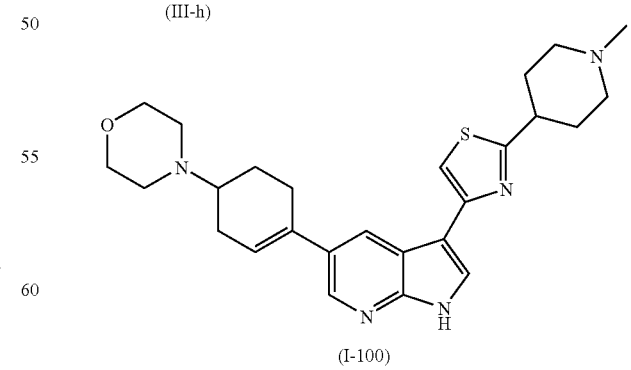
(I-100)

Bromide (III-h) (0.70 g, 1.35 mmol), boronate (VIb-54) (0.48 g, 1.62 mmol), lithium chloride (0.17 g, 4.06 mmol), and Pd(PPh₃)₂Cl₂ (0.095 g, 0.13 mmol), in EtOH (10 ml), toluene (10 ml) and 1.0 M Na$_2$CO$_3$ solution (4.05 ml) were reacted for 72 h under reflux using the general procedure A for the Suzuki reaction. Crude product was purified by SGC on amino asilica (Chromatorex NH, Fuji Silysia) using EtOAc:hexane (gradient from 50:50 to 100:0, v/v) then EtOAc:MeOH (gradient from 100:0 to 90:10, v/v) to afford (I-100) as pale red color solid (0.27 g, 43%). $^1$H NMR (400 MHz, CDCl$_3$) δ $^1$H NMR (400 MHz, CDCl$_3$) δ 1.59-1.71 (m, 1H), 1.91-2.03 (m, 2H), 2.09-2.30 (m, 6H), 2.35 (s, 3H), 2.43-2.52 (m, 1H), 2.58-2.74 (m, 7H), 2.94-3.12 (m, 3H), 3.78 (t, J=4.6 Hz, 4H), 6.06-6.10 (m, 1H), 7.23 (s, 1H), 7.85 (d, J=2.1 Hz, 1H), 8.31 (d, J=2.0 Hz, 1H), 8.42 (d, J=2.0 Hz, 1H), 11.27 (br s, NH, 1H).

4-(4-(3-(2-(1-methylpiperidin-4-yl)thiazol-4-yl)-1H-pyrrolo[2,3-b]pyridin-5-yl)cyclohex-3-enyl)-1,4-oxazepane (I-101)—see preparation of 4-(4-(3-(2-(1-methylpiperidin-4-yl)thiazol-4-yl)-1-(phenylsulfonyl)-1H-pyrrolo[2,3-b]pyridin-5-yl)cyclohex-3-enyl)-1,4-oxazepane (IIa-101)

4-((1r,4r)-4-(3-(2-(1-methylpiperidin-4-yl)thiazol-4-yl)-1H-pyrrolo[2,3-b]pyridin-5-yl)cyclohexyl)-1,4-oxazepane (I-102)

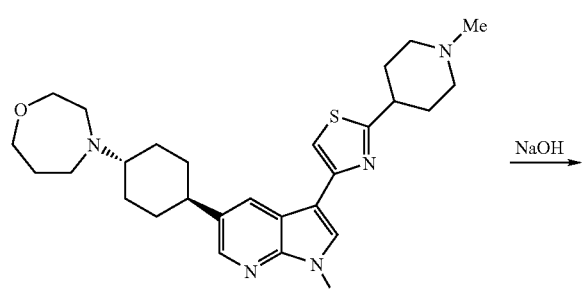
(IIb-102)

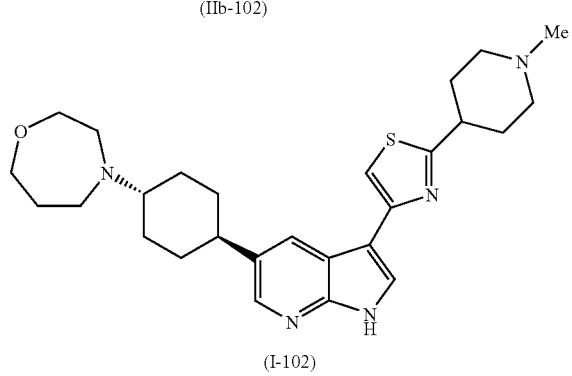
(I-102)

Compound (IIb-102) (20 mg, 0.032 mmol) in EtOH (1 mL) and 10% aqueous NaOH (0.13 mL), was deprotected as described in the general procedure A for the deprotection of 7-azaindoles by refluxing for 20 min. The crude product was purified by PTLC using CHCl$_3$:MeOH:NH$_4$OH=83:15:2 (v/v/v) as the eluent to give (I-102) (8 mg, 51%) as a white solid. $^1$H NMR (400 MHz, CDCl$_3$) δ 1.46-1.57 (q, J=11.1 Hz, 2H), 1.59-1.71 (q, J=12.3 Hz, 2H), 1.90-2.11 (m, 8H), 2.13-2.26 (m, 4H), 2.36 (s, 3H), 2.62-2.81 (m, 2H), 2.85-2.94 (m, 4H), 2.99-3.13 (m, 3H), 3.79 (t, J=4.2 Hz, 2H), 3.83 (t, J=5.9 Hz, 2H), 7.24 (s, 1H), 7.81 (d, J=1.9 Hz, 1H), 8.18. (d, J=1.7 Hz, 1H), 8.24 (d, J=1.9 Hz, 1H), 9.66 (br s, NH, 1H).

4-((1r,4r)-4-(3-(2-(1-methylpyrrolidin-2-yl)thiazol-4-yl)-1H-pyrrolo[2,3-b]pyridin-5-yl)cyclohexyl)morpholine (I-107)

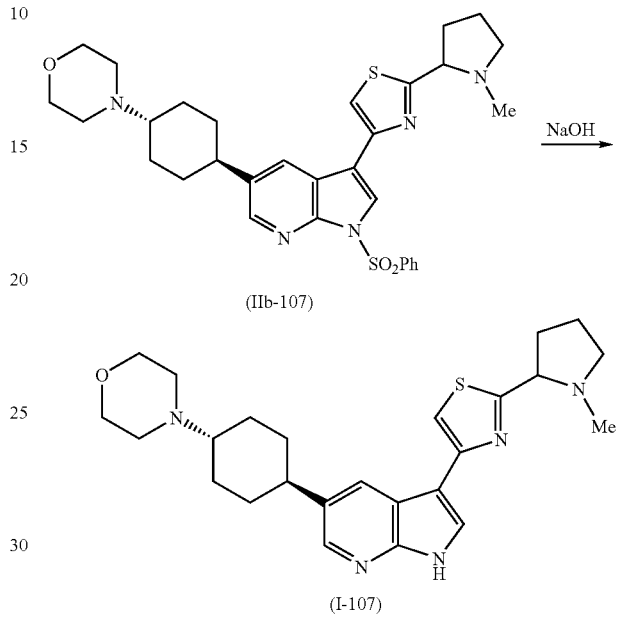

Compound (IIb-107) (53 mg, 0.09 mmol) in EtOH (1 mL) and 10% aqueous NaOH (0.36 mL), was deprotected as described in the general procedure A for the deprotection of 7-azaindoles by refluxing for 20 min. The crude product was purified by PTLC using CH$_2$Cl$_2$:MeOH=9:1 (v/v) as the eluent to give (I-107) (12 mg, 30%) as a white solid. $^1$H NMR (400 MHz, CDCl$_3$) δ 1.41-1.52 (dq, J=2.2, 12.2 Hz, 2H), 1.59-1.70 (dq, J=2.2, 12.2 Hz, 2H), 1.82-2.03 (m, 4H), 2.11 (t, J=4.5 Hz, 4H), 2.35-2.46 (m, 3H), 2.48 (s, 3H), 2.62-2.73 (m, 5H), 3.29 (tt, J=1.8, 8.1 Hz, 1H), 3.78 (t, J=4.4 Hz, 4H), 3.79-3.83 (dd, J=6.2, 8.9 Hz, 1H), 7.30 (s, 1H), 7.85 (d, J=2.4 Hz, 1H), 8.16 (d, J=1.8 Hz, 1H), 8.25 (d, J=1.9 Hz, 1H), 9.95 (br s, NH, 1H).

4-((1s,4s)-4-(3-(2-(1-methylpyrrolidin-2-yl)thiazol-4-yl)-1H-pyrrolo[2,3-b]pyridin-5-yl)cyclohexyl)morpholine (I-108)

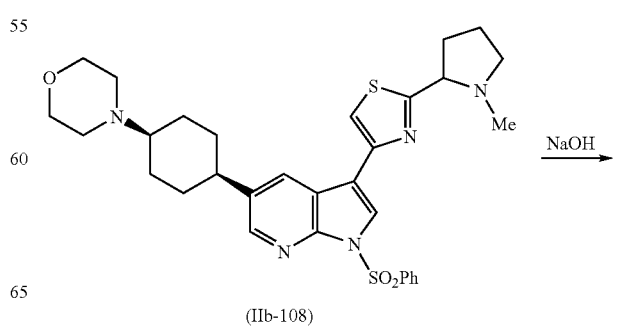
(IIb-108)

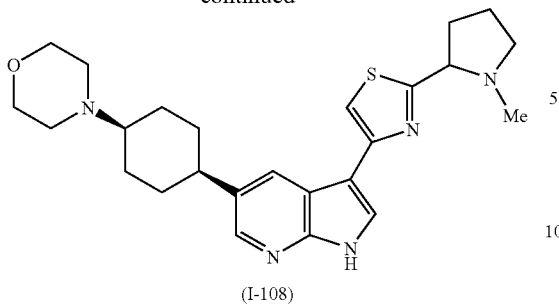

(I-108)

Compound (IIb-108) (33 mg, 56 µmol) in EtOH (1 mL) and 10% aqueous NaOH (0.36 mL), was deprotected as described in the general procedure A for the deprotection of 7-azaindoles by refluxing for 20 min. The crude product was purified by PTLC using CH$_2$Cl$_2$:MeOH=9:1 (v/v) as the eluent to give (I-108) (9.4 mg, 37%) as a white solid. $^1$H NMR (400 MHz, CDCl$_3$) δ 1.54-1.64 (m, 2H), 1.66-1.73 (m, 2H), 1.83-1.91 (m, 1H), 1.95-2.10 (m, 6H), 2.27-2.32 (m, 1H), 2.39-2.46 (m, 2H), 2.48 (s, 3H), 2.50-2.55 (br s, 4H), 2.82-2.91 (m, 1H), 3.26-3.32 (m, 1H), 3.78 (t, J=4.5 Hz, 4H), 3.80-3.84 (dd, J=6.4, 8.8 Hz, 1H), 7.30 (s, 1H), 7.83 (d, J=2.4 Hz, 1H), 8.24 (d, J=1.8 Hz, 1H), 8.29 (d, J=1.9 Hz, 1H), 9.72 (br s, NH, 1H).

4-(5-((1r,4r)-4-(4-methylpiperazin-1-yl)cyclohexyl)-1H-pyrrolo[2,3-b]pyridin-3-yl)-2-(1-methylpyrrolidin-2-yl)thiazole (I-109)

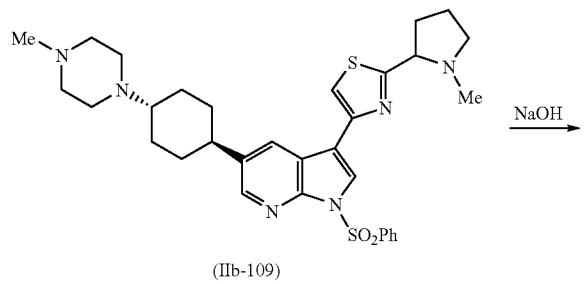

(IIb-109)

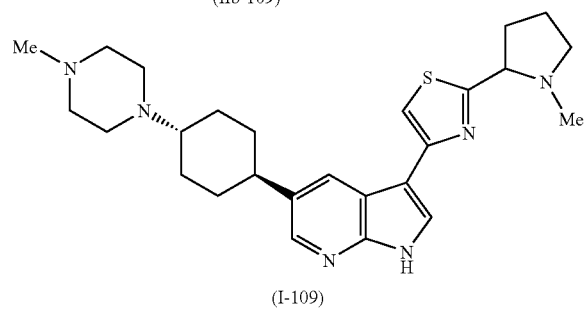

(I-109)

Compound (IIb-109) (31 mg, 51 µmol) in EtOH (2 mL) and 10% aqueous NaOH (0.51 mL), was deprotected as described in the general procedure A for the deprotection of 7-azaindoles by refluxing for 20 min. The crude product was purified by PTLC using CH$_2$Cl$_2$:MeOH=8:2 (v/v) as the eluent to give (I-109) (17 mg, 71%) as a white solid. $^1$H NMR (400 MHz, CDCl$_3$) δ 1.44-1.56 (q, J=11.2 Hz, 2H), 1.59-1.70 (q, J=12.6 Hz, 2H), 1.83-1.92 (m, 1H), 1.93-2.2.03 (m, 2H), 2.04-2.17 (m, 5H), 2.34 (s, 3H), 2.39-2.48 (m, 2H), 2.48 (s, 3H), 2.47-2.62 (br m, 5H), 3.29 (t, J=8.6 Hz, 1H), 3.79-3.84 (dd, J=6.2, 8.6 Hz, 1H), 7.30 (s, 1H), 7.83 (d, J=0.8 Hz, 1H), 8.15 (d, J=1.8 Hz, 1H), 8.23 (d, J=1.9 Hz, 1H), 9.70 (br s, NH, 1H).

4-(5-((1s,4s)-4-(4-methylpiperazin-1-yl)cyclohexyl)-1H-pyrrolo[2,3-b]pyridin-3-yl)-2-(1-methylpyrrolidin-2-yl)thiazole (I-110)

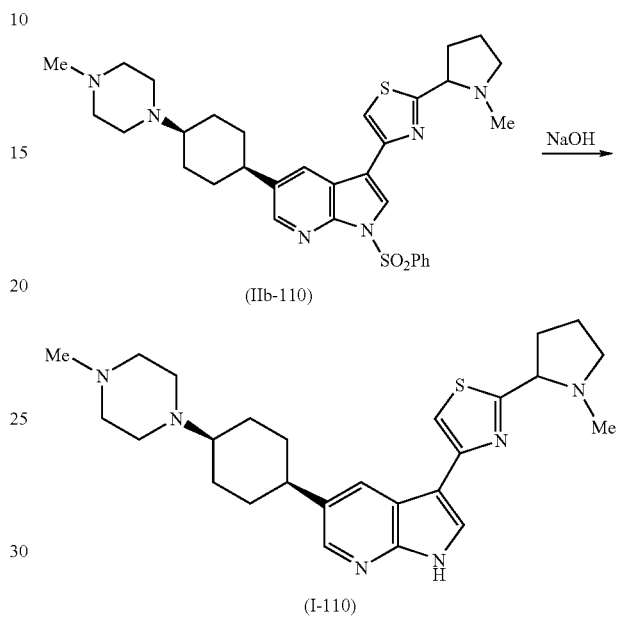

Compound (IIb-110) (23 mg, 38 µmol) in EtOH (2 mL) and 10% aqueous NaOH (0.15 mL), was deprotected as described in the general procedure A for the deprotection of 7-azaindoles by refluxing for 20 min. The crude product was purified by PTLC using CH$_2$Cl$_2$:MeOH=8:2 (v/v) as the eluent to give (I-110) (19.5 mg, 57%) as a white solid. $^1$H NMR (400 MHz, CDCl$_3$) δ 1.56-1.65 (m, 2H), 1.67-1.75 (m, 2H), 1.83-1.93 (m, 1H), 1.95-2.12 (m, 9H), 2.34 (s, 3H), 2.39-2.65 (br m, 8H), 2.48 (s, 3H), 2.83-2.92 (m, 1H), 3.29 (tt, J=1.6, 8.1 Hz, 1H), 3.79-3.84 (dd, J=6.2, 8.6 Hz, 1H), 7.31 (s, 1H), 7.83 (d, J=1.3 Hz, 1H), 8.23 (d, J=1.7 Hz, 1H), 8.29 (d, J=1.9 Hz, 1H), 9.70 (br s, NH, 1H).

2-(1-methylpyrrolidin-2-yl)-4-(5-((1r,4r)-4-(pyrrolidin-1-yl)cyclohexyl)-1H-pyrrolo[2,3-b]pyridin-3-yl)thiazole (I-111)

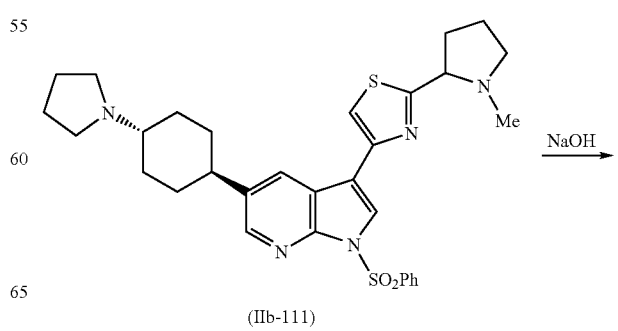

(IIb-111)

-continued

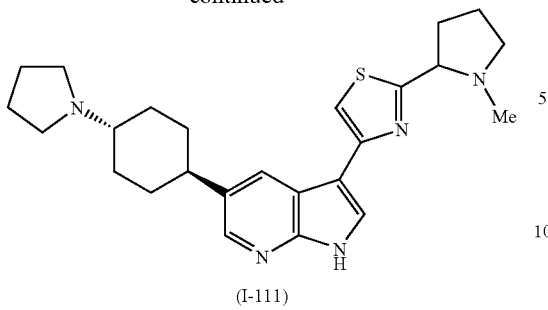
(I-111)

Compound (IIb-111) (23 mg, 40 μmol) in EtOH (1 mL) and 10% aqueous NaOH (0.16 mL), was deprotected as described in the general procedure A for the deprotection of 7-azaindoles by refluxing for 30 min. The crude product was purified by PTLC using CHCl$_3$:MeOH:NH$_4$OH=83:15:2 (v/v/v) as the eluent to give (I-111) (10 mg, 57%) as a white solid. $^1$H NMR (400 MHz, CDCl$_3$) δ 1.46-1.57 (q, J=12.0 Hz, 2H), 1.59-1.72 (q, J=12.8 Hz, 2H), 1.81-1.96 (m, 6H), 1.96-2.07 (m, 5H), 2.16-2.25 (m, 3H), 2.40-2.49 (m, 1H), 2.48 (s, 3H), 2.64-2.73 (m, 4H), 3.29 (t, J=8.0 Hz, 1H), 3.79-3.84 (dd, J=6.3, 8.7 Hz, 1H), 7.31 (s, 1H), 7.83 (d, J=2.1 Hz, 1H), 8.15 (d, J=1.7 Hz, 1H), 8.25 (d, J=1.6 Hz, 1H), 9.56 (br s, NH, 1H).

4-((1r,4r)-4-(3-(2-(1-methylpyrrolidin-2-yl)thiazol-4-yl)-1H-pyrrolo[2,3-b]pyridin-5-yl)cyclohexyl)-1,4-oxazepane (I-113)

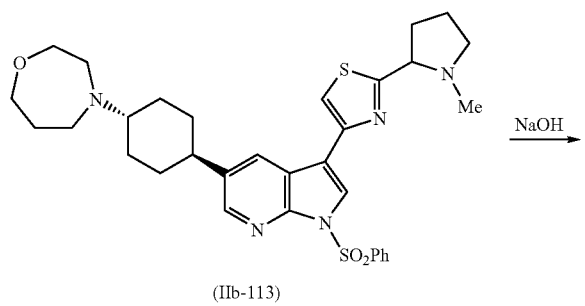

Compound (IIb-113) (46 mg, 76 μmol) in EtOH (1 mL) and 10% aqueous NaOH (0.30 mL), was deprotected as described in the general procedure A for the deprotection of 7-azaindoles by refluxing for 20 min. The crude product was purified by PTLC using CH$_2$Cl$_2$:MeOH=85:15 (v/v) as the eluent to give (I-113) (12 mg, 34%) as a white solid. $^1$H NMR (400 MHz, CDCl$_3$) δ 1.47-1.58 (q, J=11.6 Hz, 2H), 1.60-1.71 (q, J=12.6 Hz, 2H), 1.84-2.04 (m, 5H), 2.05-2.12 (br d, J=11.0 Hz, 4H), 2.38-2.48 (m, 2H), 2.48 (s, 3H), 2.62-2.72 (m, 1H), 2.73-2.83 (m, 1H), 2.87-2.96 (m, 4H), 3.29 (tt, J=1.5, 8.1 Hz, 1H), 3.78-3.82 (m, 1H), 3.80 (t, J=4.6 Hz, 2H), 3.84 (t, J=6.1 Hz, 2H), 7.30 (s, 1H), 7.84 (d, J=2.1 Hz, 1H), 8.16 (d, J=1.9 Hz, 1H), 8.23 (d, J=2.0 Hz, 1H), 9.92 (br s, NH, 1H).

4-((1s,4s)-4-(3-(2-(1-methylpyrrolidin-2-yl)thiazol-4-yl)-1H-pyrrolo[2,3-b]pyridin-5-yl)cyclohexyl)-1,4-oxazepane (I-114)

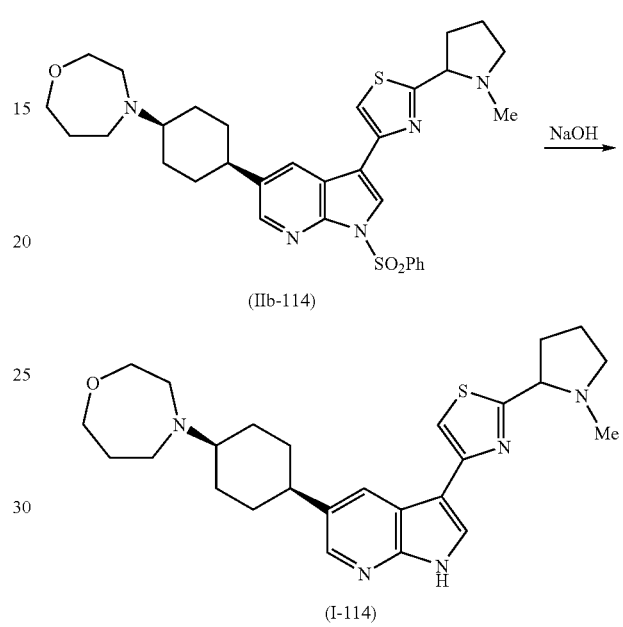

Compound (IIb-114) (30 mg, 50 μmol) in EtOH (1 mL) and 10% aqueous NaOH (0.30 mL), was deprotected as described in the general procedure A for the deprotection of 7-azaindoles by refluxing for 20 min. The crude product was purified by PTLC using CH$_2$Cl$_2$:MeOH=85:15 (v/v) as the eluent to give (I-114) (7.5 mg, 32%) as a white solid. $^1$H NMR (400 MHz, CDCl$_3$) δ 1.65-1.83 (m, 4H), 1.89-2.04 (m, 8H), 2.12 (m, 3H), 2.38-2.48 (m, 1H), 2.48 (s, 3H), 2.89-3.00 (br s, 6H), 3.29 (tt, J=2.5, 7.6 Hz, 1H), 3.78-3.85 (m, 4H), 7.34 (s, 1H), 7.84 (d, J=2.0 Hz, 1H), 8.29 (s, 1H), 8.30 (d, J=1.8 Hz, 1H), 9.63 (br s, 1H).

4-((1r,4r)-4-(3-(thiazol-4-yl)-1H-pyrrolo[2,3-b]pyridin-5-yl)cyclohexyl)-1,4-oxazepane (I-116)

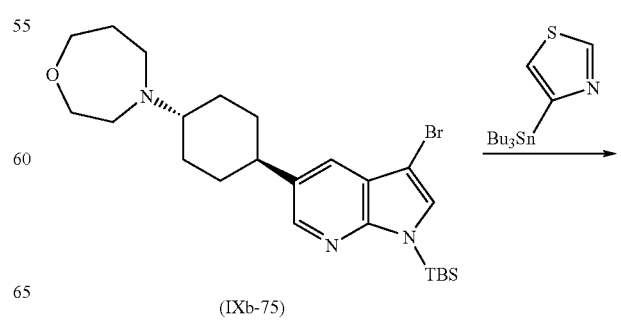

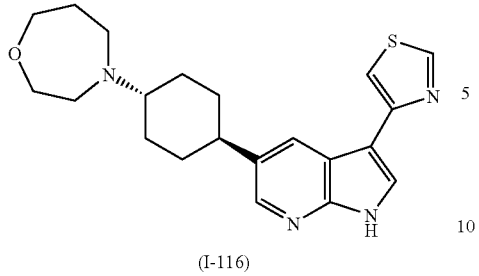

(I-116)

A mixture of bromide (IXb-75) (120 mg, 0.24 mmol), N,N-dicyclohexylmethylamine (52 mg, 0.27 mmol), 4-(tributylstannyl)thiazole (138 mg, 0.37 mmol), dihydrogen dichlorobis(di-tert-butylphosphinito-kP)palladate(2-) (7 mg, 0.01 mmol) in DMF (3 mL) was stirred at 135° C. for 19 h. The mixture was then cooled to RT and partitioned between EtOAc (20 mL) and saturated aqueous NaHCO₃ solution (10 mL). The aqueous layer was extracted with EtOAc (2×15 mL). The combined organic solutions were dried (MgSO₄), filtered and concentrated. The orange residue was purified by LCMS (column LUNA 10μ C18(2) 00G-4253-V0 250×50 mm) using water-acetonitrile (0.1% AcOH) as eluent (in gradient; flow 80 mL/min) to afford azaindole (I-116) (24.1 mg, 26%). ¹H NMR (400 MHz, CDCl₃) δ 1.51-1.67 (m, 4H), 2.03-2.16 (m, 6H), 2.57-2.64 (m, 1H), 3.04-3.12 (m, 5H), 3.82 (t, J=6.0 Hz, 2H), 3.84-3.87 (m, 2H), 6.44 (d, J=3.4 Hz, 1H), 7.31 (d, J=3.4 Hz, 1H), 7.80 (d, J=1.9 Hz, 1H), 8.01 (s, 1H), 8.05 (d, J=1.9 Hz, 1H), 10.29 (br s, 1H).

4-((1r,4r)-4-(3-(4-methylthiazol-2-yl)-1H-pyrrolo[2,3-b]pyridin-5-yl)cyclohexyl)-1,4-oxazepane (I-117)

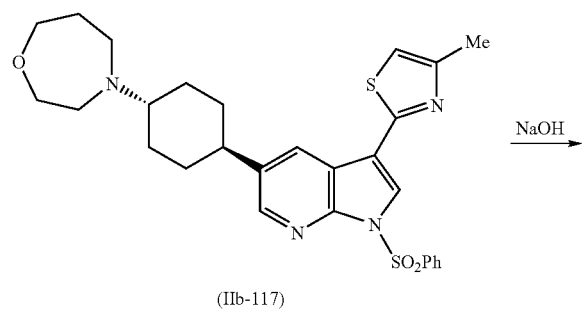

Compound (IIb-117) (38.3 mg, 0.07 mmol) in EtOH (4 mL) and 10% aqueous NaOH (0.70 mL), was deprotected as described in the general procedure A for the deprotection of 7-azaindoles by refluxing for 1.5 h. The crude product (I-117) (24.4 mg, 85%), a pale yellow powder, did not require further purification. ¹H NMR (400 MHz, CDCl₃) δ 1.45-1.56 (m, 2H), 1.60-1.71 (m, 2H), 1.86-1.94 (m, 2H), 2.00-2.11 (m, 4H), 2.54 (d, J=1.0 Hz, 3H), 2.64-2.76 (m, 2H), 2.83-2.92 (m, 4H), 3.74-3.79 (m, 2H), 3.83 (t, J=6.0 Hz, 2H), 6.78 (d, J=1.0 Hz, 1H), 7.93 (s, 1H), 8.27 (d, J=2.0 Hz, 1H), 8.38 (d, J=2.0 Hz, 1H), 10.84 (br s, 1H).

4-((1r,4r)-4-(3-(thiazol-5-yl)-1H-pyrrolo[2,3-b]pyridin-5-yl)cyclohexyl)-1,4-oxazepane (I-118)

Compound (IIb-118) (containing (XXVIIb-75)) (15.1 mg, 0.02 mmol) in EtOH (4 mL) and 10% aqueous NaOH (0.50 mL), was deprotected as described in the general procedure A for the deprotection of 7-azaindoles by stirring at 90° C. for 40 min. The crude product was purified by LCMS (column LUNA 10μ C18(2) 00G-4253-V0 250×50 mm) using water-acetonitrile (0.1% AcOH) as eluent (in gradient; flow 80 mL/min) to afford the azaindole (I-118) (6.1 mg, 77%). ¹H NMR (400 MHz, CDCl₃) δ 1.52-1.71 (m, 4H), 2.04-2.16 (m, 6H), 2.63-2.72 (m, 1H), 3.00-3.09 (m, 5H), 3.82-3.87 (m, 4H), 7.55 (s, 1H), 8.01 (d, J=2.0 Hz, 1H), 8.06 (s, 1H), 8.16 (d, J=2.0 Hz, 1H), 8.77 (s, 1H), 10.60 (br s, 1H).

4-((1r,4r)-4-(3-(thiazol-2-yl)-1H-pyrrolo[2,3-b]pyridin-5-yl)cyclohexyl)-1,4-oxazepane (I-119)

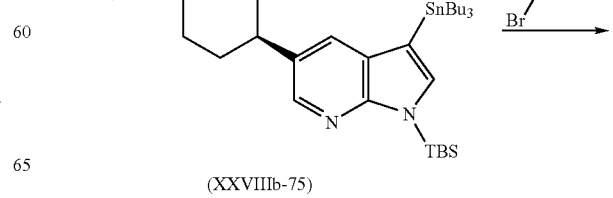

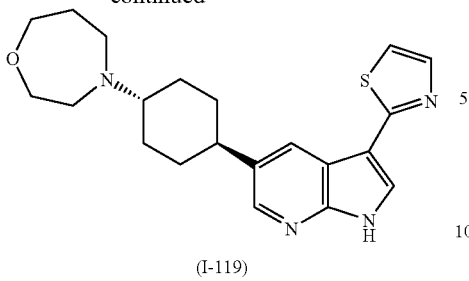

(I-119)

Crude stannane (XXVIII-75) (250 mg, about 0.30 mmol), 2-bromothiazole (88 mg, 0.53 mmol), tri-O-tolylphosphine (21 mg, 0.07 mmol), dichlorobis(acetonitrile)palladium(II) (9 mg, 0.04 mmol), and toluene (2 mL) were reacted for 20 h at 85° C. using a modification of the general procedure B for the Stille reaction. The reaction mixture was filtered and concentrated. The residual brown oil was purified by LCMS (column LUNA 10μ C18(2) 00G-4253-V0 250×50 mm) using water-acetonitrile (0.1% AcOH) as eluent (in gradient; flow 80 mL/min) followed by PTLC on amino silica plates (Chromatorex NH, Fuji Silysia) to give (I-119) (4.1 mg, 2.3%). $^1$H NMR (400 MHz, CDCl$_3$) δ 1.46-1.56 (m, 2H), 1.60-1.72 (m, 2H), 1.87-2.09 (m, 6H), 2.64-2.81 (m, 2H), 2.88-2.92 (m, 4H), 3.78-3.79 (m, 2H), 3.82 (t, J=6.0 Hz, 2H), 7.24 (d, J=3.3 Hz, 1H), 7.85 (d, J=3.4 Hz, 1H), 7.88 (s, 1H), 8.22 (d, J=2.0 Hz, 1H), 8.44 (d, J=2.0 Hz, 1H).

4-((1r,4r)-4-(3-(2-methoxythiazol-4-yl)-1H-pyrrolo[2,3-b]pyridin-5-yl)cyclohexyl)morpholine (I-120)

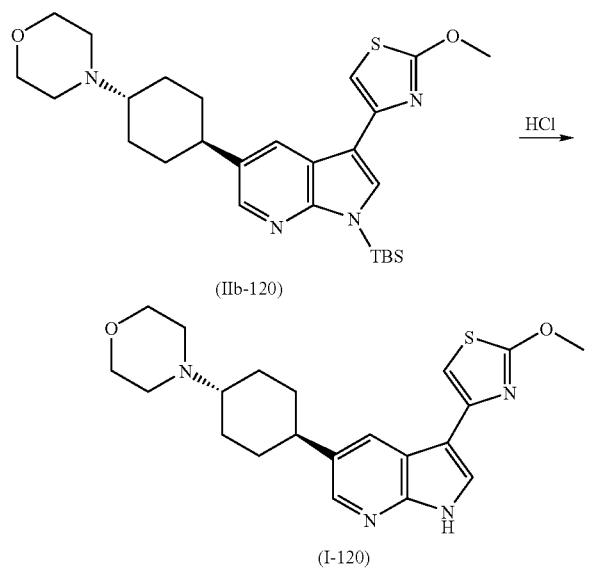

Compound (IIb-120) (289.00 mg, purity 60.00%, 0.34 mmol) was deprotected following the general procedure B for deprotection of 7-azaindoles using conc. aqueous HCl (2.00 ml, 24.00 mmol) in MeOH (20.00 mL) over 30 min. The crude product was purified by LCMS (column LUNA 10μ C18(2) 00G4253-V0 250×50 mm) using water-acetonitrile (0.1% AcOH) as eluent (in gradient; flow 80 mL/min) to give (I-120) (51.00 mg, 38%). $^1$H NMR (400 MHz, CDCl$_3$) δ 1.49 (qd, J=12.3, 2.4 Hz, 2H ), 1.65 (qd, J=12.8, 2.2 Hz, 2H ), 2.05-2.18 (m, 5H), 2.35-2.46 (m, 2H), 2.60-2.75 (m, 5H), 3.79 (t, J=4.4 Hz, 4H ) 4.20 (s, 3H), 6.76 (s, 1H), 7.78 (s, 1H), 8.17 (d, J=1.9 Hz, 1H), 8.24 (d, J=1.9 Hz, 1H), 9.81 (bs, 1H).

3-(5-methyl-1,3-thiazol-2-yl)-5-[trans-4-(1,4-oxazepan-4-yl)cyclohexyl]-1H-pyrrolo[2,3-b]pyridine (I-121)

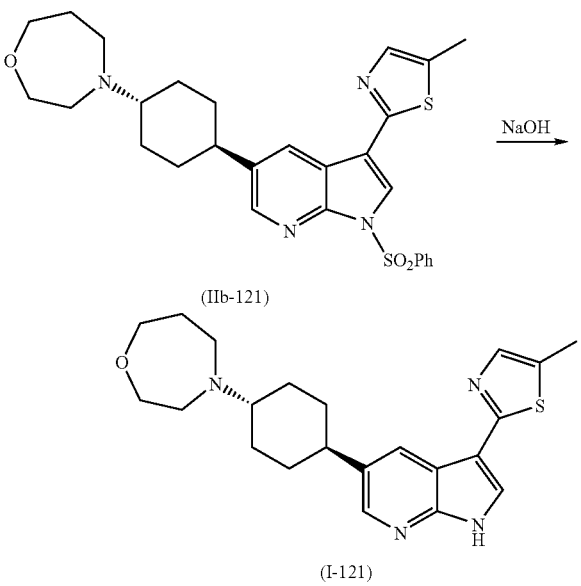

Compound (IIb-121) (18.3 mg, 0.03 mmol) in EtOH (4 mL) and 10% aqueous NaOH (0.70 mL), was deprotected as described in the general procedure A for the deprotection of 7-azaindoles by stirring at 90° C. for 1 h. Usual workup afforded crude azaindole (I-121) (10.2 mg, 75%) as a pale yellow powder. $^1$H NMR (400 MHz, CDCl$_3$) δ 1.42-1.73 (m, 4H), 1.85-1.94 (m, 2H), 1.98-2.09 (m, 4H), 2.52 (s. 3H), 2.62-2.73 (m, 2H), 2.80-2.89 (m, 4H), 3.73-3.78 (m, 2H), 3.82 (t, J=5.8 Hz, 2H), 7.47 (d, J=1.0 Hz, 1H), 7.83 (d, J=2.0 Hz, 1H), 8.27 (d, J=2.0 Hz, 1H), 8.39 (d, J=2.0 Hz, 1H), 10.15 (brs, NH).

5-[trans-4-(1,4-oxazepan-4-yl)cyclohexyl]-3-(2-pyrrolidin-1-yl-1,3-thiazol-4-yl)-1H-pyrrolo[2,3-b]pyridine (I-122)

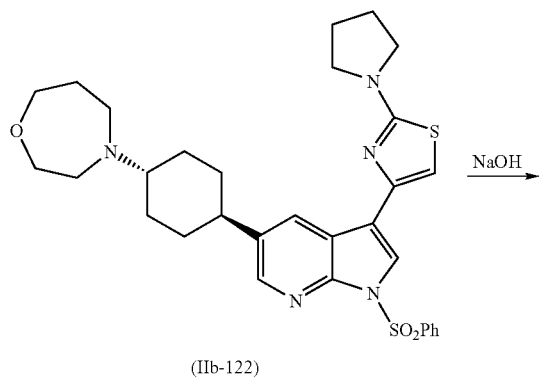

-continued

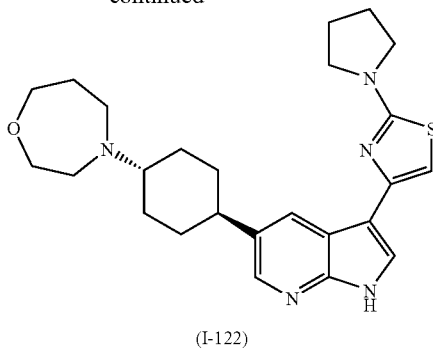

(I-122)

Compound (IIb-122) (30.1 mg, 0.05 mmol) in EtOH (5 mL) and 10% aqueous NaOH (0.70 mL), was deprotected as described in the general procedure A for the deprotection of 7-azaindoles by stirring at 90° C. for 1 h. Usual workup afforded crude azaindole (I-122) (19.3 mg, 84%) as a pale yellow powder. $^1$H NMR (400 MHz, CDCl$_3$) δ 1.43-1.54 (m, 2H), 1.57-1.69 (m, 2H), 1.70-1.80 (m, 2H), 1.85-1.93 (m, 2H), 2.05-2.10 (m, 6H), 2.59-2.72 (m, 2H), 2.81-2.89 (m, 4H), 3.53-3.58 (m, 4H), 3.73-3.77 (m, 2H), 3.82 (t, J=5.9 Hz, 2H), 6.56 (s, 1H), 7.74 (d, J=2.3 Hz, 1H), 8.17 (d, J=2.1 Hz, 1H), 8.20 (d, J=2.1 Hz, 1H), 9.29 (brs, NH).

3-(4,5-dimethyl-1,3-thiazol-2-yl)-5-[trans-4-(1,4-oxazepan-4-yl)cyclohexyl]-1H-pyrrolo[2,3-b]pyridine (I-123)

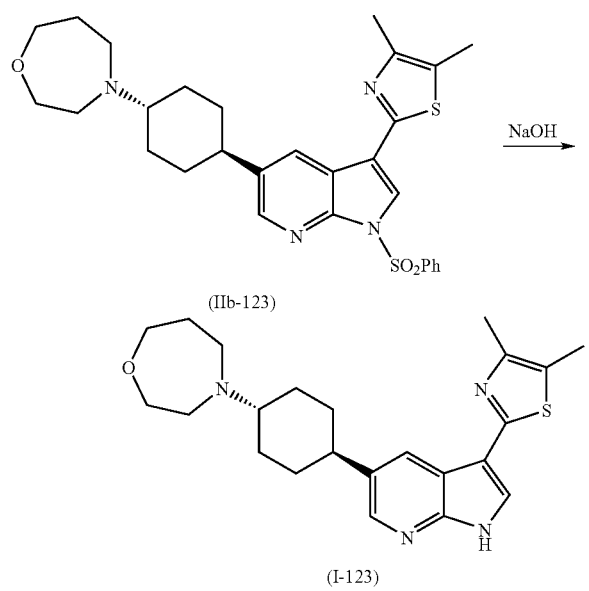

Compound (IIb-123) (70.3 mg, 0.13 mmol) in EtOH (5 mL) and 10% aqueous NaOH (0.70 mL), was deprotected as described in the general procedure A for the deprotection of 7-azaindoles by stirring at 90° C. for 1.3 h. Usual workup afforded crude azaindole (I-123) (44.4 mg, 83%) as a pale yellow powder. $^1$H NMR (400 MHz, CDCl$_3$) δ 1.43-1.56 (m, 2H), 1.59-1.72 (m, 2H), 1.84-1.94 (m, 2H), 1.99-2.10 (m, 4H), 2.41 (s, 6H), 2.63-2.74 (m, 2H), 2.82-2.89 (m, 4H), 3.73-3.78 (m, 2H), 3.82 (t, J=6.0 Hz, 2H), 7.85 (d, J=2.1 Hz, 1H), 8.25 (d, J=2.1 Hz, 1H), 8.33 (d, J=2.1 Hz, 1H), 10.50 (brs, NH).

3-(2-methoxy-1,3-thiazol-4-yl)-5-[trans-4-(1,4-oxazepan-4-yl)cyclohexyl]-1H-pyrrolo[2,3-b]pyridine (I-124)

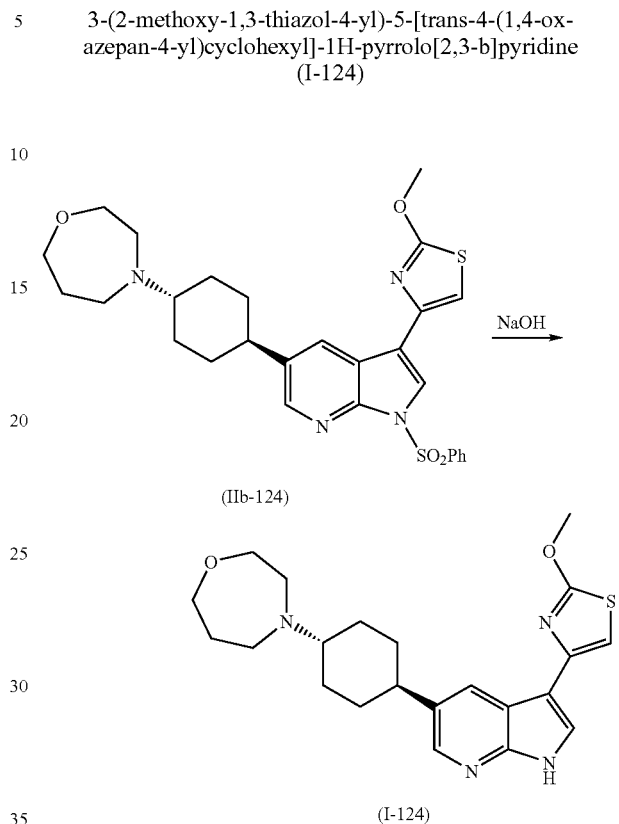

Compound (IIb-124) (94.4 mg, 0.17 mmol) in EtOH (5 mL) and 10% aqueous NaOH (0.70 mL), was deprotected as described in the general procedure A for the deprotection of 7-azaindoles by stirring at 90° C. for 1 h. Usual workup afforded crude azaindole (I-124) (55.8 mg, 78%) as a pale yellow powder. $^1$H NMR (400 MHz, CDCl$_3$) δ 1.42-1.55 (m, 2H), 1.57-1.69 (m, 2H), 1.84-1.93 (m, 2H), 1.98-2.11 (m, 4H), 2.60-2.73 (m, 2H), 2.80-2.89 (m, 4H), 3.73-3.77 (m, 2H), 3.82 (t, J=6.0 Hz, 2H), 4.18 (s, 3H), 6.73 (s, 1H), 7.77 (d, J=2.1 Hz, 1H), 8.14 (d, J=2.1 Hz, 1H), 8.24 (d, J=2.1 Hz, 1H), 10.07 (brs, NH).

3-(2-ethoxy-1,3-thiazol-4-yl)-5-[trans-4-(1,4-oxazepan-4-yl)cyclohexyl]-1H-pyrrolo[2,3-b]pyridine (I-125)

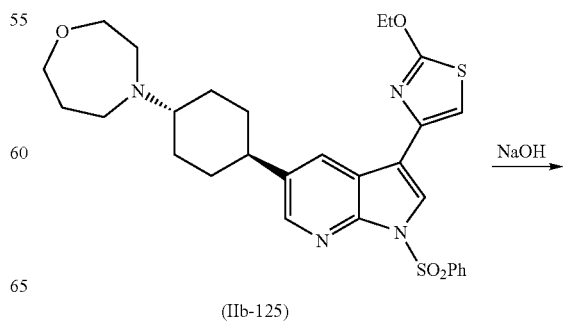

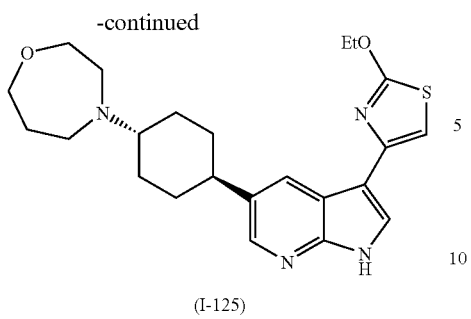

(I-125)

Compound (IIb-125) (82.3 mg, 0.14 mmol) in EtOH (5 mL) and 10% aqueous NaOH (0.70 mL), was deprotected as described in the general procedure A for the deprotection of 7-azaindoles by stirring at 90° C. for 1.5 h. Usual workup afforded crude azaindole (I-124) (24.8 mg, 40%) as a pale yellow powder. $^1$H NMR (400 MHz, CDCl$_3$) δ 1.46-1.55 (m, 2H), 1.50 (t, J=7.1 Hz, 3H), 1.57-1.69 (m, 2H), 1.85-1.93 (m, 2H), 1.98-2.11 (m, 4H), 2.60-2.72 (m, 2H), 2.81-2.88 (m, 4H), 3.73-3.78 (m, 2H), 3.82 (t, J=6.0 Hz, 2H), 4.56 (q, J=7.1, 14.2 Hz, 2H), 6.72 (s, 1H), 7.76 (d, J=2.4 Hz, 1H), 8.23 (d, J=2.0 Hz, 1H), 10.16 (brs, NH).

4-(5-cyclopentenyl-1-(phenylsulfonyl)-1H-pyrrolo[2,3-b]pyridin-3-yl)-2-(1-methylpiperidin-4-yl)thiazole (IIa-1)

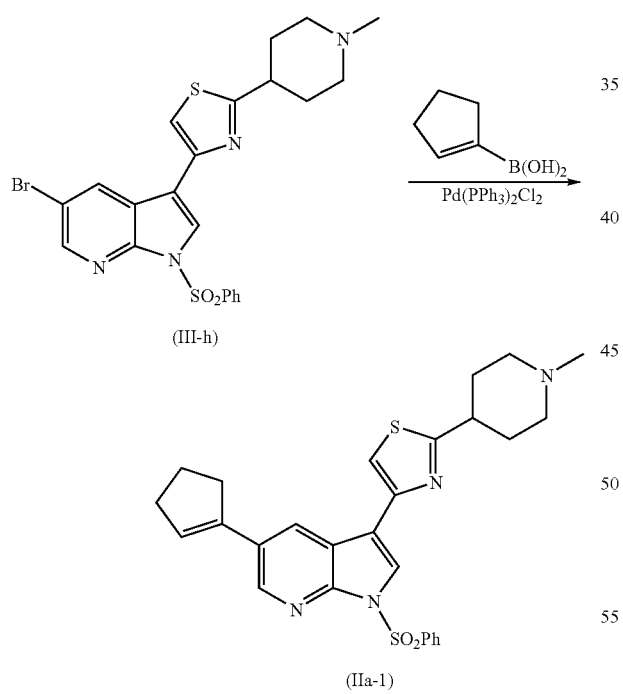

Bromide (III-h) (267 mg, 0.52 mmol), cyclopent-1-enyl boronic acid (80 mg, 0.68 mmol), lithium chloride (70 mg, 1.65 mmol), and Pd(PPh$_3$)$_2$Cl$_2$ (30 mg, 43 µmol), in EtOH (2 ml), toluene (2 ml) and 1.0 M Na$_2$CO$_3$ solution (1.0 ml) were reacted for 2 h under reflux using the general procedure A for the Suzuki reaction. Crude product (89 mg) was purified by SGC using CH$_2$Cl$_2$:MeOH 19:1 (v/v) to afford (IIa-1) (213 mg, 0.42 mmol, 81%) as a foam. $^1$H NMR (400 MHz, CDCl$_3$) δ 1.80-2.17 (m, 8H), 2.27 (s, 3H), 2.45-2.52 (m, 2H), 2.65-2.72 (m, 2H), 2.87-3.03 (m, 3H), 6.18 (pentet, J=2.2 Hz, 1H), 7.27 (s, 1H), 7.40 (t, J=7.8 Hz, 2H), 7.49 (tt, J=1.3, 7.4 Hz, 1H), 8.05 (s, 1H), 8.11-8.17 (m, 2H), 8.24 (d, J=2.1 Hz, 1H), 8.53 (d, J=2.1 Hz, 1H).

(IIb-11)—see preparation of (I-11)

4-(5-cyclohexenyl-1-(phenylsulfonyl)-1H-pyrrolo[2,3-b]pyridin-3-yl)-N,N-diethylthiazol-2-amine (IIa-12)

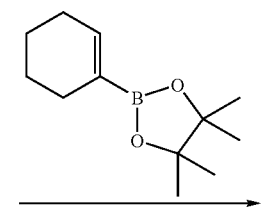

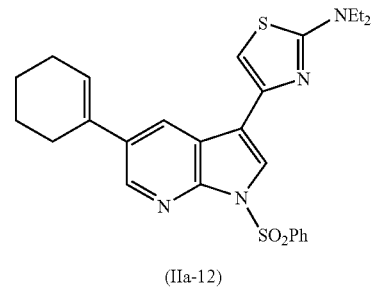

(IIa-12)

Bromide (III-i) (253 mg, ~0.45 mmol), cyclohexenyl boronic acid pinacol ester (150 mg, 0.72 mmol), lithium chloride (80 mg, 1.89 mmol), and Pd(PPh$_3$)$_2$Cl$_2$ (50 mg, 71 µmol), in EtOH (1.5 ml), toluene (1.5 ml) and 1.0 M Na$_2$CO$_3$ solution (0.75 ml) were reacted for 3 h under reflux using the general procedure A for the Suzuki reaction. Crude product (344 mg) was purified by SGC using CH$_2$Cl$_2$ to afford (IIa-12) (105 mg, 213 µmol, 47%) as a foam. $^1$H NMR (400 MHz, CDCl$_3$) δ 1.31 (t, J=7.1 Hz, 6H), 1.65-1.73 (m, 2H), 1.78-1.85 (m, 2H), 2.21-2.28 (m, 2H), 2.42-2.49 (m, 2H), 3.58 (q, J=7.2 Hz, 4H), 6.13-6.18 (m, 1H), 6.67 (s, 1H), 7.47 (t, J=7.6 Hz, 2H), 7.57 (tt, J=1.4, 7.5 Hz, 1H), 8.11 (s, 1H), 8.20 (d, J=7.8 Hz, 2H), 8.48 (d, J=2.2 Hz, 1H), 8.51 (d, J=2.2 Hz, 1H).

(IIb-18)—see preparation of (I-18)

2-(1-methylpiperidin-4-yl)-4(1-(phenylsulfonyl)-5-
(1,4-dioxaspiro[4.5]decan-8-yl)-1H-pyrrolo[2,3-b]
pyridin-3-yl)thiazole (IIb-23)

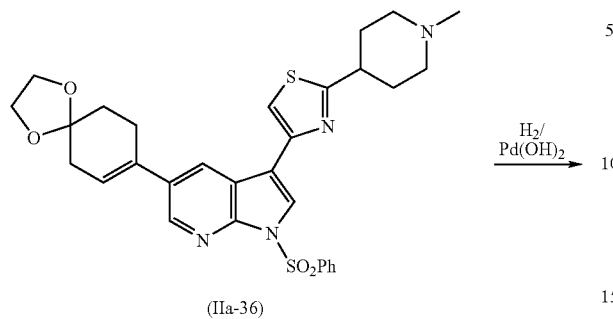

(IIa-36)

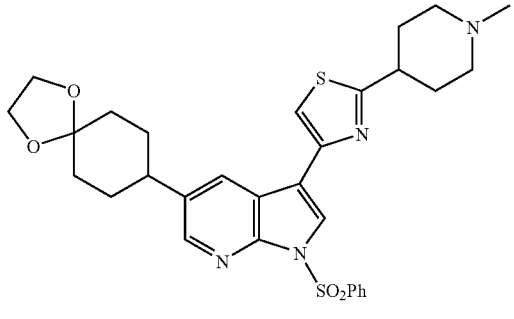

(IIb-23)

Compound (IIa-36) (1.08 g, 1.87 mmol) was hydrogenated using the general procedure for hydrogenation of 7-azaindoles using 20% Pd(OH)$_2$/C (Degussa type, 0.40 g) in MeOH (30 mL)-EtOAc (30 mL) over a period of 20 h. The reaction mixture was then filtered through Celite and was washed with copious amount of CH$_2$Cl$_2$:MeOH (1:1). The solvent was removed to give (IIb-23) (0.76 g, 70%) as a white foam. $^1$H NMR (400 MHz, CDCl$_3$) δ 1.58-1.92 (m, 10H), 2.22-2.35 (m, 2H), 2.41-2.53 (m, 2H), 2.62 (s, 3H), 2.65-2.74 (m, 2H), 3.22-3.30 (m, 2H), 3.97 (s, 4H), 7.38 (s, 1H), 7.44-7.49 (m, 2H), 7.53-7.60 (m, 1H), 8.11(s, 1H), 8.12 (s, 1H), 8.19-8.22 (m, 2H), 8.35 (d, J=2.0 Hz, 1H).

2-(1-methylpiperidin-4-yl)-4-(1-(phenylsulfonyl)-5-
(1,4-dioxaspiro[4.5]decan-8-yl)-1H-pyrrolo[2,3-b]
pyridin-3-yl)thiazole (IIb-23)—see also preparation
of (I-23)

2-(5-cyclohexenyl-1-(phenylsulfonyl)-1H-pyrrolo[2,
3-b]pyridin-3-yl)thiazole (IIa-24)

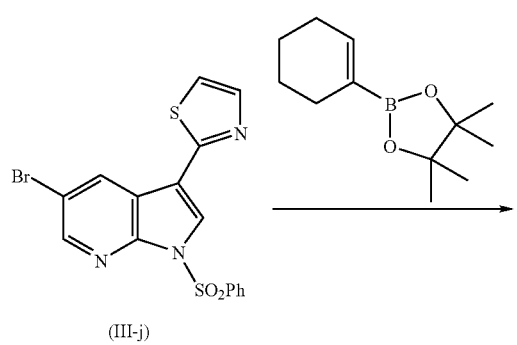

(III-j)

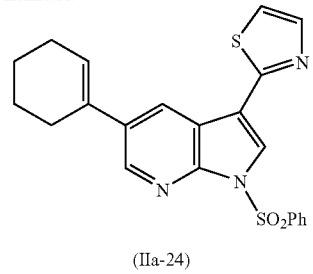

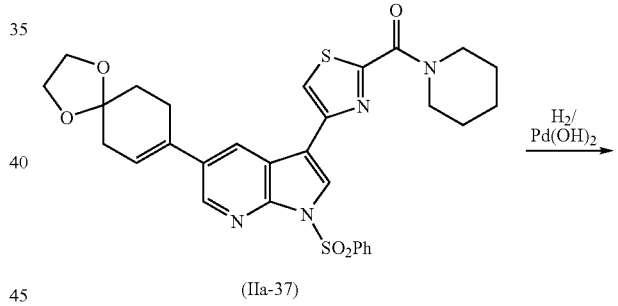

(IIa-24)

Bromide (III-j) (190 mg, 0.45 mmol), cyclohexenyl boronic acid pinacol ester (120 mg, 0.56 mmol), lithium chloride (80 mg, 1.89 mmol), and Pd(PPh$_3$)$_2$Cl$_2$ (25 mg, 36 μmol), in EtOH (1 ml), toluene (1 ml) and 1.0 M Na$_2$CO$_3$ solution (0.5 ml) were reacted for 3.5 h under reflux using the general procedure A for the Suzuki reaction. Crude product (brown oil, 385 mg) was purified by SGC using CH$_2$Cl$_2$ to afford (IIa-24) (139 mg, 0.33 mmol, 73%) as a foam. $^1$H NMR (400 MHz, CDCl$_3$) δ 1.67-1.74 (m, 2H), 1.80-1.87 (m, 2H), 2.22-2.29 (m, 2H), 2.45-2.51 (m, 2H), 6.16-6.20 (m, 1H), 7.35 (d, J=3.3 Hz, 1H), 7.53 (t, J=7.6 Hz, 2H), 7.62 (tt, J=1.5, 7.5 Hz, 1H), 7.91 (d, J=3.3 Hz, 1H), 8.24-8.29 (m, 3H), 8.44 (d, J=2.2 Hz, 1H), 8.56 (d, J=2.2 Hz, 1H).

(4-(1-(phenylsulfonyl)-5-(1,4-dioxaspiro[4.5]decan-
8-yl)-1H-pyrrolo[2,3-b]pyridin-3-yl)thiazol-2-yl)
(piperidin-1-yl)methanone (IIb-25)

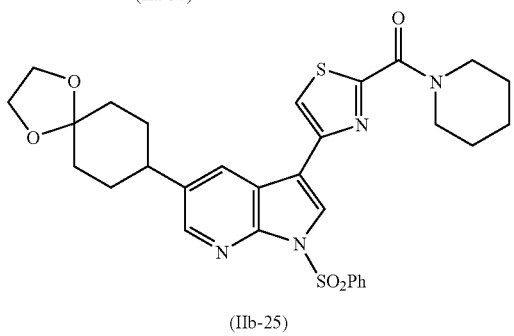

(IIa-37)

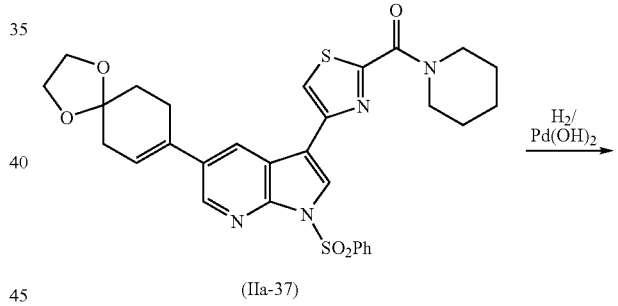

(IIb-25)

Compound (IIa-37) (115 mg, up to 0.18 mmol) was hydrogenated using the general procedure for hydrogenation of 7-azaindoles using 20% Pd(OH)$_2$/C (Degussa type, 40 mg) in MeOH (5 mL)-CH$_2$Cl$_2$ (5 mL) over a period of 20 h. The reaction mixture was then filtered through Celite, and concentrated to afford crude reduction product (IIb-25) (103 mg, 0.17 mmol, 96%) as an oil. $^1$H NMR (400 MHz, CDCl$_3$) δ $^1$H NMR (400 MHz, CDCl$_3$) δ 1.48-2.20 (m, 14H), 3.76-3.78

(m, 2H), 3.93 (s, 4H), 4.31-4.40 (m, 2H), 7.43 (t, J=7.6 Hz, 2H), 7.52 (t, J=7.2 Hz, 1H), 7.59 (s, 1H), 8.04 (s, 1H), 8.14-8.21 (m, 3H), 8.31 (s, 1H).

2-(5-cyclohexyl-1-(phenylsulfonyl)-1H-pyrrolo[2,3-b]pyridin-3-yl)thiazole (IIb-26)

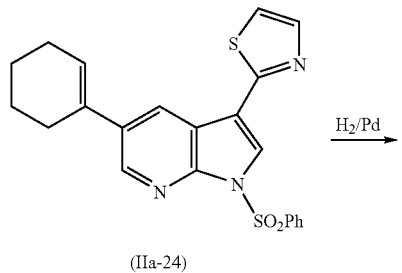

Compound (IIa-24) (114 mg, 0.27 mmol) was hydrogenated using the general procedure for hydrogenation of 7-azaindoles using 20% Pd(OH)₂/C (Degussa type, 30 mg) in MeOH (4 mL)-CH₂Cl₂ (2 mL) over a period of 4 d. The reaction mixture was then filtered through Celite, washing with MeOH:CH₂Cl₂ and concentrated to afford crude reduction product as a brown oil (92 mg). The oil was purified by SGC with CH₂Cl₂ as eluent to afford (IIb-26) (55 mg, 0.13 mmol, 48%) as a foam. ¹H NMR (400 MHz, CDCl₃) δ 1.16-1.50 (m, 5H), 1.66-1.87 (m, 5H), 2.60 (tt, J 3.3, 11.9 Hz, 1H), 7.26 (d, J=3.3 Hz, 1H), 7.43 (t, J=7.6 Hz, 2H), 7.53 (tt, J=1.4, 7.4 Hz, 1H), 7.82 (d, J=3.3 Hz, 1H), 8.15-8.20 (m, 3H), 8.30 (d, J=2.1 Hz, 1H), & 8.34 (d, J=2.1 Hz, 1H).

Ethyl 4-(5-(4,4-dimethylcyclohexa-1,5-dienyl)-1-(phenylsulfonyl)-1H-pyrrolo[2,3-b]pyridin-3-yl)thiazole-2-carboxylate (IIa-35)

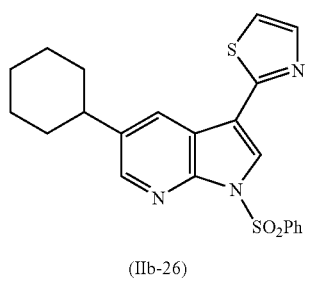

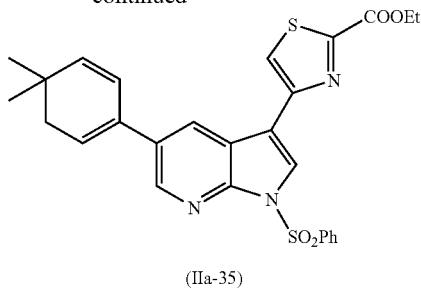

Bromide (III-a) (300 mg, up to 0.61 mmol), 4,4-dimethylcyclohexa-1,5-dienyl boronic acid pinacol ester (163 mg, 0.70 mmol), lithium chloride (80 mg, 1.89 mmol), and Pd(PPh₃)₂Cl₂ (80 mg, 0.11 mmol), in EtOH (2 ml), toluene (2 ml) and 1.0 M Na₂CO₃ solution (1.0 ml) were reacted for 2 h under reflux using the general procedure A for the Suzuki reaction. Crude product (430 mg) was purified by SGC using AcOEt:hexanes 1:4 (v/v) to afford (IIa-35) (112 mg, 0.22 mmol, 35%) as a foam. ¹H NMR (400 MHz, CDCl₃) δ 1.00 (s, 6H), 1.42 (t, J=7.1 Hz, 3H), 2.24 (d, J=4.7 Hz, 2H), 4.45 (q, J=7.1 Hz, 2H), 5.69 (dd, J=0.8, 9.6 Hz, 1H), 5.95-5.99 (m, 1H), 6.24 (dd, J=1.7, 9.7 Hz, 1H), 7.42 (t, J=7.7 Hz, 2H), 7.51 (tt, J=1.2, 7.8 Hz, 1H), 7.67 (s, 1H), 8.14-8.23 (m, 4H), 8.47 (d, J=2.1 Hz, 1H).

2-(1-methylpiperidin-4-yl)-4-(1-(phenylsulfonyl)-5-(1,4-dioxaspiro[4.5]dec-7-en-8-yl)-1H-pyrrolo[2,3-b]pyridin-3-yl)thiazole (IIa-36)

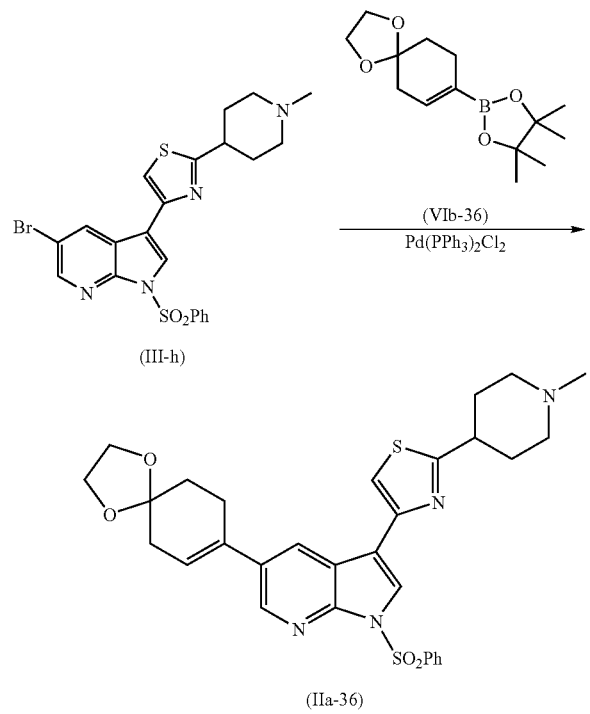

Bromide (III-h) (109 mg, 0.28 mmol), boronic acid pinacol ester (VIb-36) (75 mg, 0.28 mmol), lithium chloride (35 mg, 0.83 mmol), and Pd(PPh₃)₂Cl₂ (25 mg, 36 µmol), in EtOH (1 ml), toluene (1 ml) and 1.0 M Na₂CO₃ solution (0.5 ml) were reacted for 1 h under reflux using the general procedure A for the Suzuki reaction. Crude product (186 mg) was purified by SGC using CH$_2$Cl$_2$:MeOH 23:2 (v/v) to afford (IIa-36) (148 mg, 0.26 mmol, 92%) as a foam. $^1$H NMR (400 MHz, CDCl$_3$) δ $^1$H NMR (400 MHz, CDCl$_3$) δ 1.91-2.04 (m, 4H), 2.10-2.24 (m, 4H), 2.34 (s, 3H), 2.47-2.52 (m, 2H), 2.67-2.73 (m, 2H), 2.95-3.11 (m, 3H), 4.04 (s, 4H), 5.98-6.02 (m, 1H), 7.34 (s, 1H), 7.47 (t, J=7.4 Hz, 2H), 7.56 (t, J=7.4 Hz, 1H), 8.13 (s, 1H), 8.19-8.22 (m, 2H), 8.27 (d, J=2.2 Hz, 1H), 8.53 (d, J=2.2 Hz, 1H).

(4-(1-(phenylsulfonyl)-5-(1,4-dioxaspiro[4.5]dec-7-en-8-yl)-1H-pyrrolo[2,3-b]pyridin-3-yl)thiazol-2-yl)(piperidin-1-yl)methanone (IIa-37)

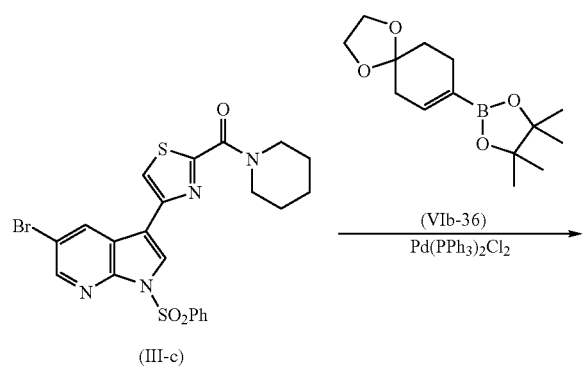

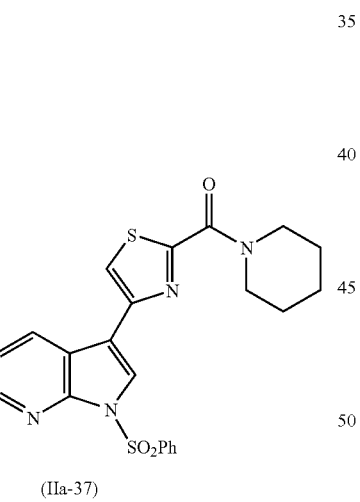

Bromide (III-c) (96 mg, 0.18 mmol), boronic acid pinacol ester (VIb-36) (65 mg, 0.24 mmol), lithium chloride (30 mg, 0.71 mmol), and Pd(PPh$_3$)$_2$Cl$_2$ (25 mg, 36 μmol), in EtOH (1 ml), toluene (1 ml) and 1.0 M Na$_2$CO$_3$ solution (0.5 ml) were reacted for 1 h under reflux using the general procedure A for the Suzuki reaction. Crude product (221 mg) was purified by SGC using AcOEt:hexanes 1:1 (v/v) to afford (IIa-37) (115 mg, crude yield >100%) as a foam. $^1$H NMR (400 MHz, CDCl$_3$) δ $^1$H NMR (400 MHz, CDCl$_3$) δ 1.71-1.81 (m, 6H), 1.96 (t, J=6.5 Hz, 2H), 2.48-2.52 (m, 2H), 2.67-2.74 (m, 2H), 3.76-3.82 (m, 2H), 4.05 (s, 4H), 4.35-4.41 (m, 2H), 5.98-6.02 (m, 1H), 7.50 (t, J=7.9 Hz, 2H), 7.60 (tt, J=1.3, 7.5 Hz, 1H), 7.67 (s, 1H), 8.14 (s, 1H), 8.22-8.26 (m, 2H), 8.32 (d, J=2.3 Hz, 1H), 8.55 (d, J=2.3 Hz, 1H).

ethyl 4-(5-(4-methylcyclohex-1-enyl)-1-(phenylsulfonyl)-1H-pyrrolo[2,3-b]pyridin-3-yl)thiazole-2-carboxylate (IIa-38)

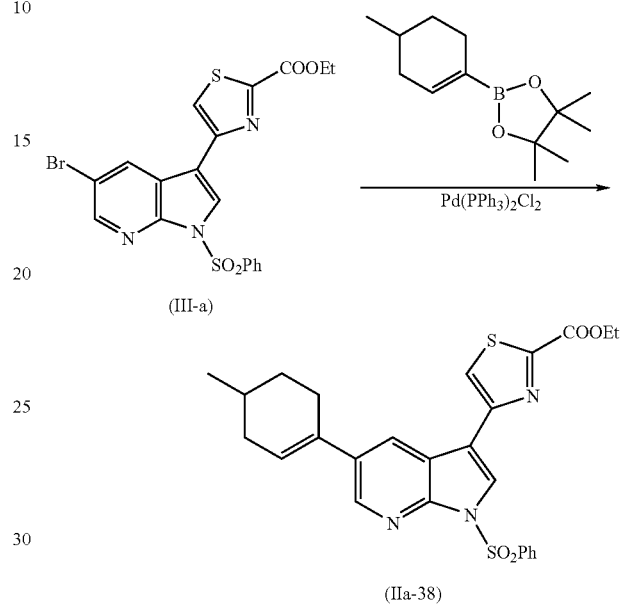

Bromide (III-a) (600 mg, 1.22 mmol), 4-methyl-cyclohex-1-enyl boronic acid pinacol ester (220 mg, 1.57 mmol), lithium chloride (180 mg, 4.24 mmol), and Pd(PPh$_3$)$_2$Cl$_2$ (75 mg, 0.11 mmol), in EtOH (5 ml), toluene (5 ml) and 1.0 M Na$_2$CO$_3$ solution (2.0 ml) were reacted for 1 h under reflux using the general procedure A for the Suzuki reaction. Crude product was purified by SGC using AcOEt:hexanes 1:2 (v/v) to afford (IIa-38) (540 mg, 0.99 mmol, 81%) as a foam. $^1$H NMR (400 MHz, CDCl$_3$) δ 1.04 (d, J 6.4 Hz, 3H), 1.38-1.59 (m, 4H), 1.72-2.00 (m, 3H), 2.29-2.40 (m, 1H), 2.46-2.61 (m, 2H), 4.54 (q, J=7.1 Hz, 2H), 6.11-6.19 (m, 1H), 7.50 (t, J=7.9 Hz, 2H), 7.59 (t, J=7.4 Hz, 1H), 7.75 (s, 1H), 8.22-8.35 (m, 4H), 8.55 (d, J=2.1 Hz, 1H).

ethyl 4-(5-cyclopentenyl-1-(phenylsulfonyl)-1H-pyrrolo[2,3-b]pyridin-3-yl)thiazole-2-carboxylate (IIa-39)

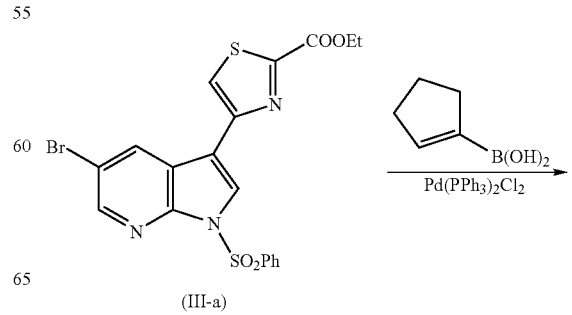

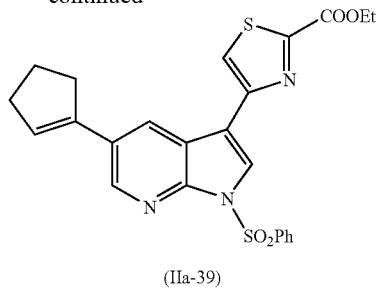

(IIa-39)

Bromide (III-a) (480 mg, 0.98 mmol), cyclopent-1-enyl boronic acid (130 mg, 1.16 mmol), lithium chloride (140 mg, 3.30 mmol), and Pd(PPh$_3$)$_2$Cl$_2$ (60 mg, 86 µmol), in EtOH (4 ml), toluene (4 ml) and 1.0 M Na$_2$CO$_3$ solution (2.0 ml) were reacted for 1.5 h under reflux using the general procedure A for the Suzuki reaction. Crude product (548 mg) was purified by SGC using AcOEt:hexanes 1:4 (v/v) to afford (IIa-39) (374 mg, 0.78 mmol, 80%) as a solid. $^1$H NMR (400 MHz, CDCl$_3$) δ 1.51 (t, J=7.1 Hz, 3H), 2.08 (pentet, J=7.5 Hz, 2H), 2.56-2.63 (m, 2H), 2.77-2.84 (m, 2H), 4.55 (q, J=7.1 Hz, 2H), 6.30 (pentet, J=2.1 Hz, 1H), 7.51 (t, J=7.7 Hz, 2H), 7.60 (tt, J=1.3, 7.4 Hz, 1H), 7.74 (s, 1H), 8.23-8.30 (m, 3H), 8.36 (d, J=2.1 Hz, 1H), 8.65 (d, J=2.1 Hz, 1H).

(IIa-40)—see preparation of (I-11)

ethyl 4-(5-cyclohexenyl-1-(phenylsulfonyl)-1H-pyrrolo[2,3-b]pyridin-3-yl)thiazole-2-carboxylate (IIIa-41)

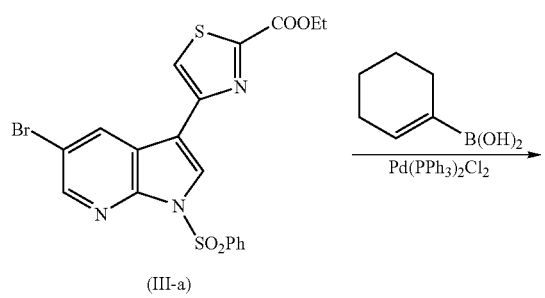

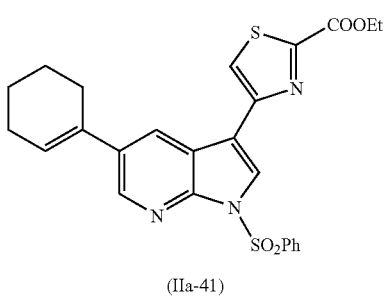

(IIa-41)

Bromide (III-a) (668 mg, 1.36 mmol), cyclohex-1-enyl boronic acid (200 mg, 1.59 mmol), lithium chloride (165 mg, 3.89 mmol), and Pd(PPh$_3$)$_2$Cl$_2$ (100 mg, 0.14 mmol), in EtOH (4 ml), toluene (4 ml) and 1.0 M Na$_2$CO$_3$ solution (2.0 ml) were reacted for 1 h under reflux using the general procedure A for the Suzuki reaction. Crude product (1.18 g) was purified by SGC using AcOEt:hexanes 1:4 (v/v) to afford (IIa-41) (600 mg, 1.22 mmol, 89%) as a solid. $^1$H NMR (400 MHz, CDCl$_3$) δ 1.50 (t, J=7.1 Hz, 3H), 1.66-1.73 (m, 2H), 1.78-1.86 (m, 2H), 2.21-2.28 (m, 2H), 2.43-2.50 (m, 2H), 4.54 (q, J=7.1 Hz, 2H), 6.14-6.17 (m, 1H), 7.49 (t, J=7.7 Hz, 2H), 7.59 (tt, J=1.3, 7.4 Hz, 1H), 7.75 (s, 1H), 8.22-8.29 (m, 3H), 8.30 (d, J=2.1 Hz, 1H), 8.54 (d, J=2.1 Hz, 1H).

ethyl 4-(5-cyclohexyl-1-(phenylsulfonyl)-1H-pyrrolo[2,3-b]pyridin-3-yl)thiazole-2-carboxylate (IIb-42)

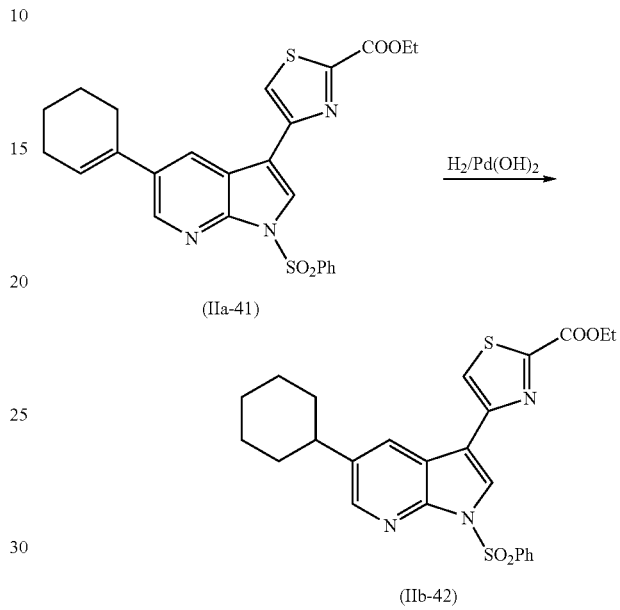

Compound (IIa-41) (600 mg, 1.22 mmol) was hydrogenated using the general procedure for hydrogenation of 7-azaindoles using 20% Pd(OH)$_2$/C (Degussa type, 100 mg) in MeOH (10 mL) over a period of 4 days. The reaction mixture was then filtered through Celite, and concentrated to afford crude reduction product (IIb-42) (650 mg, crude yield >100%) as an oil. $^1$H NMR (400 MHz, CDCl$_3$) δ 1.27-1.56 (m, 7H), 1.76-1.97 (m, 6H), 2.64-2.73 (m, 1H), 4.55 (q, J=7.1 Hz, 2H), 7.51 (t, J=7.7 Hz, 2H), 7.60 (tt, J=1.2, 7.5 Hz, 1H), 7.74 (s, 1H), 8.19 (d, J=2.1 Hz, 1H), 8.23-8.29 (m, 3H), 8.39 (d, J=2.1 Hz, 1H).

ethyl 4-(1-(phenylsulfonyl)-5-(1,4-dioxaspiro[4.5]dec-7-en-8-yl)-1H-pyrrolo[2,3-b]pyridin-3-yl)thiazole-2-carboxylate (IIa-43)

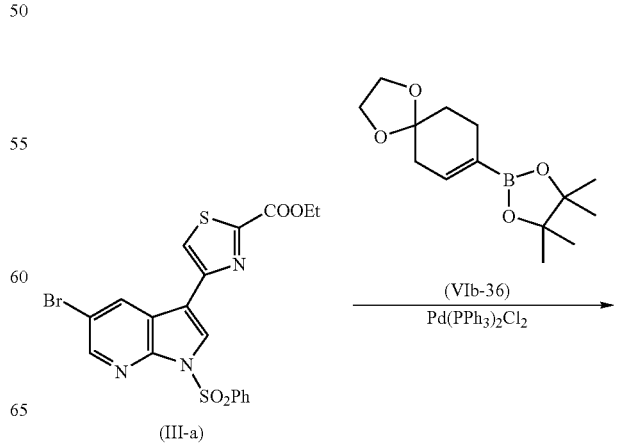

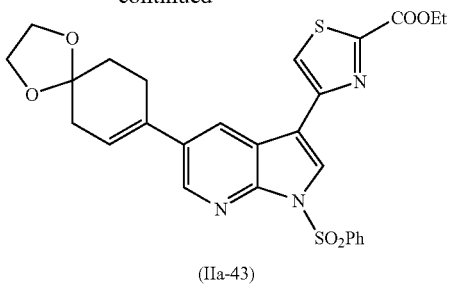

(IIa-43)

Bromide (III-a) (3.00 g, 6.09 mmol), boronic acid pinacol ester (VIb-36) (1.94 g, 7.31 mmol), lithium chloride (0.77 g, 18.27 mmol), and Pd(PPh$_3$)$_2$Cl$_2$ (0.43 g, 0.61 mmol), in EtOH (15.2 ml), toluene (15.2 ml) and 1.0 M Na$_2$CO$_3$ solution (15.2 ml) were reacted for 3 h under reflux using the general procedure A for the Suzuki reaction. Crude product (221 mg) was purified by SGC using AcOEt:hexanes (gradient elution) to afford (IIa-43) (2.30 g, 68%) as a pale brown solid. $^1$H NMR (400 MHz, CDCl$_3$) δ 1.49 (t, J=7.2 Hz, 3H), 1.95 (t, J=6.5 Hz, 2H), 2.48-2.51 (m, 2H), 2.69-2.76 (m, 2H), 4.04 (s, 4H), 4.53 (q, J=7.2 Hz, 2H), 6.01-6.04 (m, 1H), 7.46-7.51 (m, 2H), 7.55-7.60 (m, 1H), 7.73 (s, 1H), 8.21-8.24 (m, 2H), 8.27 (s, 1H), 8.33 (d, J=2.1 Hz, 1H), 8.56 (d, J=2.1 Hz, 1H).

ethyl 4-(1-(phenylsulfonyl)-5-(1,4-dioxaspiro[4.5] decan-8-yl)-1H-pyrrolo[2,3-b]pyridin-3-yl)thiazole-2-carboxylate (IIb-44)

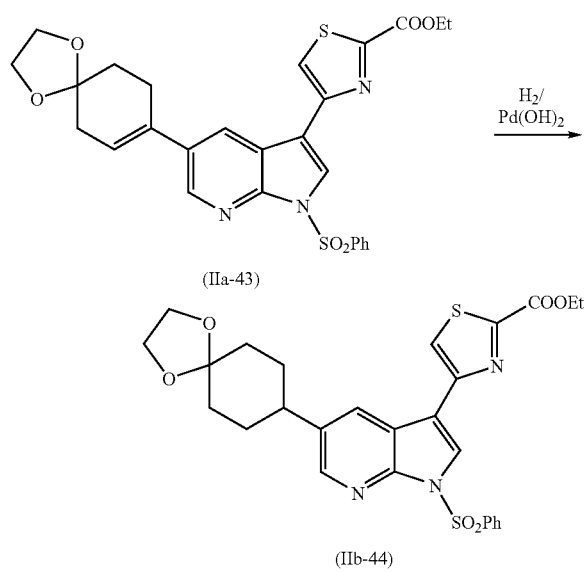

Compound (IIa-43) (2.30 g, 4.17 mmol) was hydrogenated using the general procedure for hydrogenation of 7-azaindoles using 20% Pd(OH)$_2$/C (Degussa type, 0.29 g) in MeOH (15 mL) and EtOAc (41.7 mL) over a period of 5 days. The reaction mixture was then filtered through Celite, and concentrated to afford crude reduction product (IIb-44) (2.13 g, 92%) as a yellow foam. $^1$H NMR (400 MHz, CDCl$_3$) δ 1.50 (t, J=7.1 Hz, 3H), 1.68-1.78 (m, 2H), 1.81-1.93 (m, 6H), 2.68-2.79 (m, 2H), 4.00 (s, 4H), 4.53 (q, J=7.1 Hz, 2H), 7.47-7.53 (m, 2H), 7.56-7.61 (m, 1H), 7.73 (s, 1H), 8.20 (d, J=2.0 Hz, 1H), 8.23-8.26 (m, 2H), 8.29 (s, 1H), 8.41 (d, J=2.1 Hz, 1H).

ethyl 4-(5-(4-oxocyclohexyl)-1-(phenylsulfonyl)-1H-pyrrolo[2,3-b]pyridin-3-yl) thiazole-2-carboxylate (IIb-45)

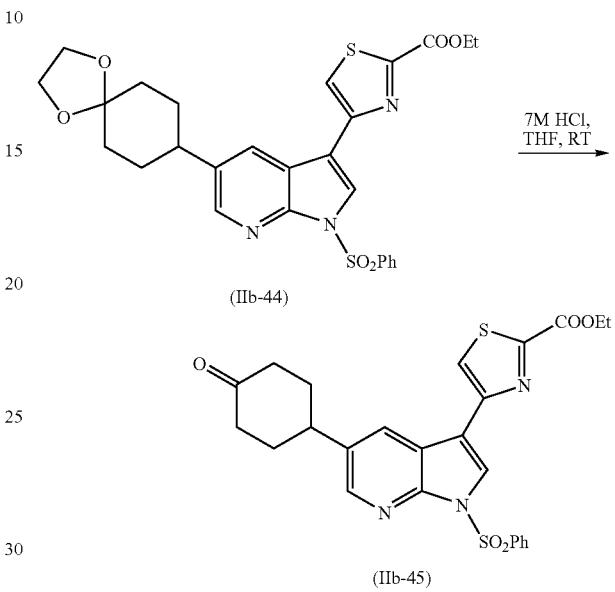

Compound (IIb-44) (2.13 g, 3.85 mmol) was dissolved in THF (38.5 mL). Then, 7 M HCl (12.8 mL) was added at room temperature in one portion. The reaction was stirred at RT overnight. It was then quenched by addition of a saturated aqueous solution of NaHCO$_3$ (100 mL) over a period of 10 min. The mixture was extracted with EtOAc (3×100 mL). The combined extracts were dried over MgSO$_4$ and concentrated to give product (IIb-45) as a yellow foam (1.92 g, 98%). $^1$H NMR (400 MHz, CDCl$_3$) δ 1.49 (t, J=7.2 Hz, 3H), 1.96-2.09 (m, 2H), 2.23-2.31 (m, 2H), 2.49-2.59 (m, 4H), 3.21 (tt, J=3.3 and 12.2 Hz, 1H), 4.53 (q, J=7.2 Hz, 2H), 7.47-7.53 (m, 2H), 7.58-7.62 (m, 1H), 7.73 (s, 1H), 8.22-8.25 (m, 2H), 8.26 (s, 1H), 8.29 (d, J=2.1 Hz, 1H), 8.43 (d, J=2.1 Hz, 1H).

methyl 4-(5-((1s,4s)-4-morpholinocyclohexyl)-1-(phenylsulfonyl)-1H-pyrrolo[2,3-b]pyridin-3-yl) thiazole-2-carboxylate (IIb-46) and methyl 4-(5-((1r,4r)-4-morpholinocyclohexyl)-1-(phenylsulfonyl)-1H-pyrrolo[2,3-b]pyridin-3-yl)thiazole-2-carboxylate (IIb-47)

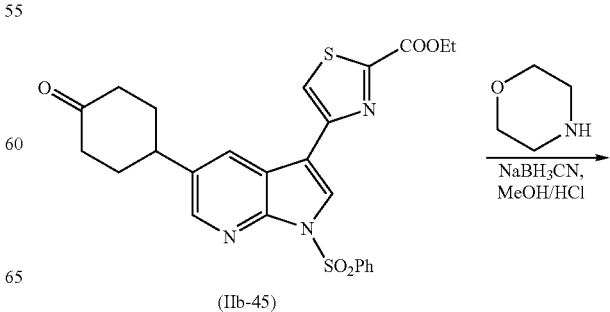

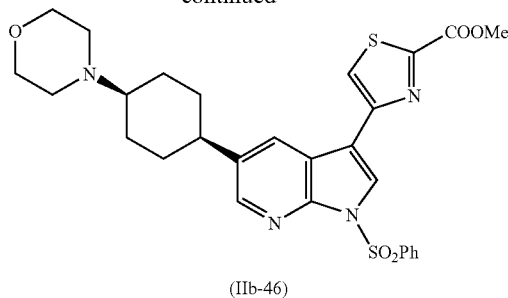

(IIb-46)

+

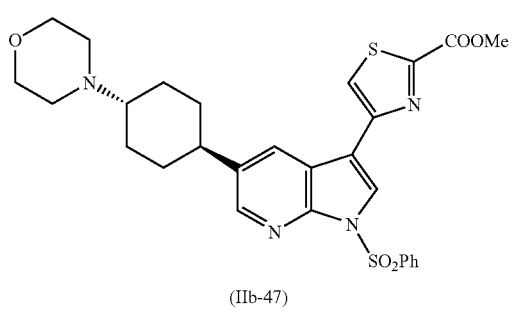

(IIb-47)

Ketone (IIb-45) (0.50 g, 0.98 mmol), morpholine (0.51 g, 5.88 mmol), 1.25 M HCl/MeOH (1.57 mL, 1.96 mmol) and NaCNBH$_3$ (0.12 g, 1.96 mmol) in anhydrous methanol (9.8 mL) were reacted following the general procedure A for the reductive amination. The crude product was purified by PTLC using CH$_2$Cl$_2$:MeOH=10:1 (v/v) to give methyl esters (IIb-46) (138 mg, 25%) and (IIb-47) (147 mg, 26%) as colorless oil.

Data for cis isomer (IIb-46): $^1$H NMR (400 MHz, CDCl$_3$) δ 1.45-1.68 (m, 4H), 1.92-2.05 (m, 4H), 2.43-2.53 (br m, 4H), 2.66-2.74 (m,1H), 2.77-2.88 (m, 1H), 3.72-3.79 (m, 4H), 4.06 (s, 3H), 7.46-7.54 (m, 2H), 7.55-7.60 (m, 1H), 7.75 (s, 1H), 8.20-8.28 (m, 4H), 8.43 (d, J=1.7 Hz, 1H).

Data for trans isomer (IIb-47): $^1$H NMR (400 MHz, CDCl$_3$) δ 1.37-1.62 (m, 4H), 1.97-2.14 (m, 4H), 2.30-2.41 (m, 1H), 2.58-2.69 (m, 5H), 3.75 (t, J=4.4 Hz, 4H), 4.06 (s, 3H), 7.46-7.51 (m, 2H), 7.55-7.60 (m, 1H), 7.73 (s, 1H), 8.19 (d, J=1.9 Hz, 1H), 8.20-8.25 (m, 2H), 8.26 (s, 1H), 8.36 (s, 1H).

4-(4-(3-(2-methylthiazol-4-yl)-1-(phenylsulfonyl)-1H-pyrrolo[2,3-b]pyridin-5-yl)cyclohex-3-enyl)morpholine (IIa-54)

Bromide (III-k) (1.07 g, 2.45 mmol), boronic acid pinacol ester (VIb-54) (863 mg, 2.94 mmol), LiCl (312 mg, 7.36 mmol), and Pd(PPh$_3$)$_2$Cl$_2$ (86 mg, 0.12 mmol), in EtOH (10 ml), toluene (10 ml) and 1.0 M Na$_2$CO$_3$ solution (4.0 ml) were reacted for 2 h under reflux using the general procedure A for the Suzuki reaction. Crude product (1.65 g; dark brown oil) was purified by SGC using AcOEt:CH$_2$Cl$_2$:MeOH (gradient elution from 50:50:0 to 45:45:10; v/v) to afford (IIa-54) (1.15 g, 2.21 mmol, 90%) as a pale brown foam. $^1$H NMR (400 MHz, CDCl$_3$) δ 1.57-1.69 (m, 1H), 2.16-2.31 (m, 2H), 2.43-2.73 (m, 8H), 2.83 (s, 3H), 3.79 (t, J=4.6 Hz, 2H), 6.07-6.12 (m, 1H), 7.32 (s, 1H), 7.49 (t, J=7.8 Hz, 2H), 7.59 (t, J=7.4 Hz, 1H), 8.17 (s, 1H), 8.17-8.21 (m, 3H), 8.53 (d, J=2.1 Hz, 1H).

4-((1r,4r)-4-(3-(2-methylthiazol-4-yl)-1-(phenylsulfonyl)-1H-pyrrolo[2,3-b]pyridin-5-yl)cyclohexyl)morpholine (IIb-55) 4-((1s,4s)-4-(3-(2-methylthiazol-4-yl)-1-(phenylsulfonyl)-1H-pyrrolo[2,3-b]pyridin-5-yl)cyclohexyl)morpholine (IIb-56)

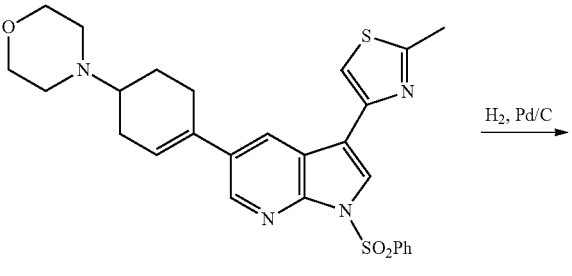

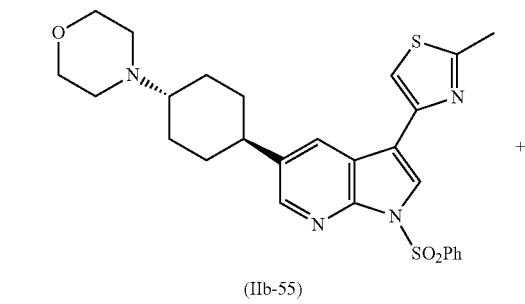

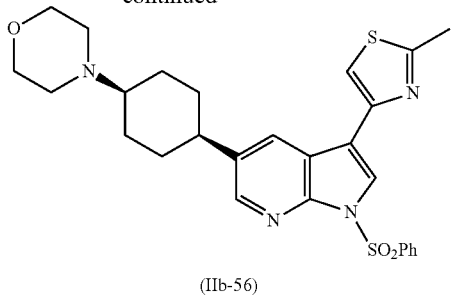

(IIb-56)

Compound (IIa-54) (140 mg, 0.27 mmol) was hydrogenated using the general procedure for hydrogenation of 7-azaindoles using 20% Pd(OH)$_2$/C (Degussa type, 50 mg) in EtOH (3 mL) and AcOEt (3 mL) over a period of 3 days. The reaction mixture was then filtered through Celite washing with ethanol (50 mL), and concentrated to afford crude reduction product as an oil (133 mg). The oil was purified by SGC using AcOEt:CH$_2$Cl$_2$:MeOH (gradient from 50:50:0 to 45:45:10 v/v). Eluting first was (IIb-56) (57 mg, 0.11 mmol, 41%) and then (IIb-55) (62 mg, 0.12 mmol, 44%).

Data for (IIb-55): $^1$H NMR (400 MHz, CDCl$_3$) δ 1.38-1.65 (m, 4H), 1.99-2.14 (m, 4H), 2.30-2.41 (m, 1H), 2.58-2.71 (m, 4H), 2.82 (s, 3H), 3.77 (t, J=4.6 Hz, 2H), 7.31 (s, 1H), 7.49 (t, J=7.6 Hz, 2H), 7.58 (tt, J=1.5, 7.4 Hz, 1H), 8.12 (d, J=2.1 Hz, 1H), 8.16 (s, 1H), 8.21-8.26 (m, 2H), 8.36 (d, J=2.1 Hz, 1H).

Data for (IIb-56): $^1$H NMR (400 MHz, CDCl$_3$) δ 1.51-1.69 (m, 4H), 1.93-2.09 (m, 4H), 2.26-2.31 (m, 1H), 2.43-2.56 (m, 4H), 2.77-2.87 (m, 4H), 3.76 (t, J=4.6 Hz, 2H), 7.32 (s, 1H), 7.49 (t, J=7.6 Hz, 2H), 7.58 (tt, J=1.5, 7.5 Hz, 1H), 8.16 (s, 1H), 8.22-8.26 (m, 2H), 8.20 (d, J=2.0 Hz, 1H), 8.43 (d, J=2.0 Hz, 1H).

4-(5-cyclohexenyl-1-(phenylsulfonyl)-1H-pyrrolo[2,3-b]pyridin-3-yl)-2-methylthiazole (IIa-57)

Bromide (III-k) (208 mg, 0.48 mmol), 2-cyclohexenyl-4,4,5,5-tetramethyl-1,3,2-dioxaborolane (130 mg, 0.62 mmol), LiCl (61 mg, 1.44 mmol), and Pd(PPh$_3$)$_2$Cl$_2$ (17 mg, 0.02 mmol), in EtOH (2 ml), toluene (2 ml) and 1.0 M Na$_2$CO$_3$ solution (0.72 mL) were reacted for 2 h under reflux using the general procedure A for the Suzuki reaction. Crude product (0.38 g; dark brown oil) was purified by SGC using AcOEt:CH$_2$Cl$_2$:MeOH (gradient elution from 50:50:0 to 45:45:10; v/v) to afford (IIa-57) (183 mg, 0.42 mmol, 88%) as a foam. $^1$H NMR (400 MHz, CDCl$_3$) δ 1.66-1.74 (m, 2H), 1.79-1.87 (m, 2H), 2.21-2.29 (m, 2H), 2.42-2.50 (m, 2H), 2.82 (s, 3H), 6.12-6.16 (m, 1H), 7.32 (s, 1H), 7.49 (t, J=7.6 Hz, 2H), 7.58 (tt, J=1.5, 7.5 Hz, 1H), 8.17 (s, 1H), 8.21-8.26 (m, 3H), 8.53 (d, J=2.2 Hz, 1H).

4-(5-cyclohexyl-1-(phenylsulfonyl)-1H-pyrrolo[2,3-b]pyridin-3-yl)-2-methylthiazole (IIb-58)

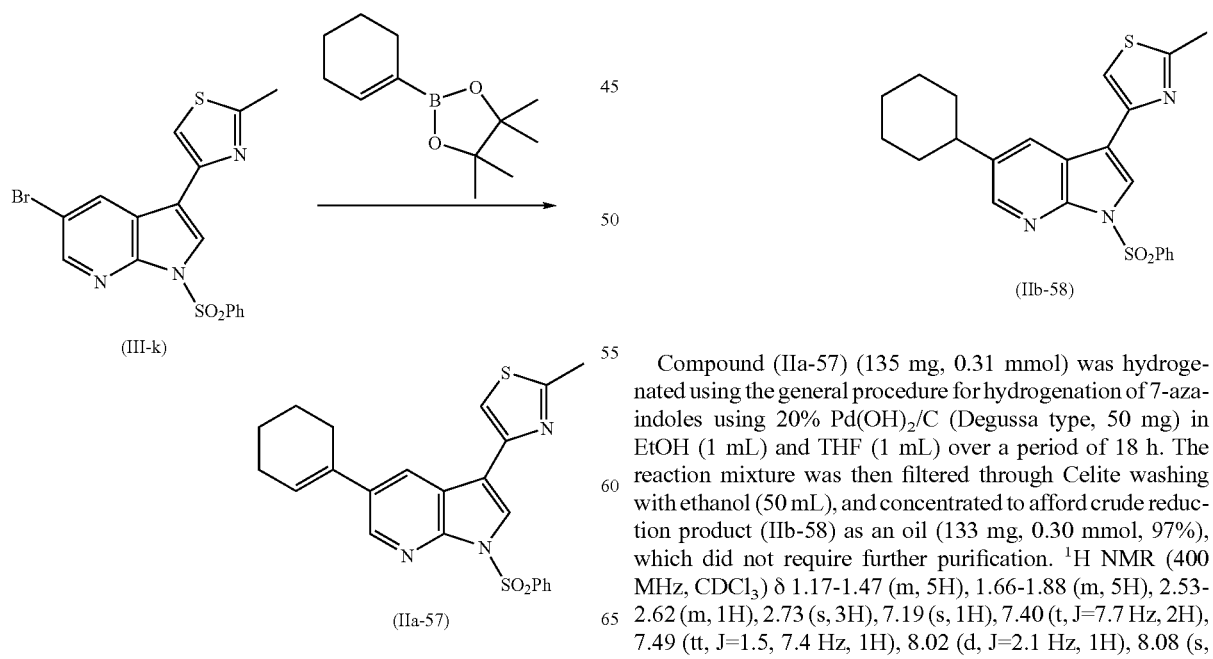

Compound (IIa-57) (135 mg, 0.31 mmol) was hydrogenated using the general procedure for hydrogenation of 7-azaindoles using 20% Pd(OH)$_2$/C (Degussa type, 50 mg) in EtOH (1 mL) and THF (1 mL) over a period of 18 h. The reaction mixture was then filtered through Celite washing with ethanol (50 mL), and concentrated to afford crude reduction product (IIb-58) as an oil (133 mg, 0.30 mmol, 97%), which did not require further purification. $^1$H NMR (400 MHz, CDCl$_3$) δ 1.17-1.47 (m, 5H), 1.66-1.88 (m, 5H), 2.53-2.62 (m, 1H), 2.73 (s, 3H), 7.19 (s, 1H), 7.40 (t, J=7.7 Hz, 2H), 7.49 (tt, J=1.5, 7.4 Hz, 1H), 8.02 (d, J=2.1 Hz, 1H), 8.08 (s, 1H), 8.13-8.17 (m, 2H), 8.28 (d, J=2.0 Hz, 1H).

4-((1r,4r)-4-(1-(tert-butyldimethylsilyl)-3-(thiazol-4-yl)-1H-pyrrolo[2,3-b]pyridin-5-yl)cyclohexyl)morpholine (IIb-59)—see preparation of (I-59)

4-((1r,4r)-4-(1-(tert-butyldimethylsilyl)-3-(thiazol-5-yl)-1H-pyrrolo[2,3-b]pyridin-5-yl)cyclohexyl)morpholinee (IIb-60)—see preparation of (I-60)

4-((1r,4r)-4-(1-(tert-butyldimethylsilyl)-3-(4-methylthiazol-2-yl)-1H-pyrrolo[2,3-b]pyridin-5-yl)cyclohexyl)morpholine (IIb-61)—see preparation of (I-61)

4-((1r,4r)-4-(1-(tert-butyldimethylsilyl)-3-(5-methylthiazol-2-yl)-1H-pyrrolo[2,3-b]pyridin-5-yl)cyclohexyl)morpholine (IIb-62)—see preparation of (I-62)

4-((1r,4r)-4-(1-(tert-butyldimethylsilyl)-3-(2-ethoxythiazol-4-yl)-1H-pyrrolo[2,3-b]pyridin-5-yl)cyclohexyl)morpholine (IIb-63)—see preparation of (I-63)

4-((1r,4r)-4-(1-(tert-butyldimethylsilyl)-3-(4,5-dimethylthiazol-2-yl)-1H-pyrrolo[2,3-b]pyridin-5-yl)cyclohexyl)morpholine (IIb-64)—see preparation of (I-64)

2-(1-(phenylsulfonyl)-5-(1,4-dioxaspiro[4.5]dec-7-en-8-yl)-1H-pyrrolo[2,3-b]pyridin-3-yl)-4-(trifluoromethyl)thiazole (IIa-65)

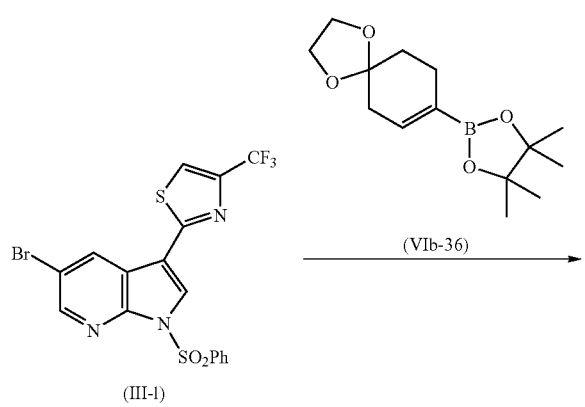

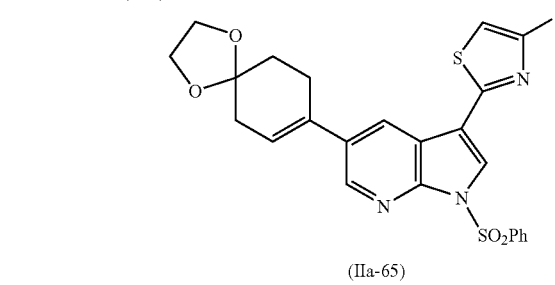

Bromide (III-I) (1.26 g, 2.58 mmol), boronate (VIb-36) (690 mg, 2.58 mmol), LiCl (330 mg, 7.74 mmol), and Pd(PPh$_3$)$_2$Cl$_2$ (110 mg, 0.15 mmol), in EtOH (8 mL), toluene (8 mL) and 1.0 M Na$_2$CO$_3$ solution (3.87 mL, 3.87 mmol) were reacted for 3 h under reflux using the general procedure A for the Suzuki reaction. Crude product (2.64 g; dark brown oil) was purified by SGC using AcOEt:hexanes=1:1 (v/v) to afford a pale brown foam, which was further purified by trituration with Et$_2$O to afford (IIa-65) as a white powder (1.26 g, 2.30 mmol, 89%) $^1$H NMR (400 MHz, CDCl$_3$) δ 1.99 (t, J=6.3 Hz, 2H), 2.51-2.56 (m, 2H), 2.71-2.78 (m, 2H), 4.06 (s, 4H), 6.05-6.09 (m, 1H), 7.54 (t, J=7.7 Hz, 2H), 7.64 (tt, J=1.5, 7.5 Hz, 1H), 7.76 (q, J=0.8 Hz, 1H), 8.25-8.30 (m, 2H), 8.32 (s, 1H), 8.53 (d, J=2.2Hz, 1H), 8.61 (d, J=2.2Hz, 1H).

2-(1-(phenylsulfonyl)-5-(1,4-dioxaspiro[4.5]decan-8-yl)-1H-pyrrolo[2,3-b]pyridin-3-yl)-4-(trifluoromethyl)thiazole (IIb-66)

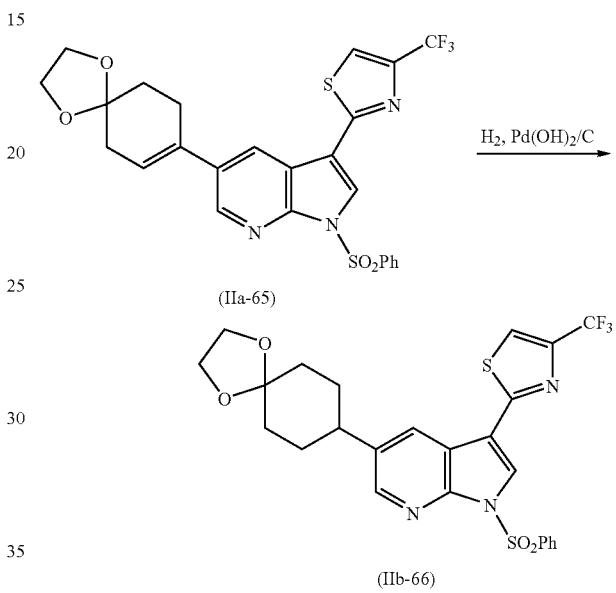

Compound (IIa-65) (1.26 g, 2.30 mmol) was hydrogenated using the general procedure for hydrogenation of 7-azaindoles using 20% Pd(OH)$_2$/C (Degussa type, 100 mg) in EtOH (5 mL) and THF (5 mL) over a period of 3 d. The reaction mixture was then filtered through Celite washing with ethanol (100 mL), and concentrated to afford the reduction product (IIb-66) (1.11 g, 2.06 mmol, 88%). $^1$H NMR (400 MHz, CDCl$_3$) δ 1.70-2.00 (m, 8H), 2.73-2.82 (m, 1H), 4.02 (s, 4H), 6.05-6.09 (m, 1H), 7.54 (t, J=7.8 Hz, 2H), 7.64 (t, J=7.5 Hz, 1H), 7.76 (s, 1H), 8.26-8.32 (m, 2H), 8.33 (s, 1H), 8.37 (d, J=2.1 Hz, 1H), 8.45 (d, J=2.1 Hz, 1H).

4-(1-(phenylsulfonyl)-3-(4-(trifluoromethyl)thiazol-2-yl)-1H-pyrrolo[2,3-b]pyridine-5-yl)cyclohexanone (IIb-67)

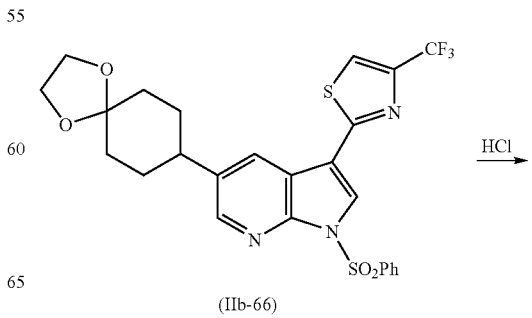

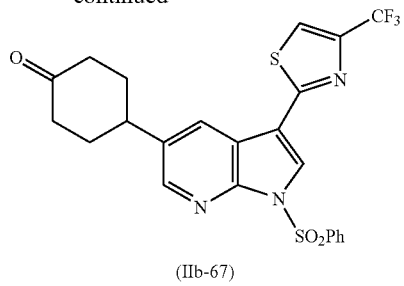

(IIb-67)

6.0 M aqueous HCl (7 mL, 42 mmol) was added to a stirred solution of (IIb-66) (1.13 g, 2.06 mmol) in THF (20 mL) and the reaction mixture was stirred at r.t. for 2 h. The solution was then added slowly to saturated aqueous NaHCO₃ (100 mL), and the mixture was extracted with AcOEt (3×100 mL). The combined organic extracts were dried over MgSO₄ and concentrated to afford (IIb-67) as a clear oil (1.04 g, 2.06 mmol, 100%). ¹H NMR (400 MHz, CDCl₃) δ 1.98-2.12 (m, 2H), 2.24-2.33 (m, 1H), 2.54-2.63 (m, 4H), 3.25 (tt, J=3.2, 12.1 Hz, 1H), 7.56 (t, J=7.7 Hz, 2H), 7.65 (t, J=7.6 Hz, 1H), 7.77 (s, 1H), 8.27-8.31 (m, 2H), 8.33 (s, 1H), 8.47 (s, 2H).

4-(4-(1-(phenylsulfonyl)-3-(4-(trifluoromethyl)thiazol-2-yl)-1H-pyrrolo[2,3-b]pyridin-5-yl)cyclohex-3-enyl)morpholine (IIa-68)

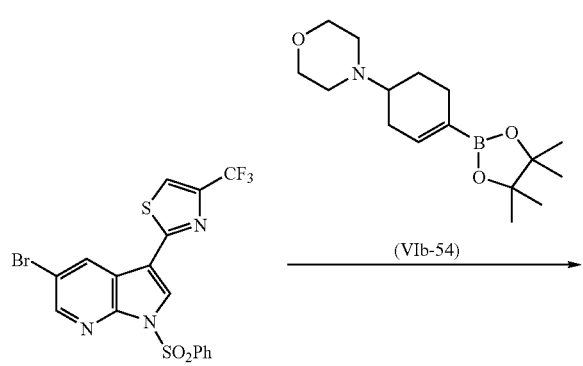

(III-1)    (VIb-54)

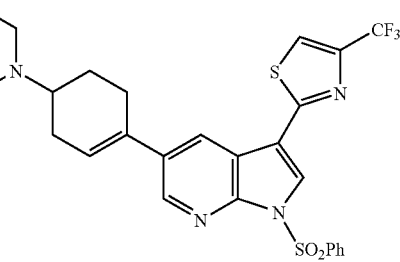

(IIa-68)

Bromide (III-I) (455 mg, 0.93 mmol), boronate (VIb-54) (360 mg, 1.23 mmol), LiCl (120 mg, 2.83 mmol), and Pd(PPh₃)₂Cl₂ (50 mg, 0.07 mmol), in EtOH (4 mL), toluene (4 mL) and 1.0 M Na₂CO₃ solution (2.0 mL, 2.0 mmol) were reacted for 16 h under reflux using the general procedure A for the Suzuki reaction. Crude product (676 mg; dark brown oil) was purified by SGC using AcOEt:CH₂Cl₂:MeOH (gradient from 50:50:0 to 45:45:10, v/v) to afford impure product (378 mg) which was further purified by trituration with Et₂O (5 mL) to afford (IIa-68) as a white powder (285 mg, 0.50 mmol, 53%). ¹H NMR (400 MHz, CDCl₃) δ 1.59-1.71 (m, 1H), 2.18-2.33 (m, 2H), 2.45-2.73 (m, 8H), 3.79 (t, J=4.6 Hz, 4H), 6.11-6.16 (m, 1H), 7.54 (t, J=7.8 Hz, 2H), 7.64 (t, J=7.5 Hz, 1H), 7.76 (s, 1H), 8.26-8.30 (m, 2H), 8.32 (s, 1H), 8.51 (d, J=2.1 Hz, 1H), 8.58 (d, J=2.1 Hz, 1H).

4-((1r,4r)-4-(1-(phenylsulfonyl)-3-(4-(trifluoromethyl)thiazol-2-yl)-1H-pyrrolo[2,3-b]pyridin-5-yl)cyclohexyl)morpholine (IIb-69) 4-((1s,4s)-4-(1-(phenylsulfonyl)-3-(4-(trifluoromethyl)thiazol-2-yl)-1H-pyrrolo[2,3-b]pyridin-5-yl)cyclohexyl)morpholine (IIb-70)

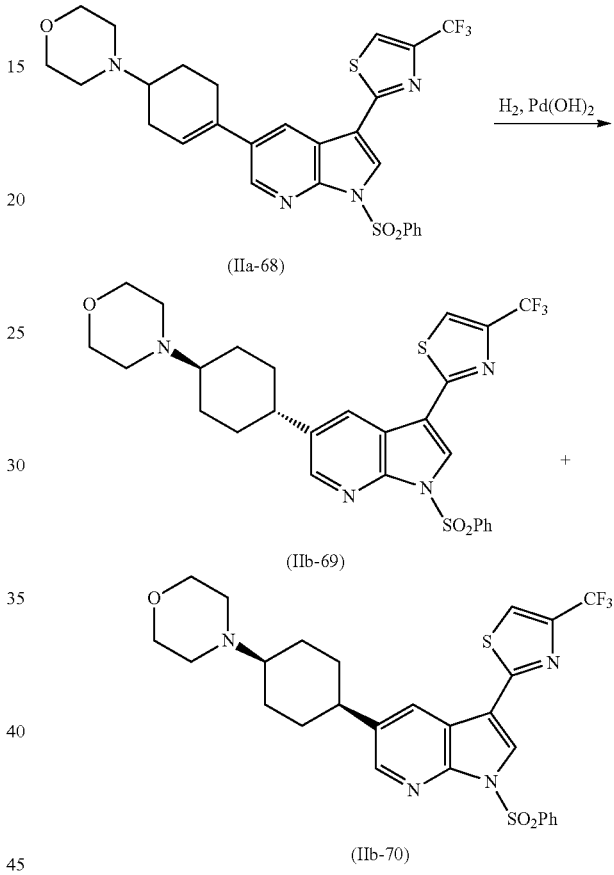

Compound (IIa-68) (285 mg, 0.50 mmol) was hydrogenated using the general procedure for hydrogenation of 7-azaindoles using 20% Pd(OH)₂/C (Degussa type, 100 mg) in EtOH (5 mL) and THF (5 mL) over a period of 4 d. The reaction mixture was then filtered through Celite washing with ethanol (100 mL), and concentrated to afford the reduction product (261 mg) as oil. The oil was purified by SGC (NH silica, Fuji Silysia) using CH₂Cl₂:hexanes (gradient from 1:2 to 2:1, v/v) to afford the cis isomer (IIb-70) (58 mg, 0.10 mmol, 20%). Next to elute was the trans isomer (IIb-69) (78 mg, 0.14 mmol, 27%).

Data for the trans isomer (IIb-69): ¹H NMR (400 MHz, CDCl₃) δ 1.39-1.66 (m, 4H), 2.00-2.15 (m, 4H), 2.32-2.42 (m, 1H), 2.59-2.74 (m, 5H), 3.77 (t, J=4.6 Hz, 4H), 7.54 (t, J=7.8 Hz, 2H), 7.64 (tt, J=1.5, 7.5 Hz, 1H), 7.76 (q, J=0.8 Hz, 1H), 8.25-8.30 (m, 2H), 8.32 (s, 1H), 8.38 (d, J=2.1 Hz, 1H), 8.41 (d, J=2.1 Hz, 1H).

Data for the cis isomer (IIb-70): ¹H NMR (400 MHz, CDCl₃) δ 1.52-1.68 (m, 4H), 1.95-2.11 (m, 4H), 2.26-2.33 (m, 1H), 2.43-2.57 (m, 4H), 2.80-2.91 (m, 1H), 3.72-3.84 (m, 4H), 6.11-6.16 (m, 1H), 7.55 (t, J=7.8 Hz, 2H), 7.65 (t, J=7.4 Hz, 1H), 7.76 (s, 1H), 8.25-8.33 (m, 3H), 8.46 (d, J=2.1 Hz, 1H), 8.51 (d, J=2.1 Hz, 1H).

2-methyl-4-(1-(phenylsulfonyl)-5-(1,4-dioxaspiro[4.5]dec-7-en-8-yl)-1H-pyrrolo[2,3-b]pyridin-3-yl)thiazole (IIa-71)

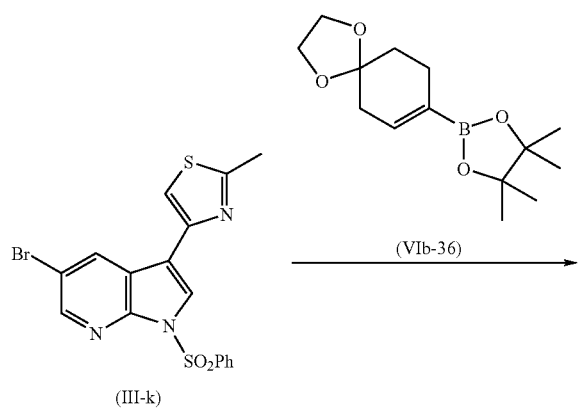

Bromide (III-k) (1.87 g, 4.31 mmol), boronate (VIb-36) (1.66 g, 6.23 mmol), LiCl (550 mg, 12.92 mmol), and Pd(PPh$_3$)$_2$Cl$_2$ (150 mg, 0.22 mmol), in EtOH (10 mL), toluene (10 mL) and 1.0 M Na$_2$CO$_3$ solution (5.2 mL, 5.2 mmol) were reacted for 2 h under reflux using the general procedure A for the Suzuki reaction. Crude product (3.61 g; dark brown oil) was purified by SGC using AcOEt:CH$_2$Cl$_2$:hexanes=1:1:2 (v/v/v) to afford a pale brown foam (2.09 g), which was further purified by trituration with Et$_2$O (25 mL) to afford (IIa-71) (1.71 g, 3.46 mmol, 80%) as a white powder. $^1$H NMR (400 MHz, CDCl$_3$) δ 1.97 (t, J=6.5 Hz, 2H), 2.50-2.54 (m, 2H), 2.70-2.76 (m, 2H), 2.82 (s, 3H), 4.06 (s, 4H), 6.00-6.04 (m, 1H), 7.49 (t, J=7.7 Hz, 2H), 7.58 (tt, J=1.5, 7.5 Hz, 1H), 8.17 (s, 1H), 8.21-8.25 (m, 2H), 8.28 (d, J=2.1 Hz, 1H), 8.55 (d, J=2.1 Hz, 1H).

2-methyl-4-(1-(phenylsulfonyl)-5-(1,4-dioxaspiro[4.5]decan-8-yl)-1H-pyrrolo[2,3-b]pyridin-3-yl)thiazole (IIb-72)

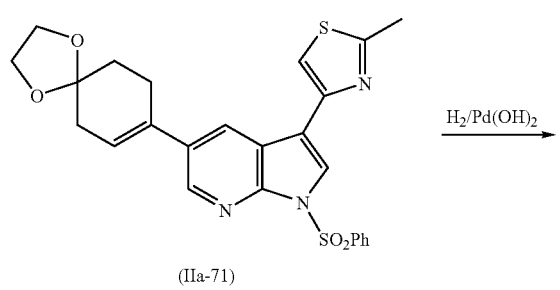

Compound (IIa-71) (1.71 g, 3.47 mmol) was hydrogenated using the general procedure for hydrogenation of 7-azaindoles using 20% Pd(OH)$_2$/C (Degussa type, 250 mg) in EtOH (10 mL) and THF (10 mL) over a period of 3 d. The reaction mixture was then filtered through Celite washing with ethanol (200 mL), and concentrated to afford (IIb-72) (1.67 g, 3.37 mmol, 97%). $^1$H NMR (400 MHz, CDCl$_3$) δ 1.70-1.96 (m, 8H), 2.70-2.80 (m, 1H), 2.83 (s, 3H), 4.02 (s, 4H), 7.32 (s, 1H), 7.49 (t, J=7.6 Hz, 2H), 7.59 (tt, J=1.5, 7.4 Hz, 1H), 8.14 (d, J=2.0 Hz, 1H), 8.18 (s, 1H), 8.22-8.26 (m, 2H), 8.39 (d, J=2.0 Hz, 1H).

4-(3-(2-methylthiazol-4-yl)-1-(phenylsulfonyl)-1H-pyrrolo[2,3-b]pyridin-5-yl)cyclohexanone (IIb-73)

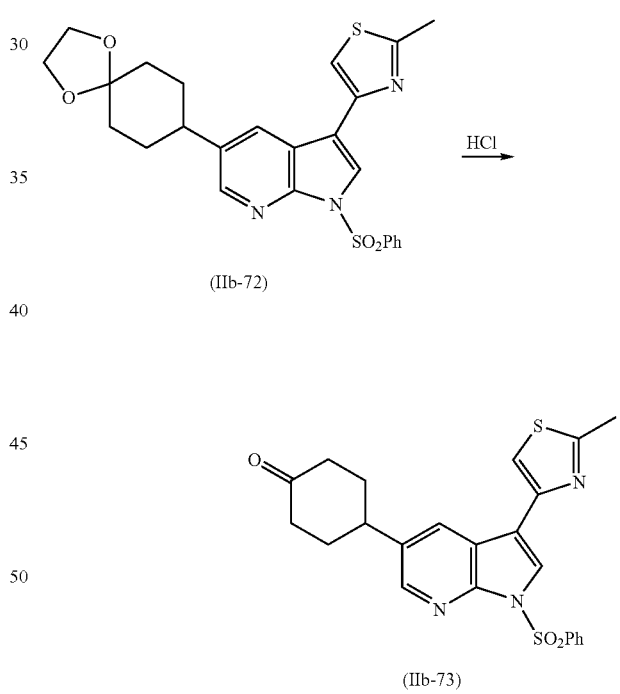

To a stirred solution of (IIb-72) (1.71 g, 3.45 mmol) in THF (50 mL) was added 6.0 M aqueous HCl (15 mL, 90 mmol) and the reaction mixture was stirred at r.t. for 2 h. The solution was then added slowly to saturated aqueous NaHCO$_3$ (200 mL), and the mixture was extracted with AcOEt (3×150 mL). The combined organic extracts were dried (MgSO$_4$) and concentrated to afford (IIb-73) (1.37 g, 3.03 mmol, 88%) as a clear oil. $^1$H NMR (400 MHz, CDCl$_3$) δ 1.98-2.10 (m, 2H), 2.24-2.33 (m, 2H), 2.52-2.61 (m, 4H), 2.83 (s, 3H), 3.22 (tt, J 3.4, 12.2 Hz, 1H), 7.32 (s, 1H), 7.51 (t, J=7.7 Hz, 2H), 7.60 (tt, J=1.5, 7.5 Hz, 1H), 8.16 (s, 1H), 8.22-8.27 (m, 3H), 8.42 (d, J=2.1 Hz, 1H).

2-methyl-4-(1-(phenylsulfonyl)-5-((1r,4r)-4-(pyrrolidin-1-yl)cyclohexyl)-1H-pyrrolo[2,3-b]pyridin-3-yl)thiazole (IIb-74)

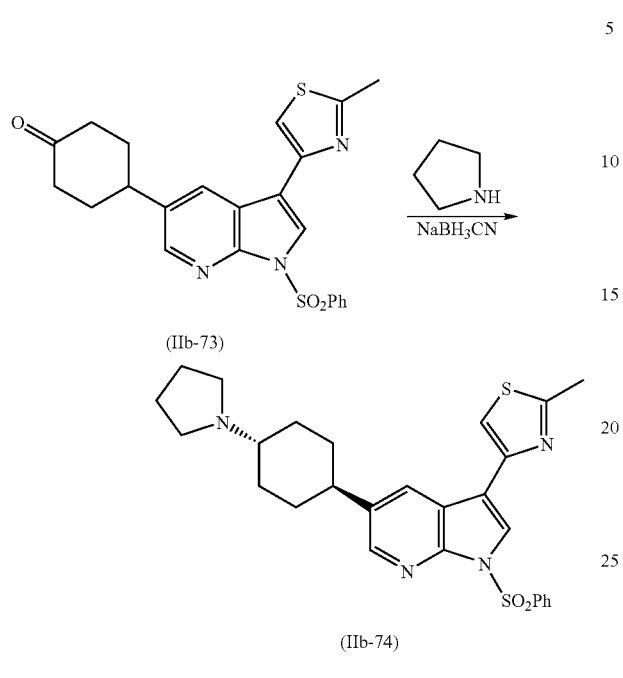

Ketone (IIb-73) (371 mg, 0.82 mmol), pyrrolidine (500 mg, 7.03 mmol), 1.25 M HCl/MeOH (2.50 mL, 3.13 mmol) in anhydrous methanol (2 mL) were reacted with NaCNBH$_3$ (100 mg, 1.59 mmol) added at −20° C. as solution in MeOH (2 mL) following the general procedure A for the reductive amination. The crude product (380 mg) was purified by SGC using AcOEt:CH$_2$Cl$_2$:MeOH:Et$_3$N as eluent (gradient from 47:47:5:1 to 42:42:15:1; v/v/v/v) to afford (IIb-74) as a white powder (177 mg, 0.35 mmol, 43%). $^1$H NMR (400 MHz, CDCl$_3$) δ 1.54-1.67 (m, 2H), 1.70-1.83 (m, 2H), 1.98-2.09 (m, 6H), 2.07-2.28 (m, 2H), 2.68-2.80 (m, 2H), 2.82 (s, 3H), 3.05-3.14 (m, 4H), 7.33 (s, 1H), 7.49 (t, J=7.7 Hz, 2H), 7.59 (tt, J=1.5, 7.5 Hz, 1H), 8.15 (d, J=2.1 Hz, 1H), 8.16 (s, 1H), 8.20-8.24 (m, 3H), 8.34 (d, J=2.1 Hz, 1H). The relevant cis isomer was also formed in the reaction but was not isolated.

4-((1r,4r)-4-(3-(2-methylthiazol-4-yl)-1-(phenylsulfonyl)-1H-pyrrolo[2,3-b]pyridin-5-yl)cyclohexyl)-1,4-oxazepane (IIb-75) and 4-((1s,4s)-4-(3-(2-methylthiazol-4-yl)-1-(phenylsulfonyl)-1H-pyrrolo[2,3-b]pyridin-5-yl)cyclohexyl)-1,4-oxazepane (IIb-76)

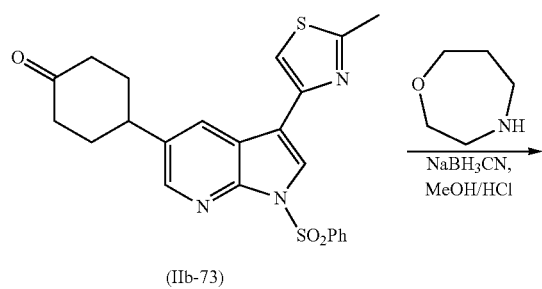

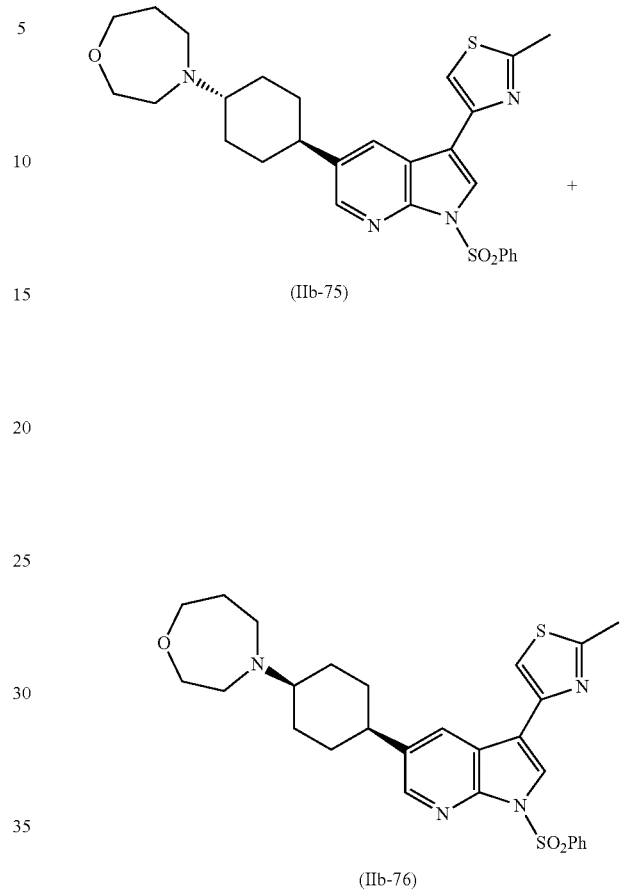

Ketone (IIb-73) (603 mg, 1.34 mmol), perhydro-1,4-oxazepine hydrochloride (1.47 g, 10.68 mmol), iPr$_2$NEt (690 mg, 5.34 mmol) in anhydrous methanol (8 mL) were reacted with NaBH$_3$CN (168 mg, 2.67 mmol) added at −20° C. as a 5 solution in MeOH (5 mL) following the general procedure A for the reductive amination. The crude product (877 mg, an oil), was purified by SGC using AcOEt:MeOH as eluent (gradient from 98:2 to 85:15, v/v). First to elute was the cis isomer (IIb-76) (223 mg, 0.42 mmol, 31%) as a clear oil. Further elution afforded the trans isomer (IIb-75) (343 mg, 0.64 mmol, 49%) as a solid. Data for trans isomer (IIb-75): $^1$H NMR (400 MHz, CDCl$_3$) δ 1.45-1.58 (m, 2H), 1.59-1.74 (m, 2H), 1.89-2.17 (m, 6H), 2.65 (tt, J=3.6, 11.7 Hz, 1H), 2.72-2.84 (m, 1H), 2.83 (s, 3H), 2.88-2.99 (m, 4H), 3.76-3.88 (m, 4H), 7.31 (s, 1H), 7.49 (t, J=7.7 Hz, 2H), 7.58 (tt, J=1.5, 7.4 Hz, 1H), 8.13 (d, J=2.1 Hz, 1H), 8.16 (s, 1H), 8.21-8.25 (m, 3H), 8.35 (d, J=2.1 Hz, 1H).

Data for cis isomer (IIb-76): $^1$H NMR (400 MHz, CDCl$_3$) δ 1.60-2.14 (m, 10H), 2.82 (s, 3H), 2.83-2.99 (m, 6H), 3.75-3.87 (m, 4H), 7.34 (s, 1H), 7.50 (t, J=7.6 Hz, 2H), 7.59 (tt, J=1.5, 7.5 Hz, 1H), 8.17 (s, 1H), 8.22-8.26 (m, 3H), 8.44 (d, J=2.1 Hz, 1H).

4-(4-(3-(4-(1-methylpiperidin-4-yl)thiazol-2-yl)-1-(phenylsulfonyl)-1H-pyrrolo[2,3-b]pyridin-5-yl)cyclohex-3-enyl)morpholine (IIa-77)

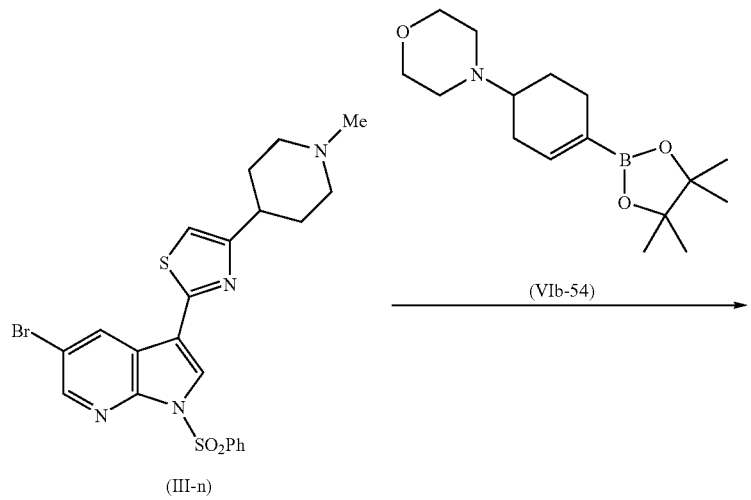

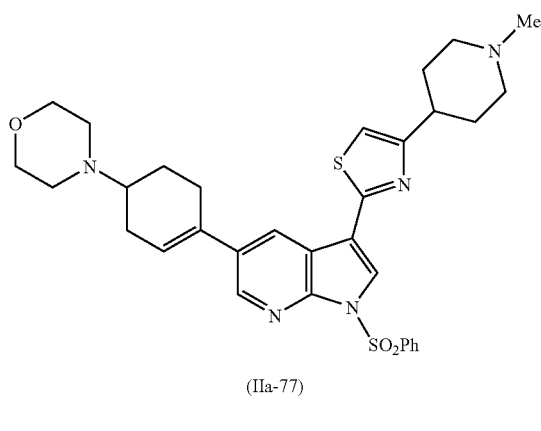

Bromide (III-n) (778 mg, 1.50 mmol), boronate (VIb-54) (510 mg, 1.73 mmol), LiCl (191 mg, 4.51 mmol), and Pd(PPh$_3$)$_2$Cl$_2$ (50 mg, 0.07 mmol), in EtOH (4 mL), toluene (4 mL) and 1.0 M Na$_2$CO$_3$ solution (2 mL, 2 mmol) were reacted for 16 h under reflux using the general procedure A for the Suzuki reaction. Crude product (1.14 g; dark brown oil) was purified by SGC using AcOEt:CH$_2$Cl$_2$:MeOH (gradient from 47.5:47:5:5 to 42.5:42.5:15, v/v/v) to afford 592 mg of nearly pure material, which was further purified by trituration with Et$_2$O (10 mL) to afford (IIa-77) (577 mg, 0.96 mmol, 64%) as a white powder. $^1$H NMR (400 MHz, CDCl$_3$) δ 1.57-1.73 (m, 2H), 1.83-1.98 (m, 2H), 2.10-2.33 (m, 6H), 2.38 (s, 3H), 2.45-2.55 (m, 1H), 2.57-2.73 (m, 6H), 2.79-2.91 (m, 1H), 2.98-3.09 (m, 2H), 3.80 (t, J=4.6 Hz, 2H), 6.09-6.13 (m, 1H), 6.92 (s, 1H), 7.51 (t, J=7.7 Hz, 2H), 7.61 (tt, J=7.4, 1.5 Hz, 1H), 8.22-8.28 (m, 3H), 8.47 (d, J=2.2 Hz, 1H), 8.55 (d, J=2.2 Hz, 1H).

4-((1r,4r)-4-(3-(4-(1-methylpiperidin-4-yl)thiazol-2-yl)-1-(phenylsulfonyl)-1H-pyrrolo[2,3-b]pyridin-5-yl)cyclohexyl)morpholine (IIb-78) and 4-((1s,4s)-4-(3-(4-(1-methylpiperidin-4-yl)thiazol-2-yl)-1-(phenylsulfonyl)-1H-pyrrolo[2,3-b]pyridin-5-yl)cyclohexyl)morpholine (IIb-79)

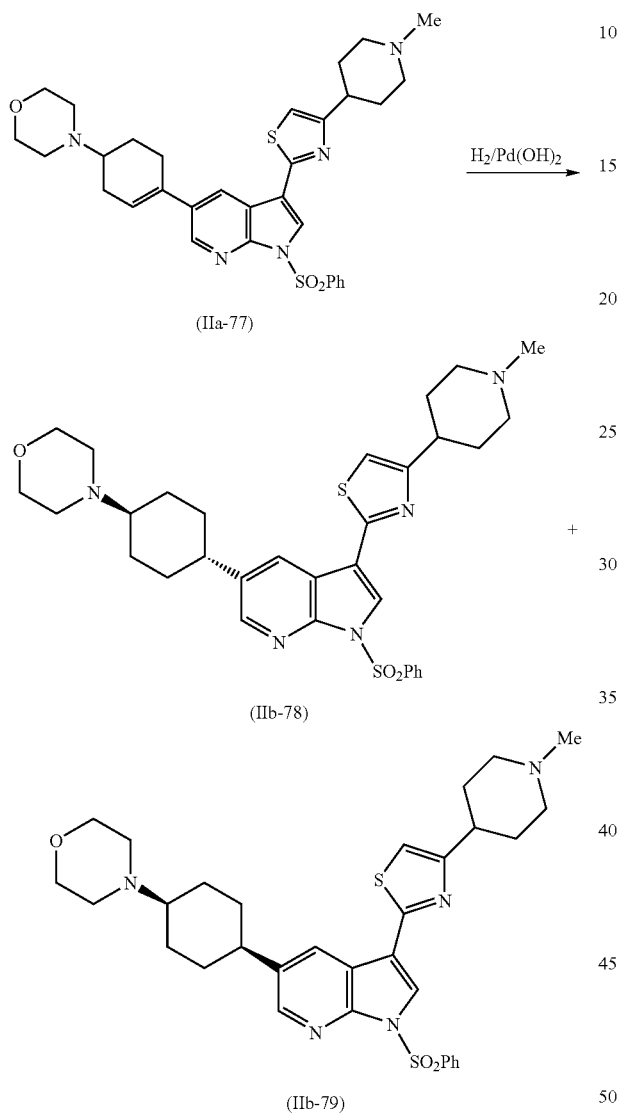

Data for the cis isomer (IIb-79): $^1$H NMR (400 MHz, CDCl$_3$) δ 1.26-1.59 (m, 4H), 1.76-1.99 (m, 6H), 2.03-2.13 (m, 4H), 2.18-2.23 (m, 1H), 2.29 (s, 3H), 2.36-2.46 (m, 4H), 2.71-2.81 (m, 2H), 2.89-2.98 (m, 2H), 3.67 (t, J=4.5 Hz, 4H), 6.83 (s, 1H), 7.43 (t, J=7.7 Hz, 2H), 7.52 (tt, J=7.4, 1.5 Hz, 1H), 8.12-8.19(m, 3H), 8.33-8.37 (m, 2H).

4-((1r,4r)-4-(1-(phenylsulfonyl)-3-(4-(trifluoromethyl)thiazol-2-yl)-1H-pyrrolo[2,3-b]pyridin-5-yl)cyclohexyl)-1,4-oxazepane (IIb-80) and 4-((1s,4s)-4-(1-(phenylsulfonyl)-3-(4-(trifluoromethyl)thiazol-2-yl)-1H-pyrrolo[2,3-b]pyridin-5-yl)cyclohexyl)-1,4-oxazepane (IIb-81)

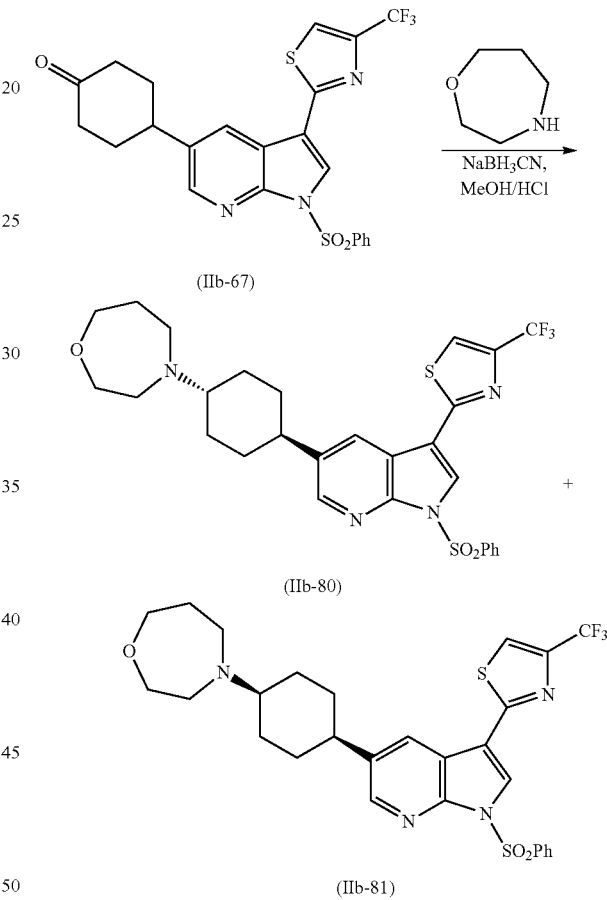

Compound (IIa-77) (577 mg, 0.96 mmol) was hydrogenated using the general procedure for hydrogenation of 7-azaindoles using 20% Pd(OH)$_2$/C (Degussa type, 100 mg) in EtOH (10 mL) and THF (10 mL) over a period of 3 d. The reaction mixture was then filtered through Celite washing with ethanol (100 mL), and concentrated to afford the reduction product (535 mg) as oil. The oil was purified by SGC using CH$_2$Cl$_2$:MeOH:Et$_3$N (gradient from 10:0:0.05 to 8:2:0.05, v/v/v) to afford the cis isomer (IIb-79) (149 mg, ~80% pure, 0.20 mmol, 21%). Next to elute was the trans isomer (IIb-78) (276 mg, ~80% pure, 0.36 mmol, 38%).

Data for the trans isomer (IIb-78): $^1$H NMR (400 MHz, CDCl$_3$) δ 1.42-1.79 (m, 4H), 1.89-2.34 (m, 6H), 2.40-2.80 (m, 1OH), 3.03-3.17 (m, 6H), 3.71-3.91 (m, 4H), 6.96 (s, 1H), 7.52 (t, J=7.6 Hz, 2H), 7.62 (t, J=7.6 Hz, 1H), 8.22-8.29 (m, 3H), 8.35-8.40 (m, 2H).

Ketone (IIb-67) (250 mg, 0.49 mmol), perhydro-1,4-oxazepine hydrochloride (400 mg, 3.96 mmol), iPr$_2$NEt (256 mg, 1.98 mmol) in anhydrous methanol (6 mL) were reacted with NaBH$_3$CN (62 mg, 0.99 mmol) added at −20° C. as a solution in MeOH (4 mL) following the general procedure A for the reductive amination. The crude product (356 mg, an oil), was purified by SGC using AcOEt:CH$_2$Cl$_2$:MeOH as eluent (gradient from 49:49:2 to 42.5:42.5:15, v/v/v). First to elute was the cis isomer (IIb-81) (74 mg, 0.13 mmol, 25%). Further elution afforded the trans isomer (IIb-80) (97 mg, 0.16 mmol, 33%) as a solid.

Data for trans isomer (IIb-80): $^1$H NMR (400 MHz, CDCl$_3$) δ 1.46-1.68 (m, 4H), 1.92-2.00 (m, 2H), 2.01-2.12 (m, 4H), 2.63-2.82 (m, 2H), 2.87-2.96 (m, 4H), 3.79 (t, J=4.6 Hz, 2H), 3.84 (t, J=6.0 Hz, 2H), 7.54 (t, J=7.7 Hz, 2H), 7.64

(tt, J=1.5, 7.5 Hz, 1H), 7.76 (q, J=0.8 Hz, 1H), 8.26-8.30 (m, 2H), 8.32 (s, 1H), 8.38 (d, J=2.1 Hz, 1H), 8.41 (d, J=2.1 Hz, 1H).

Data for cis isomer (IIb-81): $^1$H NMR (400 MHz, CDCl$_3$) δ 1.58-1.75 (m, 4H), 1.84-1.99 (m, 4H), 2.01-2.12 (m, 2H), 2.77-2.96 (m, 6H), 3.77 (t, J=4.9 Hz, 2H), 3.83 (t, J=5.9 Hz, 2H), 7.55 (t, J=7.8 Hz, 2H), 7.64 (tt, J=1.5, 7.5 Hz, 1H), 7.75 (q, J=0.8 Hz, 1H), 8.26-8.32 (m, 3H), 8.48 (d, J=2.0 Hz, 1H), 8.50 (d, J=2.0 Hz, 1H).

2-(5-((1r,4r)-4-(4-methylpiperazin-1-yl)cyclohexyl)-1-(phenylsulfonyl)-1H-pyrrolo[2,3-b]pyridin-3-yl)-4-(trifluoromethyl)thiazole (IIb-82) and 2-(5-((1s,4s)-4-(4-methylpiperazin-1-yl)cyclohexyl)-1-(phenylsulfonyl)-1H-pyrrolo[2,3-b]pyridin-3-yl)-4-(trifluoromethyl)thiazole (IIb-83)

(m, 2H), 2.48 (s, 3H), 2.65-3.00 (m, 10H), 3.03-3.02 (m, 1H), 7.54 (t, J=7.8 Hz, 2H), 7.64 (tt, J=7.4 Hz, 1H), 7.76 (q, J=0.8 Hz, 1H), 8.25-8.30 (m, 3H), 8.31 (s, 1H), 8.37 (d, J=2.0 Hz, 1H), 8.40 (d, J=2.0 Hz, 1H).

Data for cis isomer (IIb-83): $^1$H NMR (400 MHz, CDCl$_3$) δ 1.20-1.26 (m, 1H), 1.51-1.68 (m, 4H), 1.95-2.09 (m, 4H), 2.28-2.37 (m, 5H), 2.38-2.73 (m, 6H), 2.81-2.90 (m, 1H), 7.56 (t, J=7.7 Hz, 2H), 7.63 (t, J=7.4 Hz, 1H), 7.76 (s, 1H), 8.26-8.31 (m, 3H), 8.46 (d, J=2.0 Hz, 1H), 8.50 (d, J=2.0 Hz, 1H).

2-(1-(phenylsulfonyl)-5-((1r,4r)-4-(pyrrolidin-1-yl)cyclohexyl)-1H-pyrrolo[2,3-b]pyridin-3-yl)-4-(trifluoromethyl)thiazole (IIb-84) and 2-(1-(phenylsulfonyl)-5-((1s,4s)-4-(pyrrolidin-1-yl)cyclohexyl)-1H-pyrrolo[2,3-b]pyridin-3-yl)-4-(trifluoromethyl)thiazole (IIb-85)

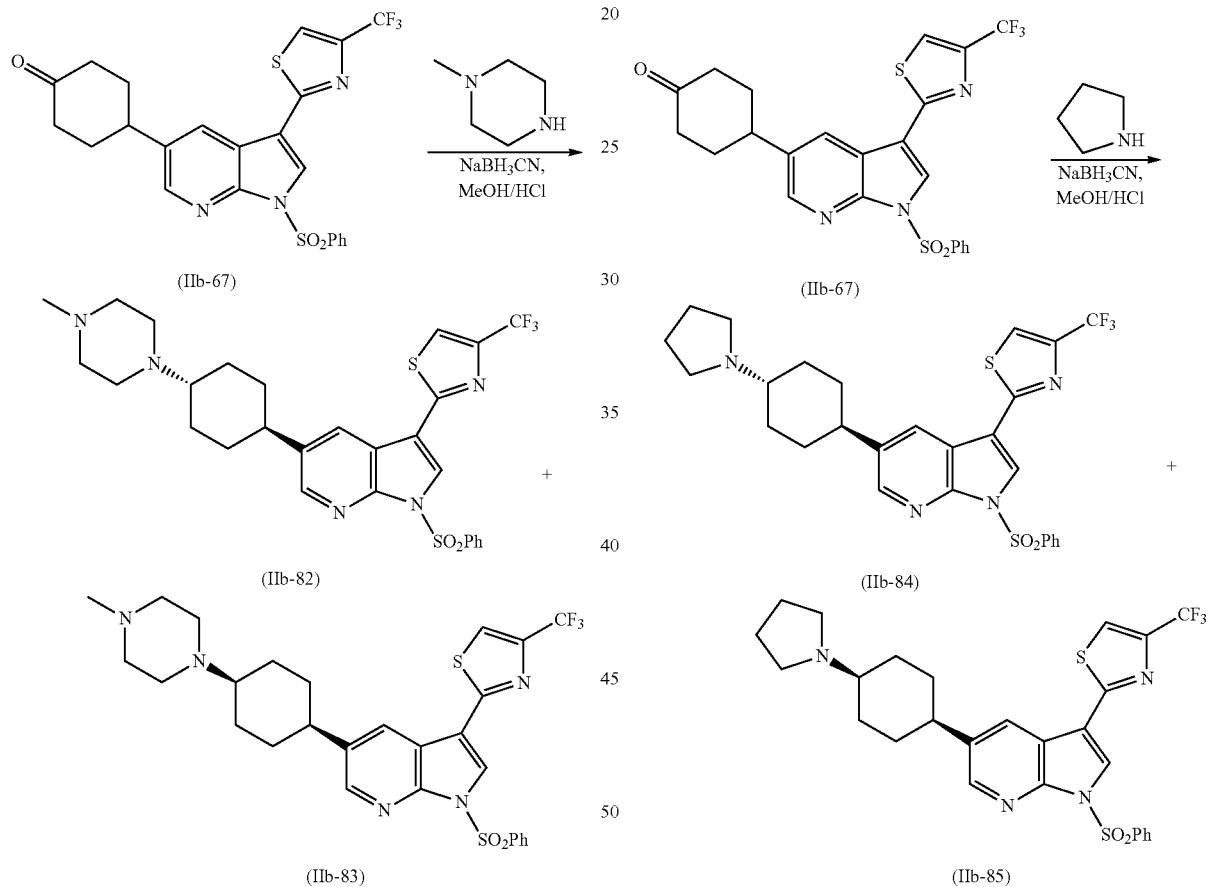

Ketone (IIb-67) (250 mg, 0.49 mmol), 1.25 M HCl in MeOH (1.60 mL, 2.00 mmol), and N-methyl-piperazine (396 mg, 3.96 mmol) in anhydrous methanol (6 mL) were reacted with NaBH$_3$CN (62 mg, 0.99 mmol) added at −20° C. as a solution in MeOH (4 mL) following the general procedure A for the reductive amination. The crude product (356 mg, an oil), was purified by SGC using AcOEt:CH$_2$Cl$_2$:MeOH as eluent (gradient from 49:49:2 to 42.5:42.5:15, v/v/v). First to elute was the cis isomer (IIb-83) (40 mg, 0.07 mmol, 14%) as clear oil. Further elution afforded the trans isomer (IIb-82) (93 mg, 0.16 mmol, 32%) as a solid.

Data for trans isomer (IIb-82): $^1$H NMR (400 MHz, CDCl$_3$) δ 1.54-1.66 (m, 4H), 2.03-2.11 (m, 2H), 2.13-2.20

Ketone (IIb-67) (250 mg, 0.49 mmol), 1.25 M HCl in MeOH (1.60 mL, 2.00 mmol), and pyrrolidine (284 mg, 3.99 mmol) in anhydrous methanol (6 mL) were reacted with NaBH$_3$CN (63 mg, 1.00 mmol) added at −20° C. as a solution in MeOH (4 mL) following the general procedure A for the reductive amination. The crude product (300 mg, an oil), was purified by SGC using CHCl$_3$:MeOH:NH$_4$OH=93:6: 1 (v/v/v). First to elute was the cis isomer (IIb-85) (54 mg, 0.100 mmol, 19%) as clear oil. Further elution afforded some mixed fractions which were discarded, and the trans isomer (IIb-84) (23 mg, 0.04 mmol, 8%) as a solid.

Data for trans isomer (IIb-84): $^1$H NMR (400 MHz, CDCl$_3$) δ 1.43-1.58 (m, 4H), 1.75-1.85 (m, 4H), 1.89-1.97

(m, 2H), 2.09-2.23 (m, 3H), 2.45-2.53 (m, 1H), 2.58-2.75 (m, 1H), 7.45 (t, J=7.8 Hz, 2H), 7.55 (tt, J=1.5, 7.4 Hz, 1H), 7.67 (q, J=0.8 Hz, 1H), 8.17-8.21 (m, 2H), 8.23 (s, 1H), 8.28 (d, J=2.1 Hz, 1H), 8.33 (d, J=2.1 Hz, 1H).

Data for cis isomer (IIb-85): $^1$H NMR (400 MHz, CDCl$_3$) δ 1.46-1.61 (m, 4H), 1.66-1.75 (m, 4H), 1.81-2.04 (m, 2H), 2.14-2.19 (m, 1H), 2.39-2.48 (m, 4H), 2.68-2.77 (m, 1H), 7.45 (t, J=7.7 Hz, 2H), 7.54 (tt, J=1.5, 7.4 Hz, 1H), 7.66 (q, J=0.8 Hz, 1H), 8.16-8.23 (m, 3H), 8.35 (d, J=2.1 Hz, 1H), 8.38 (d, J=2.1 Hz, 1H).

2-(1-(phenylsulfonyl)-5-(1,4-dioxaspiro[4.5]dec-7-en-8-yl)-1H-pyrrolo[2,3-b]pyridin-3-yl)thiazole (IIa-86)

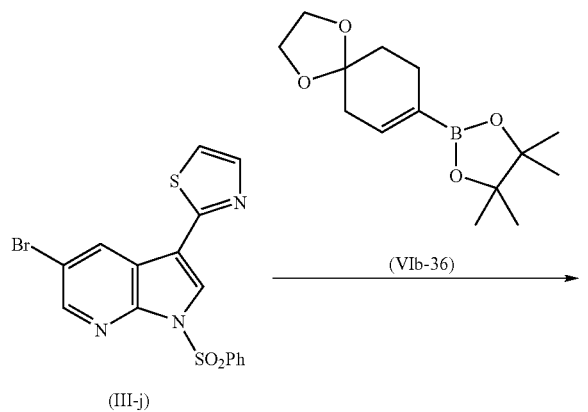

Bromide (III-j) (1.41 g, 3.35 mmol), boronate (VIb-36) (1.00 g, 3.76 mmol), LiCl (400 mg, 9.48 mmol), and Pd(PPh$_3$)$_2$Cl$_2$ (140 mg, 0.20 mmol), in EtOH (10 mL), toluene (10 mL) and 1.0 M Na$_2$CO$_3$ solution (5.0 mL, 5.0 mmol) were reacted for 3 h under reflux using the general procedure A for the Suzuki reaction. Crude product (2.35 g; dark brown oil) was purified by SGC using AcOEt:CH$_2$Cl$_2$:hexanes=1:1:2 (v/v/v) to afford (IIa-86) (1.24 g, 2.77 mmol, 83%) as a pale brown foam. $^1$H NMR (400 MHz, CDCl$_3$) δ 1.97 (t, J=6.5 Hz, 2H), 2.50-2.54 (m, 2H), 2.72-2.78 (m, 2H), 4.06 (s, 4H), 6.04-6.08 (m, 1H), 7.35 (d, J=3.3 Hz, 1H), 7.52 (t, J=7.8 Hz, 2H), 7.62 (tt, J=1.5, 7.4 Hz, 1H), 7.91 (d. J=3.3 Hz, 1H), 8.24-8.28 (m, 3H), 8.58 (d, J=2.2 Hz, 1H), 8.59 (d, J=2.2 Hz, 1H).

2-(1-(phenylsulfonyl)-5-(1,4-dioxaspiro[4.5]decan-8-yl)-1H-pyrrolo[2,3-b]pyridin-3-yl)thiazole (IIb-87)

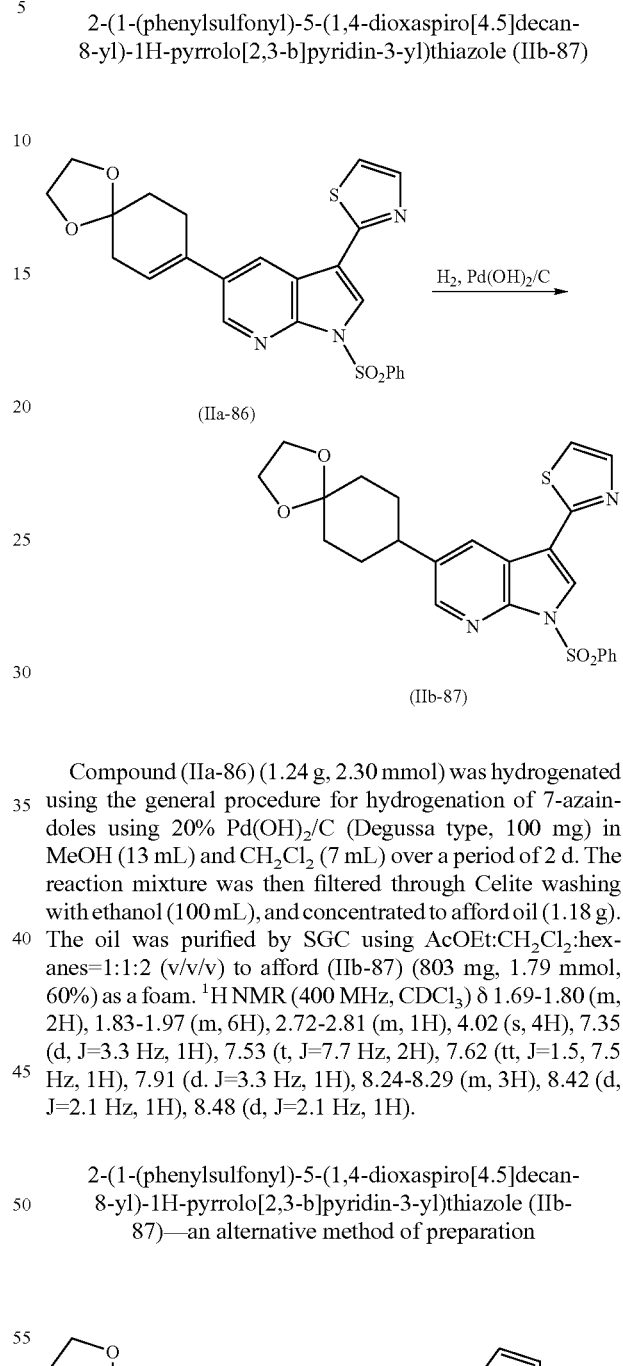

Compound (IIa-86) (1.24 g, 2.30 mmol) was hydrogenated using the general procedure for hydrogenation of 7-azaindoles using 20% Pd(OH)$_2$/C (Degussa type, 100 mg) in MeOH (13 mL) and CH$_2$Cl$_2$ (7 mL) over a period of 2 d. The reaction mixture was then filtered through Celite washing with ethanol (100 mL), and concentrated to afford oil (1.18 g). The oil was purified by SGC using AcOEt:CH$_2$Cl$_2$:hexanes=1:1:2 (v/v/v) to afford (IIb-87) (803 mg, 1.79 mmol, 60%) as a foam. $^1$H NMR (400 MHz, CDCl$_3$) δ 1.69-1.80 (m, 2H), 1.83-1.97 (m, 6H), 2.72-2.81 (m, 1H), 4.02 (s, 4H), 7.35 (d, J=3.3 Hz, 1H), 7.53 (t, J=7.7 Hz, 2H), 7.62 (tt, J=1.5, 7.5 Hz, 1H), 7.91 (d. J=3.3 Hz, 1H), 8.24-8.29 (m, 3H), 8.42 (d, J=2.1 Hz, 1H), 8.48 (d, J=2.1 Hz, 1H).

2-(1-(phenylsulfonyl)-5-(1,4-dioxaspiro[4.5]decan-8-yl)-1H-pyrrolo[2,3-b]pyridin-3-yl)thiazole (IIb-87)—an alternative method of preparation

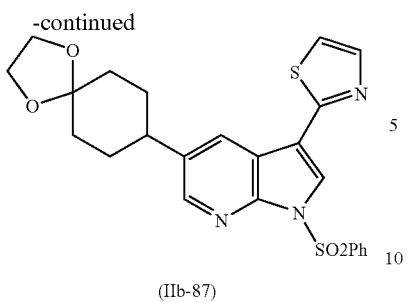

(IIb-87)

Iodide (IXb-23) (100 mg, 0.19 mmol) and 2-(tributylstannyl)thiazole (107 mg, 0.29 mmol), tri-O-tolylphosphine (7 mg, 0.02 mmol), dichlorobis(acetonitrile)palladium(II) (3 mg, 0.01 mmol) and toluene (3 mL) were reacted for 5 h at 120° C. (oil bath) in a sealed reaction vessel using the general procedure B for the Stille reaction. The reaction mixture was filtered, concentrated and purified by LCMS (column LUNA 10 µ C18(2) 00G-4253-V0 250×50 mm) using water—acetonitrile (0.1% AcOH) as eluent (in gradient; flow 80 mL/min) to give (IIb-87) (42.2 mg, 46%) as a white solid. $^1$H NMR (400 MHz, CDCl$_3$) δ 1.57-1.64 (m, 2H), 1.68-1.76 (m, 2H), 1.86-1.91 (m, 4H), 2.70-2.78 (m, 1H), 3.99 (s, 4H), 7.33 (d, J=3.3 Hz, 1H), 7.48-7.52 (m, 2H), 7.60 (tt, J=1.5, 7.4 Hz, 1H), 7.89 (d. J=3.3 Hz, 1H), 8.23 (s, 1H), 8.24-8.26 (m, 2H), 8.39 (d, J=2.1 Hz, 1H), 8.45 (d, J=2.1 Hz, 1H).

4-(1-(phenylsulfonyl)-3-(thiazol-2-yl)-1H-pyrrolo[2,3-b]pyridin-5-yl)cyclohexanone (IIb-88)

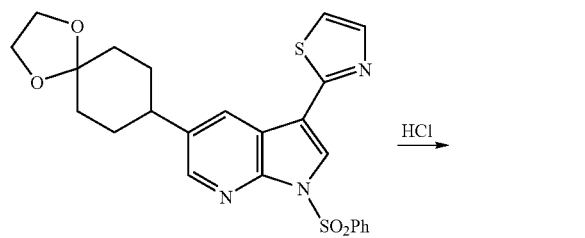

To a stirred solution of (IIb-87) (803 mg, 1.79 mmol) in THF (25 mL) was added 6.0 M aqueous HCl (10 mL, 60 mmol) and the reaction mixture was stirred at r.t. for 2 h. The solution was then added slowly to saturated aqueous NaHCO$_3$ (250 mL), and the mixture was extracted with AcOEt (3×200 mL). The combined organic extracts were dried (MgSO$_4$) and concentrated to afford (IIb-88) (740 mg, 1.83 mmol, quant.) as a clear oil. $^1$H NMR (400 MHz, CDCl$_3$) δ 2.00-2.14 (m, 2H), 2.24-2.33 (m, 2H), 2.52-2.60 (m, 4H), 3.23 (tt, J 3.4, 12.2 Hz, 1H), 7.36 (d, J=3.3 Hz, 1H), 7.54 (t, J=7.8 Hz, 2H), 7.63 (tt, J=1.5, 7.4 Hz, 1H), 7.91 (d. J=3.3 Hz, 1H), 8.25-8.30 (m, 3H), 8.45 (d, J=2.2 Hz, 1H), 8.53 (d, J=2.2 Hz, 1H).

4-((1r,4r)-4-(1-(phenylsulfonyl)-3-(thiazol-2-yl)-1H-pyrrolo[2,3-b]pyridin-5-yl)cyclohexyl)morpholine (IIb-89) and 4-((1s,4s)-4-(1-(phenylsulfonyl)-3-(thiazol-2-yl)-1H-pyrrolo[2,3-b]pyridin-5-yl)cyclohexyl)morpholine (IIb-90)

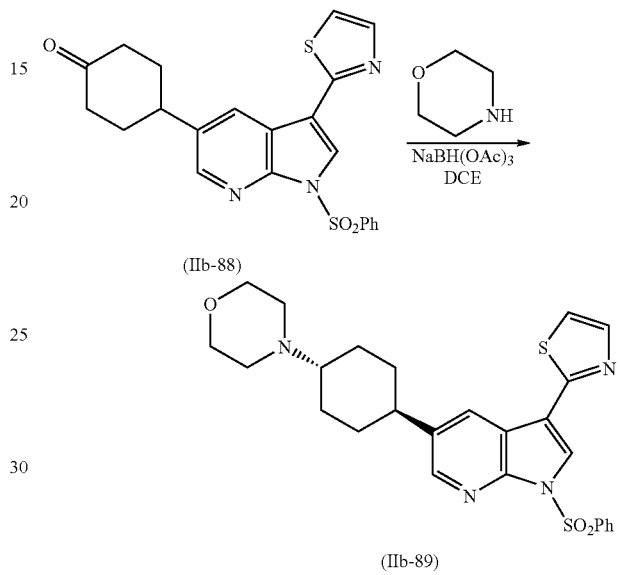

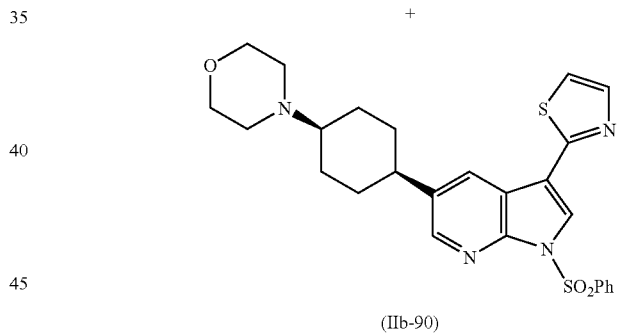

Ketone (IIb-88) (148 mg, 0.34 mmol), morpholine (88 mg, 1.01 mmol), acetic acid (41 mg, 0.68 mmol) in 1,2-dichloroethane (3 mL) were reacted with NaBH(OAc)$_3$ (143 mg, 0.68 mmol) following the general procedure B for reductive amination. The crude product (151 mg, an oil) was purified by means of SGC using AcOEt:CH$_2$Cl$_2$:MeOH as eluent (gradient elution from 50:50:0 to 45:45:10, v/v/v). First to elute was the cis isomer (IIb-90) (86 mg, 0.17 mmol, 50%). Further elution afforded the trans isomer (IIb-89) (44 mg, 0.09 mmol, 26%) as a solid.

Data for the trans isomer (IIb-89): $^1$H NMR (400 MHz, CDCl$_3$) δ 1.37-1.50 (m, 2H), 1.54-1.68 (m, 2H), 1.99-2.14 (m, 4H), 2.36 (tt, J=3.4, 11.4 Hz, 1H), 2.59-2.72 (m, 5H), 3.76 (t, J=4.6 Hz, 2H), 7.34 (d, J=3.3 Hz, 1H), 7.52 (t, J=7.7 Hz, 2H), 7.61 (tt, J=1.5, 7.5 Hz, 1H), 7.90 (d J=3.3 Hz, 1H), 8.23-8.29 (m, 3H), 8.39 (d, J=2.1 Hz, 1H), 8.44 (d, J=2.1 Hz, 1H).

Data for the cis isomer (IIb-90): $^1$H NMR (400 MHz, CDCl$_3$) δ 1.52-1.71 (m, 4H), 1.96-2.09 (m, 4H), 2.26-2.32

(m, 1H), 2.43-2.57 (m, 4H), 2.81-2.90 (m, 1H), 3.77 (t, J=4.6 Hz, 2H), 7.36 (d, J=3.3 Hz, 1H), 7.54 (t, J=7.6 Hz, 2H), 7.63 (tt, J=1.5, 7.4 Hz, 1H), 7.92 (d. J=3.3 Hz, 1H), 8.25-8.30 (m, 3H), 8.46 (d, J=2.1 Hz, 1H), 8.48 (d, J=2.1 Hz, 1H).

2-methyl-4-(5-((1r,4r)-4-(4-methylpiperazin-1-yl)cyclohexyl)-1-(phenylsulfonyl)-1H-pyrrolo[2,3-b]pyridin-3-yl)thiazole (IIb-91) and 2-methyl-4-(5-((1s,4s)-4-(4-methylpiperazin-1-yl)cyclohexyl)-1-(phenylsulfonyl)-1H-pyrrolo[2,3-b]pyridin-3-yl)thiazole (IIb-92)

Data for cis isomer (IIb-92): $^1$H NMR (400 MHz, CDCl$_3$) δ 1.63-1.75 (m, 4H), 1.94-2.06 (m, 4H), 2.55 (s, 3H), 2.52-2.59 (m, 1H), 2.80 (s, 3H), 2.63-2.98 (m, 9H), 7.36 (s, 1H), 7.46-7.51 (m, 2H), 7.55-7.60 (m, 1H), 8.15 (s, 1H), 8.18-8.22 (m, 3H), 8.42 (d, J=2.0 Hz, 1H).

4-(3-(2-(1-methylpiperidin-4-yl)thiazol-4-yl)-1-(phenylsulfonyl)-1H-pyrrolo[2,3-b]pyridin-5-yl)cyclohexanone (IIb-93)

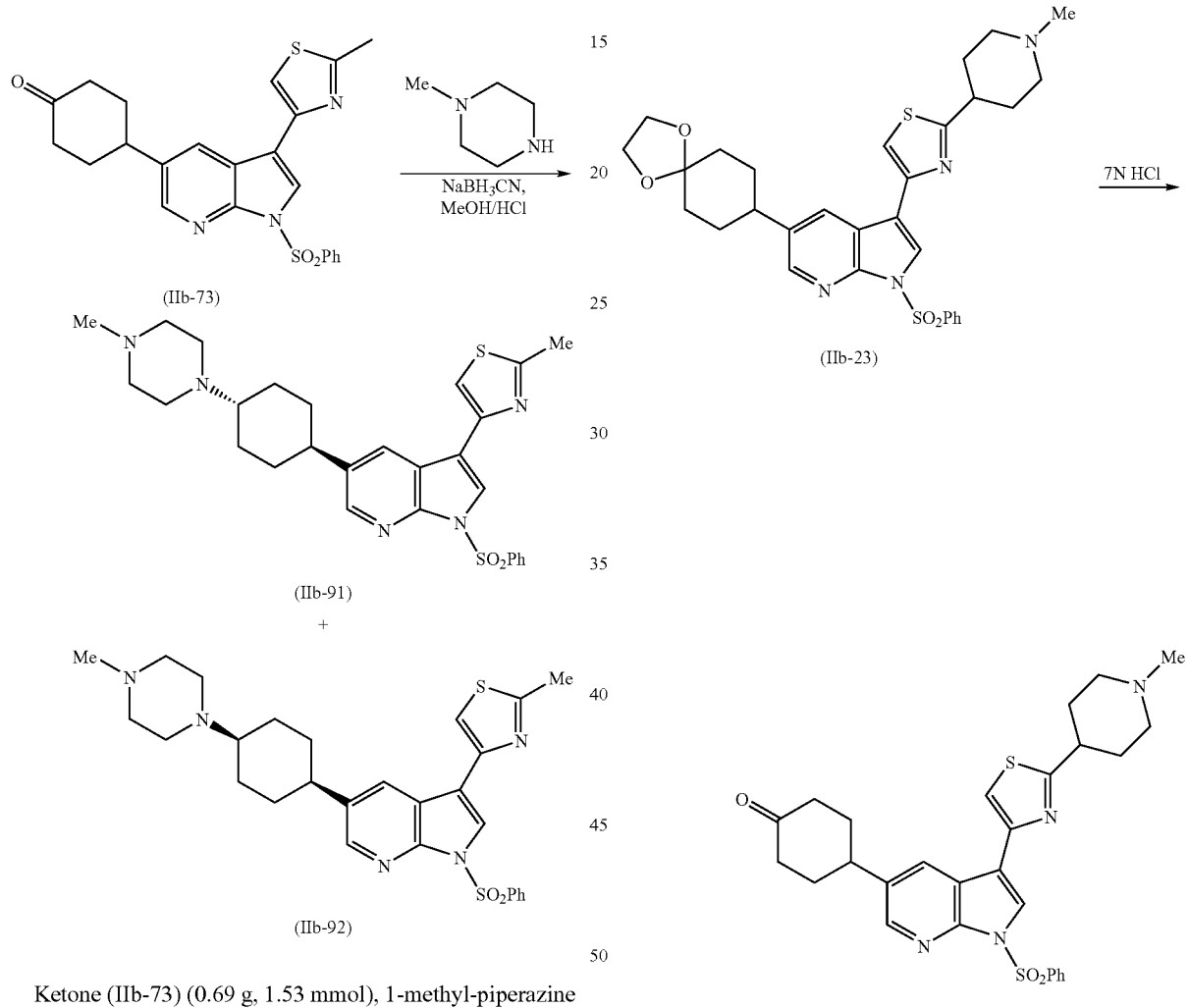

Ketone (IIb-73) (0.69 g, 1.53 mmol), 1-methyl-piperazine (1.70 mL, 15.32 mmol), 1.25 M HCl in MeOH (4.90 mL, 6.13 mmol) in anhydrous methanol (15 mL) were reacted overnight with NaBH$_3$CN (0.19 g, 3.06 mmol) added in one portion and following the general procedure A for the reductive amination. The crude product was purified by SGC using CH$_2$Cl$_2$:MeOH as eluent (gradient from 98:2 to 85:15, v/v). First to elute was the cis isomer (IIb-92) (0.178 g, 22%) as a white foam. Further elution afforded the trans isomer (IIb-91) (0.192 g, 23%) as a white foam.

Data for trans isomer (IIb-91): $^1$H NMR (400 MHz, CDCl$_3$) δ 1.41-1.65 (m, 4H), 2.03 (d, J=12 Hz, 2H), 2.36 (s, 3H), 2.45-2.69 (m, 7H), 2.72-2.80 (m, 3H), 2.70-2.79 (br s, 3H), 2.81 (s, 3H), 7.30 (s, 1H), 7.45-7.50 (m, 2H), 7.54-7.59 (m, 1H), 8.11 (d, J=2.1 Hz, 2H), 8.15, (s, 1H), 8.22-8.20 (m, 2H), 8.34 (d, J=2.1 Hz, 1H).

7 N aqueous HCl (1.88 mL, 13.13 mmol) was added in one portion at r.t. to a solution of ketal (IIb-23) (0.76 g, 1.31 mmol) in THF (10 mL) and the mixture was stirred at r.t. for 5 h. The reaction mixture was then poured slowly over 20 min into a saturated aqueous solution of NaHCO$_3$ (100 mL). It was extracted with EtOAc (4×50 mL). The combined organic extracts were dried (MgSO$_4$) and concentrated to give (IIb-93) as a white foam (0.57 g, 81%), $^1$H NMR (400 MHz, CDCl$_3$) δ 1.92-2.07 (m, 4H), 2.11-2.30 (m, 6H), 2.35 (s, 3H), 2.48-2.60 (m, 4H), 2.95-3.03 (m, 2H), 3.07 (tt, J=3.8, 11.6

Hz, 1H), 3.20 (tt, J=3.8, 11.6 Hz, 1H), 7.34 (s, 1H), 7.46-7.52 (m, 2H), 7.55-7.60 (m, 1H), 8.13 (s, 1H), 8.20-8.25 (m, 3H), 8.40 (d, J=2.0 Hz, 1H).

4-((1r,4r)-4-(3-(2-(1-methylpiperidin-4-yl)thiazol-4-yl)-1-(phenylsulfonyl)-1H-pyrrolo[2,3-b]pyridin-5-yl)cyclohexyl)morpholine (IIb-94) and 4-((1s,4s)-4-(3-(2-(1-methylpiperidin-4-yl)thiazol-4-yl)-1-(phenylsulfonyl)-1H-pyrrolo[2,3-b]pyridin-5-yl)cyclohexyl)morpholine (IIb-95)

4-(5-((1r,4r)-4-(4-methylpiperazin-1-yl)cyclohexyl)-1-(phenylsulfonyl)-1H-pyrrolo[2,3-b]pyridin-3-yl)-2-(1-methylpiperidin-4-yl)thiazole (IIb-96) and 4-(5-((1s,4s)-4-(4-methylpiperazin-1-yl)cyclohexyl)-1-(phenylsulfonyl)-1H-pyrrolo[2,3-b]pyridin-3-yl)-2-(1-methylpiperidin-4-yl)thiazole (IIb-97)

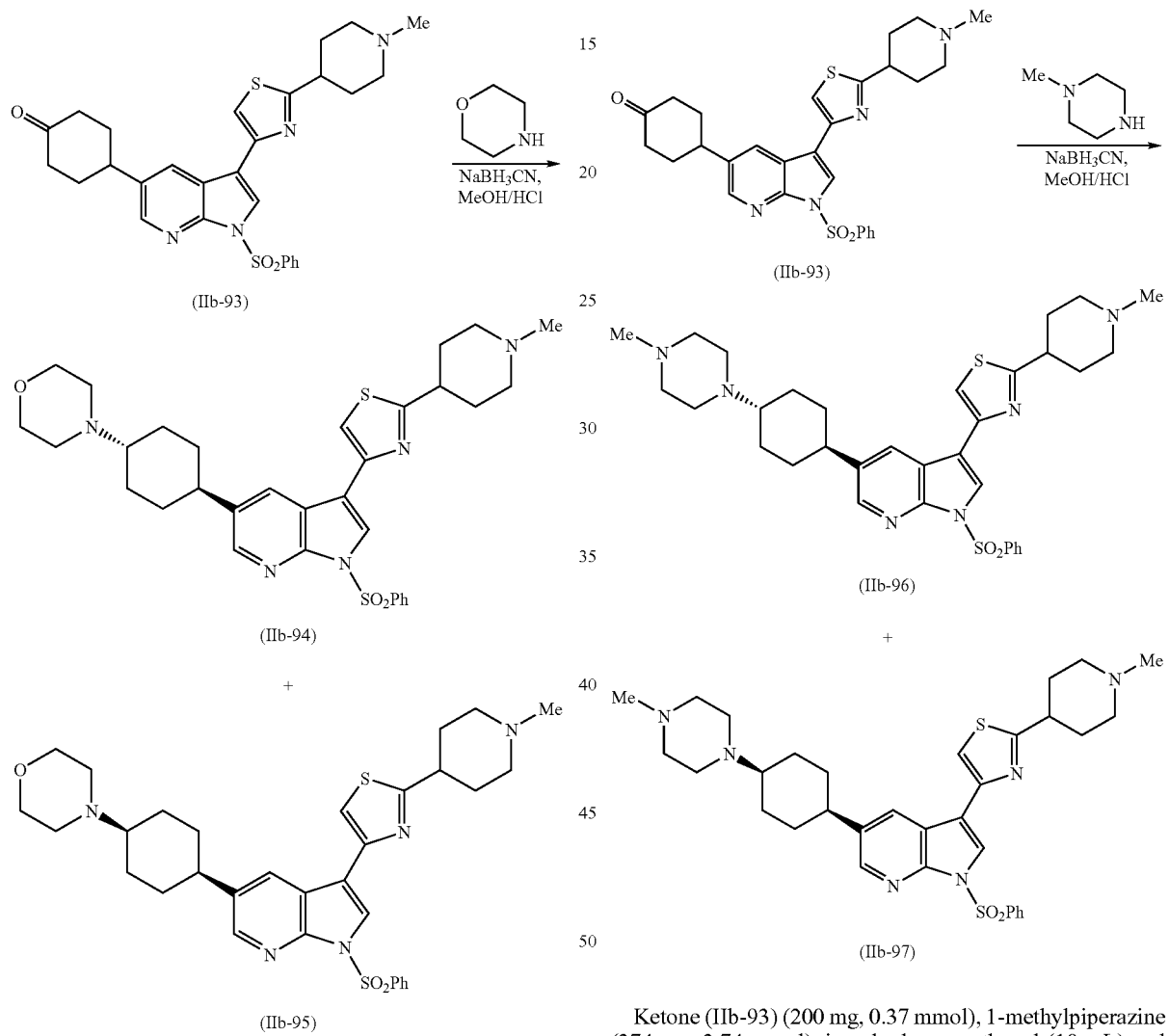

Ketone (IIb-93) (200 mg, 0.37 mmol), morpholine (326 mg, 3.75 mmol), 1.25 M HCl in MeOH (0.60 mL, 0.75 mmol) in anhydrous methanol (10 mL) were reacted overnight with NaBH$_3$CN (47 mg, 0.75 mmol) added in one portion and following the general procedure A for the reductive amination. The crude product was purified by was purified by PTLC using CH$_2$Cl$_2$:MeOH=9:1 (v/v) as the eluent to give the cis isomer (IIb-95) (45 mg, 20%) which was impure and wasn't characterized and the trans isomer (IIb-94) (48 mg, 21%).

Data for trans isomer (IIb-94): $^1$H NMR (400 MHz, CDCl$_3$) δ 1.36-1.48 (dq, J=2.1, 12.5 Hz, 2H), 1.48-1.60 (dq, J=2.1, 12.5 Hz, 2H), 1.95-2.25 (m, 12H), 2.35 (s, 3H), 2.58-

Ketone (IIb-93) (200 mg, 0.37 mmol), 1-methylpiperazine (374 mg, 3.74 mmol), in anhydrous methanol (10 mL) and 1.25 M HCl in MeOH (0.60 mL, 0.75 mmol) were reacted overnight with NaBH$_3$CN (47 mg, 0.75 mmol) added in one portion and following the general procedure A for the reductive amination. The crude product was purified by was purified by PTLC using CHCl$_3$:MeOH:NH$_4$OH=90:9:1 (v/v/v) as the eluent to give the cis isomer (IIb-97) (29 mg, 12%), which was impure and wasn't characterized and the trans isomer (IIb-96) (44 mg, 19%).

Data for trans isomer (IIb-96): $^1$H NMR (400 MHz, CDCl$_3$) δ 1.39-1.61 (m, 2H), 1.94-2.10 (m, 8H), 2.17-2.26 (m, 4H), 2.32 (s, 3H), 2.36 (s, 3H), 2.40-2.50 (tt, J=3.3, 11.2 Hz, 1H), 2.51-2.66 (m, 4H), 2.66-2.77 (m, 2H), 3.00-3.06 (m, 2H), 3.05-3.12 (tt, J=3.8, 11.5 Hz, 4H), 7.33 (s, 1H), 7.44-

7.49 (m, 2H), 7.52-7.59 (m, 1H), 8.11 (d, J=2.2 Hz, 1H), 8.12 (s, 1H), 8.19-8.22 (m, 2H), 8.33 (d, J=2.0 Hz, 1H). MS calc for $C_{33}H_{42}N_6O_2S_2$ M=618, found (M+H)$^+$=619.4.

2-(1-methylpiperidin-4-yl)-4-(1-(phenylsulfonyl)-5-((1r,4r)-4-(pyrrolidin-1-yl)cyclohexyl)-1H-pyrrolo[2,3-b]pyridin-3-yl)thiazole (IIb-98) and 2-(1-methylpiperidin-4-yl)-4-(1-(phenylsulfonyl)-5-((1s,4s)-4-(pyrrolidin-1-yl)cyclohexyl)-1H-pyrrolo[2,3-b]pyridin-3-yl)thiazole (IIb-99)

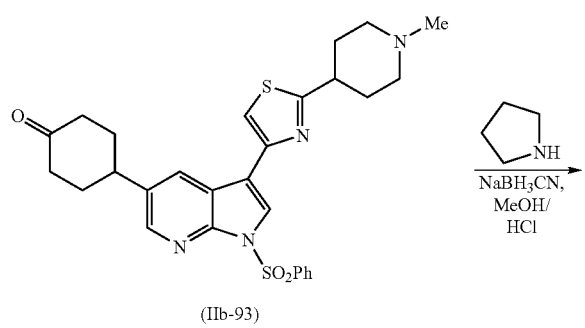

(IIb-93)

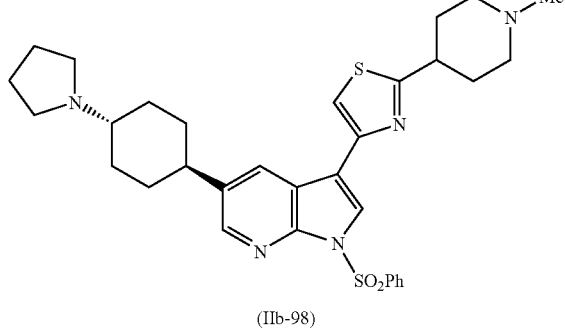

(IIb-98)

+

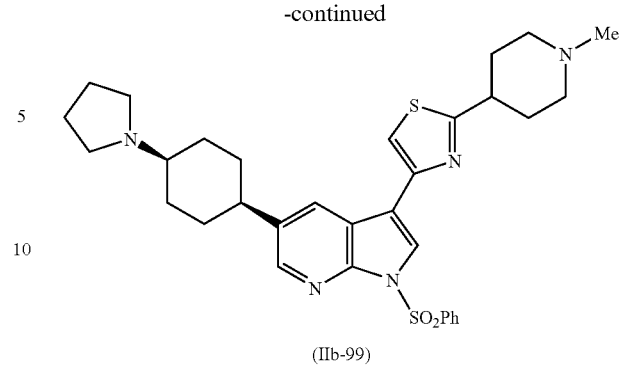

(IIb-99)

Ketone (IIb-93) (172 mg, 0.32 mmol), pyrrolidine (229 mg, 3.23 mmol), in anhydrous methanol (10 mL) and 1.25 M HCl in MeOH (0.52 mL, 0.65 mmol) were reacted overnight with NaBH$_3$CN (40.5 mg, 0.64 mmol) added in one portion and following the general procedure A for the reductive amination. The crude product was purified by was purified by PTLC using CH$_2$Cl$_2$:MeOH:NH$_4$OH=800:199:1 (v/v/v) as the eluent to give the cis isomer (IIb-99) (37 mg, 19%) and the trans isomer (IIb-98) (59 mg, 31%).

Data for trans isomer (IIb-98): $^1$H NMR (400 MHz, CDCl$_3$) δ 1.48-1.61 (m, 4H), 1.81-1.92 (m, 4H), 1.93-2.01 (m, 4H), 2.10-2.22 (m, 7H), 2.34 (s, 3H), 2.64-2.81 (m, 4H), 2.93-3.01 (m, 3H), 3.0-3.10 (tt, J=3.7, 11.5 Hz, 1H), 7.34 (s, 1H), 7.44-7.50 (m, 2H), 7.54-7.59 (m, 1H), 8.12 (s, 1H), 8.13 (s, 1H), 8.19-8.23 (m, 2H), 8.34 (d, J=2.0 Hz, 1H).

Data for cis isomer (IIb-99): $^1$H NMR (400 MHz, CDCl$_3$) δ 1.62-1.73 (m, 4H), 1.88-2.05 (m, 10H), 2.11-2.25 (m, 6H), 2.34 (s, 3H), 2.67-2.84 (m, 4H), 2.93-3.10 (m, 3H), 7.45-7.50 (m, 3H), 7.53-7.59 (m, 1H), 8.17 (m, 1H), 8.20-8.23 (m, 2H), 8.27 (d, J=2.0 Hz, 1H), 8.37 (d, J=2.0 Hz, 1H).

4-(4-(3-(2-(1-methylpiperidin-4-yl)thiazol-4-yl)-1-(phenylsulfonyl)-1H-pyrrolo[2,3-b]pyridin-5-yl)cyclohex-3-enyl)-1,4-oxazepane (IIa-101) and 4-(4-(3-(2-(1-methylpiperidin-4-yl)thiazol-4-yl)-1H-pyrrolo[2,3-b]pyridin-5-yl)cyclohex-3-enyl)-1,4-oxazepane (I-101)

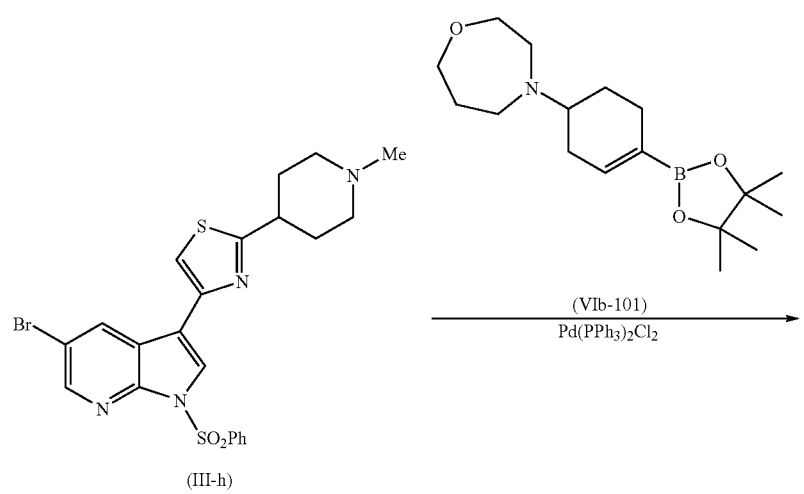

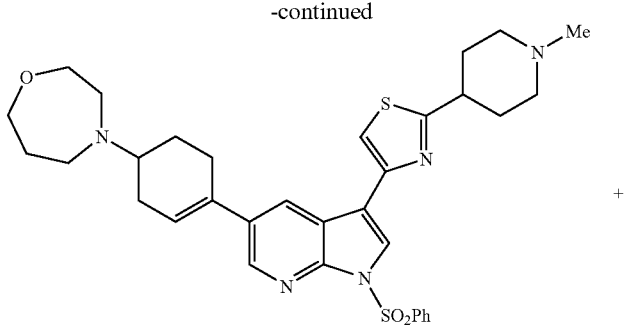

(IIa-101)

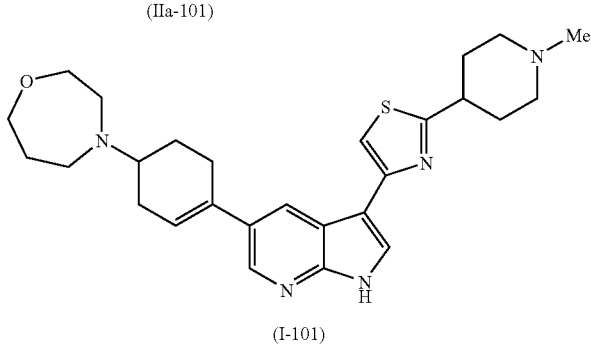

(I-101)

Bromide (III-h) (1.00 g, 1.93 mmol), boronate (VIb-101) (0.71 g, 2.32 mmol), LiCl (0.25 g, 5.80 mmol), and Pd(PPh$_3$)$_2$Cl$_2$ (0.13 g, 0.19 mmol) in EtOH (30 mL), toluene (30 mL) and 1.0 M Na$_2$CO$_3$ solution (19.3 mL, 19.3 mmol) were reacted for 72 h under reflux using the general procedure A for the Suzuki reaction. Crude product was purified by SGC using AcOEt:hexanes (gradient from 50:50 to 100:0, v/v) then AcOEt:MeOH (gradient from 100:0 to 90:10, v/v) to afford (IIa-101) (0.14 g, 12%) and (I-101) (0.23 g, 25%) as pale red color solid.

Data for (IIa-101): $^1$H NMR (400 MHz, CDCl$_3$) δ 1.81-2.00 (m, 5H), 2.04-2.28 (m, 5H), 2.32 (s, 3H), 2.36-2.44 (m, 1H), 2.53-2.59 (m, 2H), 2.76-2.87 (m, 5H), 2.90-3.07 (m, 4H), 3.73 (t, J=4.6 Hz, 2H), 3.80 (t, J=6.1 Hz, 2H), 6.04-6.09 (m, 1H), 7.33 (s, 1H), 7.42-7.46 (m, 2H), 7.51-7.57 (m, 1H), 8.12 (s, 1H), 8.17-8.20 (m, 2H), 8.23 (d, J=2.1 Hz, 1H), 8.48 (d, J=2.1 Hz, 1H).

Data for (I-101): $^1$H NMR (400 MHz, CDCl$_3$) δ 1.68-1.76 (m, 1R), 1.89-2.03 (m, 4H), 2.08-2.16 (m, 2H), 2.17-2.31 (m, 4H), 2.35 (s, 3H), 2.40-2.49 (m, 1H), 2.63-2.73 (m, 2H), 2.86-2.90 (m, 4H), 2.94-3.03 (m, 3H), 3.03-3.12 (m, 1H), 3.78 (t, J=4.7 Hz, 2H), 3.85 (t, J=6.0 Hz, 2H), 6.08-6.11 (m, 1H), 7.24 (s, 1H), 7.82 (d, J=2.4 Hz, 1H), 8.31 (d, J=2.0 Hz, 1H), 8.42 (d, J=2.0Hz, 1H), 9.82 (br s, NH, 1H).

4-((1r,4r)-4-(3-(2-(1-methylpiperidin-4-yl)thiazol-4-yl)-1-(phenylsulfonyl)-1H-pyrrolo[2,3-b]pyridin-5-yl)cyclohexyl)-1,4-oxazepane (IIb-102) and 4-((1s,4s)-4-(3-(2-(1-methylpiperidin-4-yl)thiazol-4-yl)-1-(phenylsulfonyl)-1H-pyrrolo[2,3-b]pyridin-5-yl)cyclohexyl)-1,4-oxazepane (IIb-103)

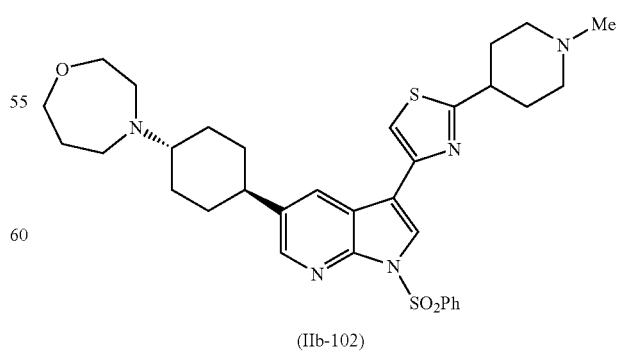

(IIa-101)

$\xrightarrow{\text{H}_2/\text{Pd(OH)}_2}$ (IIb-102)

+

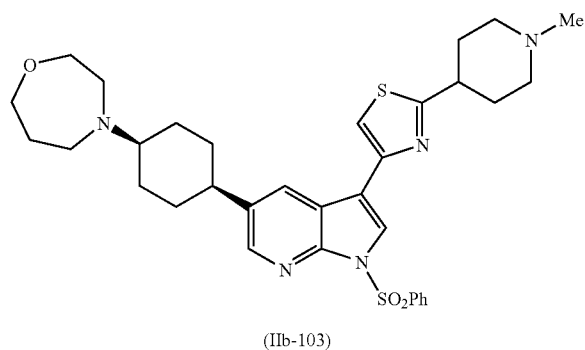

(IIb-103)

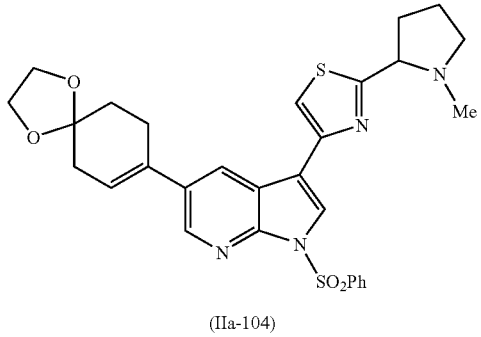

(IIa-104)

Compound (IIa-101) (100 mg, 1.87 mmol) was hydrogenated using the general procedure for hydrogenation of 7-azaindoles using 20% Pd(OH)$_2$/C (Degussa type, 30 mg) in MeOH (5 mL) and AcOEt (5 mL) over a period of 20 h. The reaction mixture was then filtered through Celite washing with CH$_2$Cl$_2$:MeOH=1:1 and concentrated to afford a white foam. The foam was purified by PTLC SGC using CHCl$_3$:MeOH:NH$_4$OH=90:9:1 (v/v/v) to afford the cis isomer (IIb-103) (10 mg, 10%; higher R$_f$) as white foam and the trans isomer (IIb-102) (20 mg, 20%; lower R$_f$) as white foam.

Data for the trans isomer (IIb-102) $^1$H NMR (400 MHz, CDCl$_3$) δ 1.40-1.65 (m, 4H), 1.85-2.07 (m, 8H), 2.10-2.25 (m, 4H), 2.35 (s, 3H), 2.60-2.70 (m, 2H), 2.81-2.90 (m, 4H), 2.97-3.10 (m, 3H), 3.74 (t, J=4.6 Hz, 2H), 3.81 (t, J=5.9 Hz, 2H), 7.33 (s, 1H), 7.45-7.50 (m, 2H), 7.54-7.59 (m, 1H), 8.13 (s, 2H), 8.20-8.23 (m, 2H), 8.34 (d, J=2.1 Hz, 1H).

Data for the cis isomer (IIb-102) $^1$H NMR (400 MHz, CDCl$_3$) δ 1.59-1.75 (m, 4H), 1.86-2.14 (m, 10H), 2.14-2.25 (m, 4H), 2.36 (s, 3H), 2.83-2.92 (m, 4H), 2.97-3.12 (m, 3H), 3.76 (t, J=4.7 Hz, 2H), 3.80 (t, J=5.8 Hz, 2H), 7.39 (s, 1H), 7.46-7.51 (m, 2H), 7.54-7.59 (m, 1H), 8.13 (s, 1H), 8.21-8.24 (m, 2H), 8.27 (s, 1H), 8.41 (d, J=1.9 Hz, 1H).

2-(1-methylpyrrolidin-2-yl)-4-(1-(phenylsulfonyl)-5-(1,4-dioxaspiro[4.5]dec-7-en-8-yl)-1H-pyrrolo[2,3-b]pyridin-3-yl)thiazole (IIa-104)

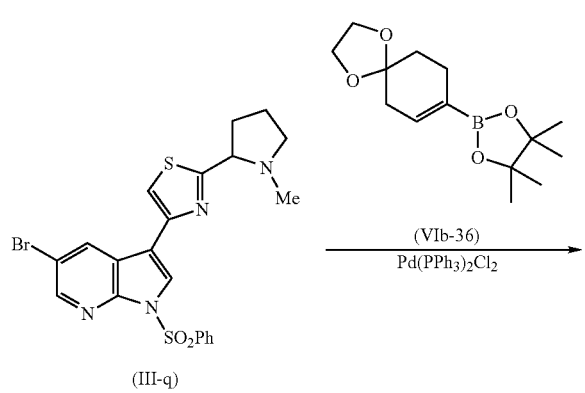

Bromide (III-q) (1.10 g, 2.18 mmol), boronate (VIb-36) (0.70 g, 2.62 mmol), LiCl (0.28 g, 6.55 mmol), and Pd(PPh$_3$)$_2$Cl$_2$ (0.15 g, 0.22 mmol) in EtOH (21.8 ml), toluene (21.8 ml) and 1.0 M Na$_2$CO$_3$ solution (5.5 mL, 5.5 mmol) were reacted for 72 h under reflux using the general procedure A for the Suzuki reaction. Crude product was purified by SGC using AcOEt:hexane (gradient from 0:100 to 100:0, v/v) to afford (IIa-104) (0.91 g, 74%) as a grey solid. $^1$H NMR (400 MHz, CDCl$_3$) δ $^1$H NMR (400 MHz, CDCl$_3$) δ 1.83-2.03 (m, 3H), 1.96 (t, J=6.3 Hz, 2H), 2.39-2.45 (m, 1H), 2.45-2.48 (m, 1H), 2.47 (s, 3H), 2.48-2.52 (m, 2H), 2.68-2.76 (m, 2H), 3.25-3.33 (tt, J=1.6, 7.2 Hz, 1H), 3.78-3.82 (dd, J=6.3, 8.8 Hz, 1H), 4.04 (s, 4H), 5.98-6.02 (tt, J=1.5, 3.9 Hz, 1H), 7.39 (s, 1H), 7.44-7.49 (m, 2H), 7.54-7.58 (m, 1H), 8.16 (s, 1H), 8.19-8.23 (m, 2H), 8.25 (d, J=2.1 Hz, 1H), 8.53 (d, J=2.1 Hz, 1H).

2-(1-methylpyrrolidin-2-yl)-4-(1-(phenylsulfonyl)-5-(1,4-dioxaspiro[4.5]decan-8-yl)-1H-pyrrolo[2,3-b]pyridin-3-yl)thiazole (IIb-105)

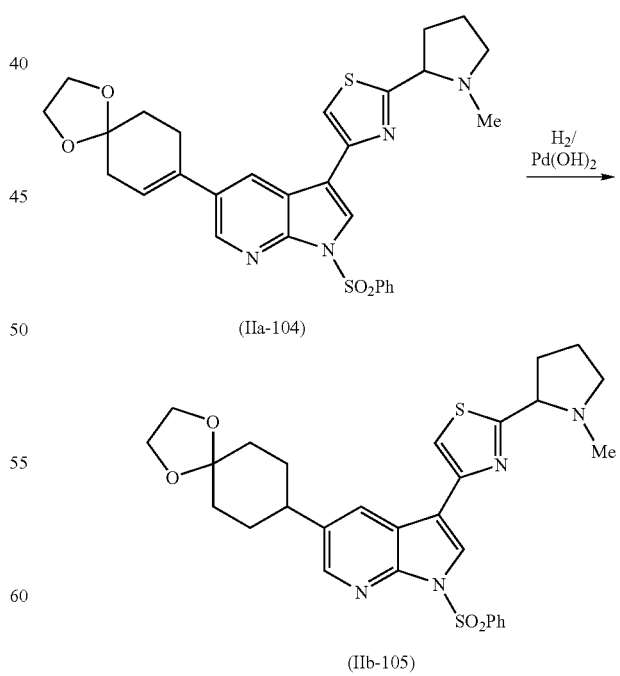

Compound (IIa-104) (0.91 g, 1.62 mmol) was hydrogenated using the general procedure for hydrogenation of 7-azaindoles using 20% Pd(OH)$_2$/C (Degussa type, 0.35 g ) in MeOH (50 mL)—EtOAc (50 mL) over a period of 20 h. The reaction mixture was then filtered through Celite washing with CH₂Cl₂:MeOH=1:1 and concentrated to afford crude (IIb-105) (0.81 g, 89%) as a white solid, which did not require further purification. ¹H NMR (400 MHz, CDCl₃) δ 1.66-1.78 (m, 3H), 1.81-1.95 (m, 5H), 1.97-2.15 (m, 2H), 2.45-2.59 (m, 2H), 2.71 (s, 3H), 2.70-2.77 (m, 1H), 3.05 (t, J=7.3 Hz, 1H), 3.13 (t, J=7.3 Hz, 1H), 3.26-3.38 (m, 1H), 3.99 (s, 4H), 7.42 (s, 1H), 7.45-7.51 (m, 2H), 7.54-7.59 (m, 1H), 8.12 (s, 1H), 8.17 (s, 1H), 8.21-8.25 (m, 2H), 8.37 (d, J=2.1 Hz, 1H).

4-(3-(2-(1-methylpyrrolidin-2-yl)thiazol-4-yl)-1-(phenylsulfonyl)-1H-pyrrolo[2,3-b]pyridin-5-yl)cyclohexanone (IIb-106)

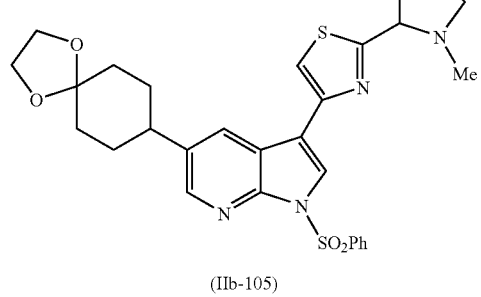

(IIb-105)

7N HCl →

(dd, J=6.0, 8.6 Hz, 1H), 7.38 (s, 1H), 7.44-7.50 (m, 2H), 7.56-7.59 (m, 1H), 8.15 (s, 1H), 8.18-8.22 (m, 3H), 8.39 (d, J=2.1 Hz, 1H).

4-((1r,4r)-4-(3-(2-(1-methylpyrrolidin-2-yl)thiazol-4-yl)-1-(phenylsulfonyl)-1H-pyrrolo[2,3-b]pyridin-5-yl)cyclohexyl)morpholine (IIb-107) and 4-((1s,4s)-4-(3-(2-(1-methylpyrrolidin-2-yl)thiazol-4-yl)-1-(phenylsulfonyl)-1H-pyrrolo[2,3-b]pyridin-5-yl)cyclohexyl)morpholine (IIb-108)

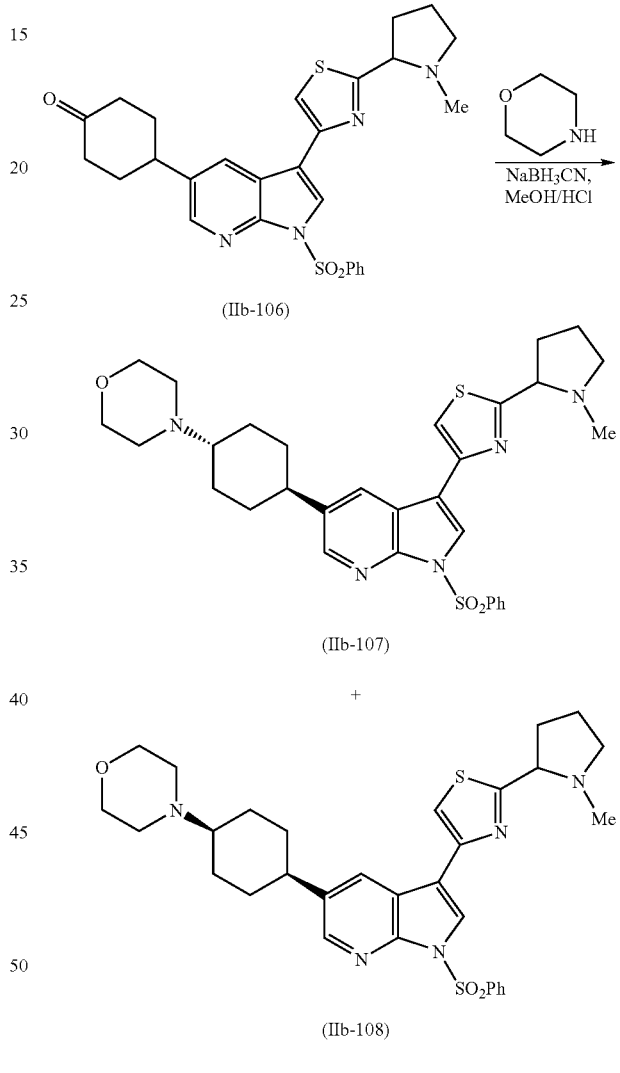

7 N aqueous HCl (1.02 mL, 7.17 mmol) was added in one portion at r.t. to a solution of ketal (IIb-105) (0.81 g, 1.43 mmol) in THF (4 mL) and the mixture was stirred at r.t. overnight. The reaction mixture was then poured slowly over 30 min into a saturated aqueous solution of NaHCO₃ (100 mL). It was extracted with EtOAc (4×50 mL). The combined organic extracts were dried (MgSO₄) and concentrated to give (IIb-106) (0.74 g, 99%), ¹H NMR (400 MHz, CDCl₃) δ 1.66-1.76 (m, 1H), 1.83-2.05 (m, 5H), 2.20-2.29 (m, 2H), 2.44-2.48 (m, 1H), 2.46 (s, 3H), 2.51-2.57 (m, 4H), 3.19 (tt, J=3.2, 12.4 Hz, 1H), 3.27 (tt, J=1.6, 7.1 Hz, 1H), 3.77-3.82

Ketone (IIb-106) (170 mg, 0.33 mmol), morpholine (284 mg, 3.26 mmol) in anhydrous methanol (10 mL) and 1.25 M HCl in MeOH (0.52 mL, 0.65 mmol) were reacted overnight with NaBH₃CN (41 mg, 0.65 mmol) added in one portion and following the general procedure A for the reductive amination. The crude product was purified by was purified by PTLC using CH₂Cl₂:MeOH=95:5 (v/v) as the eluent to give the cis isomer (IIb-108) (37 mg, 19%) as a white foam and the trans isomer (IIb-107) (53 mg, 27%) as a white foam.

Data for trans isomer (IIb-107): ¹H NMR (400 MHz, CDCl₃) δ 1.37-1.49 (dq, J=2.2, 12.5 Hz, 2H), 1.50-1.62 (dq, J=2.2, 12.9 Hz, 2H), 1.83-2.13 (m, 8H), 2.31-2.50 (m, 2H), 2.46 (s, 3H), 2.59-2.67 (m, 5H), 3.27 (tt, J=1.9, 7.2 Hz, 1H), 3.76 (t, J=4.5 Hz, 4H), 3.78 (dd, J=6.1, 8.7 Hz, 1H), 7.38 (s, 1H), 7.44-7.50 (m, 2H), 7.53-7.58 (m, 1H), 8.09 (d, J=2.0 Hz, 1H), 8.16 (s, 1H), 8.20-8.23 (m, 2H), 8.34 (d, J=2.0 Hz, 1H).

Data for cis isomer (IIb-108): $^1$H NMR (400 MHz, CDCl$_3$) δ 1.49-1.65 (m, 4H), 1.83-2.05 (m, 8H), 2.37-2.52 (m, 6H), 2.47 (s, 3H), 2.81 (tt, J=3.8, 10.5 Hz, 1H), 3.28 (tt, J=1.7, 7.9 Hz, 1H), 3.75 (t, J=4.2 Hz, 4H), 3.78-3.82 (dd, J=6.1, 8.9 Hz, 1H), 7.39 (s, 1H), 7.45-7.50 (m, 2H), 7.54-7.59 (m, 1H), 8.15 (m, 1H), 8.18 (s, 1H), 8.20-8.23 (m, 2H), 8.40 (d, J=2.0 Hz, 1H).

4-(5-((1r,4r)-4-(4-methylpiperazin-1-yl)cyclohexyl)-1-(phenylsulfonyl)-1H-pyrrolo[2,3-b]pyridin-3-yl)-2-(1-methylpyrrolidin-2-yl)thiazole (IIb-109) and 4-(5-((1s,4s)-4-(4-methylpiperazin-1-yl)cyclohexyl)-1-(phenylsulfonyl)-1H-pyrrolo[2,3-b]pyridin-3-yl)-2-(1-methylpyrrolidin-2-yl)thiazole (IIb-110)

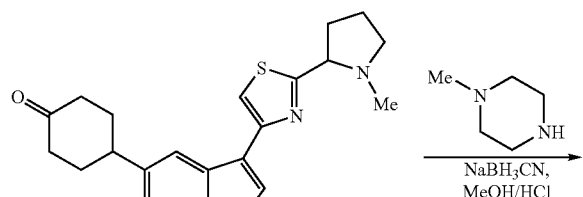

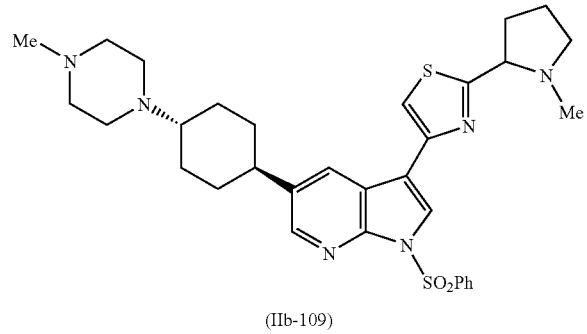

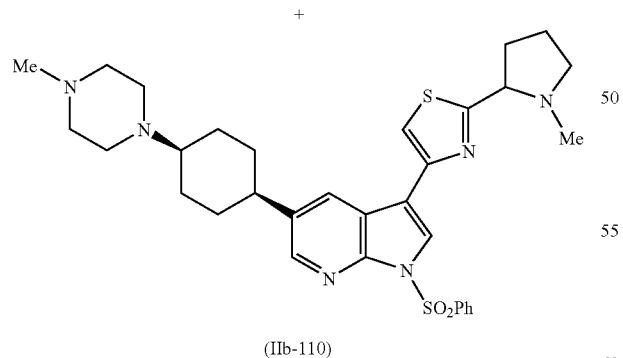

Ketone (IIb-106) (163 mg, 0.31 mmol), 1-methylpiperazine (313 mg, 3.13 mmol) in anhydrous methanol (10 mL) and 1.25 M HCl in MeOH (0.50 mL, 0.63 mmol) were reacted overnight with NaBH$_3$CN (39 mg, 0.63 mmol) added in one portion and following the general procedure A for the reductive amination. The crude product was purified by was puri- fied by PTLC using CH$_2$Cl$_2$:MeOH=90:10 (v/v) as the eluent to give the cis isomer (IIb-110) (23 mg, 12%) and the trans isomer (IIb-109) (31 mg, 16%).

Data for trans isomer (IIb-109): $^1$H NMR (400 MHz, CDCl$_3$) δ 1.42 (m, 4H), 1.83-2.06 (m, 6H), 2.06-2.13 (d, J=11.5 Hz, 2H), 2.35 (s, 3H), 2.46 (s, 3H), 2.54-2.70 (m, 6H), 2.71-2.82 (br s, 5H), 3.27 (t, J=7.9 Hz, 1H), 3.78-3.83 (dd, J=6.2, 8.8 Hz, 1H), 7.38 (s, 1H), 7.45-7.50 (m, 2H), 7.54-7.59 (m, 1H), 8.09 (d, J=2.0 Hz, 1H), 8.16 (s, 1H), 8.19-8.23 (m, 2H), 8.33 (d, J=2.0 Hz, 1H).

Data for cis isomer (IIb-110): $^1$H NMR (400 MHz, CDCl$_3$) δ 1.51-1.67 (m, 4H), 1.85-1.92 (m, 1H), 1.93-2.05 (m, 7H), 2.28-2.34 (m, 2H), 2.32 (s, 3H), 2.47 (s, 3H), 2.40-2.65 (br m, 8H), 2.82 (tt, J=3.8, 10.2 Hz, 1H), 3.25 (t, J=7.9 Hz, 1H), 3.78-3.83 (dd, J=6.1, 8.7 Hz, 1H), 7.40 (s, 1H), 7.46-7.50 (m, 2H), 7.55-7.59 (m, 1H), 8.15 (s, 1H), 8.18 (d, J=2.0 Hz, 1H), 8.20-8.23 (m, 2H), 8.41 (d, J=2.0 Hz, 1H).

2-(1-methylpyrrolidin-2-yl)-4-(1-(phenylsulfonyl)-5-((1r,4r)-4-(pyrrolidin-1-yl)cyclohexyl)-1H-pyrrolo[2,3-b]pyridin-3-yl)thiazole (IIb-111) and 2-(1-methylpyrrolidin-2-yl)-4-(1-(phenylsulfonyl)-5-((1s,4s)-4-(pyrrolidin-1-yl)cyclohexyl)-1H-pyrrolo[2,3-b]pyridin-3-yl)thiazole (IIb-112)

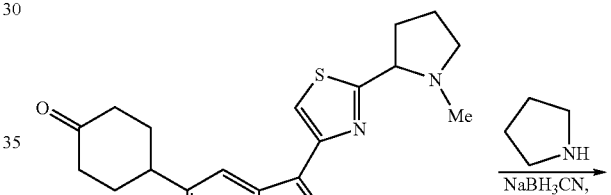

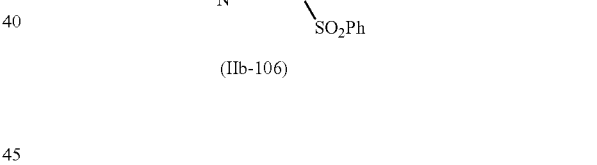

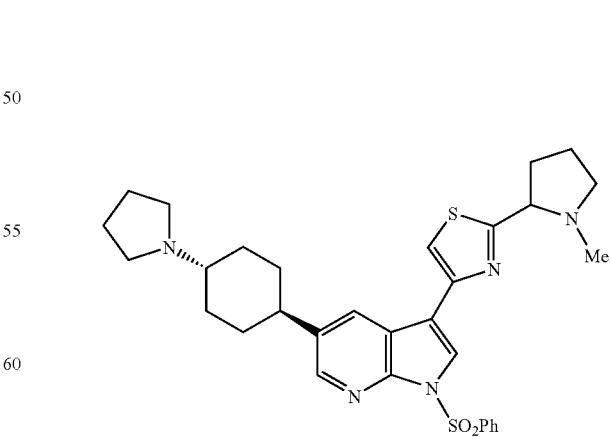

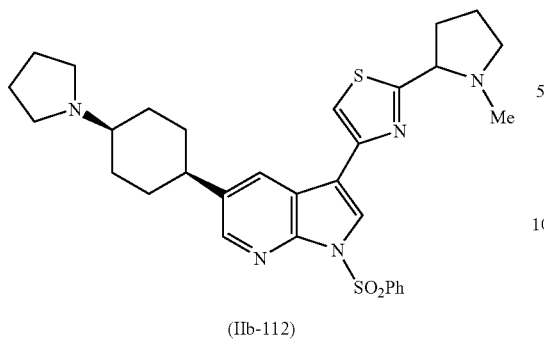

(IIb-112)

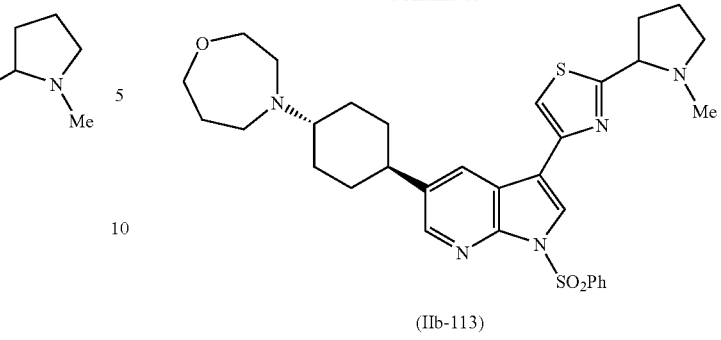

(IIb-113)

Ketone (IIb-106) (140 mg, 0.27 mmol), pyrrolidine (191 mg, 2.69 mmol) in anhydrous methanol (10 mL) and 1.25 M HCl in MeOH (0.43 mL, 0.54 mmol) were reacted overnight with NaBH₃CN (34 mg, 0.54 mmol) added in one portion and following the general procedure A for the reductive amination. The crude product was purified by was purified by PTLC using CH₂Cl₂:MeOH=90:10 (v/v) as the eluent to give the cis isomer (IIb-112) (10 mg, 6%) and the trans isomer (IIb-111) (23 mg, 15%).

Data for trans isomer (IIb-111): ¹H NMR (400 MHz, CDCl₃) δ 1.50-1.62 (dq, J=2.6, 12.4 Hz, 2H), 1.75-2.07 (m, 15H), 2.18-2.27 (m, 2H), 2.38-2.47 (m, 1H), 2.46 (s, 3H), 2.57-2.68 (m, 1H), 2.73 (tt, J=3.1, 12.4 Hz, 1H), 2.95 (br s, 2H), 3.27 (tt, J=1.8, 8.0 Hz, 1H), 3.79-3.84 (dd, J=6.1, 8.8 Hz, 1H), 7.38 (s, 1H), 7.45-7.50 (m, 2H), 7.54-7.59 (m, 1H), 8.12 (d, J=2.0 Hz, 1H), 8.15 (s, 1H), 8.19-8.22 (m, 2H), 8.32 (d, J=2.0 Hz, 1H).

Data for cis isomer (IIb-112): ¹H NMR (400 MHz, CDCl₃) δ 1.72-1.80 (m, 4H), 1.81-1.89 (m, 4H), 1.92-2.00 (m, 2H), 2.08-2.18 (br m, 5H), 2.34-2.64 (m, 10H), 2.44 (s, 3H), 2.74-2.84 (m, 1H), 3.27 (tt, J=1.5, 7.2 Hz, 1H), 3.78 (dd, J=6.4 Hz, 8.2 Hz, 1H), 7.44-7.52 (m, 3H), 7.53-7.58 (m, 1H), 8.20-8.23 ((m, 2H), 8.27 (, s, 1H), 8.33 (d, J=1.8 Hz, 1H), 8.68 (br s, 1H).

4-((1r,4r)-4- (3-(2- (1-methylpyrrolidin-2-yl)thiazol-4-yl)-1-(phenylsulfonyl)-1H-pyrrolo[2,3-b]pyridin-5-yl)cyclohexyl)-1,4-oxazepane (IIb-113) and 4-((1s,4s)-4-(3-(2-(1-methylpyrrolidin-2-yl)thiazol-4-yl)-1-(phenylsulfonyl)-1H-pyrrolo[2,3-b]pyridin-5-yl) cyclohexyl)-1,4-oxazepane (IIb-114)

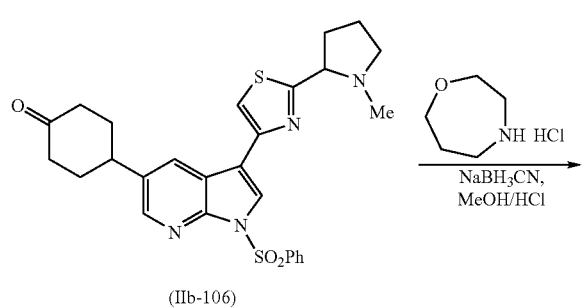 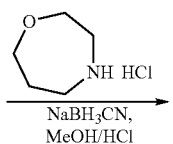

(IIb-106)

Ketone (IIb-106) (200 mg, 0.38 mmol), homomorpholine hydrochloride (310 mg, 2.25 mmol) and N-ethyldiisopropylamine (0.27 mL, 1.53 mmol) in anhydrous methanol (5 mL) and 1.25 M HCl in MeOH (0.43 mL, 0.54 mmol) were reacted overnight with NaBH₃CN (34 mg, 0.54 mmol), which was added at −20° C. as a solution in MeOH (2 mL), and following the general procedure A for the reductive amination. The crude product was purified by was purified by PTLC using CH₂Cl₂:MeOH=90:10 (v/v) as the eluent to give the cis isomer (IIb-114) (32 mg, 14%) as a colorless thick oil and the trans isomer (IIb-113) (46 mg, 20%).

Data for trans isomer (IIb-113): ¹H NMR (400 MHz, CDCl₃) δ 1.49-1.67 (m, 4H), 1.83-2.15 (m, 10H), 2.39-2.48 (m, 1H), 2.47 (s, 3H), 2.61-2.67 (m, 1H), 2.84-2.94 (m, 1H), 2.95-3.06 (m, 4H), 3.28 (t, J=7.4 Hz, 1H), 3.78-3.85 (m, 5H), 7.40 (s, 1H), 7.46-7.50 (m, 2H), 7.54-7.59 (m, 1H), 8.1 1 (d, J=2.0 Hz, 1H), 8.16 (s, 1H), 8.19-8.23 (m, 2H), 8.33 (d, J=2.0 Hz, 1H).

Data for cis isomer (IIb-114): ¹H NMR (400 MHz, CDCl₃) δ 1.71-1.81 (m, 4H), 1.85-2.04 (m, 8H), 2.08-2.20 (m, 2H), 2.37-2.45 (m, 1H), 2.47 (s, 3H), 2.90-2.98 (m, 1H), 2.98-3.13 (m, 5H), 3.27 (tt, J=1.7, 7.8 Hz, 1H), 3.77-3.86 (m, 5H), 7.44-7.51 (m, 2H), 7.54-7.59 (m, 1H), 8.17 (s, 1H), 8.20-8.24 (m, 2H), 8.25n (d, J=1.9 Hz, 1H), 8.41 (d, J=2.1 Hz, 1H).

4-(1-(phenylsulfonyl)-5-(1,4-dioxaspiro[4.5]decan-8-yl)-1H-pyrrolo[2,3-b]pyridin-3-yl)thiazole (IIb-115)

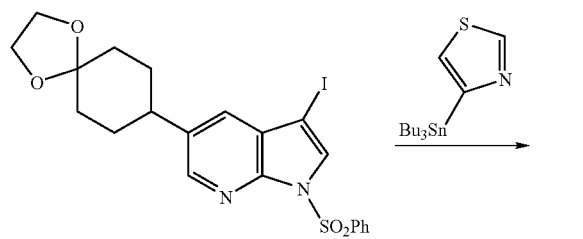

(IXb-23)

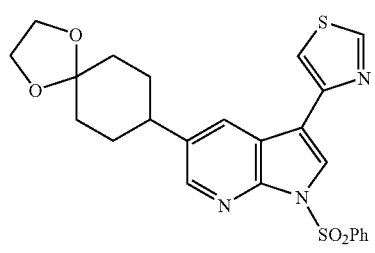

(IIb-115)

Iodide (IXb-23) (100 mg, 0.19 mmol) and 4-(tributylstannyl)thiazole (107 mg, 0.29 mmol), tri-O-tolylphosphine (7 mg, 0.02 mmol), dichlorobis(acetonitrile)palladium(II) (3 mg, 0.01 mmol) and toluene (3 mL) were reacted for 1 h at 120° C. (oil bath) in a sealed reaction vessel using the general procedure B for the Stille reaction. The reaction mixture was filtered, concentrated and purified by LCMS (column LUNA 10 μ C18(2) 00G-4253-V0 250×50 mm) using water—acetonitrile (0.1% AcOH) as eluent (in gradient; flow 80 mL/min) to give (IIb-115) (22.2 mg, 24%) as a white solid. $^1$H NMR (400 MHz, CDCl$_3$) δ 1.68-1.90 (m, 8H), 2.69-2.76 (m, 1H), 3.99 (m, 4H), 7.46-7.50 (m, 2H), 7.52 (d, J=1.9 Hz, 1H), 7.57 (tt, J=7.4, 1.5 Hz, 1H), 8.17 (s, 1H), 8.22-8.25 (m, 3H), 8.38 (d, J=1.9 Hz, 1H), 8.93 (d, J=1.9 Hz, 1H).

4-((1r,4r)-4-(3-(4-methylthiazol-2-yl)-1-(phenylsulfonyl)-1H-pyrrolo[2,3-b]pyridin-5-yl)cyclohexyl)-1,4-oxazepane (IIb-117)

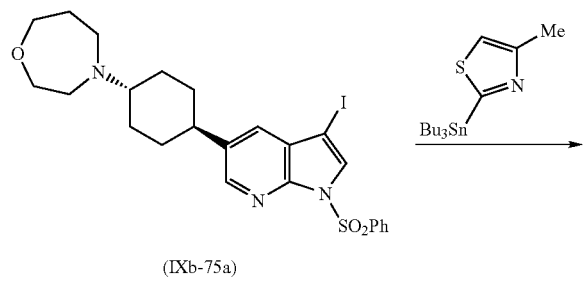

(IXb-75a)

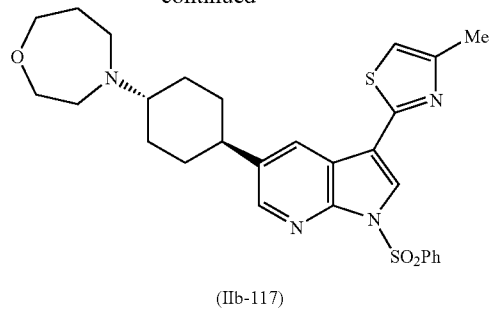

(IIb-117)

Iodide (IXb-75a) (150 mg, 0.27 mmol), 4-methyl-2-(tributylstannyl)thiazole (154 mg, 0.40 mmol), tri-O-tolylphosphine (10 mg, 0.03 mmol), dichlorobis(acetonitrile)palladium(II) (4 mg, 0.02 mmol) and toluene (3 mL) were reacted for 5 h at 120° C. (oil bath) in a sealed reaction vessel using the general procedure B for the Stille reaction. The reaction mixture was filtered, concentrated and purified by LCMS (column LUNA 10 μ C18(2) 00G-4253-V0 250×50 mm) using water—acetonitrile (0.1% AcOH) as eluent (in gradient; flow 80 mL/min) followed by PTLC on amino silica plates (Chromatorex NH, Fuji Silysia) to give (IIb-117) (38.8 mg, 26.9%). $^1$H NMR (400 MHz, CDCl$_3$) δ 1.41-1.63 (m, 4H), 1.84-1.90 (m, 2H), 1.96-2.03 (m, 4H), 2.53 (d, J=1.0 Hz, 3H), 2.58-2.69 (m, 2H), 2.79-2.84 (m, 4H), 3.71-3.74 (m, 2H), 3.81 (t, J=6.1 Hz, 2H), 6.87 (d, J=1.0 Hz, 1H), 7.47-7.52 (m, 2H), 7.58 (tt, J=7.5, 1.5 Hz, 1H), 8.21-8.24 (m, 3H), 8.31-8.36 (m, 2H).

4-((1r,4r)-4-(1-(tert-butyldimethylsilyl)-3-(thiazol-5-yl)-1H-pyrrolo[2,3-b]pyridin-5-yl)cyclohexyl)-1,4-oxazepane (IIb-118)

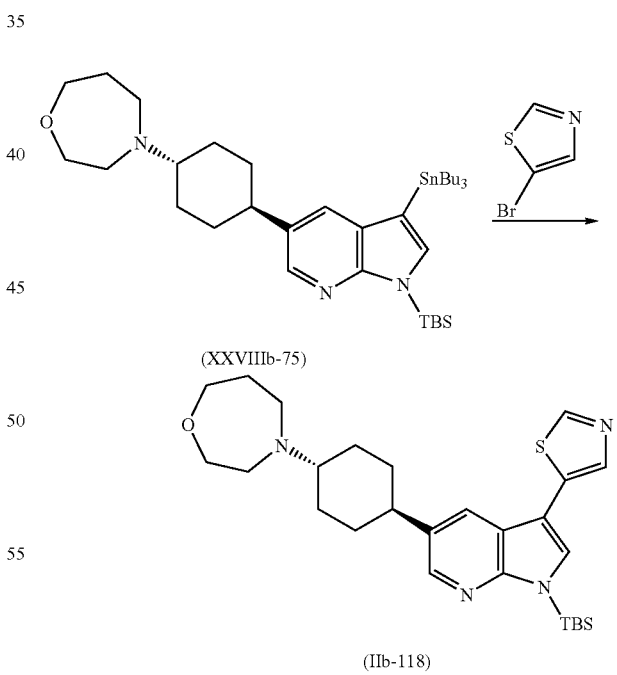

Crude stannane (XXVIII-75) (250 mg, about 0.30 mmol), 5-bromothiazole (88 mg, 0.53 mmol), tri-O-tolylphosphine (21 mg, 0.07 mmol), dichlorobis(acetonitrile)palladium(II) (9 mg, 0.04 mmol), and toluene (2 mL) were reacted for 18 h at 85° C. using a modification of the general procedure B for the Stille reaction. The crude product was purified by PTLC using LCMS CHCl$_3$:MeOH:NH$_4$OH=93:6:1 (v/v/v) to give a mixture of (Ib-118) and (XXVIIb-75) (15.10 mg), which was used directly in further steps without additional purification. Selected resonances in $^1$H NMR (400 MHz, CDCl$_3$) spectrum: δ 0.65 (s, 6H), 0.96 (s, 9H), 1.46-1.67 (m, 4H), 1.91-2.10 (m, 6H), 2.53-2.77 (m, 2H), 2.85-2.95 (m, 4H), 3.75-3.80 (m, 2H), 3.82 (t, J=6.0 Hz, 2H), 7.41 (s, 1H), 7.88 (d, J=2.1 Hz, 1H), 8.03 (s, 1H), 8.22 (d, J=2.1 Hz, 1H), 8.74 (s, 1H).

4-((1r,4r)-4-(1-(tert-butyldimethylsilyl)-3-(2-methoxythiazol-4-yl)-1H-pyrrolo[2,3-b]pyridin-5-yl)cyclohexyl)morpholine (IIb-120)

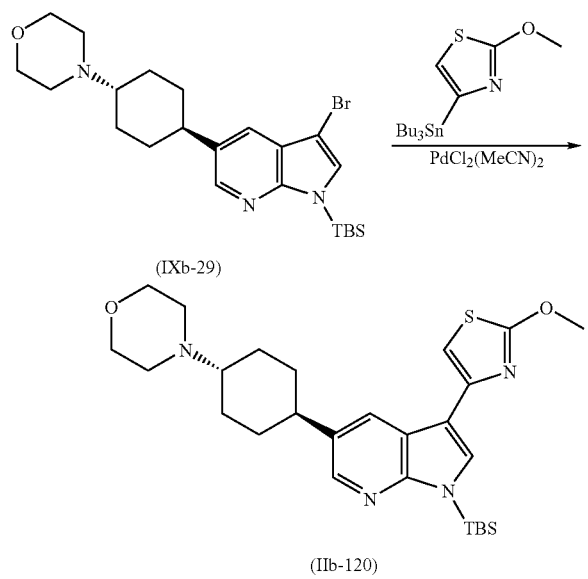

Bromide (IXb-29) (312.00 mg, 0.65 mmol), tri-O-tolylphosphine (39.69 mg, 0.13 mmol), PdCl$_2$(MeCN)$_2$ (16.91 mg, 0.07 mmol) and 2-methoxy-4-(tributylstannyl) thiazole (289.88 mg, 0.72 mmol) in toluene (3.0 mL) were reacted for 18 h using the general procedure B for the Stille reaction. The crude product was purified by LCMS (column LUNA 10 μ C18(2) 00G-4253-V0 250×50 mm) using water—acetonitrile (0.1% AcOH) as eluent (in gradient; flow 80 mL/min) followed by SGC using CH$_2$Cl$_2$:EtOAc:MeOH as eluent (gradient elution from 50:50:0 to 45:45:10; v/v/v) to give (IIb-120) (289.00 mg, 60.00% pure, 0.34 mmol, 52%).

4-((1r,4r)-4-(3-(5-methylthiazol-2-yl)-1-(phenylsulfonyl)-1H-pyrrolo[2,3-b]pyridin-5-yl)cyclohexyl)-1,4-oxazepane (IIb-121)

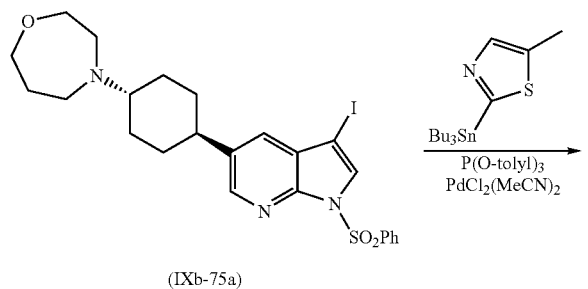

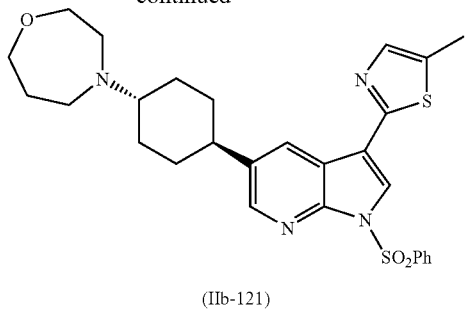

Iodide (IXb-75a) (101 mg, 0.18 mmol), 5-methyl-2-(tributylstannyl)thiazole (104 mg, 0.27 mmol), tri-O-tolylphosphine (7 mg, 0.02 mmol), dichlorobis(acetonitrile)palladium (II) (3 mg, 0.01 mmol) and toluene (3 mL) were reacted for 5.5 h at 120° C. (oil bath) in a sealed reaction vessel using the general procedure B for the Stille reaction. The reaction mixture was filtered, concentrated and purified by PTLC on amino silica plates (Chromatorex NH, Fuji Silysia) to give (IIb-121) (18.3 mg, 19%). $^1$H NMR (400 MHz, CDCl$_3$) δ 1.38-1.61 (m, 4H), 1.83-1.90 (m, 2H), 1.95-2.01 (m, 4H), 2.53 (s, 3H), 2.57-2.68 (m, 2H), 2.78-2.84 (m, 4H), 3.71-3.75 (m, 2H), 3.81 (t, J=5.9 Hz, 2H), 7.49-7.52 (m, 3H), 7.56-7.61 (m, 1H), 8.13 (s, 1H), 8.21-8.24 (m, 2H) and 8.33-8.37 (m, 2H).

4-((1r,4r)-4-(1-(phenylsulfonyl)-3-(2-(pyrrolidin-1-yl)thiazol-4-yl)-1H-pyrrolo[2,3-b]pyridin-5-yl)cyclohexyl)-1,4-oxazepane (IIb-122)

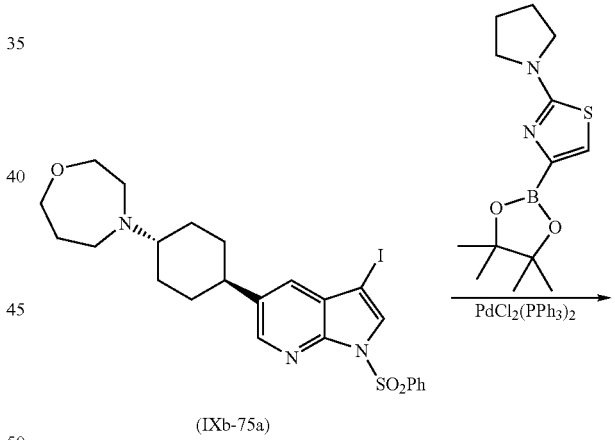

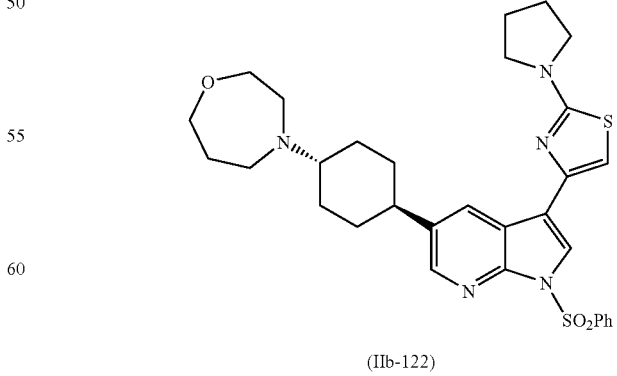

A mixture of iodide (IXb-75a) (100 mg, 0.18 mmol), 2-(pyrrolidin-1-yl)-4-(4,4,5,5-tetramethyl-1,3,2-dioxaborolan-2-yl)thiazole (55 mg, 0.19 mmol), LiCl (22 mg, 0.53 mmol), Pd(PPh$_3$)$_2$Cl$_2$ (6 mg, 0.008 mmol) and 1.0 M Na$_2$CO$_3$ solution (0.44 mL, 0.44 mmol) in EtOH (2 mL) and toluene (2 mL) was reacted for 4.5 h following the general procedure B for the Suzuki reaction. The product was purified by PTLC on amino silica plates (Fuji Silysia, Chromatorex NH) to afford (IIb-122) (30.1 mg, 28%); $^1$H NMR (400 MHz, CDCl$_3$) δ 1.39-1.61 (m, 4H), 1.66-1.79 (m, 2H), 1.88 (t, J=5.4 Hz, 2H), 1.95-2.03 (m, 4H), 2.06-2.11 (m, 4H), 2.54-2.68 (m, 2H), 2.79-2.86 (m, 2H), 3.51-3.56 (m, 4H), 3.72-3.75 (m, 2H), 3.81 (t, J=5.9 Hz, 2H), 6.63 (s, 1H), 7.43-7.48 (m, 2H), 7.54 (tt, J=7.4 and 1.6 Hz, 11H), 8.03 (s, 1H), 8.10 (d, J=2.1 Hz, 1H), 8.18-8.22 (m, 2H), 8.30 (d, J=2.1 Hz, 1H).

4-((1r,4r)-4-(3-(4,5-dimethylthiazol-2-yl)-1-(phenyl-sulfonyl)-1H-pyrrolo[2,3-b]pyridin-5-yl)cyclo-hexyl)-1,4-oxazepane (IIb-123)

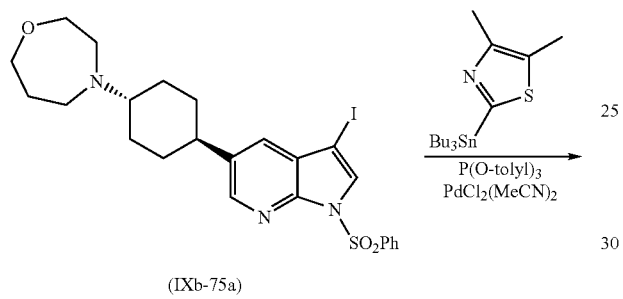

(IIb-123)

Iodide (IXb-75a) (150 mg, 0.26 mmol), 4,5-dimethyl-2-(tributylstannyl)thiazole (160 mg, 0.39 mmol), tri-O-tolylphosphine (10 mg, 0.03 mmol), dichlorobis(acetonitrile)palladium(II) (4 mg, 0.02 mmol) and toluene (3 mL) were reacted for 4 h at 120° C. (oil bath) in a sealed reaction vessel using the general procedure B for the Stille reaction. The reaction mixture was filtered, concentrated and purified by PTLC on amino silica plates (Chromatorex NH, Fuji Silysia) using hexane:EtOAc=1:1 (v/v) as eluent to give (IIb-123) (70.3 mg, 48%). $^1$H NMR (400 MHz, CDCl$_3$) δ 1.38-1.63 (m, 4H), 1.83-1.91 (m, 2H), 1.95-2.03 (m, 4H), 2.40 (s, 3H), 2.41 (s, 3H), 2.57-2.69 (m, 2H), 2.79-2.85 (m, 4H), 3.71-3.75 (m, 2H), 3.81 (t, J=6.0 Hz, 2H), 7.46-7.51 (m, 2H), 7.58 (tt, J=7.4, 1.6 Hz, 1H), 8.14 (s, 1H), 8.20-8.23 (m, 2H), 8.29 (d, J=2.1 Hz, 1H), 8.34 (d, J=2.1 Hz, 1H).

4-((1r,4r)-4-(3-(2-methoxythiazol-4-yl)-1-(phenyl-sulfonyl)-1H-pyrrolo[2,3-b]pyridin-5-yl)cyclo-hexyl)-1,4-oxazepane (IIb-124)

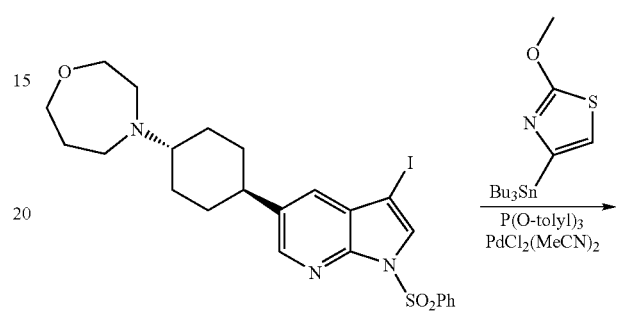

(IIb-124)

Iodide (IXb-75a) (150 mg, 0.26 mmol), 2-methoxy-4-(tributylstannyl)thiazole (161 mg, 0.39 mmol), tri-O-tolylphosphine (10 mg, 0.03 mmol), dichlorobis(acetonitrile)palladium(II) (4 mg, 0.02 mmol) and toluene (3 mL) were reacted for 2 h at 120° C. (oil bath) in a sealed reaction vessel using the general procedure B for the Stille reaction. The reaction mixture was filtered, concentrated and purified by PTLC on amino silica plates (Chromatorex NH, Fuji Silysia) using hexane:EtOAc=1:1 (v/v) as eluent to give (IIb-124) (94.4 mg, 64%). $^1$H NMR (400 MHz, CDCl$_3$) δ 1.38-1.61 (m, 4H), 1.82 (m, 2H), 1.95-2.02 (m, 4H), 2.55-2.67 (m, 2H), 2.78-2.84 (m, 4H), 3.70-3.75 (m, 2H), 3.80 (t, J=6.0 Hz, 2H), 4.17 (s, 3H), 6.83 (s, 1H), 7.44-7.50 (m, 2H), 7.56 (tt, J=7.4, 1.6 Hz, 1H), 8.06 (d, J=2.0 Hz, 1H), 8.09 (s, 1H), 8.19-8.23 (m, 2H), 8.32 (d, J=2.0 Hz, 1H).

4-((1r,4r)-4-(3-(2-ethoxythiazol-4-yl)-1-(phenylsulfonyl)-1H-pyrrolo[2,3-b]pyridin-5-yl)cyclohexyl)-1,4-oxazepane (IIb-125)

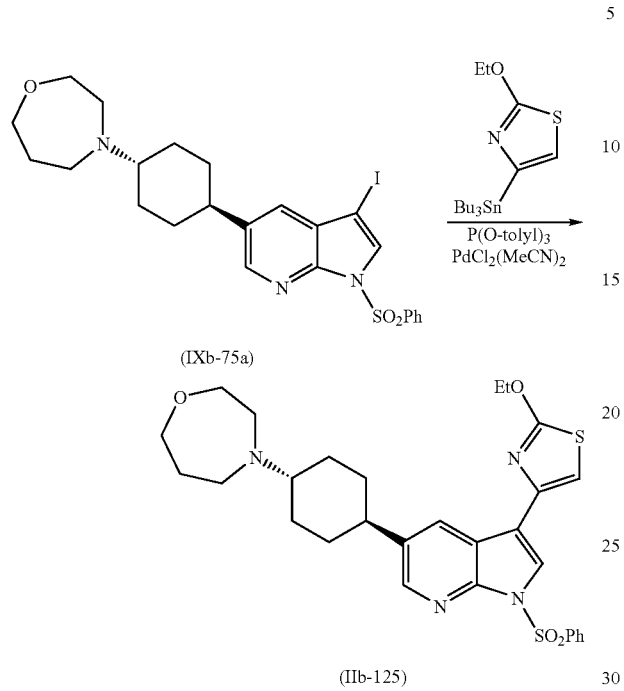

Iodide (IXb-75a) (150 mg, 0.26 mmol), 2-ethoxy-4-(tributylstannyl)thiazole (166 mg, 0.39 mmol), tri-O-tolylphosphine (10 mg, 0.03 mmol), dichlorobis(acetonitrile)palladium(II) (4 mg, 0.02 mmol) and toluene (3 mL) were reacted for 4.3 h at 120° C. (oil bath) in a sealed reaction vessel using the general procedure B for the Stille reaction. The reaction mixture was filtered, concentrated and purified by PTLC on amino silica plates (Chromatorex NH, Fuji Silysia) using hexane:EtOAc=1:1 (v/v) as eluent to give (IIb-125) (82.3 mg, 54%). $^1$H NMR (400 MHz, CDCl$_3$) δ 1.39-1.60 (m, 4H), 1.49 (t, J=7.1 Hz, 3H), 1.83-1.90 (m, 2H), 1.95-2.02 (m, 4H), 2.55-2.67 (m, 2H), 2.78-2.84 (m, 4H), 3.70-3.75 (m, 2H), 3.80 (t, J=6.0 Hz, 2H), 4.12 (q, J=7.1, 14.2 Hz, 2H), 6.81 (s, 1H), 7.45-7.50 (m, 2H), 7.56 (tt, J=7.4, 1.6 Hz, 1H), 8.05 (d, J=2.1 Hz, 1H), 8.08 (s, 1H), 8.19-8.23 (m, 2H), 8.32 (d, J=2.1 Hz, 1H).

4-(1-Benzenesulfonyl-5-bromo-1H-pyrrolo[2,3-b]pyridin-3-yl)-thiazole-2-carboxylic acid ethyl ester (III-a)

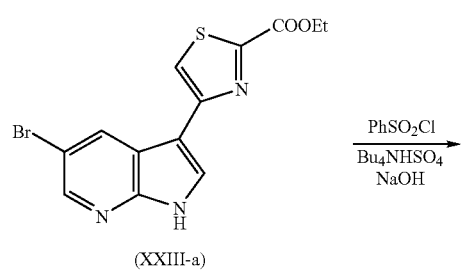

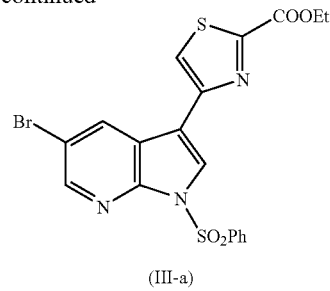

Compound (XXIII-a) (6.08 g, 14.0 mmol), n-Bu$_4$NHSO$_4$ (100 mg, cat.), PhSO$_2$Cl (2.50 mL, 19.5 mmol) and 50% aqueous NaOH (2 mL) in CH$_2$Cl$_2$ (75 mL) were reacted at RT for 1.5 h following the general procedure for the protection of (XXIII). The crude product was recystallized from CH$_2$Cl$_2$/hexane to afford pure (III-a) (2.33 g) as a yellow solid. More product was obtained from the mother liquor by SGC using hexane:CH$_2$Cl$_2$:EtOAc (2:1:1, v/v/v) as eluent. Total yield of (III-a) (4.40 g, 8.94 mmol, 57%). $^1$H NMR (400 MHz, CDCl$_3$) δ 1.51 (t, J=7.2 Hz, 3H), 4.55 (q, J=7.1 Hz, 2H), 7.53 (t, J=7.8 Hz, 2H), 7.63 (t, J=7.5 Hz, 1H), 7.74 (s, 1H), 8.24 (d, J=7.8 Hz, 1H), 8.30 (s, 1H), 8.54 (d, J=2.1 Hz, 1H), 8.56 (d, J=2.1 Hz, 1H).

(4-(5-bromo-1-(phenylsulfonyl)-1H-pyrrolo[2,3-b]pyridin-3-yl)thiazol-2-yl)(piperidin-1-yl)methanone (III-c)

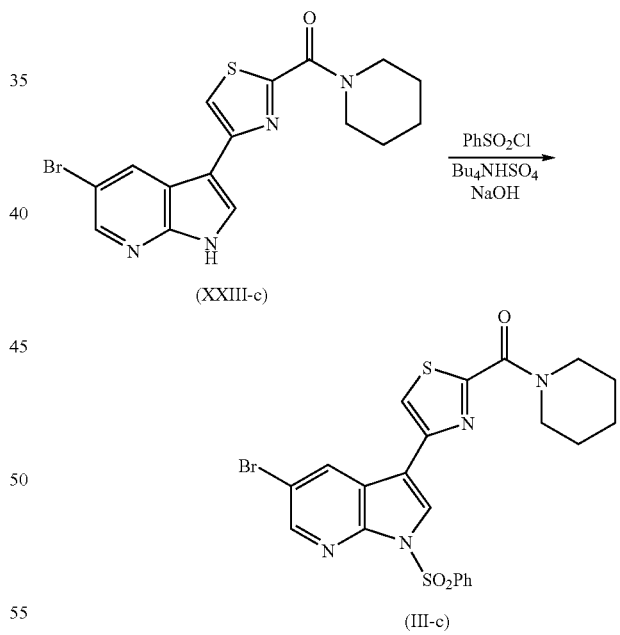

Compound (XXIII-c) (770 mg, 1.97 mmol), n-Bu$_4$NHSO$_4$ (100 mg, 0.294 mmol), PhSO$_2$Cl (0.40 mL, 554mg, 3.12 mmol) and 50% aqueous NaOH (1 mL) in CH$_2$Cl$_2$ (10 mL) were reacted at RT for 1.5 h following the general procedure for the protection of (XXIII). The crude brown oil (738 mg) was purified by SGC using AcOEt:hexanes 1:4 (v/v) to afford (III-c) (385 mg, 0.72 mmol, 37%) as a solid. $^1$H NMR (400 MHz, CDCl$_3$) δ 1.71-1.88 (m, 6H), 3.76-3.84 (m, 2H), 4.31-4.39 (m, 2H), 7.53 (t, J 7.7 Hz, 2H), 7.63 (tt, J 1.2, 7.5 Hz, 1H), 7.68 (s, 1H), 8.16 (s, 1H), 8.21-8.26 (m, 2H), 8.52 (d, J=2.2 Hz, 1H), 8.58 (d, J=2.2Hz, 1H).

4-[4-(1-Benzenesulfonyl-5-bromo-1H-pyrrolo[2,3-b]pyridin-3-yl)-thiazol-2-yl]-piperidine-1-carboxylic acid tert-butyl ester (III-f)

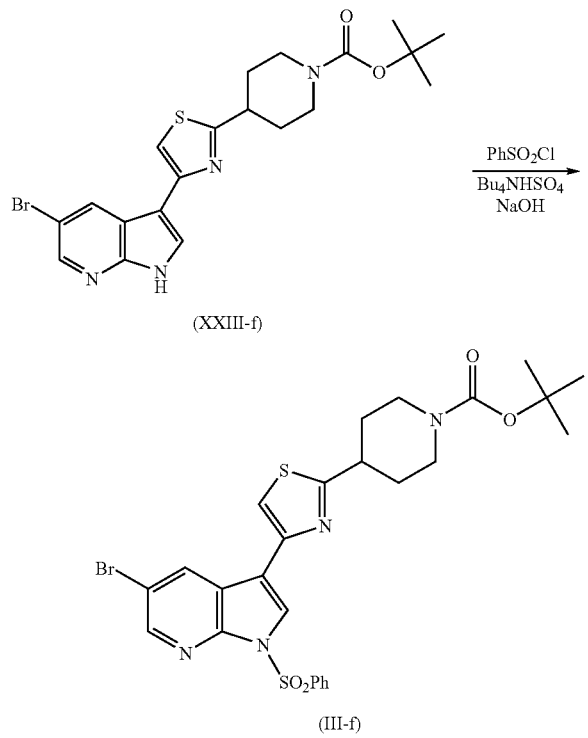

Compound (XXIII-f) (1.24 g, 2.68 mmol), n-Bu₄NHSO₄ (120 mg, 0.35 mmol), PhSO₂Cl (0.50 mL, 690 mg, 3.90 mmol) and 50% aqueous NaOH (0.5 mL) in CH₂Cl₂ (15 mL) were reacted at RT overnight following the general procedure for the protection of (XXIII). The crude (III-f) (840 mg) was obtained as pale yellow solid. On standing overnight, a precipitate appeared in the aqueous extract, which was filtered to afford additional (III-f) (710 mg) as a white powder. The two solids were combined to afford (III-f) as an off-white solid (1.55 g, 2.57 mmol, 96%). $^1$H NMR (400 MHz, CDCl₃) δ 1.51 (s, 9H), 1.79 (dd, J=4.4, 12.6 Hz, 2×1H), 1.84 (dd, J=4.4, 12.6 Hz, 2×1H), 2.19 (br d, J=12.6 Hz, 2H), 2.95 (br t, J=12.3 Hz, 2H), 3.25 (tt, J=3.8, 11.6 Hz, 1H), 4.26 (br s, 2H), 7.37 (s, 1H), 7.52 (t, J=7.8 Hz, 2H), 7.62 (t, J=7.5 Hz, 1H), 8.17 (s, 1H), 8.22 (d, J=7.8 Hz, 1H), 8.52 (d, J=2.4 Hz, 1H), 8.54 (d, J=2.4 Hz, 1H).

4-(5-bromo-1-(phenylsulfonyl)-1H-pyrrolo[2,3-b]pyridin-3-yl)-2-(piperidin-4-yl)thiazole (III-g)

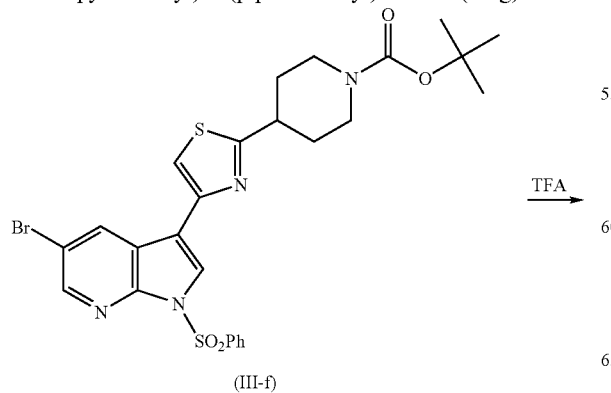

To a stirred solution of (III-f) (5.80 g, 9.61 mmol) in CH₂Cl₂ (40 mL) was added CF₃COOH (5 mL). The reaction was stirred at r.t. for 2 h. The reaction mixture was then poured slowly into a saturated solution of NaHCO3 (300 mL) and the mixture was stirred for 20 min. It was extracted with EtOAc (3×300 mL). The combined organic extracts were dried (MgSO₄) and concentrated to give the crude product which was triturated with MeOH (20 mL). The solid was filtered to give (III-g) (4.80 g, 99%) as an yellow solid. $^1$H NMR (400 MHz, CDCl₃) δ 1.95-2.06 (dq, J=3.8 and 12.5 Hz, 2H), 2.20-2.29 (dd, J=2.4 and 13.3 Hz, 2H), 2.48-2.57 (dt, J=2.4 and 11.8 Hz, 2H), 2.99-3.08 (tt, J=3.8 and 11.4 Hz, 1H), 3.90-3.97 (m, 2H), 7.35 (s, 1H), 7.47-7.51 (m, 2H), 7.55-7.60 (m, 1H), 8.12 (s, 1H), 8.18-5.21 (m, 2H), 8.48 (d, J=2.2 Hz, 1H), 8.49 (d, J=2.2 Hz, 1H).

1-Benzenesulfonyl-5-bromo-3-[2-(1-methyl-piperidin-4-yl)-thiazol-4-yl]-1H pyrrolo[2,3-b]pyridine (III-h)

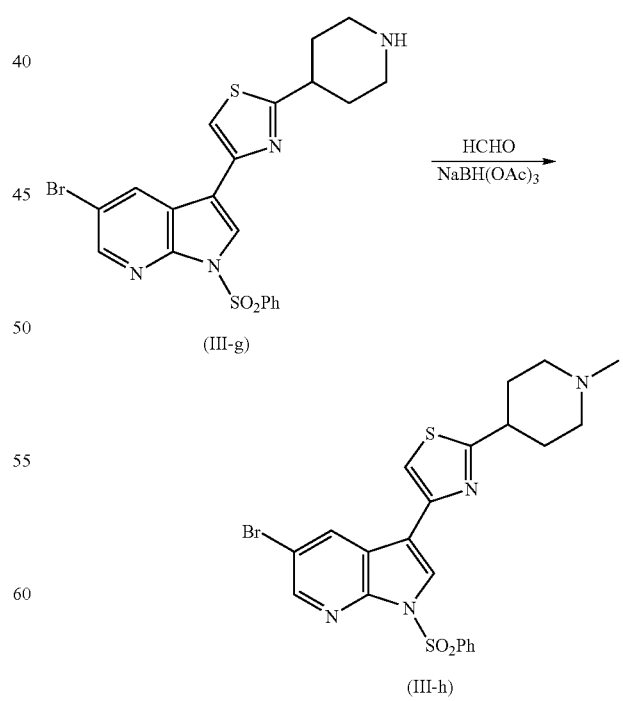

To a stirred solution of (III-g) (4.80 g, 9.53 mmol) in THF (40 mL) was added a 40% aqueous solution of formaldehyde (10 mL). Acetic acid (0.03 mL, 0.48 mmol) was added. The mixture was stirred at room temperature for 30 mins. NaBH(OAc)₃ (4.04 g, 19.07 mmol) was added in one portion. The reaction was stirred at r.t. overnight. A saturated solution of NaHCO₃ (400 mL) was added slowly over 20 min into the reaction mixture until the gas evolution ceased. It was extracted with CH₂Cl₂ (3×400 mL). The combined organic extracts were dried (MgSO₄) and concentrated to give (III-h) (3.81 g, 77%). ¹H NMR (400 MHz, CDCl₃) δ 1.90-2.02 (m, 2H), 2.11-2.18 (m, 4H), 2.33 (s, 3H), 2.95-3.10 (m, 3H), 7.27 (s, 1H), 7.42 (t, J=7.7 Hz, 2H), 7.52 (t, J=7.4 Hz, 1H), 8.06 (s, 1H), 8.12 (d, J=7.7 Hz, 1H), 8.41 (d, J=2.0 Hz, 1H), 8.45 (d, J=2.0 Hz, 1H).

1-Benzenesulfonyl-5-bromo-3-[2-(1-methyl-piperidin-4-yl)-thiazol-4-yl]-1H pyrrolo[2,3-b]pyridine (III-h)—alternative preparation without isolation of (III-g)

added formaldehyde (40% aq., 1 mL, excess), acetic acid (3 drops, cat.) and NaBH(OAc)₃ (800 mg, 3.77 mmol). The reaction mixture was allowed to stir overnight, and was then quenched by the addition of 1.0 N aqueous HCl (10 mL, 10 mmol). The mixture was then neutralized with 1.0 N aqueous NaOH (about 10 mL, 10 mmol) and extracted with AcOEt (3×50 mL). The organic extracts were combined, dried (MgSO₄) and concentrated to afford (III-h) (840 mg, 1.62 mmol, 63%) as a pale yellow solid. ¹H NMR (400 MHz, CDCl₃) δ 1.85-2.00 (m, 2H), 2.07-2.23 (m, 4H), 2.33 (s, 3H), 2.93-3.07 (m, 3H), 7.27 (s, 1H), 7.42 (t, J=7.7 Hz, 2H), 7.52 (t, J=7.4 Hz, 1H), 8.06 (s, 1H), 8.12 (d, J=7.7 Hz, 1H), 8.41 (d, J=2.0 Hz, 1H), 8.45 (d, J=2.0 Hz, 1H).

4-(5-bromo-1-(phenylsulfonyl)-1H-pyrrolo[2,3-b]pyridin-3-yl)-N,N-diethylthiazol-2-amine (III-i)

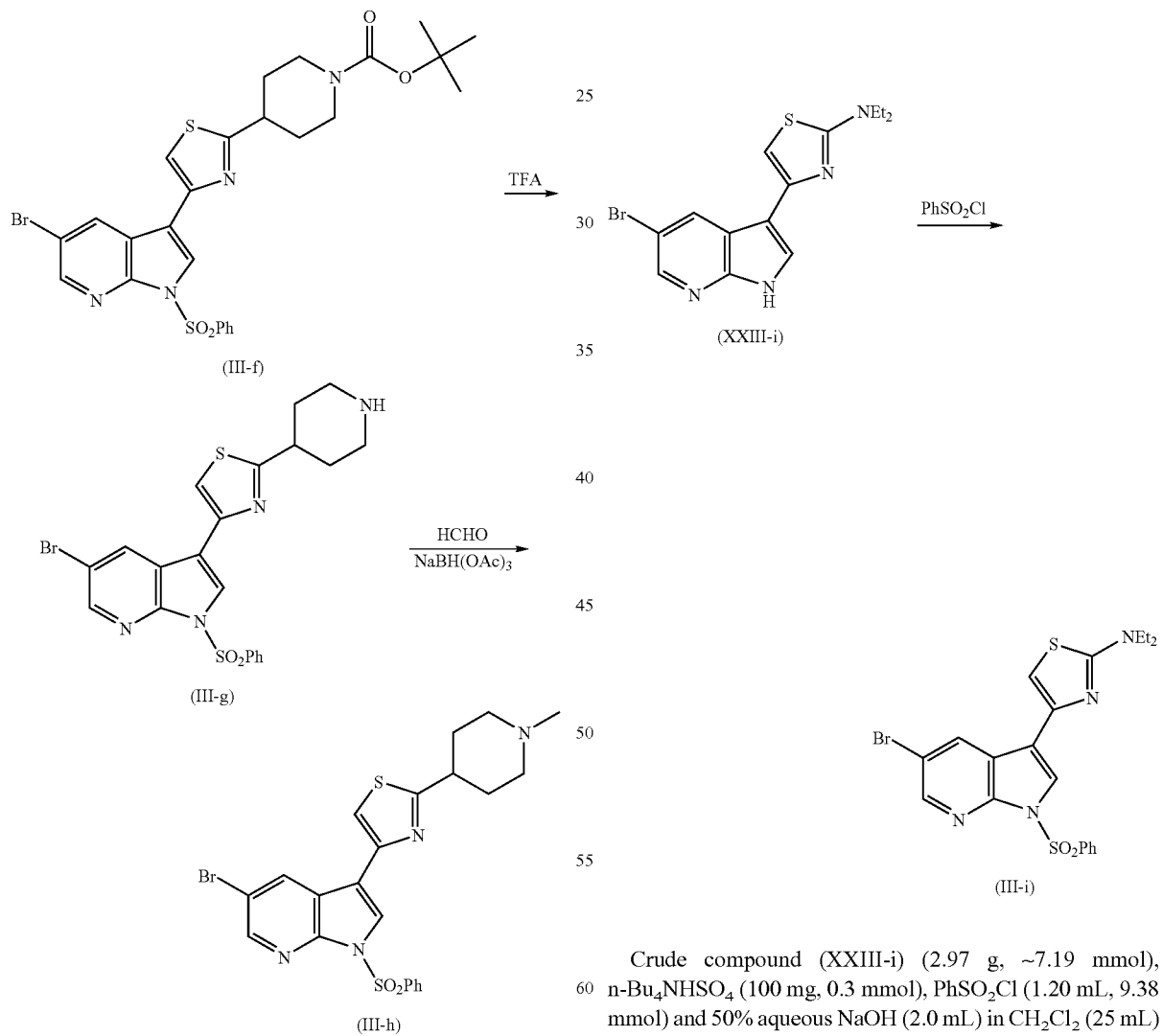

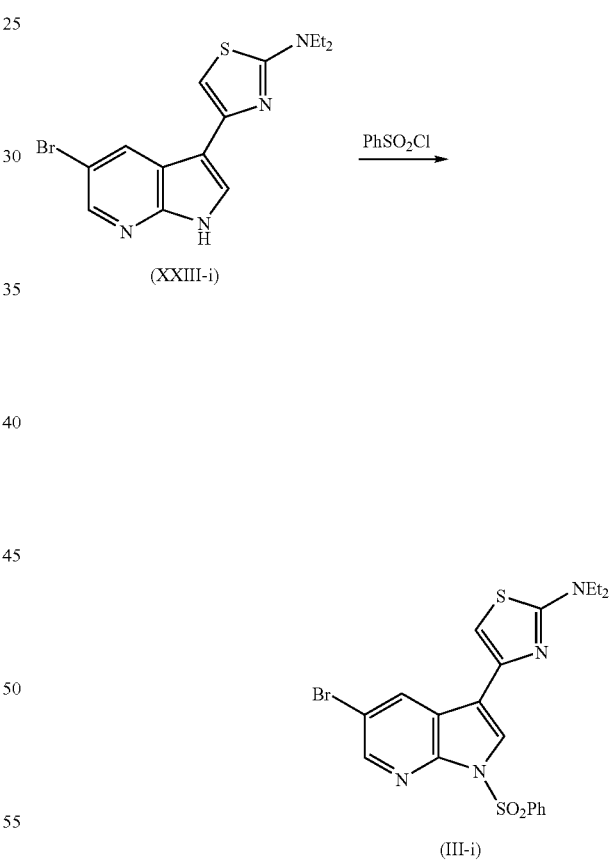

To a stirred solution of (III-f) (1.55 g, 2.57 mmol) in CH₂Cl₂ (10 mL) was added CF₃COOH (5 mL). After 1 h, the solution was concentrated to dryness and THF (5 mL) was added. To the resulting suspension of (III-g) TFA salt was Crude compound (XXIII-i) (2.97 g, ~7.19 mmol), n-Bu₄NHSO₄ (100 mg, 0.3 mmol), PhSO₂Cl (1.20 mL, 9.38 mmol) and 50% aqueous NaOH (2.0 mL) in CH₂Cl₂ (25 mL) were reacted at RT for 2 h following the general procedure for the protection of (XXIII). The crude product (3.87 g) was triturated with MeOH (50 mL) to give (III-i) (2.14 g, estimated purity 85%) as a pale brown powder. ¹H NMR (400 MHz, CDCl₃) δ 1.31 (t, J=7.1 Hz, 6H), 3.57 (q, J=7.1 Hz, 4H), 6.64 (s, 1H), 7.50 (t, J=7.7 Hz, 2H), 7.60 (tt, J=1.5, 7.5 Hz, 1H), 8.11 (s, 1H), 8.20 (d, J=7.8 Hz, 2H), 8.48 (d, J=2.2 Hz, 1H), 8.51 (d, J=2.2 Hz, 1H).

2-(5-bromo-1-(phenylsulfonyl)-1H-pyrrolo[2,3-b]pyridin-3-yl)thiazole (III-j)

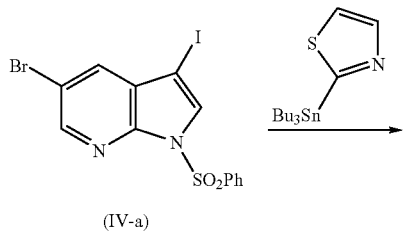
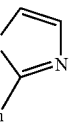
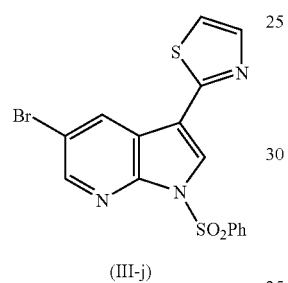

Bromide (IV-a) (4.35 g, 9.39 mmol; preparation disclosed in WO2004/078756), 2-(tributylstannyl)thiazole (3.71 g, 9.92 mmol), tri-o-tolylphosphine (355 mg, 1.17 mmol) and bis(acetonitrile)dichloropalladium (II) (150 mg, 0.58 mmol) in toluene (30 mL) were reacted for 6 h (bath temperature 110° C.) using the general procedure A for the Stille reaction. The crude product (dark brown oil, 8.89 g) was purified by silicagel chromatography using $CH_2Cl_2$ as eluent to afford the (III-j) as a pale yellow foam (1.72 g, 4.09 mmol, 44%). $^1$H NMR (400 MHz, $CDCl_3$) δ 7.37 (d, J=3.3 Hz, 11H), 7.55 (t, J=7.7 Hz, 2H), 7.65 (tt, J=1.5, 7.5 Hz, 1H), 7.91 (d, J=3.3 Hz, 1H), 8.22-8.29 (m, 3H), 8.55 (d, J=2.2 Hz, 1H), 8.83 (d, J=2.2 Hz, 1H).

4-(5-bromo-1-(phenylsulfonyl)-1H-pyrrolo[2,3-b]pyridin-3-yl)-2-methylthiazole (III-k)

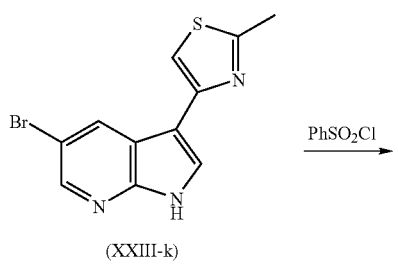

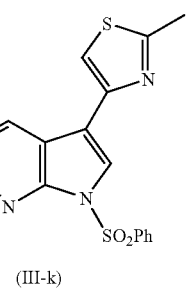

Compound (XXIII-k) (2.63 g, 8.94 mmol), n-$Bu_4NHSO_4$ (250 mg, 0.74 mmol), $PhSO_2Cl$ (2.21 g, 12.52 mmol) and 50% aqueous NaOH (1.0 mL) in $CH_2Cl_2$ (50 mL) were reacted at RT for 2 h following the general procedure for the protection of (XXIII). The solution was then poured onto saturated aqueous $NaHCO_3$ (100 mL), and extracted with AcOEt (2×100 mL). The combined organic portions were dried over $MgSO_4$ and concentrated to afford a brown solid. The solid was triturated with MeOH (50 mL) to afford (III-k) as a white powder (3.28 g, 7.54 mmol, 84%). $^1$H NMR (400 MHz, $CDCl_3$) δ 2.72 (s, 3H), 7.22 (s, 1H), 7.42 (t, J=7.7 Hz, 2H), 7.53 (tt, J=1.5, 7.5 Hz, 1H), 8.08 (s, 1H), 8.10-8.13 (m, 2H), 8.42 (d, J=2.2 Hz, 1H), 8.45 (d, J=2.2 Hz, 1H).

2-(5-bromo-1-(phenylsulfonyl)-1H-pyrrolo[2,3-b]pyridin-3-yl)-4-(trifluoromethyl)thiazole (III-l)

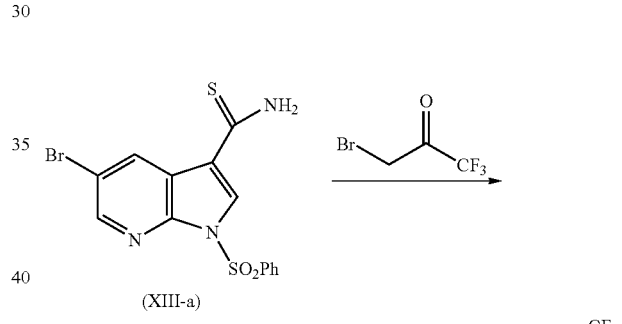

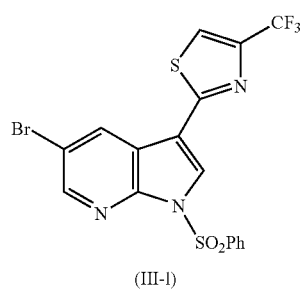

To a stirred solution of (XIII-a) (5.65 g, 14.26 mmol) in THF (50 mL) was added 3-bromo-1,1,1-trifluoro-propan-2-one (3.01 g, 15.74 mmol) dropwise over 10 min. The reaction mixture was then stirred at r.t. for 18 h, added to saturated aqueous $NaHCO_3$ (100 mL) and extracted with AcOEt (2×100 mL). The combined organic portions were dried ($MgSO_4$) and concentrated to afford a crude hydroxythiazoline (10.16 g). Elimination to the thiazole was effected by dissolving in THF (100 mL), adding trifluoroacetic anhydride (5 mL) and stirring at room temperature for 18 h. The mixture was then poured onto saturated aqueous $NaHCO_3$ (250 mL) and extracted with AcOEt (2×250 mL). The combined organic portions were dried over $MgSO_4$ and concentrated to give an oil (8.34 g) which was purified by SGC using AcOEt:

hexane=1:4 (v/v) as eluent to afford impure product (5.11 g, estimated purity 85%). The product was further purified by trituration with Et₂O (100 mL) to afford (III-l) as a white powder (1.71 g, 3.50 mmol, 25%). ¹H NMR (400 MHz, CDCl₃) δ 7.56 (t, J=7.8 Hz, 2H), 7.67 (tt, J=1.5, 7.5 Hz, 1H), 7.78 (q, J=0.8 Hz, 1H), 8.24-8.29 (m, 2H), 8.33 (s, 1H), 8.57 (d, J=2.3 Hz, 1H), 8.76 (d, J=2.3 Hz, 1H).

tert-butyl 4-(2-(5-bromo-1-(phenylsulfonyl)-1H-pyrrolo[2,3-b]pyridin-3-yl)thiazol-4-yl)piperidine-1-carboxylate (III-m)

2-(5-bromo-1-(phenylsulfonyl)-1H-pyrrolo[2,3-b]pyridin-3-yl)-4-(1-methylpiperidin-4-yl)thiazole (III-n)

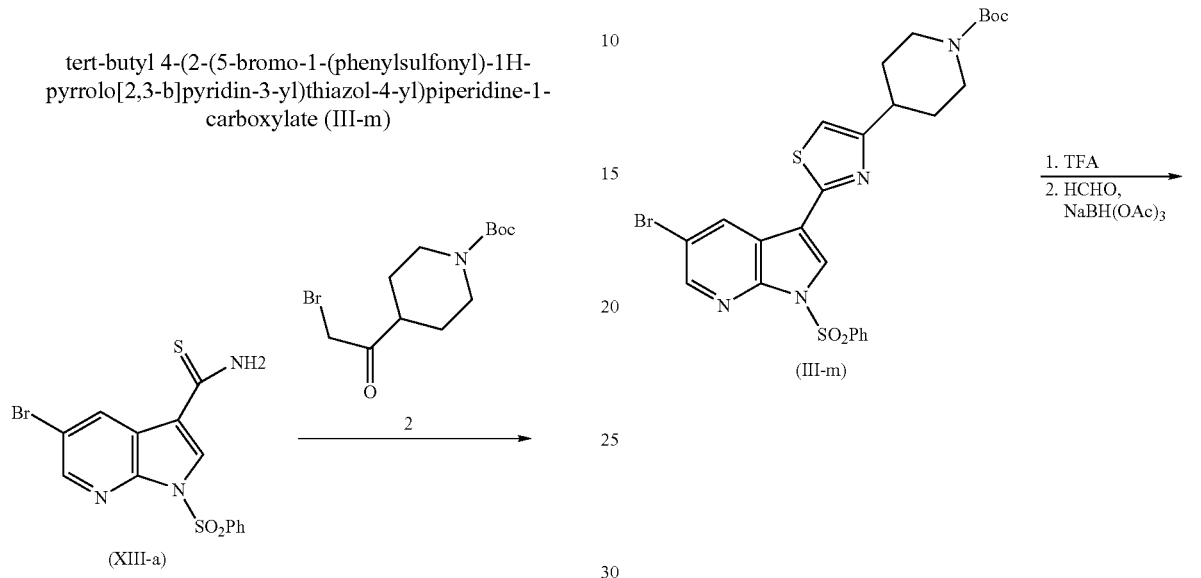

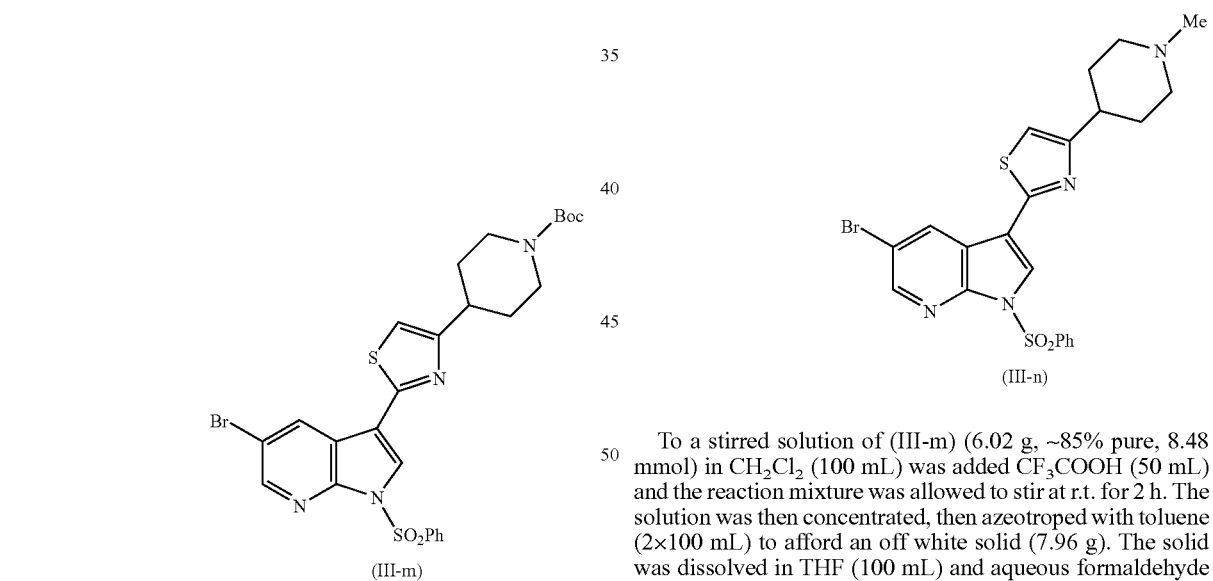

To a solution of (XIII-a) (3.60 g, 9.08 mmol) in THF (50 mL) was added tert-butyl 4-(2-bromoacetyl)piperidine-1-carboxylate (2) (3.03 g, 9.90 mmol; preparation described in *Bioorg. Med. Chem. Lett.* 2004, 14, 3419, *ibid.* 2005, 15, 2129) and the reaction mixture stirred at r.t. for 11 d. Saturated aqueous NaHCO₃ (100 mL) was then added, and the mixture extracted with AcOEt (2×150 mL). The combined organic extracts were dried (MgSO₄) and concentrated to afford (III-m) (6.02 g, 85% pure, 8.48 mmol, 93%) as a yellow solid, which was used without additional purification.

To a stirred solution of (III-m) (6.02 g, ~85% pure, 8.48 mmol) in CH₂Cl₂ (100 mL) was added CF₃COOH (50 mL) and the reaction mixture was allowed to stir at r.t. for 2 h. The solution was then concentrated, then azeotroped with toluene (2×100 mL) to afford an off white solid (7.96 g). The solid was dissolved in THF (100 mL) and aqueous formaldehyde (37%, 3.0 mL). After stirring at r.t. for 10 mins, NaBH(OAc)₃ (2.70 g, 12.72 mmol) was added, and the solution allowed to stir for 18 h. The mixture was then diluted with AcOEt (300 mL) and washed with saturated aqueous NaHCO₃ (3×100 mL). The organic layer was dried (MgSO₄) and concentrated to afford a solid (4.39 g). The solid was triturated with Et₂O (50 mL), discarding the off-white powder and evaporating the filtrate to afford (III-n) (3.04 g, purity ~92%, 5.40 mmol, 64%) as an oil. ¹H NMR (400 MHz, CDCl₃) δ 1.83-1.95 (m, 2H), 2.08-2.20 (m, 4H), 2.37 (s, 3H), 2.78-2.88 (m, 1H), 2.98-3.08 (m, 2H), 6.91 (s, 1H), 7.54 (t, J=7.8 Hz, 2H), 7.64 (tt, J=1.5, 7.5 Hz, 1H), 8.21-8.27 (m, 3H), 8.54 (d, J=2.1 Hz, 1H), 8.75 (d, J=2.1 Hz, 1H).

4-[4tert-butyl 2-(4-(5-bromo-1-(phenylsulfonyl)-1H-pyrrolo[2,3-b]pyridin-3-yl)thiazol-2-yl)pyrrolidine-1-carboxylate (III-o)

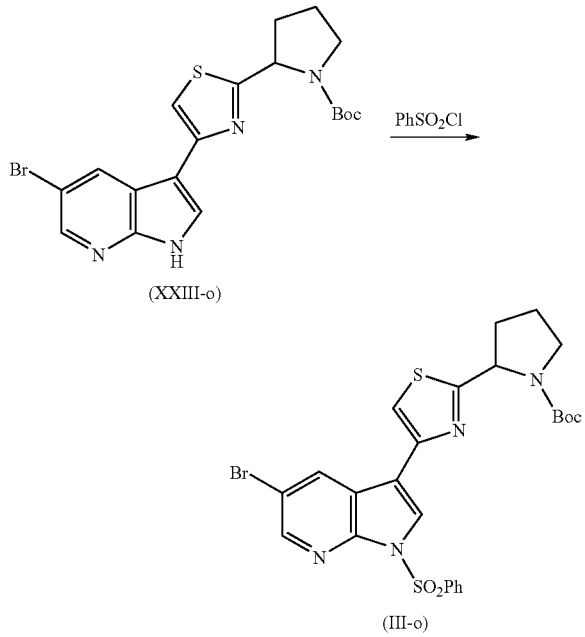

Compound (XXIII-o) (2.44 g, 5.44 mmol), n-Bu₄NHSO₄ (185 mg, 0.54 mmol), PhSO₂Cl (0.97 mL, 7.61 mmol) and 50% aqueous NaOH (2.17 mL) in CH₂Cl₂ (20 mL) were reacted at RT overnight following the general procedure for the protection of (XXIII). The solution was then poured onto saturated aqueous NaHCO₃ (100 mL), and extracted with CH₂Cl₂ (3×100 mL). The combined organic portions were dried (MgSO₄) and concentrated to afford a brown solid. The solid was purified by SCG using EtOAc:hexane as the eluent (gradient elution from 0:100 to 100:0, v/v) to give the product (III-o) as a yellow solid (2.65 g, 83%). Compound exists as rotamers ¹H NMR (400 MHz, CDCl₃) δ 1.35 (s, 6H), 1.50 (s, 3H), 1.93-2.04 (m, 2H), 2.24-2.47 (m, 2H), 3.45-3.70 (m, 2H), 5.21 (d, J=6 Hz, 0.6H), 5.26-5.33 (br s, 0.4H), 7.36 (br s, 1H), 7.50 (t, J=7.7 Hz, 2H), 7.60 (t, J=7.2 Hz, 1H), 8.10-8.24 (m, 3H), 8.49 (s, 1H), 8.52 (s, 0.6H), 8.53 (s, 0.4H).

4-(5-bromo-1-(phenylsulfonyl)-1H-pyrrolo[2,3-b]pyridin-3-yl)-2-(pyrrolidin-2-yl)thiazole (III-p)

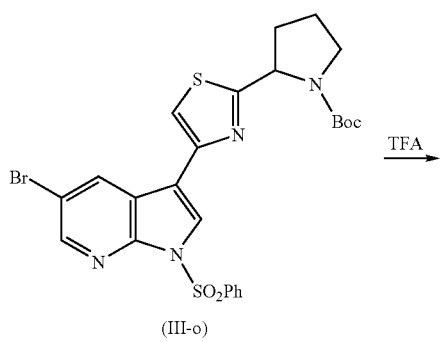

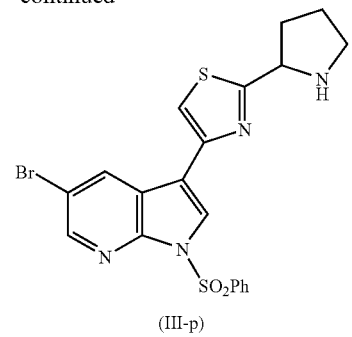

To a stirred solution of (III-o) (2.65 g, 4.50 mmol) in CH₂Cl₂ (20 mL) was added CF₃COOH (3.46 mL). The reaction was stirred at RT for 30 min. The reaction mixture was then poured slowly into a saturated aqueous solution of NaHCO₃ (300 mL) and the mixture was stirred for 20 min. It was extracted with EtOAc (3×300 mL). The combined organic extracts were dried (MgSO₄) and concentrated to give the crude product (III-p) (1.65 g, 75%). ¹H NMR (400 MHz, CDCl₃+ few drops of CD₃OD) δ 1.88-2.00 (m, 2H), 2.04-2.13 (m, 2H), 2.34-2.49 (m, 1H), 3.12-3.26 (m, 2H), 4.68-4.72 (dd, J=6.0, 8.5 Hz, 1H), 7.37 (s, 1H), 7.45-7.50 (m, 2H), 7.55-7.61 (m, 1H), 8.15 (s, 1H), 8.15-5.18 (m, 2H), 8.45 (d, J=2.1 Hz, 1H), 8.46 (d, J=2.1 Hz, 1H).

4-(5-bromo-1-(phenylsulfonyl)-1H-pyrrolo[2,3-b]pyridin-3-yl)-2-(1-methylpyrrolidin-2-yl)thiazole (III-q)

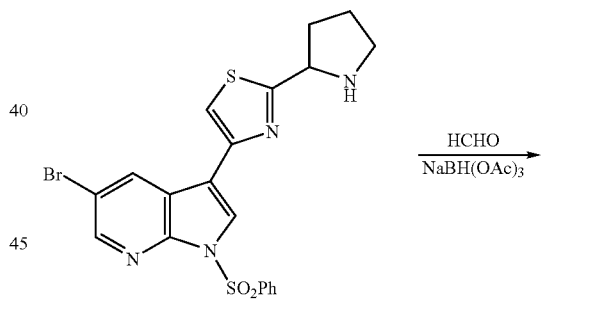

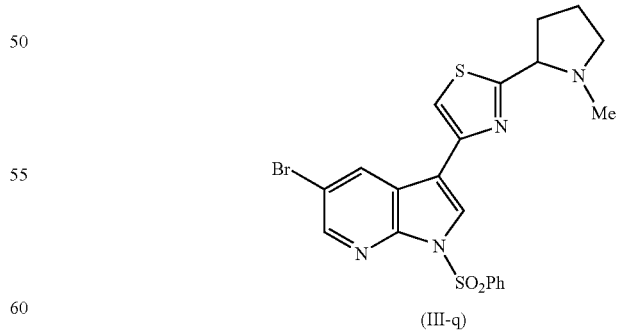

To a stirred solution of (III-p) (1.65 g, 3.37 mmol) in THF (50 mL) was added a 40% aqueous solution of formaldehyde (5 mL) and AcOH (0.02 mL, 0.33 mmol). The mixture was stirred at RT for 30 min. NaBH(AcO)₃ (2.14 g, 10.11 mmol) was added in one portion at RT. The reaction was stirred at RT overnight. A saturated solution of NaHCO$_3$ (150 mL) was added slowly over 20 min into the reaction until the gas evolution ceased. The mixture was extracted with EtOAc (3×150 mL). The combined organic extracts were dried (MgSO$_4$) and concentrated. The crude product was purified by SGC using CH$_2$Cl$_2$:hexane (gradient elution from 0:100 to 100:0, v/v) to afford (III-q) (1.11 g, 65%). $^1$H NMR (400 MHz, CDCl$_3$) δ 1.82-2.04 (m, 3H), 2.37-2.51 (m, 2H), 2.46 (s, 3H), 3.24-3.33 (tt, J=1.5, 7.4 Hz, 1H), 3.78-3.82 (dd, J=6.0, 8.5 Hz, 1H), 7.38 (s, 1H), 7.47-7.52 (m, 2H), 7.57-7.62 (m, 1H), 8.17 (s, 1H), 8.19-8.21 (m, 2H), 8.49 (d, J=2.1 Hz, 1H), 8.51 (d, J=2.1 Hz, 1H).

Synthesis of boronic ester (VIb-54)

A mixture of 1,4-dioxaspiro[4.5]decan-8-one (10.0 g, 64.0 mmol), morpholine (20 mL) and AcOH (1.0 mL) was stirred for 2.5 h. Sodium cyanoborohydride (8.05 g, 128.0 mmol) was then added in one portion followed by more morpholine (15 mL). An exothermic reaction occurred and the mixture was cooled for 2 min with an ice-bath. Then the mixture was stirred at room temperature for 16 h. Ethanol (120 mL) and water (28 mL) were added to the resulting thick slurry and the white solid filtered, washed with ethanol (2×) and the filtrate concentrated. Ethyl acetate was then added, the precipitate filtered off, washed with ethyl acetate and the filtrate concen-

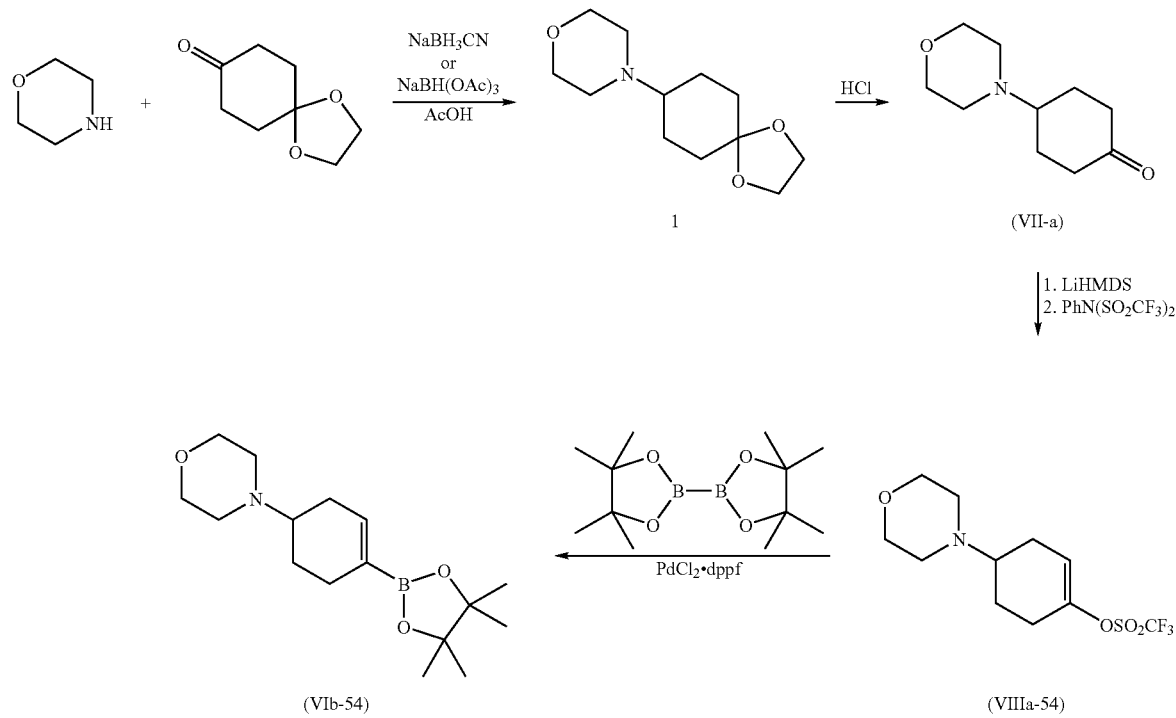

4-(1,4-Dioxa-spiro[4.5]dec-8-yl)-morpholine (1)

trated. The residual oil was purified by Kugelrohr distillation to give 1 (9.03 g, 62%; b.p.140° C./0.05 mmHg) as a clear oil which solidifies on standing.

4-(1,4-Dioxa-spiro[4.5]dec-8-yl)-morpholine (1)—an alternative method

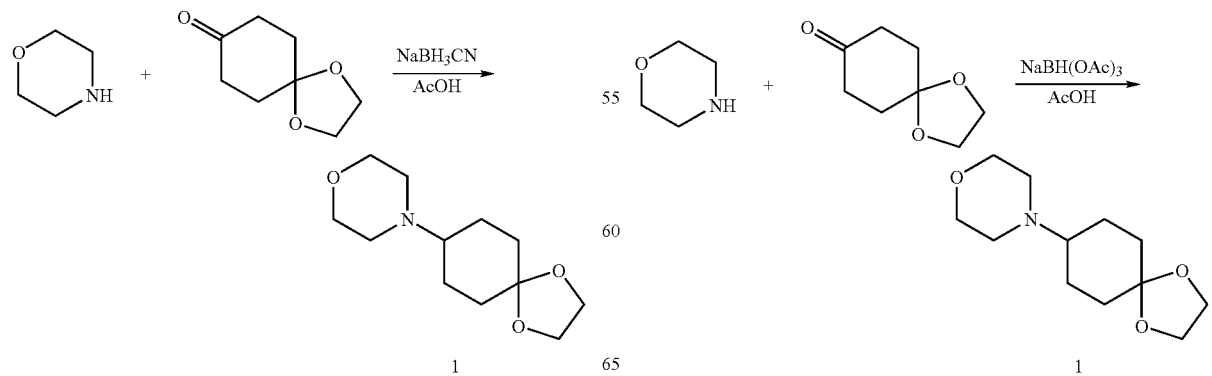

Sodium triacetoxyborohydride (382 g, 1.8 mol) was added in one portion to a mixture of 1,4-dioxaspiro[4.5]decan-8-one (200.0 g, 1.28 mol), morpholine (111.4 g, 1.28 mol) and glacial AcOH (73.2 mL, 1.28 mol) in 1,2-dichloroethane (4 L). A slightly exothermic reaction occurred accompanied by increase in temperature by 12° C. Then the mixture was stirred at room temperature overnight. The reaction was quenched by the addition of 10% aqueous NaOH (1.8 L) over a period of 20 min. The organic layer was separated, washed with brine (1 L), dried over MgSO$_4$ and concentrated to afford 1 (237.66 g) as white solid. The aqueous layer was extracted with AcOEt (4×300 mL). Combined extracts were washed with brine (1 L), dried over MgSO$_4$ and concentrated to furnish additional portion of 1 (44 g) as an off-white solid. Total yield of 1 (281.66 g, 97%). $^1$H NMR data identical with the data obtained earlier.

4-Morpholin-4-yl-cyclohexanone (VII-a)

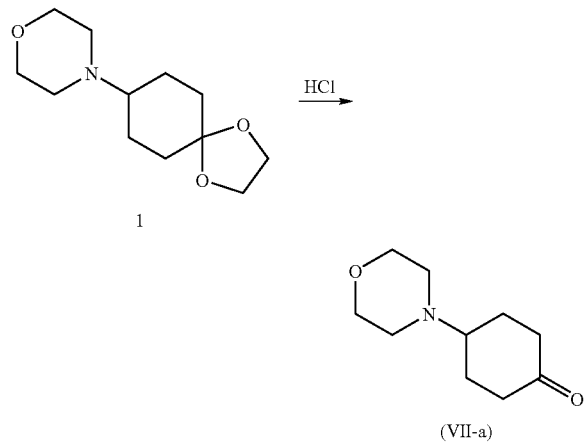

To a solution of 1 (4.50 g, 19.8 mmol) in THF (100 mL) was added 7 N aqueous HCl (40 mL). The reaction mixture was stirred for 17 h and the reaction was quenched by pouring onto saturated aqueous NaHCO$_3$ (475 mL). The mixture was extracted with ethyl acetate (1×) then CH$_2$Cl$_2$ (3×) and the combined organic extracts dried (MgSO$_4$) and concentrated. The resulting oil was purified by Kugelrohr distillation to give (VII-a) (3.17 g, 87%) as a clear oil; $^1$H NMR (400 MHz, CDCl$_3$) δ 1.80-1.94 (m, 2H), 1.80-2.10 (m, 2H), 2.30 (m, 1H), 2.45-2.65 (m, 8H), 3.74 (t, J=4.7 Hz, 4H).

Trifluoromethanesulfonic acid
4-morpholin-4-yl-cyclohex-1-enyl ester (VIIIa-36)

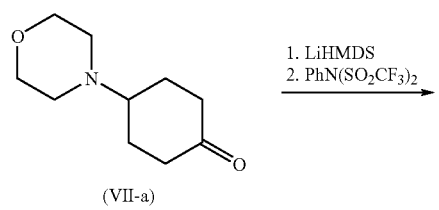

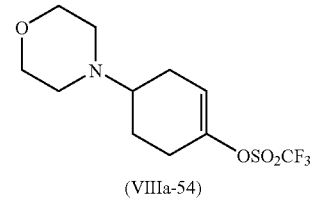

(VIIIa-54)

Triflate (VIIIa-54) was prepared using the general procedure for the synthesis of enol triflates using ketone (VII-a) (5.30 g, 28.9 mmol), 1 M solution of LiHMDS in THF (34.7 mL, 34.7 mmol) and N-phenylbis(trifluoromethanesulfinimide) (11.37 g, 31.8 mmol) in dry THF (100 mL). The crude product was purified by SGC using Ethyl acetate:hexane:Et$_3$N=39:60:1 (v/v/v) as eluent (gradient elution starting with 19:80:1) to give triflate (VIIIa-54) (7.66 g, 84%) as an orange oil; $^1$H NMR (400 MHz, CDCl$_3$) δ 1.61-1.72 (m, 1H), 2.07 (m, 1H), 2.20 (m, 1H), 2.30-2.48 (m, 3H), 2.50-2.65 (m, 5H), 3.72 (t, J=4.7 Hz, 4H), 5.72 (m, 1H).

4-[4-(4,4,5,5-Tetramethyl-[1,3,2]dioxazolidin-2-yl)-cyclohex-3-enyl]-morpholine (VIb-54)

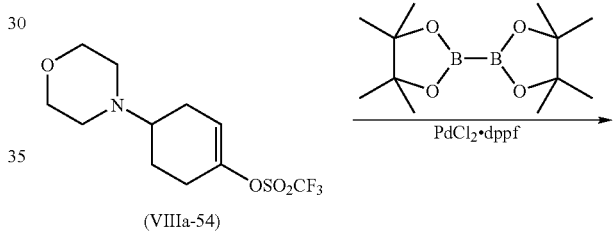

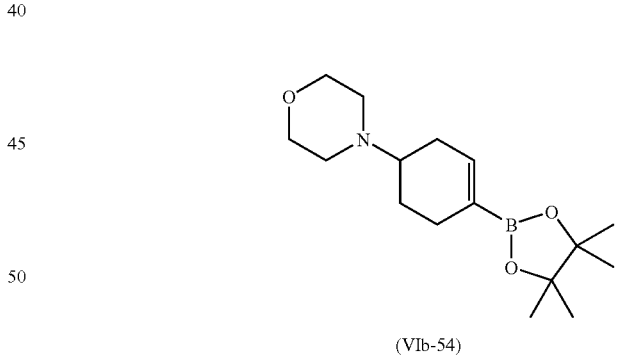

(VIb-54)

The compound was prepared using the general procedure for the synthesis of boronic pinacol esters. Triflate (VIIIa-54) (8.00 g, 25.4 mmol), bis(pinacolatodiboron) (9.66 g, 38.1 mmol), potassium acetate (7.47 g, 76.1 mmol) and dichloro [1,1'-bis(diphenylphosphino)ferrocene]palladium (II) dichloromethane adduct (1.04 g, 1.27 mmol) in DMF (110 mL) was stirred at 85° C. for 17 h. The crude product was purified by SGC using ethyl acetate:hexane=1:1 (v/v) as eluent (gradient elution) to give (VIb-54) (4.95 g, 67%) as a light orange solid; $^1$H NMR (400 MHz, CDCl$_3$) δ 1.26 (s, 12H), 1.95-2.10 (m, 2H), 2.05-2.20 (m, 2H), 2.80-2.40 (m, 2H), 2.43-2.65 (m, 5H), 3.74 (t, J=4.7 Hz, 4H), 6.51 (m, 1H).

Synthesis of boronic ester (VIb-101)

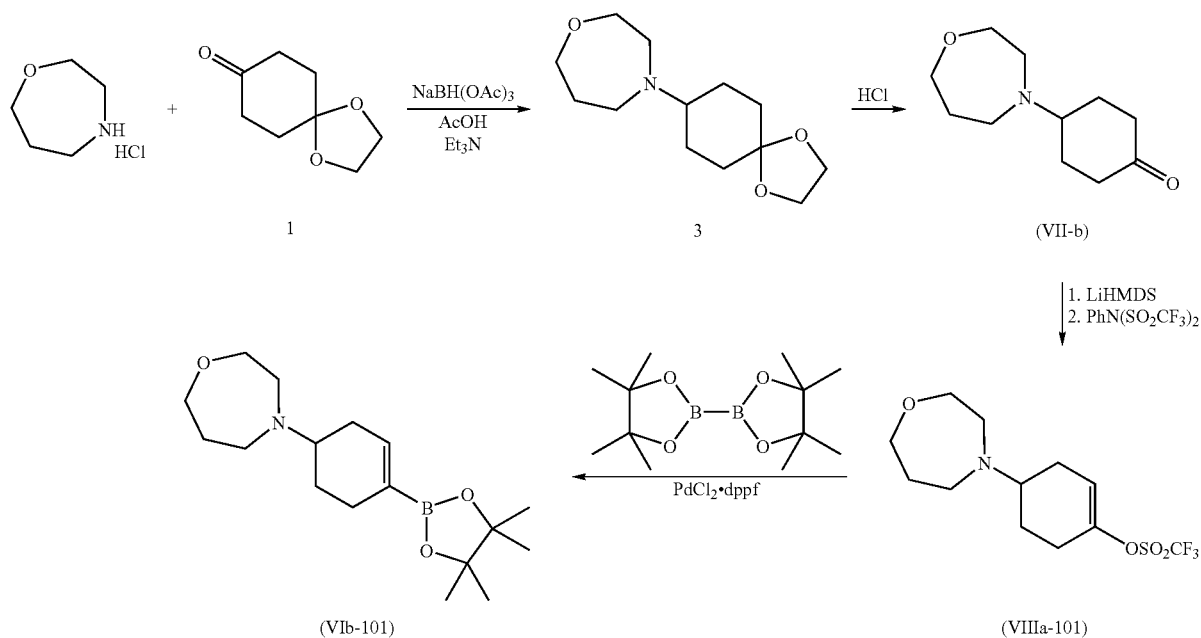

4-(1,4-dioxaspiro[4.5]decan-8-yl)-1,4-oxazepane (3)

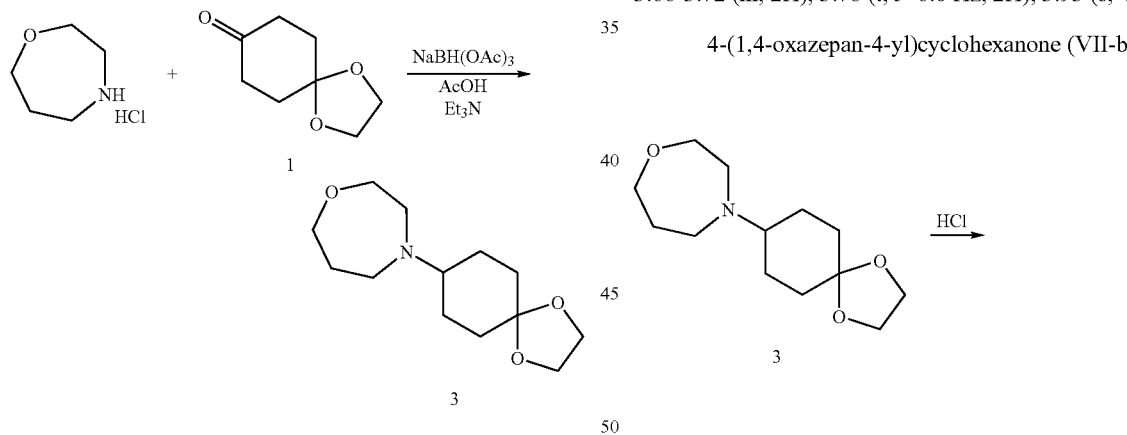

Et$_3$N (96.9 mL, 0.695 mol) was added in one portion to a stirred suspension of homomorpholine hydrochloride (79.76 g, 0.579 mol) and ketone 1 (90.5 g, 0.579 mol) in 1,2-dichloroethane (1.81 L). Then glacial acetic acid (34.8 mL, 0.607 mol) was added in one portion followed by solid NaBH(OAc)$_3$ (154 g, 0.727 mol) in one portion as well. This was accompanied by 5° C. increase in the temperature of the reaction mixture. After 2 h 45 min the reaction was quenched by addition of 10% aqueous NaOH (800 mL). The mixture was stirred for 10 min. The organic layer was separated, washed with brine (100 mL), dried (MgSO$_4$) and concentrated to afford an oil (142.36 g) with some suspended solid, which was filtered off (3.00 g). The aqueous part of the reaction mixture was combined with the brine washings and extracted with AcOEt (4×500 mL). Combined extracts were washed with brine (100 mL), dried (MgSO$_4$) and concentrated to afford additional portion of oil (16.82 g). The two oily products were combined and distilled in vacuum to give 3 (101.07 g, 72%) as colorless liquid, b.p. 122° C./8.9·10$^{-3}$ mbar. $^1$H NMR (400 MHz, CDCl$_3$) δ 1.48-1.64 (m, 4H), 1.70-1.88 (m, 6H), 2.50-2.63 (m, 1H), 2.71-2.81 (m, 4H), 3.66-3.72 (m, 2H), 3.78 (t, J=6.0 Hz, 2H), 3.93 (s, 4H).

4-(1,4-oxazepan-4-yl)cyclohexanone (VII-b)

To a cooled (<15° C.) solution of 3 (10.31 g, 42.75 mmol) in THF (216 mL) was added 7 N aqueous HCl (86 mL, 0.602 mol) over a period of 5 min. Cooling bath was then removed and the reaction mixture was stirred overnight at r.t. Then, the reaction mixture was basified to pH 8 by dropwise addition of 50% aqueous NaOH (48 g, 0.602 mol) over a period of 30 min while maintaining the internal temperature at 10-13° C. using an external cooling bath (0° C.). Hexane (50 mL) was added and the organic layer was separated, dried over MgSO$_4$ and concentrated to afford yellowish liquid (7.21 g). The aqueous layer was extracted with AcOEt (4×50 mL). The extracts were combined, dried (MgSO$_4$) and concentrated to afford the second portion of crude product (1.58 g). Both portions of crude product were combined and distilled in vacuum to afford ketone (VII-b) (7.27 g, 86%) as colorless liquid b.p. 98° C./5.3·10$^{-3}$ mbar; $^1$H NMR (400 MHz, CDCl$_3$) δ 1.73-1.85 (m, 2H), 1.89 (quintet, J=5.9 Hz, 2H), 2.05-2.15 (m, 2H), 2.30-2.42 (m, 2H), 2.43-2.52 (m, 2H), 2.79-2.85 (m, 4H), 3.03 (tt, J=10.4, 6.6 Hz, 1H), 3.72-3.77 (m, 2H), 3.82 (t, J=6.0 Hz, 2H).

4-(1,4-oxazepan-4-yl)cyclohex-1-enyl trifluoromethanesulfonate (VIIIa-101)

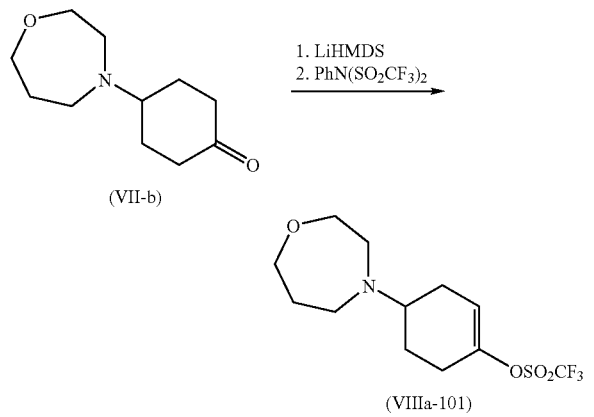

Triflate (VIIIa-101) was prepared using the general procedure for the synthesis of enol triflates using ketone (VII-b) (6.49 g, 32.9 mmol), 1 M solution of LiHMDS in THF (39.5 mL, 39.5 mmol) and N-phenylbis(trifluoromethanesulfinimide) (12.94 g, 36.2 mmol) in dry THF (115 mL). The crude reaction mixture was diluted with hexane:AcOEt=4:1 (115 mL) (v/v) and washed with water (50 mL), brine (50 mL), dried (MgSO$_4$) and concentrated. The liquid residue was distilled in vacuum to afford (VIIIa-101) (6.98 g, 64%) as colorless liquid b.p 114° C./5.7·10$^{-3}$ mbar. Purity about 85% by $^1$H NMR. $^1$H NMR (400 MHz, CDCl$_3$) δ 1.63-1.76 (m, 1H), 1.86 (quintet, J=6.0 Hz, 2H), 1.95-2.05 (m, 1H), 2.12-2.24 (m, 1H), 2.26-2.56 (m, 3H), 2.74-2.80 (m, 4H), 2.82-2.92 (m, 1H), 3.68-3.74 (m, 2H), 3.79 (t, J=6.0 Hz, 2H), 5.72 (dt, J=5.7, 2.4 Hz, 1H).

4-(4-(4,4,5,5-tetramethyl-1,3,2-dioxaborolan-2-yl)cyclohex-3-enyl)-1,4-oxazepane (VIb-101)

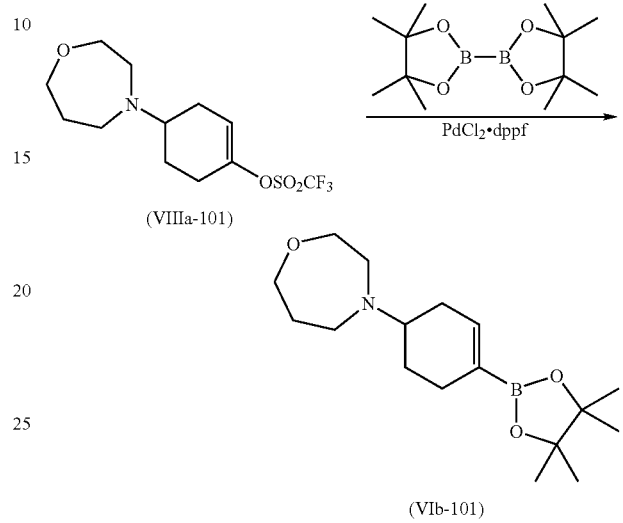

The compound was prepared using the general procedure for the synthesis of boronic pinacol esters. Triflate (VIIIa-101) (6.60 g, 20.06 mmol), bis(pinacolatodiboron) (7.62 g, 30.09 mmol), AcOK (5.90 g, 60.2 mmol) and dichloro[1,1'-bis(diphenylphosphino)ferrocene]palladium (II) dichloromethane adduct (0.82 g, 1.0 mmol) in DMF (86 mL) was stirred at 85° C. for 1 h 45 min when TLC showed absence of the remaining starting material. The mixture was concentrated and separated between AcOEt (125 mL)—water (125 mL). The organic layer was washed with water (120 mL), dried (MgSO$_4$), concentrated and separated by means of chromatography on amino silica (Chromatorex NH, Fuji Silysia) using hexane-AcOEt as eluent (gradient elution) to afford (VIb-101) (2.149 g, 35%) as white solid; $^1$H NMR (400 MHz, CDCl$_3$) δ 1.26 (s, 12H), 1.33-1.47 (m, 1H), 1.83-1.93 (m, 3H), 2.04-2.22 (m, 2H), 2.23-2.38 (m, 2H), 2.75-2.84 (m, 5H), 3.71 (t, J=4.7 Hz, 2H), 3.80 (t, J=6.0 Hz, 2H), 6.52 (m, 1H).

Synthesis of boronic ester (VIb-126)

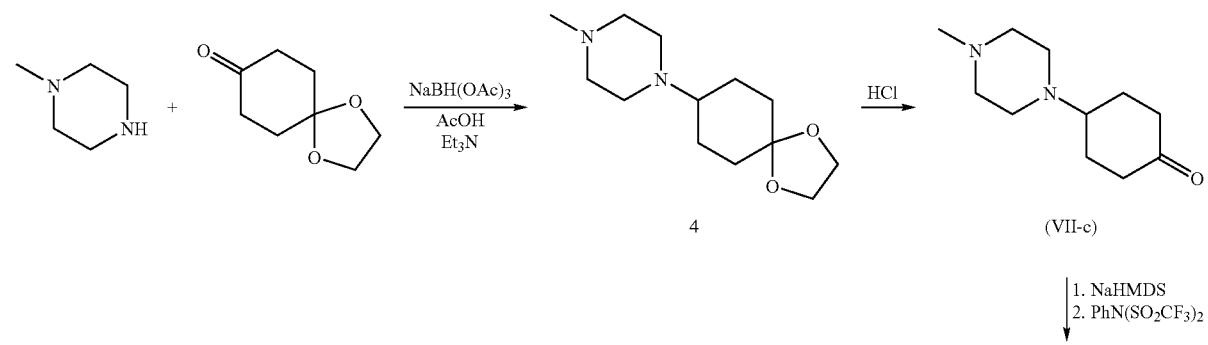

-continued

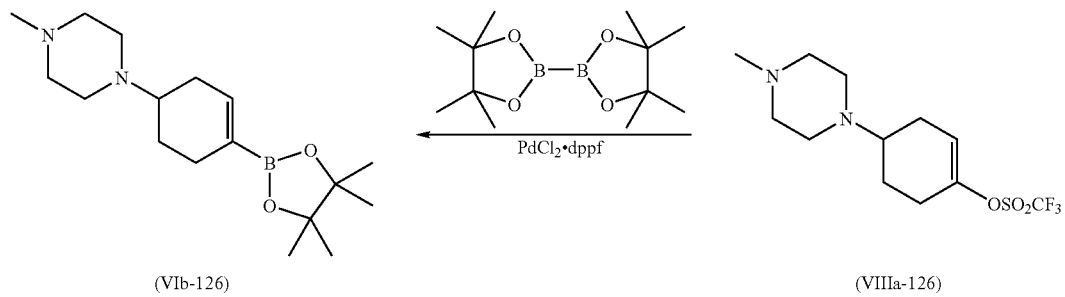

(VIb-126)     (VIIIa-126)

1-methyl-4-(1,4-dioxaspiro[4.5]decan-8-yl)piperazine (4)

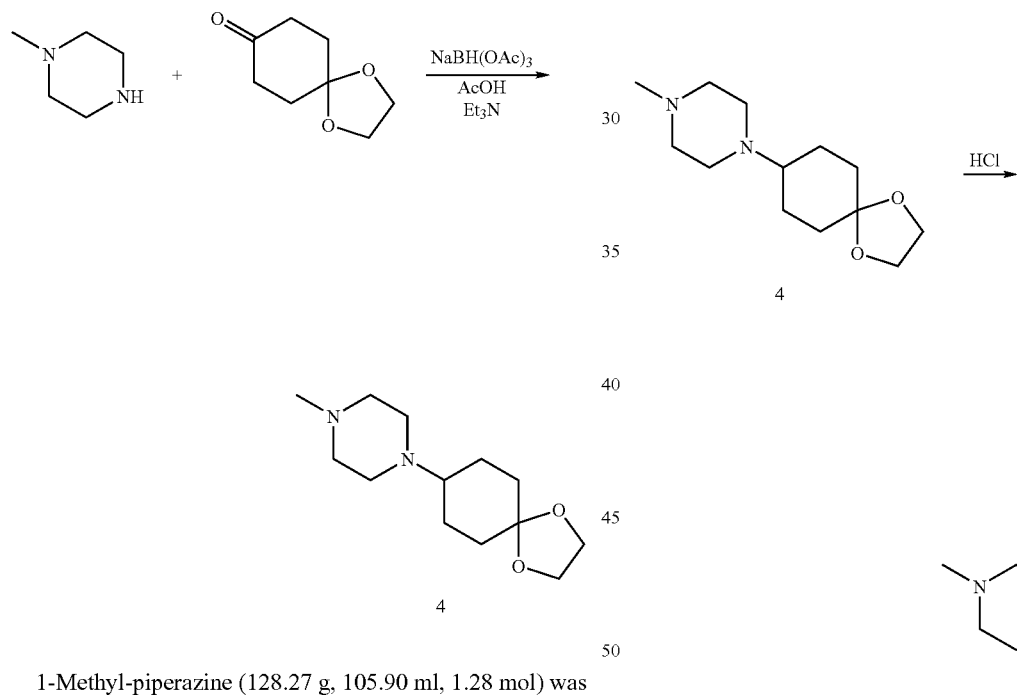

1-Methyl-piperazine (128.27 g, 105.90 ml, 1.28 mol) was added in one portion to a stirred and cooled (3° C.) solution of 1,4-dioxaspiro[4.5]decan-8-one (200.00 g, 1.28 mol) in 1,2-dichloroethane (2.0 L). Then glacial acetic acid (76.90 g, 73.31 ml, 1.28 mol) was added in one portion followed by solid NaBH(OAc)$_3$ (379.97 g, 1.79 mol) portionwise over 20 min. The reaction was slowly allowed to warm to RT and was stirred overnight. The reaction was quenched by addition of 10% aqueous NaOH (3×450 mL) with stirring over a period of 25 min. An exotherm of ca. 10° C. was observed. The mixture was stirred for 30 min. The organic layer was separated. Aqueous layer was further extracted with CH$_2$Cl$_2$ (3×1 L). Brine (1000 mL) was added to the aqueous layer and extracted with EtOAc (2×1000 mL). The combined organic solutions were dried (MgSO$_4$) and concentrated to afford 4 (305.00 g, 1.27 mol, 99.10% yield) as brown/orange oil. $^1$H NMR (400 MHz, CDCl$_3$) δ 1.45-1.68 (m, 4H), 1.72-1.90 (m, 4H), 1.99 (s, 3H), 2.45 (s, 2H), 2.56-2.67 (m, 1H), 2.87 (bs, 6H), 3.86-3.95 (m, 4H).

4-(4-methylpiperazin-1-yl)cyclohexanone (VII-c)

To a cooled (0-5° C.) mixture of 4 (270.00 g, 1,123.39 mmol) and water (1283.00 mL) was added 7 N aqueous HCl (1,283.87 ml, 8,987.08 mmol). Cooling bath was then removed and the reaction mixture was stirred overnight at r.t. Then, the reaction mixture was basified to pH 9 by dropwise addition of 50% aqueous NaOH while maintaining the internal temperature at below 35° C. with an ice bath. The mixture was extracted with EtOAc (3×2 L) followed by CH$_2$Cl$_2$ (2×2 L). The extracts were dried (MgSO$_4$) and concentrated to afford (VII-c) (142.50 g, 725.96 mmol, 64.62%) as an orange white solid; $^1$H NMR (400 MHz, CDCl$_3$) δ 1.68-1.81 (m, 2H), 1.88-1.99 (m, 2H), 2.13-2.25 (m, 2H), 2.17 (s, 3H), 2.25-2.43 (m, 5H), 2.43-2.70 (m, 5H).

4-(4-methylpiperazin-1-yl)cyclohex-1-enyl trifluoromethanesulfonate (VIIIa-126)

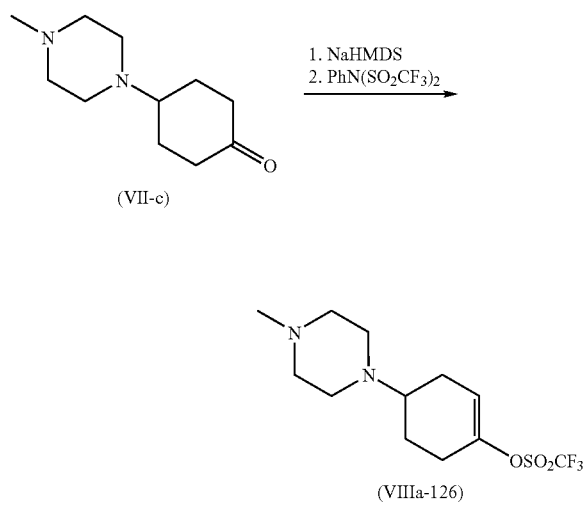

Triflate (VIIIa-126) was prepared using a modified procedure for the synthesis of enol triflates using ketone (VII-c) (50.00 g, 254.72 mmol) in THF (1000 mL), 1 M solution of NaHMDS in THF (382.08 ml, 1.00 M, 382.08 mmol), which was added at below −40° C., and N-phenylbis(trifluoromethanesulfinimide) (109.20 g, 305.67 mmol), which was added at −78° C. as a solution in THF (750 mL). The crude reaction mixture was stirred at RT overnight. The reaction was quenched by addition of 5% NaOH solution (1500 mL). The mixture was stirred for 5 min. and extracted with EtOAc (3×2 L). The combined organic extracts were dried over MgSO$_4$ and concentrated. The residue was purified by means of SGC on amino silica (Chromatorex NH, Fuji Silysia) using EtOAc:hexane as eluent (gradient elution from 0:100 to 60:40, v/v) to give (VIIIa-126) (62.00 g, 74%) as a pale yellow oil. $^1$H NMR (400 MHz, CDCl$_3$) δ 1.58-1.73 (m, 1H), 1.99-2.08 (m, 1H), 2.13-2.25 (m, 1H), 2.26-2.70 (m, 12H), 2.33 (s, 3H), 5.72 (dt, J=5.7, 2.4 Hz, 1H).

1-methyl-4-(4-(4,4,5,5-tetramethyl-1,3,2-dioxaborolan-2-yl)cyclohex-3-enyl)piperazine (VIb-126)

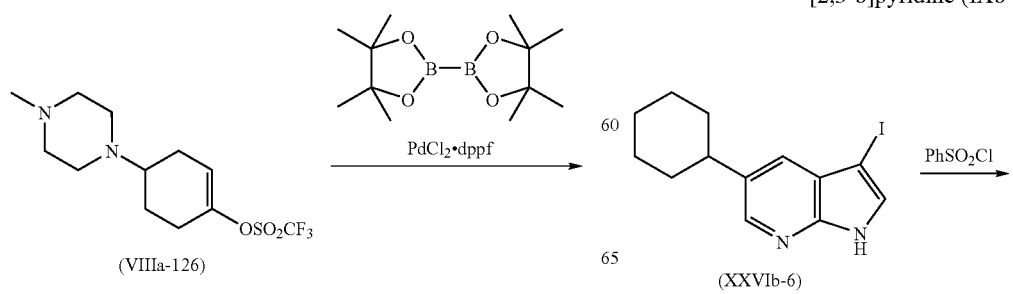

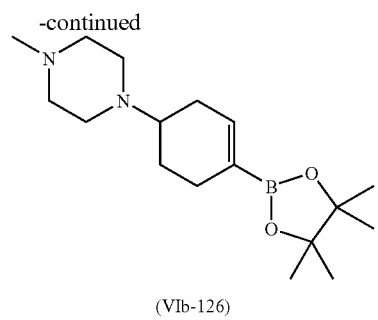

Compound (VIb-126) was prepared using the general procedure for the synthesis of boronic pinacol esters. Triflate (VIIIa-126) (66.0 g, 201 mmol), bis(pinacolatodiboron) (61.25 g, 241 mmol), AcOK (59.19 g, 603 mmol) and dichloro[1,1'-bis(diphenylphosphino)ferrocene]palladium (II) dichloromethane adduct (8.28 g, 10.05 mmol) in DMF (500 mL) was stirred at 85° C. for 3 h when TLC showed absence of the remaining starting material. The mixture was concentrated and separated between EtOAc (1000 mL)—water (1000 mL). The organic layer was washed with water (1000 mL), dried (MgSO$_4$), concentrated and separated by means of chromatography on amino silica (Chromatorex NH, Fuji Silysia) using hexane:EtOAc as eluent (gradient elution from 100:0 to 40:60, v/v) to afford (VIb-126) (32.2 g, 52%) as white solid; $^1$H NMR (400 MHz, CDCl$_3$) δ 1.24 (s, 12H), 1.29-1.44 (m, 1H), 1.92-2.03 (m, 1H), 2.04-2.19 (m, 2H), 2.29 (s, 3H), 2.24-2.39 (m, 3H), 2.39-2.55 (m, 4H), 2.55-2.83 (m, 4H), 6.47-6.55 (m, 1H).

4-Morpholin-4-yl-cyclohexanone (VII-a)—see preparation of (VIb-54)

4-(1,4-oxazepan-4-yl)cyclohexanone (VII-b)—see preparation of (VIb-101)

4-(4-methylpiperazin-1-yl)cyclohexanone (VII-c)—see preparation of (VIb-126)

Trifluoromethanesulfonic acid 4-morpholin-4-yl-cyclohex-1-enyl ester (VIIIa-36)—see preparation of (VIb-54)

4-(1,4-oxazepan-4-yl)cyclohex-1-enyl trifluoromethanesulfonate (VIIIa-101)—see preparation of (VIb-101)

4-(4-methylpiperazin-1-yl)cyclohex-1-enyl trifluoromethanesulfonate (VIIIa-126)—see preparation of (VIb-126)

5-Cyclohexyl-3-iodo-1-(phenylsulfonyl)-1H-pyrrolo[2,3-b]pyridine (IXb-6)

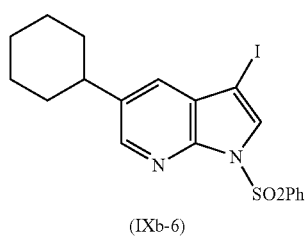

(IXb-6)

Compound (XXVIb-6) (1.92 g, 5.89 mmol), n-Bu$_4$NHSO$_4$ (0.10 g, 0.29 mmol), PhSO$_2$Cl (1.56 g, 8.83 mmol) and 50% aqueous NaOH (0.66 mL) in CH$_2$Cl$_2$ (30 mL) were reacted at RT for 1 h following the general procedure for the protection of (XXIII). The crude product (3.38 g, oil) was purified by SGC using CH$_2$Cl$_2$:hexane as eluent (gradient from 3:1 v/v to neat CH$_2$Cl$_2$) to afford (IXb-6) as a foam (2.39 g, 5.13 mmol, 87%). $^1$H NMR (400 MHz, CDCl$_3$) δ 1.25-1.53 (m, 5H), 1.76-1.93 (m, 2H), 2.66 (tt, J=3.0, 11.6 Hz, 1H), 7.47 (d, J=2.1 Hz, 1H), 7.52 (t, J=7.7 Hz, 2H), 7.61 (tt, J=1.5, 7.4 Hz, 1H), 7.84 (s, 1H), 8.20-8.25 (m, 2H), 8.32 (d, J=2.0 Hz, 1H).

3-iodo-1-(phenylsulfonyl)-5-(1,4-dioxaspiro[4.5]decan-8-yl)-1H-pyrrolo[2,3-b]pyridine (IXb-23)

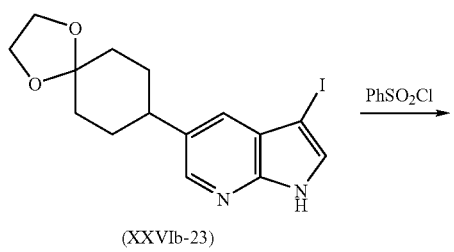

Compound (XXVIb-23) (3.73 g, 9.72 mmol; crude), n-Bu$_4$NHSO$_4$ (0.494 g, 1.46 mmol), PhSO$_2$Cl (1.92 mL, 15.0 mmol) and 50% aqueous NaOH (4.0 mL) in CH$_2$Cl$_2$ (60 mL) were reacted at RT for 3.5 h following the general procedure for the protection of (XXIII). The crude product (orange oil) was stirred with cold MeOH (70 mL) for 1.5 h. The resulting solid was filtered off to afford the azaindole (IXb-23) (3.96 g, 78% over 2 steps from (XXVb-23)) as a white powder.

4-((1r,4r)-4-(3-bromo-1-(tert-butyldimethylsilyl)-1H-pyrrolo[2,3-b]pyridin-5-yl)cyclohexyl)morpholine (IXb-29)

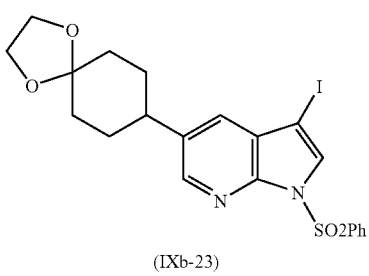

To a stirred solution of (XXVIIb-29) (6.67 g, 16.69 mmol) in CH$_2$Cl$_2$ (75 mL) was added pyridine (1.50 g, 18.96 mmol) followed by bromine (2.93 g, 18.36 mmol) dropwise over 20 min as a solution in CH$_2$Cl$_2$ (25 mL). After stirring at r.t. for 2 h, the reaction was quenched by the addition of saturated aqueous Na$_2$S$_2$O$_3$ (50 mL), brine (100 mL) and NaHCO$_3$ (100 mL), and extracted with AcOEt (2×200 mL). The combined organic portions dried over MgSO$_4$ and concentrated to give crude product (7.44 g). Purification by SGC using CH$_2$Cl$_2$:MeOH=95:5 (v/v) afforded (IXb-29) as a foam (6.19 g, 12.93 mmol, 78%). $^1$H NMR (400 MHz, CDCl$_3$) δ 0.50 (s, 6H), 0.83 (s, 9H), 1.26-1.57 (m, 5H), 1.88-2.03 (m, 4H), 2.19-2.29 (m, 1H), 2.45-2.57 (m, 5H), 3.61-3.69 (m, 4H), 7.10 (s, 1H), 7.50 (d, J=1.9 Hz, 1H), 8.07 (d, J=2.0 Hz, 1H).

4-((1r,4r)-4-(3-bromo-1-(tert-butyldimethylsilyl)-1H-pyrrolo[2,3-b]pyridin-5-yl)cyclohexyl)-1,4-oxazepane (IXb-75)

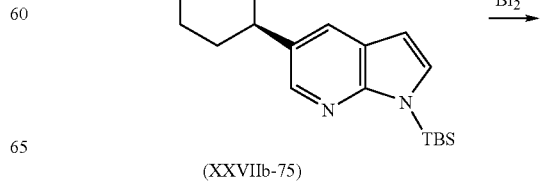

-continued

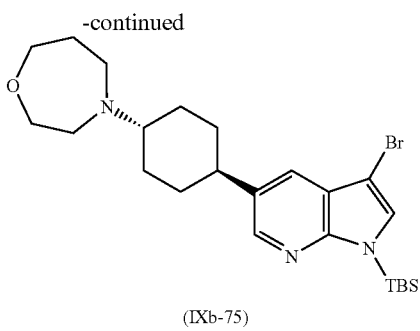

(IXb-75)

To a stirred solution of azaindole (XXVIIb-75) (0.50 g, 1.21 mmol) in CH$_2$Cl$_2$ (5 mL) and pyridine (0.12 mL, 1.45 mmol) was added Br$_2$ (0.21 g, 1.33 mmol) in CH$_2$Cl$_2$ (5 mL) over 4 min. After 2.5 h additional stirring the mixture was washed with saturated Na$_2$S$_2$O$_3$ solution (2×15 mL) and saturated NaHCO$_3$ solution (2×15 mL). The aqueous layers were extracted with EtOAc (4×25 mL). The combined organic solutions were dried (MgSO$_4$), filtered and concentrated to afford bromide (IXb-75) (0.65 g, 100%) as a viscous honey-colored oil. $^1$H NMR (400 MHz, CDCl$_3$) δ 0.60 (s, 6H), 0.93 (s, 9H), 1.43-1.65 (m, 4H), 1.90 (m, 2H), 2.00-2.05 (m, 4H), 2.57-2.66 (m, 2H), 2.84 (m, 4H), 3.75 (m, 2H), 3.82 (t, J=6.0 Hz, 2H), 7.20 (s, 1H), 7.60 (d, J=2.0 Hz, 1H), 8.17 (d, J=2.0 Hz, 1H).

4-((1r,4r)-4-(3-iodo-1-(phenylsulfonyl)-1H-pyrrolo[2,3-b]pyridin-5-yl)cyclohexyl)-1,4-oxazepane (IXb-75a)

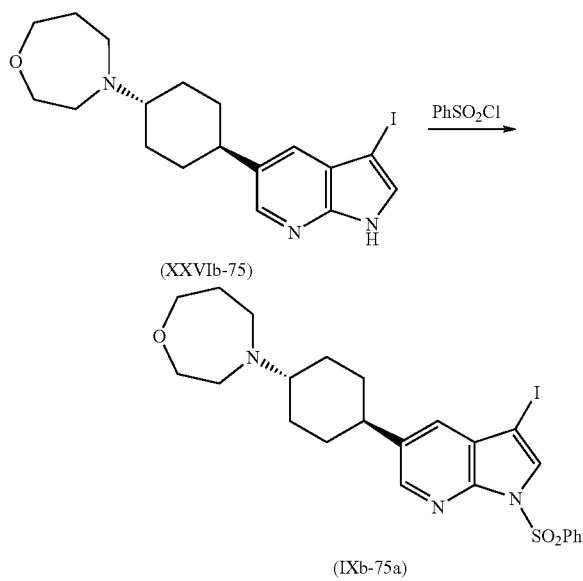

Compound (XXVIb-75) (1.55 g, 3.6 mmol), n-Bu$_4$NHSO$_4$ (0.19 g, 0.55 mmol), PhSO$_2$Cl (0.72 mL, 5.6 mmol) and 50% aqueous NaOH (2.0 mL) in CH$_2$Cl$_2$ (60 mL) were reacted at RT for 2.5 h following the general procedure for the protection of (XXIII). The resulting orange oil was purified by SGC on amino silica (Chromatorex NH, Fuji Silysia) using hexane:AcOEt (gradient elution, from 75:25 to 50:50, v/v) to afford azaindole (IXb-75a) (1.06 g, 51% for 3 steps from (XXVIIb-75)) as a white powder.

5-bromo-1-(phenylsulfonyl)-1H-pyrrolo[2,3-b]pyridine-3-carboxylic acid (X-a)

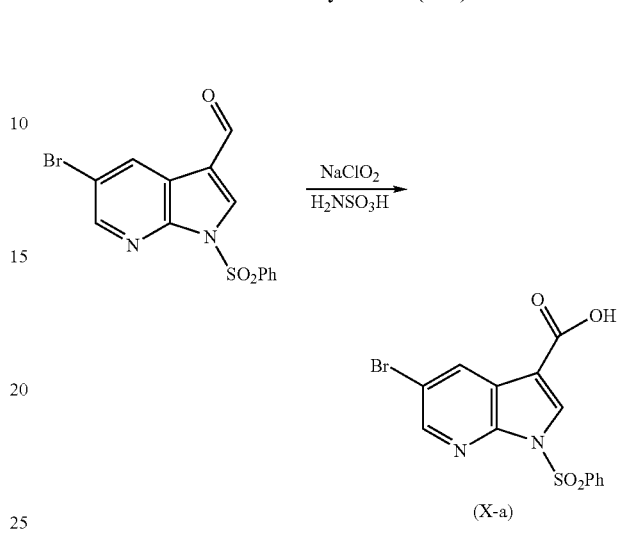

A solution of sodium chlorite (9.71 g, 107.3 mmol) in water (100 mL) was added dropwise over a period of 1 h to a stirred mixture of 5-bromo-1-(phenylsulfonyl-1H-pyrrolo[2,3-b]pyridine-3-carbaldehyde (28.00 g, 76.67 mmol; preparation disclosed in WO2004101565) and sulfamic acid (10.42 g, 107.3 mmol) in water (100 mL)—1,4-dioxane (250 mL). The temperature of the reaction mixture was maintained below 25° C. with an external cooling bath. The mixture was then stirred at r.t. for 1 h and diluted with ice-water (300 mL). The solid was filtered off, washed with cold water (100 mL) and diethyl ether (50 mL) and dried overnight in vacuum to afford (X-a) (28.55 g, 98%) as white solid. $^1$H NMR (400 MHz, DMSO-d$_6$) δ 7.64-7.72 (m, 2H), 7.76-7.83 (m, 1H), 8.18-8.25 (m, 2H), 8.45-8.49 (m, 2H), 8.55-8.59 (m, 1H), 13.34 (bs, 1H).

5-bromo-1-(phenylsulfonyl)-1H-pyrrolo[2,3-b]pyridine-3-carboxamide (XII-a)

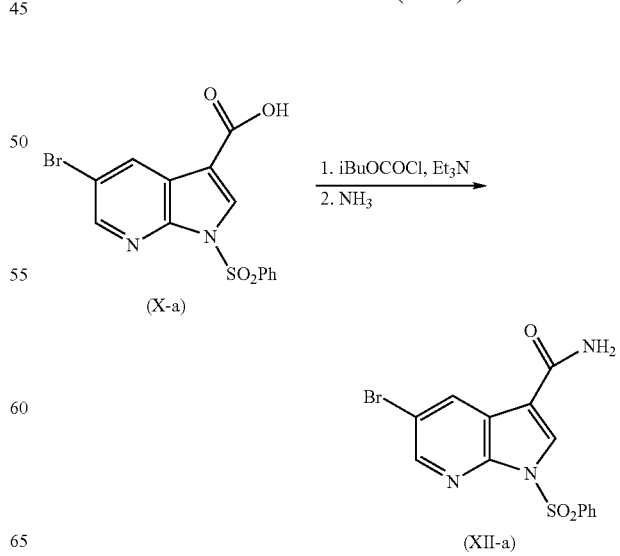

Et₃N (13.5 g, 18.6 mL, 133 mmol) was added to a stirred suspension of (X-a) (28.26 g, 74.13 mmol) in CH₂Cl₂ (400 mL). A clear solution formed. The solution was cooled to 0° C. and isobutyl chloroformate (13.16 g, 12.50 mL, 96.4 mmol) was added dropwise over 7 min while the temperature of the mixture was maintained at 0° C. Stirring continued for 30 min at 0° C. The mixture was then cooled to −10° C. and gaseous ammonia (7.31 g, 429 mmol) was introduced rapidly. Cooling bath was removed. After 6 h the excess ammonia was evaporated and the solid was filtered off to afford (XII-a) (27.94 g, purity 71%, yield 70%) as a white powder. ¹H NMR (400 MHz, DMSO-d₆) δ 7.48 (bs, 1H), 7.60-7.70 (m, 2H), 7.72-7.80 (m, 1H), 8.08-8.15 (m, 2H), 8.10 (bs, 1H), 8.57 (d, J=2.3 Hz, 1H), 8.63 (d, J=2.3 Hz, 1H), 8.79 (m, 1H).

5-bromo-1-(phenylsulfonyl)-1H-pyrrolo[2,3-b]pyridine-3-carbothioamide (XIII-a)

A mixture of (XII-a) (26.66 g; purity 71%, about 49.1 mmol) and Lawesson's reagent (42.54 g, 105.18 mmol) in THF (560 mL) was stirred at 70° C. under nitrogen for 1 h 15 min. The mixture was concentrated in vacuum and the semi-solid residue was stirred for 10 min with saturated aqueous NaHCO₃ (350 mL):AcOEt (350 mL). The organic layer was separated and the aqueous phase was extracted with AcOEt (3×300 mL). Combined organic solutions were washed with saturated aqueous NaHCO₃ (100 mL), dried (MgSO₄), concentrated and separated by means of SGC using hexane: AcOEt=1:3 (v/v). Fractions containing the desired product were combined and concentrated to afford a solid, which was washed with hexane:AcOEt=1:1 (v/v) (100 mL) followed by diethyl ether (50 mL) to afford (XIII-a) (13.91 g, purity 94%). Purification of the combined mixed fractions and washings by means of SGC using NH silica (Chromatorex, Fuji Silysia) and hexane:AcOEt as eluent (gradient elution) afforded additional (XIII-a) (2.02 g) Total yield 15.93 g (82%). ¹H NMR (400 MHz, DMSO-d₆) δ 7.64-7.70 (m, 2H), 7.76-7.81 (m, 1H), 8.13-8.18 (m, 2H), 8.53 (d, J=2.3 Hz, 1H), 8.69 (s, 1H), 9.15 (d, J=2.3 Hz, 1H), 9.57 (bs, 1H), 9.77 (bs, 1H).

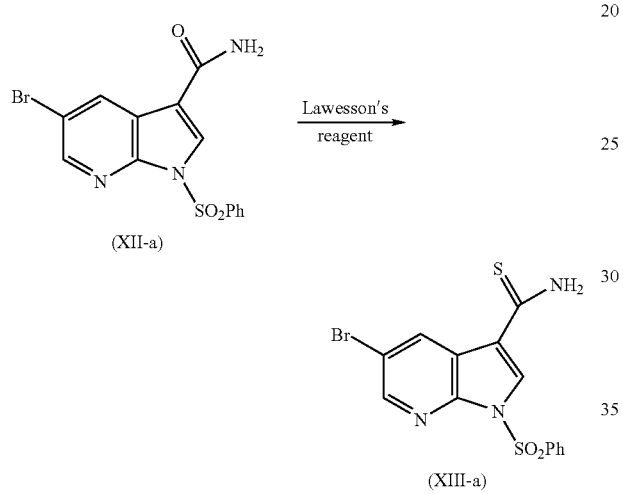

2-Bromo-1-(5-bromo-1H-pyrrolo[2,3-b]pyridin-3-yl)-ethanone (XXI-a)—see preparation of (XXIII-a)

Synthesis of intermediates (XXIII-a)-(XXIII-b)

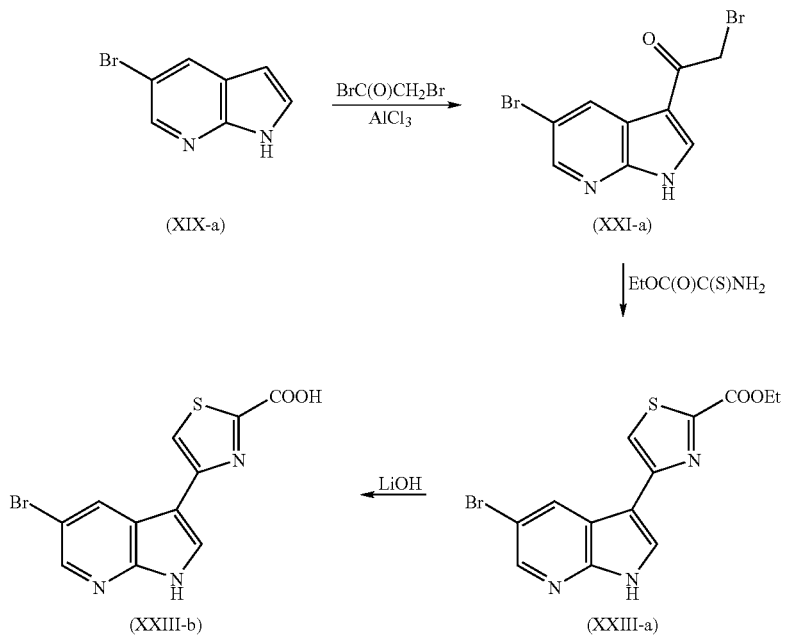

2-Bromo-1-(5-bromo-1H-pyrrolo[2,3-b]pyridin-3-yl)-ethanone (XXI-a)

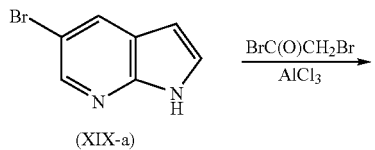

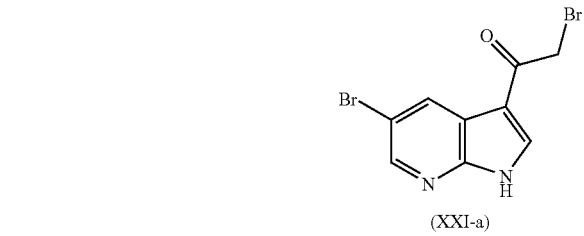

To a stirred solution of (XIX-a) (6.65 g, 33.8 mmol) in anhydrous $CS_2$ (125 mL) was added $AlCl_3$ (15.60 g, 117.0 mmol) in a single portion. The reaction vessel was equipped with a reflux condenser, the temperature was brought to 50° C., and bromoacetyl bromide (3.00 mL, 6.95 g, 34.4 mmol) was added dropwise over 10 min. After stirring at 50° C. for a further 1 h, the reaction mixture was cooled to 0° C., and 100 mL water was added (very cautiously at first). Once effervescence had ceased, AcOEt (300 mL) and THF (100 mL) were added. Solid $NaHCO_3$ was then added to adjust the pH of the aqueous layer from 1 to 3. The layers were separated, and the organic layer washed with saturated aqueous $NaHCO_3$ (150 mL) and brine (150 mL). Solvent was then removed in vacuo to afford a yellow solid (8.32 g), which was further purified by trituration with MeOH (100 mL) to afford (XXI-a) as an off-white powder (7.16 g, 22.5 mmol, 67%). $^1H$ NMR (400 MHz, $CDCl_3$) δ 4.31 (s, 2H), 8.10 (d, J=3.1 Hz, 1H), 8.48 (d, J=2.2 Hz, 1H), 8.83 (d, J=0.4, 2.2 Hz, 1H), 9.34 (br s, 1H).

4-(5-Bromo-1H-pyrrolo[2,3-b]pyridin-3-yl)-thiazole-2-carboxylic acid ethyl ester (XXIII-a)

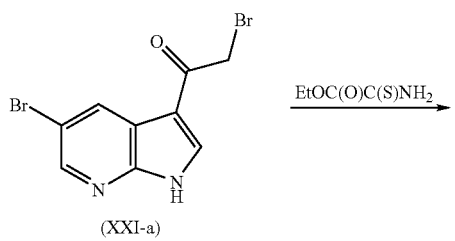

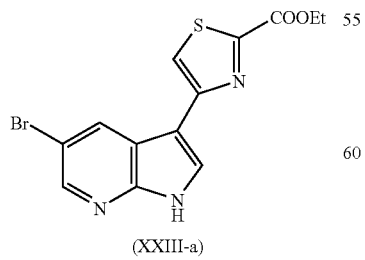

To a stirred solution of (XXI-a) (4.97 g, 15.6 mmol) in dioxane (55 mL) was added ethyl thiooxamate (2.29 g, 17.2 mmol). The reaction mixture was stirred vigorously at 95° C. for 18 h. The hot reaction mixture was filtered and the collected product was washed with cold dioxane (25 mL) to afford the hydrobromide salt of (XXIII-a) as a yellow powder (6.08 g, 14.0 mmol, 90%). $^1H$ NMR (400 MHz, $CDCl_3$) δ 1.48 (t, J=7.1 Hz, 3H), 4.52 (q, J=7.1 Hz, 2H), 7.77 (s, 1H), 8.05 (s, 1H), 8.43 (d, J=1.8 Hz, 1H), 9.21 (s, 1H).

4-(5-bromo-1H-pyrrolo[2,3-b]pyridin-3-yl)thiazole-2-carboxylic acid (XXIII-b)

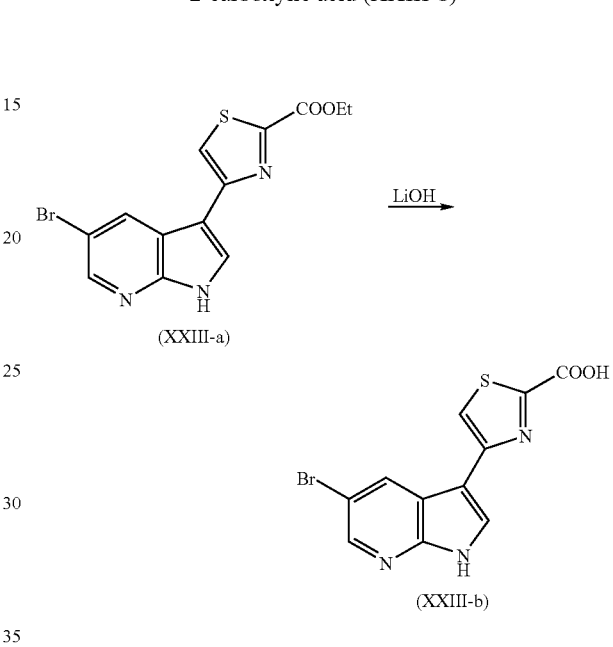

To a stirred solution of ethyl 4-(5-bromo-1H-pyrrolo[2,3-b]pyridin-3-yl)thiazole-2-carboxylate hydrobromide (XXIII-a) (4.03 g, 9.30 mmol) in water:THF 1:1 (50 mL) was added $LiOH \cdot H_2O$ (900 mg, 21.45 mmol) portionwise over 30 min. After stirring for 3 h, the reaction mixture was filtered to afford a yellow solid (2.49 g). The filtrate was then concentration to ~20 mL by evaporation, and filtered again to afford a further 820 mg of yellow solid. The solids were combined to afford (XXIII-b) (3.31g, crude yield >100%). $^1H$ NMR (400 MHz, D-6 DMSO) δ 7.76 (s, 1H), 8.03 (s, 1H), 7.73-7.78 (m, 3H), 8.32 (d, J=2.3 Hz, 1H), 8.74 (d, J=2.3 Hz, 1H), 12.09 (br s, 1H).

(4-(5-bromo-1H-pyrrolo[2,3-b]pyridin-3-yl)thiazol-2-yl)(piperidin-1-yl)methanone (XXIII-c)

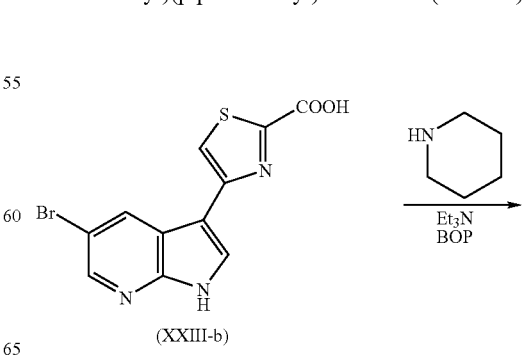

-continued

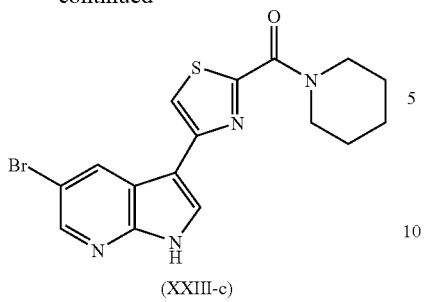

(XXIII-c)

Compound (XXIII-b) (1.14 g, up to 3.54 mmol), triethylamine (1.00 mL, 726 mg, 7.17 mmol), piperidine (0.70 mL, 603 mg, 7.09 mmol) and BOP (2.25 g, 5.09 mmol) in DMF (15 mL) were converted into (XXIII-c) by stirring for 18 h and following the general procedure for the formation of amides. The crude reaction mixture was treated with AcOEt (100 mL), washed with NaHCO$_3$ (2×50 mL), concentrated, and purified by SGC using MeOH:CH$_2$Cl$_2$=1:19 (v/v) to afford crude (XXIII-c) as an off-white powder (1.26 g, up to 3.52 mmol) which was used in subsequent reactions without further purification. $^1$H NMR (400 MHz, CDCl$_3$) δ 1.72-1.91 (m, 6H), 3.78-3.84 (m, 2H), 4.39-4.45 (m, 2H), 7.54 (s, 1H), 7.80 (s, 1H), 8.44 (d, J=2.0 Hz, 1H), 8.62 (d, J=2.0 Hz, 1H), 9.25 (s, 1H).

(4-(5-bromo-1H-pyrrolo[2,3-b]pyridin-3-yl)thiazol-2-yl)(morpholino)methanone (XXIII-d)

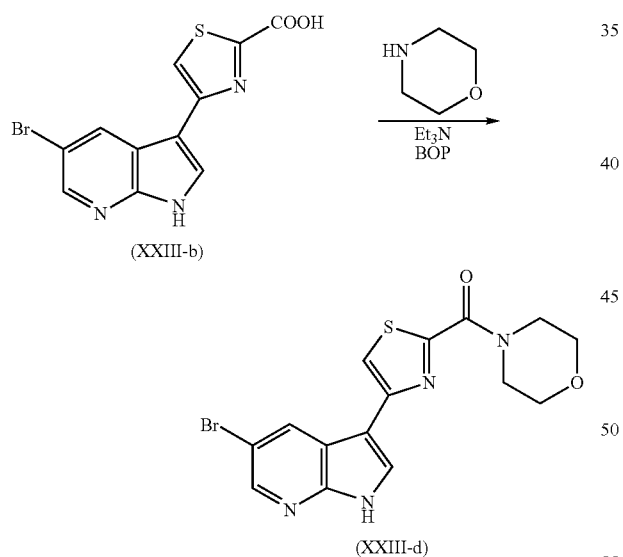

Compound (XXIII-b) (0.85 g, up to 2.62 mmol), triethylamine (0.70 mL, 508 mg, 5.02 mmol), morpholine (448 mg, 5.14 mmol) and BOP (1.60 g, 3.62 mmol) in DMF (10 mL) were converted into (XXIII-d) by stirring for 4 d and following the general procedure for the formation of amides. The crude reaction mixture was treated with AcOEt (100 mL), and washed with NaHCO$_3$ (3×25 mL). On standing, a precipitate formed in the aqueous layer which was filtered to afford crude (XXIII-d) as a white powder (1.96 g, crude yield >100%) which was used in subsequent reactions without further purification. $^1$H NMR (400 MHz, DMSO-d$_6$) δ 3.67-3.84 (m, 6H), 4.40-4.50 (m, 2H), 8.18 (s, 1H), 8.22 (s, 1H), 8.35 (d, J=2.2 Hz, 1H), 8.59 (d, J=2.2 Hz, 1H).

(4-(5-bromo-1H-pyrrolo[2,3-b]pyridin-3-yl)thiazol-2-yl)(4-methylpiperazin-1-yl)methanone (XXIII-e)

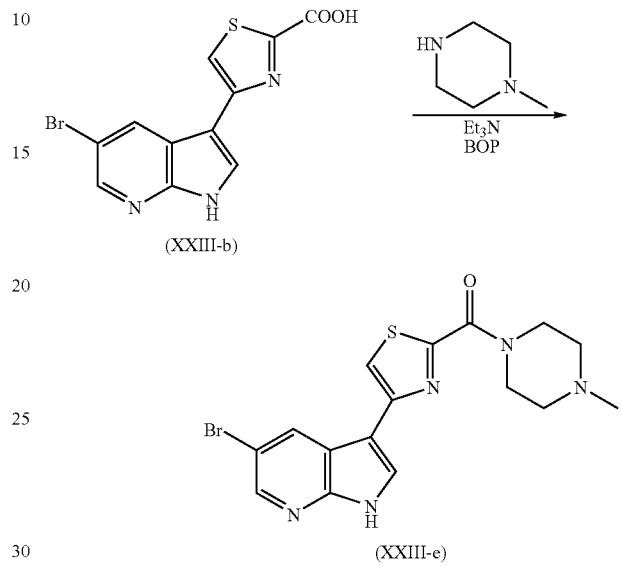

Compound (XXIII-b) (1.46 g, up to 4.10 mmol), triethylamine (1.30 mL, 944 mg, 9.33 mmol), -methyl-piperazine (1.00 mL, 903 mg, 9.01 mmol) and BOP (2.70 g, 6.10 mmol) in DMF (20 mL) were converted into (XXIII-e) by stirring for 4 d and following the general procedure for the formation of amides. The crude reaction mixture was treated with AcOEt (100 mL), extracted with NaHCO$_3$ (3×50 mL) and evaporated to afford crude (XXIII-e) as an off-white powder (1.80 g, up to 4.43 mmol) which was used in subsequent reactions without further purification. $^1$H NMR (400 MHz, DMSO-d$_6$) δ 2.26 (s, 3H), 2.41-2.48 (m, 2H), 2.93-3.04 (m, 2H), 3.67-3.75 (m, 2H), 4.35-4.43 (m, 2H), 8.19 (d, J=2.6 Hz, 1H), 8.23 (s, 1H), 8.37 (d, J=2.2 Hz, 1H), 8.64 (d, J=2.2 Hz, 1H).

4-[4-(5-Bromo-1H-pyrrolo[2,3-b]pyridin-3-yl)-thiazol-2-yl]-piperidine-1-carboxylic acid tert-butyl ester (XXIII-f)

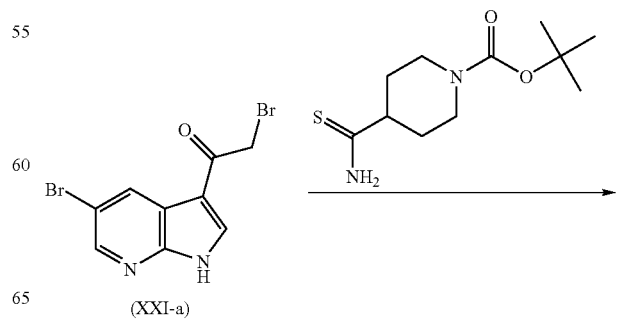

(XXI-a)

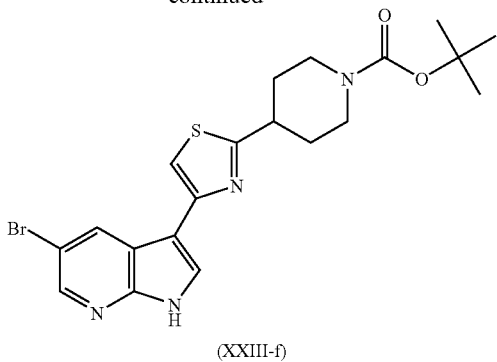

(XXIII-f)

To a solution of (XXI-a) (1.71 g, 5.38 mmol) in THF (20 mL) was added 1-Boc-4-aminothiocarbonyl piperidine (1.31 g, 5.36 mmol) and the solution was allowed to stir at RT for 3 h. The reaction mixture was then poured onto saturated aqueous NaHCO$_3$ (50 mL) and extracted with AcOEt (2×50 mL). The combined organic extracts were then evaporated to afford (XXIII-f) (2.58 g, 5.41 mmol, 100%) as a white powder. $^1$H NMR (400 MHz, CDCl$_3$) δ 1.43 (s, 9H), 1.64-1.84 (m, 4H), 2.07-2.17 (m, 2H), 2.81-2.94 (m, 2H), 3.13-3.24 (m, 1H), 7.17 (s, 1H), 7.74 (d, J=2.4 Hz, 1H), 8.32 (d, J=2.1 Hz, 1H), 8.48 (d, J=2.1 Hz, 1H), 8.97 (br s, 1H).

4-(5-bromo-1H-pyrrolo[2,3-b]pyridin-3-yl)-N,N-diethylthiazol-2-amine (XXIII-i)

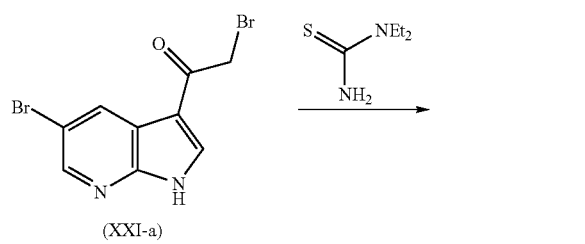

(XXIII-i)

To a stirred solution of (XXI-a) (2.30 g, 7.24 mmol) in 1,4-dioxane (20 mL) was added N,N-diethylthiourea (1.00 g, 7.56 mmol), and the reaction mixture was allowed to stir at room temperature overnight. After 24 hrs, NaHCO$_3$ (sat., aq., 50 mL) was added, and the solution extracted with AcOEt (2×75 mL). The combined organic portions were dried over MgSO$_4$ and evaporated to afford the crude product (2.97 g, estimated purity 85%). $^1$H NMR (400 MHz, CDCl$_3$) δ 1.32 (t, J=7.2 Hz, 6H), 3.59 (q, J=7.1 Hz, 4H), 6.55 (s, 1H), 7.75 (d, J=2.6 Hz, 1H), 8.38 (d, J=2.1 Hz, 1H), 8.55 (d, J=2.1 Hz, 1H), 9.13 (br s, 1H).

4-(5-bromo-1H-pyrrolo[2,3-b]pyridin-3-yl)-2-methylthiazole (XXIII-k)

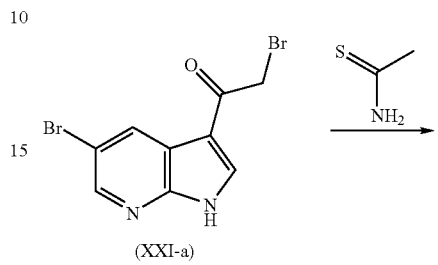

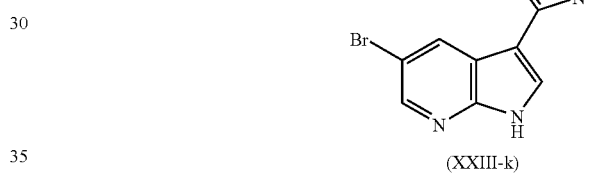

(XXIII-k)

To a stirred solution of (XXI-a) (2.89 g, 9.09 mmol) in THF (25 mL) was added thioacetamide (0.69 g, 9.18 mmol) and the reaction mixture heated to reflux. After 6 h, the reaction mixture was cooled, diluted with AcOEt (200 mL) and washed with saturated aqueous (3×25 mL). The organic layer was dried (MgSO$_4$) and concentrated to afford (XXIII-k) as a yellow powder (2.63 g, 8.94 mmol, 98%). $^1$H NMR (400 MHz, CDCl$_3$) δ 2.73 (s, 3H), 7.12 (s, 1H), 7.73 (d, J=2.7 Hz, 1H), 8.32 (d, J=2.1 Hz, 1H), 8.46 (d, J=2.0 Hz, 1H), 8.93 (br s, 1H).

tert-butyl 2-(4-(5-bromo-1H-pyrrolo[2,3-b]pyridin-3-yl)thiazol-2-yl)pyrrolidine-1-carboxylate (XXIII-o)

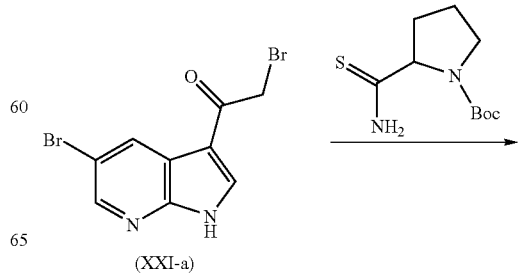

(XXI-a)

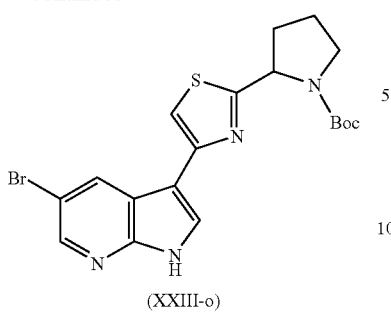

(XXIII-o)

To a solution of (XXI-a) (2.80 g, 8.81 mmol) in THF (80 mL) was added tert-butyl 2-carbamothioylpyrrolidine-1-carboxylate (3.04 g, 13.21 mmol) and the solution was heated to reflux overnight. It was allowed to cool and was then poured onto saturated aqueous NaHCO$_3$ (100 mL) and extracted with AcOEt (3×100 mL). The combined organic extracts were dried over MgSO$_4$ and concentrated. The crude product was purified by SCG using 0%-100% EtOAc:hexane as the eluent (gradient from 0:100 to 100:0, v/v) to give the product (XXIII-o) (2.44 g, 61%) as a yellow foam. Compound exists as rotamers $^1$H NMR (400 MHz, CDCl$_3$) δ 1.36 (s, 6H), 1.51 (s, 3H), 1.93-2.08 (m, 2H), 2.28-2.46 (m, 2H), 2.46-2.61 (m, 1H), 3.64-3.73 (m, 1H), 5.23 (d, J=6 Hz, 0.6H), 5.32-5.37 (br s, 0.4H), 7.15 (s, 0.4H), 7.23 (s, 0.6H), 7.76 (s, 0.4H), 7.84 (s, 0.6H), 8.37 (s, 0.4H), 8.40 (s, 0.6H), 8.50 (s, 0.4H), 8.55 (s, 0.6H), 10.79 (br s, NH, 0.4H), 10.84 (br s, NH, 0.6H).

5-Cyclohexyl-1H-pyrrolo[2,3-b]pyridine (XXVb-6)

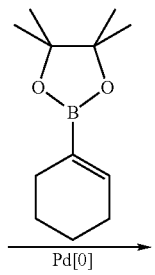

(XXVa-12)

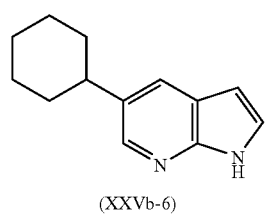

(XXVb-6)

Compound (XXVa-12) was hydrogenated using the general procedure for hydrogenation of 7-azaindoles. Thus, (XXVa-12) (1.50 g, 7.57 mmol), methanol (100 mL) and 20% Pd(OH)$_2$/C (Degussa type) (0.25 g) were stirred at RT under H$_2$ for 4 days. Filtration through a pad of Celite using MeOH:CH$_2$Cl$_2$=1:1 (200 mL) and concentration of the filtrate gave (XXVb-6) as a brown solid (1.37 g, 6.84 mmol, 90%). $^1$H NMR (400 MHz, CDCl$_3$) δ 1.24-1.59 (m, 5H), 1.76-2.00 (m, 5H), 2.66 (tt, J 3.4, 11.6 Hz, 1H), 6.48 (d, J 3.4 Hz, 1H), 7.33 (d, J=3.4 Hz, 1H), 7.81 (d, J=1.8 Hz, 1H), 8.22 (d, J=1.8 Hz, 1H), 9.58 (br s, 1H).

5-Cyclohexenyl-1H-pyrrolo[2,3-b]pyridine (XXVa-12)

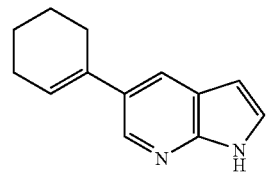

(XXVa-12)

A mixture of (XIX-a) (2.90 g, 14.70 mmol), cyclohexenyl boronic acid pinacol ester (3.40 g, 16.34 mmol), PdCl$_2$(PPh$_3$)$_2$ (0.52 g, 0.74 mmol), LiCl (1.87 g, 44.11 mmol), and 1.0 M aq. Na$_2$CO$_3$ (20 mL, 20 mmol), in EtOH (30 mL) and toluene (30 mL) was reacted for 4 h using the general procedure A for the Suzuki reaction. The crude product (5.74 g; dark brown oil) was purified by SGC using ethyl acetate:CH$_2$Cl$_2$=1:4 (v/v) as eluent to give (XXVa-12) as a pale yellow powder (1.50 g, 7.57 mmol, 51%). $^1$H NMR (400 MHz, CDCl$_3$) δ 1.68-1.75 (m, 2H), 1.81-1.88 (m, 2H), 2.23-2.29 (m, 2H), 2.47-2.53 (m, 2H), 6.10-6.14 (m, 1H), 6.50 (dd, J2.0, 3.5 Hz, 1H), 7.30 (d, J=2.4 Hz, 1H), 7.92 (d, J=1.7 Hz, 1H), 8.40 (d, J=1.8 Hz, 1H), 7.88 (s, 1H), 9.07 (br s, 1H).

5-(1,4-Dioxa-spiro[4.5]dec-8-yl)-1H-pyrrolo[2,3-b]pyridine (XXVb-23)

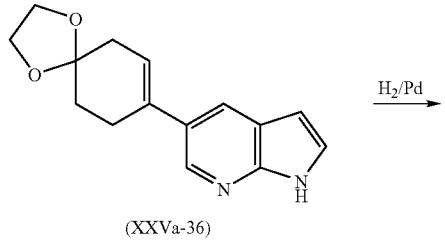

(XXVa-36)

-continued

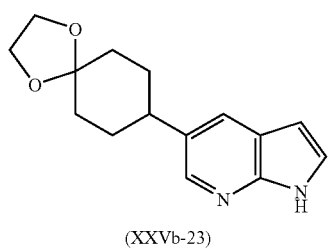
(XXVb-23)

Compound (XXVa-36) was hydrogenated using the general procedure for hydrogenation of 7-azaindoles. Thus, (XXVa-36) (800 mg, 3.12 mmol), methanol (100 mL) and a $CH_2Cl_2$ (10 mL), and 10% Pd/C (catalytic amount) was stirred at RT under $H_2$ for 16.5 h. Filtration through a pad of Celite using MeOH:$CH_2Cl_2$ and concentration of the filtrate gave (XXVb-23) as a white solid (795 mg, 99%); $^1$H NMR (400 MHz, CDCl$_3$) δ 1.70-1.80 (m, 2H), 1.86-2.00 (m, 6H), 2.72 (m, 1H), 4.01 (s, 4H), 6.46 (dd, J=1.4 , 3.4Hz, 1H), 7.34 (m, 1H), 7.84 (d, J=1.5 Hz, 1H), 8.25 (bs, 1H), 10.21 (bs, NH).

5-(1,4-Dioxa-spiro[4.5]dec-8-yl)-1H-pyrrolo[2,3-b]pyridine (XXVb-23)—alternative method of preparation

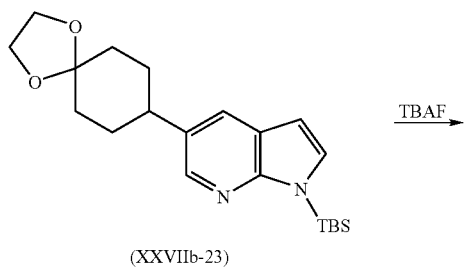
(XXVIIb-23)

→ TBAF

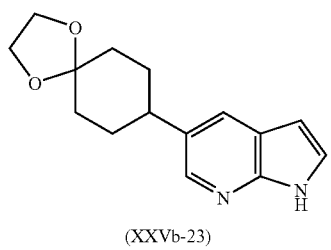
(XXVb-23)

To a stirred solution of the azaindole (XXVIIb-23) (4.23 g, 11.4 mmol) in THF (50 mL) was added 1 M nBu$_4$NF in THF (22.7 mL, 22.7 mmol). After 75 min the mixture was concentrated and separated by means of SGC using hexane:AcOEt as eluent (gradient from 100:0 to 0:100, v/v) to afford azaindole (XXVb-23) (2.51 g, 86%) indistinguishable by NMR from the compound prepared earlier via reduction of (XXVa-36).

5-(1,4-Dioxa-spiro[4.5]dec-7-en-8-yl)-1H-pyrrolo[2,3-b]pyridine (XXVa-36)

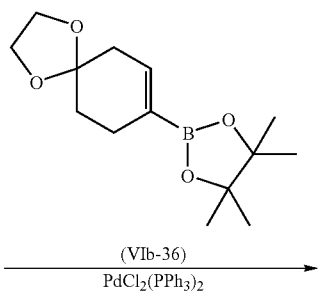

(VIb-36)
PdCl$_2$(PPh$_3$)$_2$
→

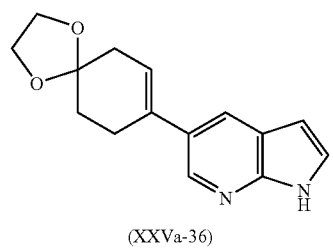
(XXVa-36)

A mixture of (XIX-a) (1.00 g, 5.08 mmol), boronic ester (VIb-36) (2.15 g, 8.07 mmol), PdCl$_2$(PPh$_3$)$_2$ (378 mg, 0.54 mmol), LiCl (684 mg, 16.1 mmol), and 1.0 M aq. Na$_2$CO$_3$ (13.5 mL, 13.5 mmol), in EtOH (25 mL) and toluene (25 mL) was reacted for 3.5 h using the general procedure A for the Suzuki reaction. The crude product was purified by SGC using ethyl acetate:hexane=6:4 (v/v) as eluent (gradient elution) to give brown solid. This solid was washed with 10% then 20% and finally 30% ethyl acetate in hexane to give (XXVa-36) (881 mg, 68%) as a white solid; $^1$H NMR (400 MHz, CDCl$_3$) δ 1.98 (t, J=6.46 Hz, 2H), 2.52 (m, 2H), 2.76 (m, 2H), 4.06 (s, 4H), 6.00 (m, 1H), 6.49 (dd, J=1.9, 3.46 Hz, 1H), 7.33 (t, J=2.91 Hz, 1H), 7.94 (d, J=1.97 Hz, 1H), 8.42 (d, J=2.1 Hz, 1H), 9.88 (bs, NH).

4-(4-(1H-pyrrolo[2,3-b]pyridin-5-yl)cyclohex-3-enyl)morpholine (XXVa-54)

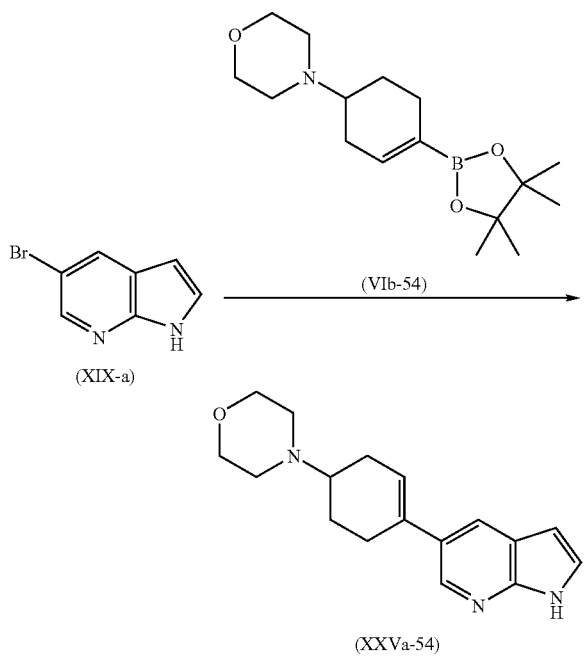

A mixture of (XIX-a) (18.00 g, 91.35 mmol), boronic ester (VIb-54) (31.40 g, 107.09 mmol), PdCl$_2$(PPh$_3$)$_2$ (3.21 g, 4.57 mmol), LiCl (11.62 g, 274.06 mmol), and 1.0 M aq. Na$_2$CO$_3$ (91.4 mL, 91.4 mmol), in EtOH (150 mL) and toluene (150 mL) was reacted for 5 h using the general procedure A for the Suzuki reaction. The reaction mixture was cooled, poured onto AcOEt (500 mL) and saturated aqueous NaHCO$_3$ (200 mL). The layers were separated and allowed to stand overnight. After 18 hrs, the aqueous layer was filtered to afford (XXVa-54) as a pale brown powder (13.59 g). The aqueous filtrate was then further extracted with AcOEt (500 mL), the combined organic portions were dried over MgSO$_4$ and evaporated to afford a dark brown oil (33.37 g), which was triturated with MeOH (250 mL) to afford more (XXVa-54) as a pale brown powder (2.76 g). Total yield of (XXVa-54) 17.23 g (60.80 mmol, 63%). $^1$H NMR (400 MHz, CDCl$_3$) δ 1.57-1.73 (m, 1H), 2.17-2.31 (m, 2H), 2.44-2.75 (m, 8H), 3.80 (t, J=4.6 Hz, 4H), 6.05-6.09 (m, 1H), 6.50 (dd, J=2.0, 3.5 Hz, 1H), 7.31 (dd, J=2.5, 3.4 Hz, 1H), 7.92 (d, J=1.9 Hz, 1H), 8.40 (d, J=2.0 Hz, 1H), 8.82 (br s, 1H).

4-((1r,4r)-4-(1H-pyrrolo[2,3-b]pyridin-5-yl)cyclohexyl)-1,4-oxazepane (XXVb-75)

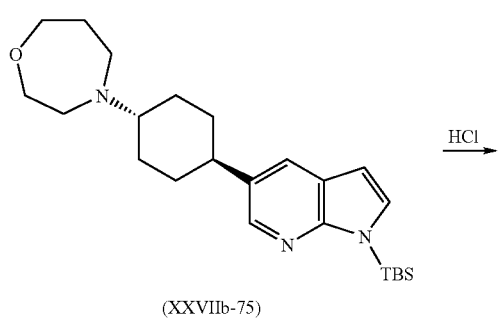

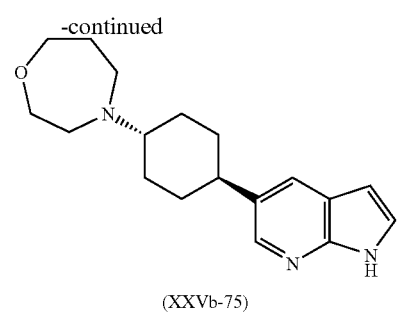

Azaindole (XXVIIb-75) (1.5 g, 3.6 mmol) in MeOH (80 mL) and 12 M HCl (1.50 mL, 18.0 mmol) was deprotected over 45 min using the general procedure B for the deprotection of 7-azaindoles to afford azaindole (XXVb-75) (1.27 g) an off-white powder that was used directly for the next transformations without further purification. $^1$H NMR (400 MHz, CDCl$_3$) δ 1.42-1.65 (m, 4H), 1.84-1.92 (m, 2H), 1.97-2.06 (m, 4H), 2.56-2.70 (m, 2H), 3.73-3.75 (m, 2H), 3.82 (t, J=6.0 Hz, 2H), 6.43 (q, J=2.0 Hz, 1H), 7.29 (q, J=2.5 Hz, 1H), 7.76 (d, J=2.0 Hz, 1H), 8.19 (d, J=2.0 Hz, 1H), 9.35 (brs, 1H).

4-(4-(1H-pyrrolo[2,3-b]pyridin-5-yl)cyclohex-3-enyl)-1,4-oxazepane (XXVa-101)

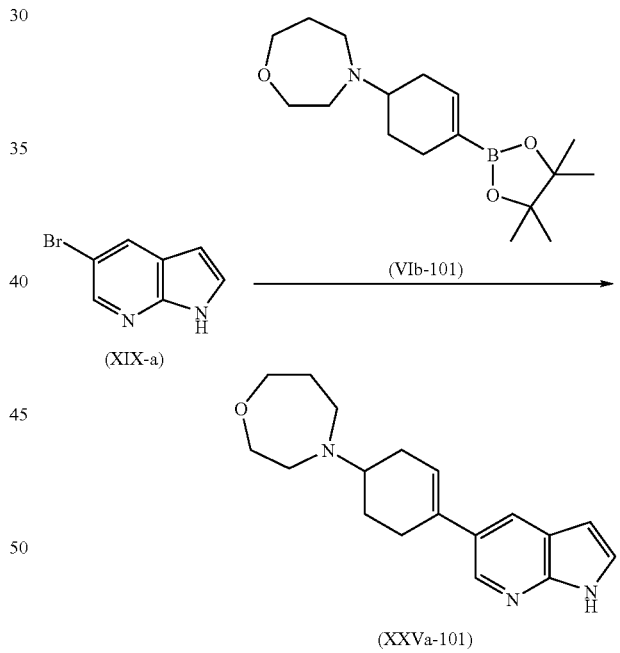

A mixture of (XIX-a) (10 g, 50.8 mmol), boronic ester (VIb-101) (17.15 g, 55.8 mmol), PdCl$_2$(PPh$_3$)$_2$ (3.92 g, 5.6 mmol), LiCl (6.93 g, 163.4 mmol), and 1.0 M aq. Na$_2$CO$_3$ (137 mL, 137 mmol) in EtOH (200 mL) and toluene (200 mL) was reacted for 2.5 h using the general procedure A for the Suzuki reaction. The reaction mixture was cooled, and partitioned between saturated brine (100 mL) and EtOAc (200 mL). The aqueous layer was extracted with EtOAc (3×150 mL). The combined organic solutions were dried (MgSO$_4$), filtered and concentrated to afford an orange powder. This was triturated with cold EtOAc and filtered to yield the Suzuki adduct (XXVa-101) (12.65 g, 84%) as a tan solid. $^1$H NMR (400 MHz, CDCl₃) δ 1.64-1.74 (m, 1H), 1.89-1.92 (m, 2H), 2.10 (m, 1H), 2.20-2.27 (m, 1H), 2.39-2.46 (m, 1H), 2.60-2.64 (m, 2H), 2.86 (m, 4H), 2.95 (m, 1H), 3.76 (t, J=4.6 Hz, 2H), 3.83 (t, J=6.0 Hz, 2H), 6.05 (m, 1H), 6.4 (dd, J=2.0, 3.5 Hz, 1H), 7.29-7.30 (m, 1H), 7.89 (d, J=2.0 Hz, 1H), 8.37 (d, J=2.0 Hz, 1H), 9.21 (br s, 1H).

5-Cyclohexyl-3-iodo-1H-pyrrolo[2,3-b]pyridine (XXVIb-6)

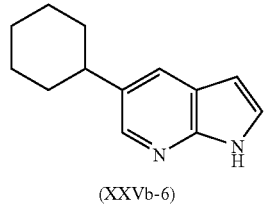

(XXVb-6)

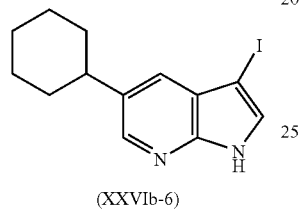

(XXVIb-6)

To a solution of (XXVb-6) (1.37 g, 6.84 mmol) in DMF (30 mL) was added KOH (0.77 g, 13.68 mmol) and the mixture was stirred for 5 min. Iodine (1.77 g, 6.98 mmol) was then added portionwise over 10 min, and the reaction was stirred at room temperature for 2 h. The solution was then diluted with AcOEt (250 mL) and washed with saturated aqueous Na₂S₂O₃ (2×50 mL). The organic layer was dried (MgSO₄) and concentrated to afford (XXVIb-6) (1.92 g, 5.89 mmol, 86%) as a yellow powder. ¹H NMR (400 MHz, CDCl₃) δ 1.27-1.61 (m, 5H), 1.78-2.00 (m, 5H), 2.70 (tt, J=3.3, 11.5 Hz, 1H), 7.40 (d, J=2.0 Hz, 1H), 7.57 (d, J=2.0 Hz, 1H), 8.22 (d, J=2.0 Hz, 1H), 8.95 (br s, 1H).

3-iodo-5-(1,4-dioxaspiro[4.5]decan-8-yl)-1H-pyrrolo[2,3-b]pyridine (XXVIb-23)

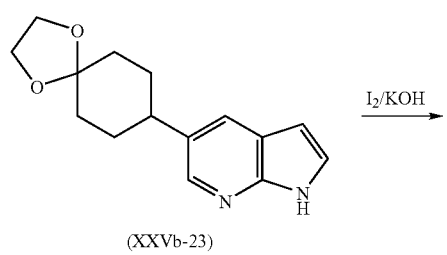

(XXVb-23)

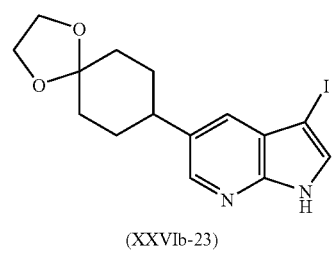

(XXVIb-23)

To a stirred mixture of azaindole (XXVb-23) (2.51 g, 9.72 mmol) and crushed KOH pellets (2.05 g, 36.6 mmol) in DMF (40 mL) was added iodine (2.22 g, 8.7 mmol). After 3.5 h the mixture was concentrated and partitioned between EtOAc (100 mL) and satd NaHCO3 solution (40 mL). The aqueous layer was extracted with EtOAc (3×60 mL) and the combined organic extracts dried (MgSO₄), filtered and concentrated to afford crude iodide (XXVIb-23), which was used directly in further steps without any purification.

4-((1r,4r)-4-(3-iodo-1H-pyrrolo[2,3-b]pyridin-5-yl)cyclohexyl)-1,4-oxazepane (XXVIb-75)

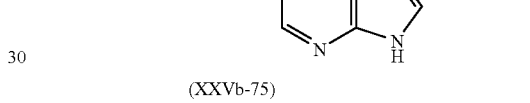

(XXVb-75)

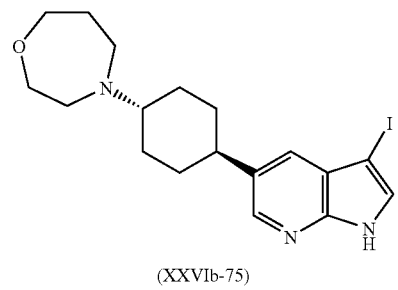

(XXVIb-75)

To a stirred mixture of (XXVb-75) (1.09 g, 3.6 mmol) and solid KOH (0.77 g, 13.7 mmol) in DMF (40 mL) was added iodine (0.83 g, 3.3 mmol) was added and the mixture was stirred for 3 h. The reaction mixture was partially concentrated in vacuo and partitioned between EtOAc (100 mL) and saturated NaHCO₃ (40 mL). The aqueous layer was extracted with EtOAc (3×60 mL). The combined organic solutions were dried (MgSO₄) and concentrated to afford iodide (XXVIb-75), which was used directly in further steps without any additional purification. ¹H NMR (400 MHz, CDCl₃) δ 1.42-1.52 (m, 2H), 1.56-1.67 (m, 2H), 1.84-1.91 (m, 2H), 1.98-2.04 (m, 4H), 2.59-2.71 (m, 2H), 2.81-2.85 (m, 4H), 3.73-

3.75 (m, 2H), 3.81 (t, J=6.0 Hz, 2H), 7.39 (d, J=2.0 Hz, 1H), 7.54 (d, J=2.0 Hz, 1H), 8.18 (d, J=2.0 Hz, 1H), 9.83 (br s, 1H).

1-(tert-butyldimethylsilyl)-5-(1,4-dioxaspiro[4.5] decan-8-yl)-1H-pyrrolo[2,3-b]pyridine (XXVIIb-23)

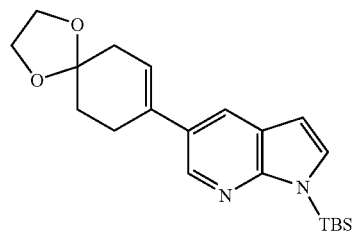

(XXVIIa-36)

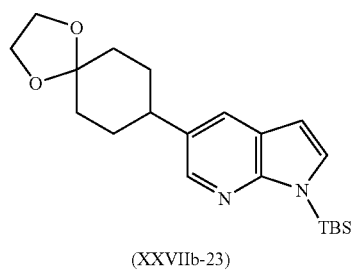

(XXVIIb-23)

Compound (XXVIIa-36) was hydrogenated using the general procedure for hydrogenation of 7-azaindoles. Thus, (XXVIIa-36) (4.37 g, 11.8 mmol), EtOH (35 mL) and THF (35 mL), and Pd(OH)$_2$ (20% on carbon, Degussa-type) (1.00 g) was stirred at RT under H$_2$ for 24 h. Filtration through a pad of Celite using EtOH (500 mL), AcOEt (500 mL) and concentration of the filtrate gave (XXVIIb-23) (4.23 g, 96%).

4-((1s,4s)-4-(1-(tert-butyldimethylsilyl)-1H-pyrrolo [2,3-b]pyridin-5-yl)cyclohexyl)morpholine (XXVIIb-28) and 4-((1r,4r)-4-(1-(tert-butyldimethylsilyl)-1H-pyrrolo[2,3-b]pyridin-5-yl)cyclohexyl) morpholine (XXVIIb-29)

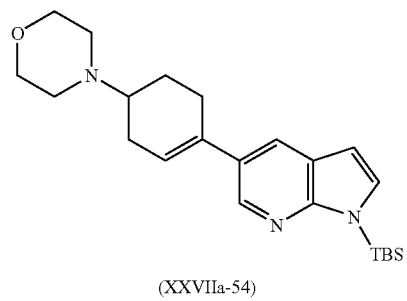

(XXVIIa-54)

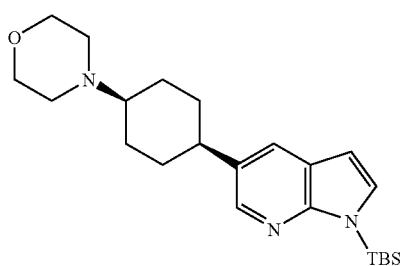

(XXVIIb-28)

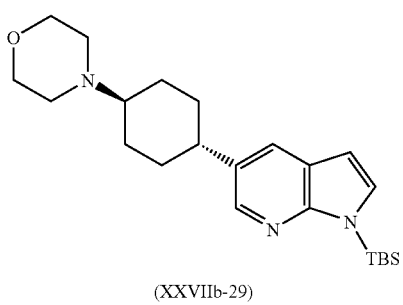

(XXVIIb-29)

Compound (XXVIIa-54) was hydrogenated using the general procedure for hydrogenation of 7-azaindoles. Thus, (XXVIIa-54) (11.00 g, 27.66 mmol), ethanol (100 mL) and THF (100 mL), and Pd(OH)$_2$ (20% on carbon, Degussa-type) (2.00 g) was stirred at RT under H$_2$ for 22 h. Filtration through a pad of Celite using ethanol (500 mL) and concentration of the filtrate gave the crude mixture of cis and trans isomers. The isomers were separated by SGC using AcOEt:CH$_2$Cl$_2$ (gradient from 1:2 to 2:1 v/v) to give (XXVIIb-28) (4.08 g, 10.21 mmol, 37%), followed by (XXVIIb-29) (6.67 g, 16.69 mmol, 60%). Data for the trans isomer (XXVIIb-29): $^1$H NMR (400 MHz, CDCl$_3$) δ 0.56 (s, 6H), 0.87 (s, 9H), 1.30-1.65 (m, 5H), 1.89-2.13 (m, 4H), 2.38-2.76 (m, 5H), 3.58-3.94 (m, 4H), 6.42 (d, J=3.5 Hz, 1H), 7.16 (d, J=3.5 Hz, 1H), 7.61 (d, J=1.9 Hz, 1H), 8.08 (d, J=2.0 Hz, 1H).

1-(tert-butyldimethylsilyl)-5-(1,4-dioxaspiro[4.5] dec-7-en-8-yl)-1H-pyrrolo[2,3-b]pyridine (XXVIIa-36)

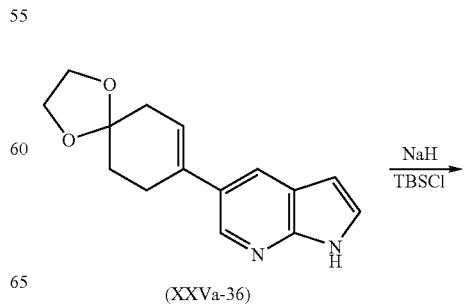

(XXVa-36)

-continued

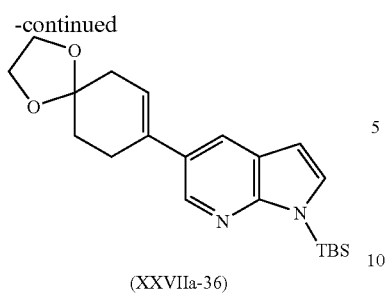

(XXVIIa-36)

To a solution of azaindole (XXVa-36) (4.0 g, 15.6 mmol) in DMF (35 mL) was added NaH (0.749 g, 18.7 mmol; 60% in oil) in one portion. After 10 min, tetrabutyldimethylsilyl chloride (3.06 g, 20.3 mmol) was added in 2 portions over 1 min. Following a further 19.5 h the mixture was diluted with EtOAc (100 mL) and saturated aqueous NaHCO₃ solution (35 mL) and partitioned. The aqueous layer was extracted with EtOAc (2×40 mL). The combined organic extracts were dried (MgSO₄), filtered and concentrated to afford a honey-coloured viscous oil. This was purified by SGC using hexane: AcOEt (gradient elution) to afford the silylated derivative (XXVIIa-36) (4.37 g, 76%).

4-(4-(1-(tert-butyldimethylsilyl)-1H-pyrrolo[2,3-b]pyridin-5-yl)cyclohex-3-enyl)morpholine (XXVIIa-54)

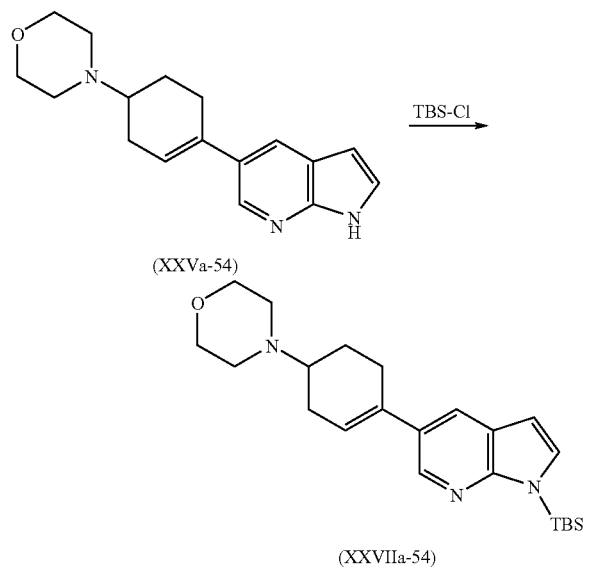

To a solution of (XXVa-54) (17.23 g, 60.80 mmol) in DMF (250 mL) was added NaH (2.67 g, 60% in mineral oil, 66.67 mmol) portionwise over 30 min. The reaction mixture was allowed to stir for 10 min, then tert-butyldimethylchlorosilane (11.00 g, 72.96 mmol) was added portionwise over 10 min. After stirring at room temperature for 3 d, the reaction was quenched with saturated aqueous NaHCO₃ (250 mL) and extracted with AcOEt (800 mL). The organic layer was further washed with saturated aqueous NaHCO₃ (2×250 mL), dried over MgSO₄, and concentrated to give an oil (17.45 g). The crude product was purified by flash column chromatography to afford (XXVIIa-54) (11.00 g, 27.66 mmol, 46%) as a colourless oil. $^1$H NMR (400 MHz, CDCl₃) δ 0.60 (s, 6H), 0.89 (s, 9H), 1.53-1.64 (m, 1H), 2.10-2.25 (m, 2H), 2.37-2.68 (m, 8H), 3.74 (t, J=4.7 Hz, 4H), 5.99-6.03 (m, 1H), 6.46 (d, J=3.4 Hz, 1H), 7.18 (d, J=3.5 Hz, 1H), 7.79 (d, J=2.3 Hz, 1H), 8.32 (d, J=2.3 Hz, 1H).

4-((1r,4r)-4-(1-(tert-butyldimethylsilyl)-1H-pyrrolo[2,3-b]pyridin-5-yl)cyclohexyl)-1,4-oxazepane (XXVIIb-75) and 4-((1s,4s)-4-(1-(tert-butyldimethylsilyl)-1H-pyrrolo[2,3-b]pyridin-5-yl)cyclohexyl)-1,4-oxazepane (XXVIIb-76)

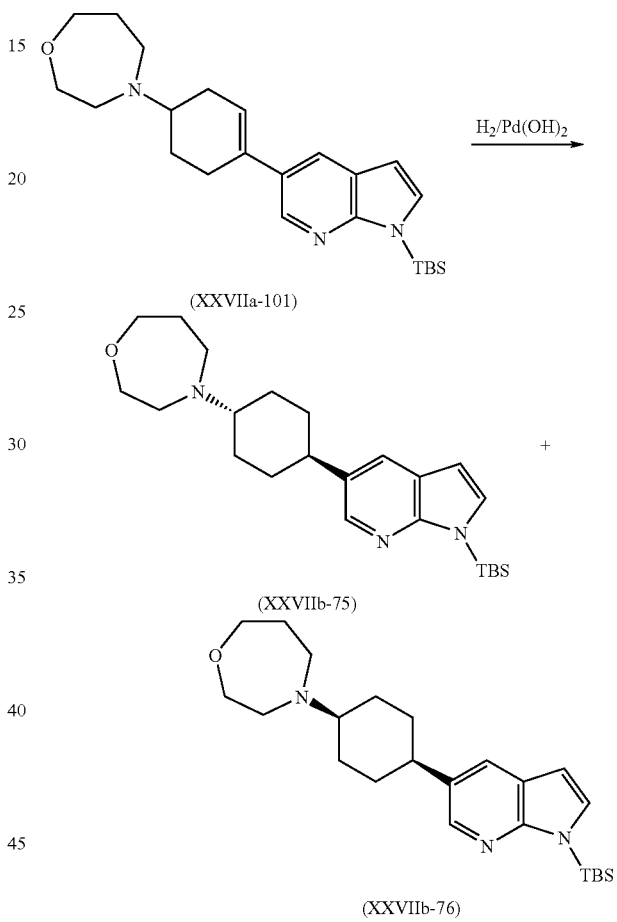

Compound (XXVIIa-101) was hydrogenated using the general procedure for hydrogenation of 7-azaindoles. Thus, (XXVIIa-101) (15.37 g, 37.3 mmol), ethanol (120 mL) and THF (120 mL), and Pd(OH)₂ (20% on carbon, Degussa-type) (3.50 g) was stirred at RT under H₂ for 23 h. Another portion of the catalyst (2.00 g) was added and stirring under H₂ continued for 23.5 h. Filtration through a pad of Celite using EtOH (500 mL), EtOAc (500 mL), DCM (500 mL), 10% MeOH/DCM (500 mL) and 10% MeOH/EtOAc (300 mL) and concentration of the filtrate gave the crude mixture of cis and trans isomers (15.44 g) as a viscous honey-coloured oil. The isomers were separated by SGC using AcOEt: MeOH=9:1 (v/v) to give (XXVIIb-76) (5.91 g, 38%), followed by mixed fractions (2.01 g, 13%) and (XXVIIb-75) (4.19 g, 27%).

Data for the trans isomer (XXVIIb-75): $^1$H NMR (400 MHz, CDCl₃) δ 0.62 (s, 6H), 0.93 (s, 9H), 1.42-1.62 (m, 4H), 1.88 (m, 1H), 1.99-2.02 (m, 4H), 2.52-2.66 (m, 2H), 2.83 (m, 4H), 3.74 (m, 12H), 3.82 (t, J=6.0 Hz, 2H), 6.46 (d, J=3.4 Hz, 1H), 7.20 (d, J=3.4 Hz, 1H), 7.67 (d, J=2.1 Hz, 1H), 8.14 (d, J=2.1 Hz, 1H).

4-(4-(1-(tert-butyldimethylsilyl)-1H-pyrrolo[2,3-b]pyridin-5-yl)cyclohex-3-enyl)-1,4-oxazepane (XXVIIa-101)

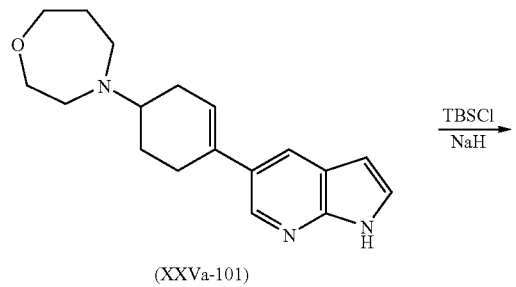

(XXVa-101)

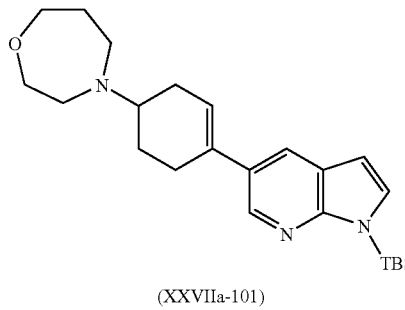

(XXVIIa-101)

To a stirred solution of azaindole (XXVa-101) (12.65 g, 42.5 mmol) in DMF (120 mL) was added 60% NaH dispersion in mineral oil (2.04 g, 51.0 mmol) portionwise over 3 min. After 15 min, tert-butyldimethylchlorosilane (8.33 g, 55.3 mmol) was added and the mixture stirred for a further 66 h. The mixture was diluted with EtOAc (150 mL) and saturated NaHCO₃ solution (100 mL) and partitioned. The aqueous layer was extracted with EtOAc (4×150 mL) and CH₂Cl₂ (100 mL). The combined organic extracts were dried (MgSO₄), filtered and concentrated to yield a honey coloured viscous oil. This was purified by means of SGC using hexane:CH₂Cl₂ (gradient elution from 100:0 to 0:100, v/v) followed by CH₂Cl₂:MeOH (gradient elution from 100:0 to 90:10, v/v) to afford the silylated azaindole (XXVIIa-101) (15.37 g, 87%). ¹H NMR (400 MHz, CDCl₃) δ 0.62 (s, 6H), 0.92 (s, 9H), 1.68 (m, 1H), 1.87-1.93 (m, 2H), 2.05-2.10 (m, 1H), 2.18-2.26 (m, 1H), 2.36-2.43 (m, 1H), 2.57-2.63 (m, 2H), 2.83-2.86 (m, 5H), 3.75 (t, J=4.7 Hz, 2H), 3.82 (t, J=6.0 Hz, 2H), 6.02-6.05 (m, 1H), 6.49 (d, J=3.5 Hz, 1H), 7.21 (d, J=3.5 Hz, 1H), 7.81 (d, J=2.3 Hz, 1H), 8.33 (d, J=2.3 Hz, 1H).

4-((1r,4r)-4-(1-(tert-butyldimethylsilyl)-3-(tributylstannyl)-1H-pyrrolo[2,3-b]pyridin-5-yl)cyclohexyl)-1,4-oxazepane (XXVIIIb-75)

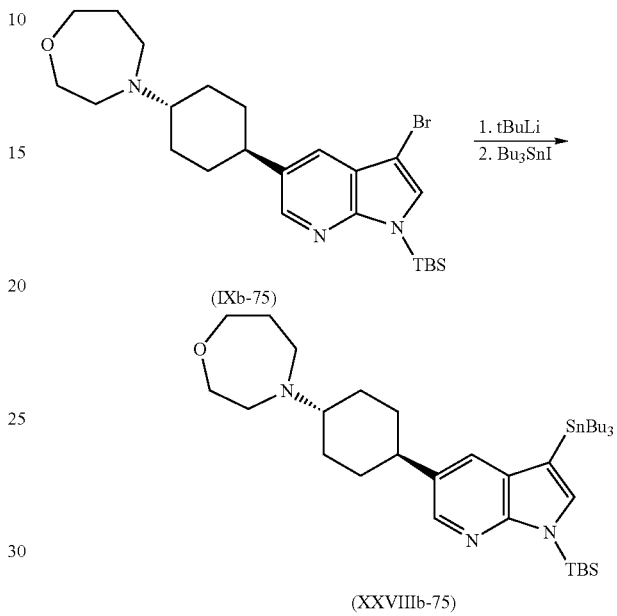

1.7 M tert-Butyllithium in pentane (1.5 mL, 2.5 mmol) was added dropwise over 2 min to a solution of bromide (IXb-75) (585 mg, 1.2 mmol) in THF (5 mL) and stirred at −78° C. under a nitrogen atmosphere. After a further 15 min, iodotributyltin (0.41 mL, 1.4 mmol) was added quickly in one portion. The mixture was stirred at −78° C. for 40 min and then allowed to warm up to RT over 40 min. The mixture was partitioned between saturated aqueous NaHCO₃ solution (15 mL) and EtOAc (20 mL). The aqueous layer was extracted with EtOAc (2×15 mL) and the combined organic solutions dried (MgSO₄) and concentrated. The residue was azeotroped from PhMe (1×35 mL) to afford a viscous yellow oil (1.0 g) (5:1 mixture of the stannane (XXVIIIb-75) and azaindole (XXVIIb-75)), which was used in further transformations without any additional purification. Selected resonances in the ¹H NMR (400 MHz, CDCl₃) spectrum: δ 0.62 (s, 6H), 0.88 (s, 9H), 0.92 (s, 9H), 1.07-1.11 (m, 6H), 1.27-1.39 (m, 6H), 1.45-1.64 (m, 10H), 1.85-1.91 (m, 2H), 1.96-2.05 (m, 4H), 2.51-2.68 (m, 2H), 2.81-2.86 (m, 4H), 3.72-3.76 (m, 2H), 3.82 (t, J=6.0 Hz, 2H), 7.08 (d, J=2.0 Hz, 1H), 8.11 (d, J=2.0 Hz, 1H).

Biological Activity
JNK1, JNK2, JNK3—SPA Assay
JNK1, JNK2, JNK3—SPA Assay
1. Compound is dissolved in DMSO to a convenient concentration and this is diluted in 10% DMSO to a five times concentrate of the desired starting concentration (frequently 1:100).
2. 10 μl of 500 mM EDTA is added to alternative wells of the Opti-plate row, which will receive kinase reaction plus DMSO. This creates the negative control.
3. For the JNK2 and JNK3 assay, compounds are prepared in six 2-fold dilutions with water and each concentration is tested in duplicate. For the JNK1 assay compounds are prepared in four 5-fold dilutions with water which are tested in triplicate. Controls are treated identically.

4. 20 µl per well of each compound concentration is transferred to an Opti-plate, in duplicate.
5. 30 µl (JNK2/3 SPA) or 50 µl (JNK1 SPA) of substrate solution (25 mM HEPES pH 7.5, 10 mM magnesium acetate with 3.33 µM ATP (JNK2/3) or 2 µM ATP (JNK1), approximately 7.5 kBq [$\gamma$-$^{33}$P] ATP, GST-c-Jun, in water) is added to each well.
6. 50 µl (JNK2/3 SPA) or 30 µl (JNK1 SPA) of kinase solution (JNK in 25 mM HEPES pH 7.5, 10 mM Mg Acetate) is added to each well.

| Kinase | Kinase per well (µg) | GST-c-Jun per well (µg) |
|---|---|---|
| JNK1 | 0.25 | 1 |
| JNK2 | 0.2 | 1.2 |
| JNK3 | 0.16 | 1.2 |

7. The plate is incubated for 30 minutes at room temperature.
8. 100 µl of bead/stop solution is added to each well (5 mg/ml glutathione-PVT-SPA beads, 40 mM ATP in PBS).
9. Plates are sealed and incubated for 30 minutes at room temperature, centrifuged for 10 minutes at 2500 g and counted.
10. The $IC_{50}$ values are calculated as the concentration of the compound being tested at which the phosphorylation of c-Jun is decreased to 50% of the control value. Example $IC_{50}$ values for the compounds of this invention are given in Tables 1 and 2.

TABLE 1

$IC_{50}$ values for compounds (I) against JNK3.

| Cpd # I- | $IC_{50}$ [nM] |
|---|---|
| 1 | 434 |
| 3 | 38 |
| 4 | 251 |
| 5 | 86 |
| 7 | 238 |
| 8 | 111 |
| 9 | 147 |
| 10 | 63 |
| 11 | 240 |
| 12 | 1000 |
| 13 | 151 |
| 14 | 105 |
| 16 | 395 |
| 17 | 40 |
| 19 | 117 |
| 20 | 138 |
| 21 | 123 |
| 22 | 16 |
| 23 | 724 |
| 24 | 229 |
| 25 | 16 |
| 26 | 324 |
| 27 | 447 |
| 30 | 229 |
| 31 | 1330 |
| 32 | 955 |
| 33 | 198 |
| 34 | 162 |
| 48 | 580 |
| 49 | 89 |
| 50 | 891 |
| 51 | 933 |
| 55 | 2000 |
| 56 | >2000 |
| 57 | 2000 |
| 58 | >2000 |
| 59 | 813 |
| 60 | 110 |
| 61 | 575 |
| 62 | 871 |
| 63 | 302 |
| 64 | 1000 |
| 69 | 447 |
| 70 | 1096 |
| 74 | 3310 |
| 75 | >1000 |
| 76 | >1000 |
| 78 | 295 |
| 79 | 309 |
| 80 | 513 |
| 81 | 1000 |
| 82 | 269 |
| 83 | 603 |
| 84 | 692 |
| 85 | 1820 |
| 89 | 575 |
| 90 | 1318 |
| 91 | 1000 |
| 92 | >1000 |
| 94 | 692 |
| 96 | 229 |
| 98 | 794 |
| 100 | 447 |
| 101 | 363 |
| 102 | 550 |
| 107 | 1259 |
| 108 | 1230 |
| 109 | 1738 |
| 110 | >2000 |
| 111 | 1738 |
| 113 | 1230 |
| 114 | 1445 |
| 116 | >2000 |
| 117 | 832 |
| 118 | 219 |
| 119 | 1047 |
| 120 | 479 |
| 121 | 1450 |
| 122 | 1290 |
| 123 | 1070 |
| 124 | 520 |
| 125 | 520 |

TABLE 2

$IC_{50}$ values for compounds (I) against JNK2 and JNK1.

| Cpd # | JNK2 $IC_{50}$ [nM] | JNK1 $IC_{50}$ [nM] |
|---|---|---|
| 1 | 831 | 302 |
| 5 | 126 | 117 |
| 7 | 513 | 347 |
| 8 | 214 | 166 |
| 9 | 195 | 209 |
| 10 | 83 | 93 |
| 14 | 191 | 174 |
| 16 | 661 | 457 |
| 33 | 209 | 209 |

Selectivity of Compounds (I) Against a Panel of Kinases

Inhibitory potency of compound (I-8) and (I-60) at a concentration of 1 micromolar and (I-69) and (I-70) at a concentration of 5 micromolar with ATP concentration of 10 micromolar was determined at Upstate/Millipore against a panel of 100 kinases representing all major families within the kinome. The results are presented in Table 3 and are expressed as percentage of remaining activity.

TABLE 3

Inhibitory profile of (I-8), (I-60), (I-69) and (I-70) against a panel of 100 kinases. Numbers represent the percentage of remaining activity.

| | (I-8) | (I-60) | (I-69) | (I-70) |
|---|---|---|---|---|
| Abl(h) | | 97 | 96 | 81 |
| AMPK(r) | | 85 | 116 | 93 |
| ARK5(h) | | | | 83 |
| Aurora-A(h) | 77 | 75 | 73 | 92 |
| BrSK1(h) | 91 | | | |
| BTK(h) | | | | |
| CaMKII(r) | | 80 | 75 | 97 |
| CDK1/cyclinB(h) | | | 80 | |
| CDK2/cyclinA(h) | | | 73 | |
| CDK2/cyclinE(h) | | | 72 | |
| CDK5/p35(h) | | | 48 | |
| CKD6/cyclinD3(h) | 72 | | | 97 |
| CDK7/cyclinH/MAT1(h) | | | | |
| CHK1(h) | 102 | 96 | | |
| CK1δ(h) | | | | 80 |
| CK2(h) | 100 | 102 | 93 | 103 |
| c-RAF(h) | | 103 | 94 | 107 |
| CSK(h) | 86 | 80 | 93 | |
| cSRC(h) | | 96 | 84 | |
| DAPK1(h) | 87 | 107 | 109 | 110 |
| cEF-2K(h) | 94 | 111 | 95 | 110 |
| EGFR(h) | 108 | 100 | 113 | 120 |
| EphB2(h) | 74 | 94 | 89 | 99 |
| FAK(h) | | 91 | 81 | 96 |
| FGFR3(h) | 94 | 75 | 82 | |
| Fgr(h) | | 83 | 108 | 77 |
| Fms(h) | | 75 | | 103 |
| Fyn(h) | | 84 | 110 | 105 |
| GRK5(h) | 98 | 93 | 94 | 105 |
| GRK6(h) | 102 | 86 | 94 | 89 |
| GSK3a(h) | | | | |
| GSK3B(h) | | 83 | 94 | 112 |
| HIPK3(h) | | 89 | 91 | 100 |
| IGF-1R(h) | | 89 | 103 | 104 |
| IKKa(h) | | 71 | | |
| IKKβ(h) | 75 | | 99 | 142 |
| IR(h) | 81 | 99 | | |
| IRAK1(h) | | | | 98 |
| Irk(h) | | | | |
| JAK2(h) | 87 | 94 | 102 | 118 |
| JAK3(h) | | 102 | 93 | 106 |
| JNK1α1(h) | | | | |
| JNK2α2(h) | | | | 90 |
| JNK3(h) | | | | |
| KDR(h) | | | | 73 |
| Lck(h) | | | | |
| LIMK1(h) | | 102 | 85 | |
| Lyn(h) | | 73 | 80 | |
| MAPK1(h) | | 90 | 97 | 99 |
| MAPK2(h) | | 91 | 92 | 84 |
| MAPKAP-K2(h) | 94 | 103 | 97 | 113 |
| MAPKAP-K3(h) | 107 | 89 | 93 | 110 |
| MEK1(h) | 95 | 111 | 89 | 115 |
| Met(h) | 83 | 82 | | 105 |
| MKK4(m) | 90 | 74 | | |
| MKK6(h) | | 86 | 99 | 100 |
| MKK7β(h) | | | | |
| MLCK(h) | | | | |
| MLK1(h) | | 107 | | |

TABLE 3-continued

Inhibitory profile of (I-8), (I-60), (I-69) and (I-70) against a panel of 100 kinases. Numbers represent the percentage of remaining activity.

| | | | | |
|---|---|---|---|---|
| MST2(h) | | 88 | | 96 |
| MuSK(h) | 70 | 84 | | 82 |
| p70S6K(h) | 86 | 95 | 82 | 97 |
| PAK2(h) | 83 | 93 | 71 | 78 |
| PAK3(h) | 78 | 72 | | |
| PAK5(h) | | | | 94 |

| | | | | |
|---|---|---|---|---|
| PAK6(h) | | 88 | 80 | 70 |
| PAR-1Bα(h) | | | | 77 |
| PDGFRα(h) | 98 | 100 | 100 | 104 |
| PDGFRβ(h) | 95 | 103 | 103 | 78 |
| PDK1(h) | 83 | 118 | 93 | 111 |
| PKA(h) | 76 | 98 | 92 | 99 |
| PKBα(h) | 98 | 87 | 91 | 103 |

| | | | | |
|---|---|---|---|---|
| PKCα(h) | | 88 | 93 | 78 |
| PKCβII(h) | 91 | 87 | 75 | |
| PKCγ(h) | 82 | 95 | 83 | 74 |
| PKCδ(h) | 96 | 95 | 76 | 99 |
| PKCε(h) | 100 | 84 | 92 | 82 |
| PDK2(h) | 83 | | | 24 |

| | | | | |
|---|---|---|---|---|
| Plk3(h) | 111 | 103 | 101 | 103 |
| PRAK(h) | 109 | 86 | 73 | 82 |
| Pyk2(h) | 89 | 84 | 90 | 92 |
| Ret(h) | 79 | 92 | 87 | 80 |
| RIPK2(h) | 74 | | | 92 |
| ROCK-I(h) | | | 86 | 82 |

| | | | | |
|---|---|---|---|---|
| ROCK-II(h) | | | | 62 |
| Rsk1(h) | 82 | | | |
| SAPK2a(h) | 96 | 112 | 98 | 106 |
| SAPK2b(h) | 106 | 110 | 87 | 102 |
| SAPK3(h) | 81 | 84 | 88 | 88 |
| SAPK4(h) | 99 | 90 | 90 | 108 |

TABLE 3-continued

Inhibitory profile of (I-8), (I-60), (I-69) and (I-70) against a panel of 100 kinases. Numbers represent the percentage of remaining activity.

| | | | | |
|---|---|---|---|---|
| SGK(h) | 84 | | | 79 |
| SRPK1(h) | 101 | 92 | 97 | 98 |
| Syk(h) | 95 | 91 | 99 | 94 |
| TBK1(h) | | 86 | 87 | 99 |
| Tie2(h) | 83 | | 76 | 82 |
| TrkA(h) | | | | |

| | | | | |
|---|---|---|---|---|
| TrkB(h) | | 96 | 93 | |
| WNK2(h) | | 73 | 74 | |
| ZAP-70(h) | 102 | 109 | 93 | 103 |
| ZIPK(h) | 97 | 109 | 97 | 104 |
| PI3Kβ(h) | 98 | 102 | 106 | 107 |
| PI3Kγ(h) | | 97 | 105 | 107 |
| PI3Kδ(h) | 81 | 100 | 106 | 108 |

▓ <30 activity

▒ 30-70% activity

░ >70% activity

For comparison purposes Table 4 contains the relevant inhibitory data for reference compounds A-L containing a (hetero)aromatic ring at C(5) of the 7-azaindole system.

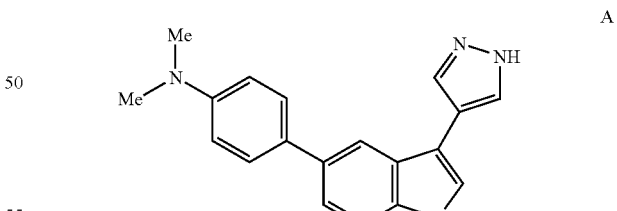

A

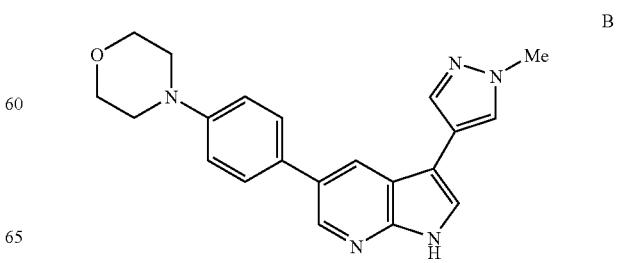

B

245
-continued
C
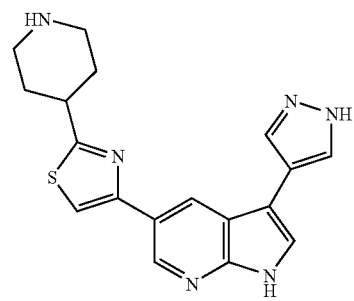
D
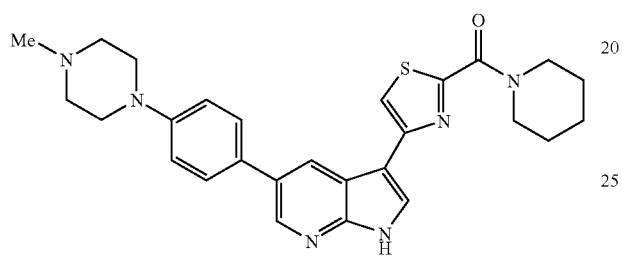
E
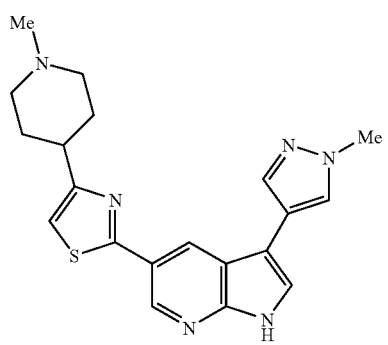
F
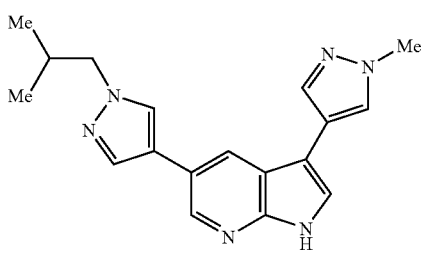
G
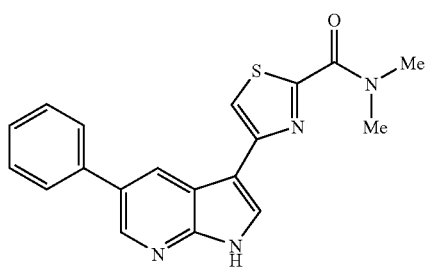
246
-continued
H
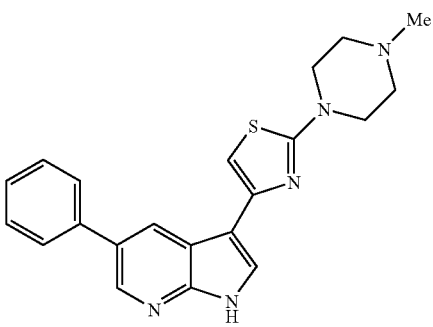
J
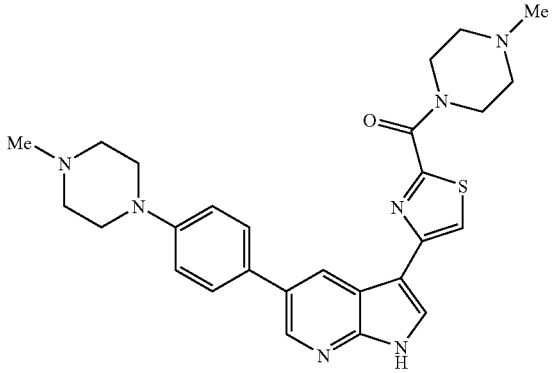
K
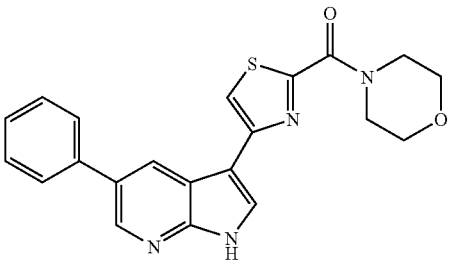
L
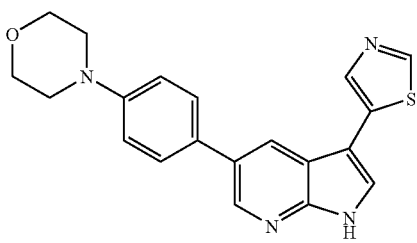

TABLE 4

Inhibitory profile of reference compounds A, B, C, D, E, F, G, H, J, K and L against a panel of 100 kinases.
Numbers represent the percentage of remaining activity.

|  | A | B | C | D | E | F | G | H | J | K | L |
|---|---|---|---|---|---|---|---|---|---|---|---|
| Abl(h) | 16 | 34 | 36 | 22 | 47 | 39 | 18 | 82 | 42 | 76 | 29 |
| AMPK(r) | 22 | 18 | 31 | 13 | 14 | 24 |  |  |  |  | 41 |
| ARK5(h) |  | 10 | 9 |  | 4 | 30 | 8 | 1 | 5 | 4 |  |
| Aurora-A(h) | 12 | 14 | 14 | 11 | 20 | 5 | 22 | 106 | 55 | 49 | 7 |
| BrSK1(h) |  |  |  |  |  |  | 59 | 81 | 76 | 55 |  |
| BTK(h) |  |  |  |  |  |  | 78 | 104 | 34 | 45 |  |
| CaMKII(r) | 62 | 51 | 82 | 18 | 74 | 66 | 33 | 72 | 34 | 37 | 43 |
| CDK1/cyclinB(h) | 5 | 8 | 41 | 10 | 43 | 5 | 5 | 10 | 17 | 5 | 6 |
| CDK2/cyclinB(h) | 5 | 10 | 37 |  |  | 7 | 10 | 22 | 19 | 4 | 5 |
| CDK3/cyclin(h) | 17 | 19 | 41 |  |  | 13 | 9 | 34 | 29 | 4 | 5 |
| CDK5/p35(h) | 5 | 12 | 35 |  |  | 11 | 8 | 7 | 24 | 8 | 4 |
| CDK6/cyclinD3(h) | 11 | 46 | 77 |  |  | 70 | 37 | 71 | 15 | 32 | 33 |
| CDK7/cyclinH/MAT1(h) | 15 | 19 | 8 |  |  | 14 | 25 | 52 | 5 | 14 | 14 |
| CHK1(h) | 17 | 12 | 14 | 36 | 12 | 16 | 62 | 63 | 46 | 59 | 21 |
| CK1a(h) | 20 | 12 | 18 | 1 | 10 | 26 | 6 | 20 | 10 | 6 | 14 |
| CK2(h) |  | 84 | 82 |  |  | 64 | 119 | 118 | 81 | 113 | 95 |
| c-RAF(h) | 88 | 95 | 106 | 94 | 101 | 41 | 73 | 98 | 90 | 57 | 99 |
| CSK(h) |  | 109 | 102 |  |  | 107 | 102 | 87 | 97 | 109 | 84 |
| cSRC(h) | 46 | 56 | 25 | 5 | 73 | 66 | 44 | 45 | 5 | 13 | 23 |
| DAPK1(h) |  | 4 | 2 |  |  | 5 | 68 | 79 | 29 | 49 | 88 |
| cEF-2K(h) |  | 105 | 113 |  |  | 107 | 99 | 92 | 97 | 102 | 102 |
| EGFR(h) | 114 | 89 | 107 | 113 | 112 | 117 | 108 | 113 | 104 | 95 | 126 |
| EphB2(h) | 66 | 80 | 97 | 78 | 77 | 109 | 69 | 91 | 65 | 101 | 68 |
| FAK(h) |  | 23 | 37 |  |  | 53 | 12 | 22 | 5 | 7 | 33 |
| FGFR3(h) | 21 | 40 | 41 |  |  | 13 | 33 | 71 | 23 | 25 | 14 |
| Fgr(h) |  | 21 | 31 |  |  | 33 | 53 | 29 | 10 | 39 | 30 |
| Fma(h) | 14 | 25 | 24 | 10 | 39 | 10 | 25 | 53 | 13 | 12 | 9 |
| Fen(h) | 19 | 51 | 42 | 19 | 54 | 63 | 55 | 66 | 13 | 36 | 36 |
| GRK5(h) |  | 112 | 84 |  |  | 72 | 108 | 111 | 109 | 109 | 98 |
| GRK6(h) |  | 94 | 75 |  |  | 75 | 95 | 87 | 77 | 59 | 96 |

TABLE 4-continued

Inhibitory profile of reference compounds A, B, C, D, E, F, G, H, J, K and L against a panel of 100 kinases.
Numbers represent the percentage of remaining activity.

| | | | | | | | | | | | |
|---|---|---|---|---|---|---|---|---|---|---|---|
| GSK3α(h) | 6 | 6 | 5 | 15 | 16 | 1 | 13 | 44 | 14 | 5 | 5 |
| GSK3β(h) | 8 | 22 | 16 | | | 5 | 47 | 125 | 34 | 9 | 15 |
| HIPK3(h) | | 13 | 30 | | | 32 | 5 | 92 | 6 | 11 | 25 |
| IGF-1R(h) | 71 | 79 | 61 | 5 | 107 | 82 | 35 | 56 | 5 | 5 | 85 |
| IKKa(h) | 5 | 13 | 23 | | | 8 | 5 | 5 | 5 | 4 | 18 |

| | | | | | | | | | | | |
|---|---|---|---|---|---|---|---|---|---|---|---|
| IKKA(h) | | 51 | 57 | 13 | 55 | 58 | 12 | 39 | 15 | 12 | 84 |
| JR(h) | | 121 | 108 | | | 143 | 62 | 118 | 27 | 36 | 44 |
| IRAK1(h) | | 7 | 14 | | | 5 | 30 | 66 | 37 | 21 | 16 |
| Ak(h) | | | | | | 5 | 43 | 2 | 5 | | |
| JAK2(h) | | 17 | 57 | | | 19 | 18 | 22 | 5 | 5 | 13 |
| JAK3(h) | | 13 | 45 | | | 31 | 16 | 34 | 11 | 6 | 10 |

| | | | | | | | | | | | |
|---|---|---|---|---|---|---|---|---|---|---|---|
| JNK1(h) | | 4 | 38 | | | 8 | | | | | 5 |
| JNK2(h) | | 13 | 61 | | | 38 | | | | | 43 |
| JNK3(h) | | 1 | 21 | 7 | 17 | 5 | 6 | 11 | 5 | 0 | 7 |
| KDR(h) | | 13 | 25 | 17 | 20 | 9 | 13 | 34 | 11 | 4 | 5 |
| Lrk(h) | | 42 | 31 | 25 | 38 | 38 | 34 | 37 | 5 | 20 | 18 |
| LIMK1(h) | | 77 | 94 | | | 81 | 43 | 88 | 109 | 38 | 46 |

| | | | | | | | | | | | |
|---|---|---|---|---|---|---|---|---|---|---|---|
| Lyn(h) | | 105 | 94 | | | 75 | 67 | 44 | 22 | 51 | 18 |
| MAPK1(h) | 41 | 30 | 49 | | | 15 | 56 | 74 | 74 | 30 | 68 |
| MAPK2(h) | | 43 | 63 | | | 12 | 55 | 61 | 73 | 22 | 56 |
| MAPKAP-K2(h) | 90 | 107 | 96 | 99 | 107 | 98 | 92 | 101 | 106 | 119 | 94 |
| MAPKAP-K3(h) | | 104 | 115 | | | 104 | 95 | 101 | 109 | 101 | 113 |
| MEK1(h) | 88 | 56 | 59 | 39 | 24 | 31 | 68 | 65 | 60 | 23 | 93 |

| | | | | | | | | | | | |
|---|---|---|---|---|---|---|---|---|---|---|---|
| Met(h) | | 25 | 101 | | | 25 | 31 | 34 | 5 | 15 | 14 |
| MKK4(m) | 53 | 42 | 97 | 122 | 82 | 61 | 40 | 79 | 56 | 12 | 67 |
| MKK6(h) | 58 | 58 | 114 | | | 20 | 44 | 59 | 70 | 13 | 61 |
| MKK7B(h) | 49 | 40 | 89 | | | 41 | 26 | 83 | 21 | 6 | 56 |
| MLCK(h) | | 46 | 34 | 9 | 19 | 44 | 25 | 48 | 5 | 13 | 32 |
| MLK1(h) | | 5 | 31 | | | 6 | 4 | 5 | 5 | 5 | 5 |

TABLE 4-continued

Inhibitory profile of reference compounds A, B, C, D, E, F, G, H, J, K and L against a panel of 100 kinases.
Numbers represent the percentage of remaining activity.

| | A | B | C | D | E | F | G | H | J | K | L |
|---|---|---|---|---|---|---|---|---|---|---|---|
| MST2(h) | 6 | | 48 | 37 | 17 | 7 | 1 | 10 | 10 | 25 | 89 |
| MuSK(h) | | 43 | 62 | | | 47 | 28 | 36 | 15 | 35 | 49 |
| p7058k(h) | 34 | 25 | 25 | 16 | 11 | 35 | 47 | 71 | 42 | 37 | 46 |
| PAK2(h) | | 106 | 92 | 39 | 43 | 94 | 85 | 63 | 39 | 55 | 4 |
| PAK3(h) | | 60 | 56 | | | 85 | 57 | 30 | 3 | 34 | 48 |
| PAK5(h) | | 34 | 51 | | | 30 | 9 | 10 | 44 | 5 | 16 |
| PAK6(h) | | 70 | 59 | | | 56 | 40 | 74 | 34 | 35 | 72 |
| PAR-1Ba(h) | | 43 | 35 | | | 32 | 32 | 69 | 5 | 30 | 6 |
| PDGFRa(h) | 77 | 93 | 104 | | | 80 | 70 | 77 | 48 | 68 | 35 |
| PDGFRB(h) | 30 | 97 | 104 | 37 | 89 | 93 | 82 | 80 | 59 | 90 | 78 |
| PDK1(h) | 5 | 40 | 61 | 92 | 73 | 59 | 69 | 83 | 89 | 60 | 70 |
| PKA(h) | 91 | 98 | 113 | 64 | 93 | 112 | 94 | 91 | 64 | 67 | 85 |
| PKBa(h) | | 102 | 96 | | | 107 | 86 | 89 | 89 | 85 | 98 |
| PKCa(h) | | 85 | 60 | 37 | | | 65 | 70 | 95 | 35 | 35 | 84 |
| PKCoII(h) | 87 | 78 | 53 | 32 | 65 | 81 | 111 | 119 | 87 | 119 | 82 |
| PKCy(h) | 76 | 92 | 85 | | | 39 | 91 | 91 | 38 | 77 | 65 |
| PKCo(h) | 92 | 53 | 61 | | | 66 | 96 | 96 | 76 | 93 | 92 |
| PKCc(h) | 103 | 60 | 68 | | | 80 | 79 | 98 | 35 | 88 | 73 |
| PKD2(h) | 11 | 6 | 6 | 11 | 5 | 14 | 22 | 34 | 1 | 25 | 21 |
| P1k3(h) | | 122 | 121 | | | 125 | 96 | 110 | 106 | 88 | 110 |
| PRAK(h) | | 43 | 61 | | | 31 | 56 | 54 | 64 | 49 | 50 |
| Pyk2(h) | | 18 | 25 | | | 38 | 23 | 23 | 8 | 30 | 23 |
| Ret(h) | 11 | 4 | 19 | 6 | 31 | 17 | 12 | 11 | 2 | 5 | 7 |
| RIPK2(h) | | 30 | 44 | | | 26 | 42 | 56 | 42 | 36 | 11 |
| ROCK-1(h) | | 26 | 31 | | | 41 | 30 | 68 | 36 | 37 | 32 |
| ROCK-11(h) | 4 | 2 | 33 | 6 | 7 | 7 | 5 | 6 | 1 | 1 | 6 |
| Rak2(h) | 34 | 35 | 27 | 18 | 23 | 16 | 26 | 38 | 27 | 27 | 35 |
| SAPK2a(h) | | 116 | 109 | | | 103 | 95 | 100 | 109 | 100 | 101 |
| SAPK3b(h) | 37 | 94 | 112 | | | 102 | 67 | 100 | 96 | 88 | 83 |
| SAPK3(h) | 77 | 90 | 121 | | | 121 | 49 | 51 | 74 | 33 | 75 |
| SAPK4(h) | 89 | 92 | 108 | | | 84 | 95 | 108 | 75 | 33 | 103 |

TABLE 4-continued

Inhibitory profile of reference compounds A, B, C, D, E, F, G, H, J, K and L against a panel of 100 kinases.
Numbers represent the percentage of remaining activity.

| | | | | | | | | | | | |
|---|---|---|---|---|---|---|---|---|---|---|---|
| SGK(h) | | | 41 | | | | 56 | 119 | 56 | 61 | |
| SRPK1(h) | | 127 | 107 | | | 93 | 67 | 98 | 92 | 51 | 78 |
| Syk(h) | | 47 | 72 | | 86 | 81 | 35 | 71 | | | 37 |
| TRK1(h) | | | | | | | | | | | |
| Tir2(h) | | 75 | 77 | | | 58 | 131 | 132 | 49 | 72 | 43 |
| TrKA(h) | | | | | | | | | | | |
| TrkB(h) | | | | | 116 | 125 | | | | | |
| WNK2(h) | | 77 | 88 | | | 85 | 71 | 87 | 84 | | 73 |
| ZAP-70(h) | 98 | 119 | 119 | 92 | 103 | 108 | 97 | 97 | 112 | 109 | 105 |
| ZIPK(h) | | 71 | 45 | | | 87 | 59 | | | 30 | 81 |
| P13Kβ(h) | | 100 | | | | 97 | 101 | 100 | 98 | 94 | 106 |
| P13Kγ(h) | 72 | 88 | | | | 73 | | 91 | 71 | | 75 |
| P13KB(h) | 72 | 94 | | | | 73 | 53 | 93 | 79 | 32 | 99 |

 <30 activity

 30-70% activity

 >70% activity

Selectivity Expressed as Gini Coefficient

Selectivity of compounds according to the present invention and reference compounds expressed as Gini coefficient (*J. Med. Chem.* 2007, 50, 5773-5779) is shown in Table 5. The individual Gini coefficients have been calculated using the data in Tables 3 and 4. Value Gini=0 corresponds to a totally non-selective compound; value Gini=1 reflects perfect selectivity (inhibition of a single target only)

TABLE 5

Selectivity of compounds (I) and reference compounds expressed as Gini coefficient (with mean ± st. dev.).

| Non-aromatic C(5) group | | Aromatic C(5) group | |
|---|---|---|---|
| Compound (I) | Gini | Reference | Gini |
| 8 | 0.4929 | A | 0.3368 |
| 60 | 0.5791 | B | 0.3920 |
| 69 | 0.5375 | C | 0.4129 |
| 70 | 0.6353 | D | 0.2705 |
| | | E | 0.3757 |
| | | F | 0.3777 |
| | | G | 0.3501 |

TABLE 5-continued

Selectivity of compounds (I) and reference compounds expressed as Gini coefficient (with mean ± st. dev.).

| Non-aromatic C(5) group | | Aromatic C(5) group | |
|---|---|---|---|
| Compound (I) | Gini | Reference | Gini |
| | | H | 0.4917 |
| | | J | 0.3286 |
| | | K | 0.2968 |
| | | L | 0.3642 |
| Mean | 0.5612 ± 0.061 | Mean | 0.3634 ± 0.059 |

LPS-Induced TNFα Suppression in Mice

Experimental Protocol

The studies were carried out in male C57/B16 mice. Compounds (20 mg/kg; p.o.) were administered 30 minutes before injection of lipopolysaccharide (LPS). LPS was administered intraperitoneally at a dose of 10 mg/kg. Animals were sacrificed 1 hour following LPS injection. Blood was collected into heparinized tubes for measurement of plasma TNFα levels and spleens were collected for the measurement of c-Jun phosphorylation. Plasma TNFα was measured using an ELISA kit purchased from R&D systems. Spleens were homogenised, extracted in high salt (250 mM NaCl) lysis buffer with phosphatase inhibitors and c-Jun phosphorylation was measured using HTRF. The suppressive effect of compounds was calculated as the percentage reduction of the TNFα level in plasma and P-c-Jun level in spleen as compared with the vehicle-treated animals.

Results

The results are presented in Table 6.

TABLE 6

Percentage reduction in the level of TNFα and P-c-Jun for compounds (I).

| Cpd # | TNFα [%] | P-c-Jun [%] |
|---|---|---|
| 1 | 77 | 15 |
| 3 | 49 | 30 |
| 5 | 66 | −32 |
| 7 | 41 | 14 |
| 8 | 21 | 7 |
| 9 | 56 | 20 |
| 10 | 47 | 20 |
| 14 | 64 | 12 |
| 16 | 56 | 32 |
| 78 | 45 | n.d. |
| 80 | 78 | n.d. | n.d.—not determined

MOG (35-55)-Induced Experimental Autoimmune Encephalomyelitis (EAE) in C57/B16J Mice Experimental Protocol Reagents PBS 0.01M phosphate buffer, 0.0027M potassium chloride, 0.137M sodium chloride pH 7.4 (prepared from tablets—Sigma, Poole, Dorset. UK.)

*Mycobacterium tuberculosis* H37 RA: Difco Laboratories, Detroit Mich., USA

MOG peptide (35-55) synthesised by Rachel Striesow, Advanced Biotechnology Centre, Imperial College Faculty of Medicine, Charing Cross Campus, Fulham Palace Road, London, W6 8RF.

Pertussis Toxin—Calbiochem (Merck Bioscience (UK), Beeston, Nottingham. UK)

Freund's Incomplete Adjuvant (Difco Laboratories, Detroit Mich., USA)

Animals

Specific pathogen-free male C57/B16J mice will be obtained at the age of 6-8 weeks (20-24 g) from Charles River UK Ltd. (Margate, UK). Mice will be purchased and acclimatised for a period of at least 3 days before the start of the experiment. The mice will be housed in transparent plastic cages with wire covers (270 W×370 L×230 H mm) 2 animals per cage, in a room with a constant temperature (20-24° C.) and humidity (40-70%) and a 12 h light-dark cycle (lightened from 6 A.M. to 6 P.M.). Animals will be provided with pellet food (RM1 E, Specialist Diet Services, Witham, UK) and tap water ad libitum.

Methods

MOG (35-55) Adjuvant was Prepared as Follows:—
1. Prepare a 20 ml syringe by removing the plunger and plugging the injection end with a bung (we use the cut off end of a Treff Pellet Mixer (2.5 mL), Anachem, Lutons, Bedfordshire. UK.)
2. Add 5 ml of 2 mg/ml MOG 35-55 in PBS
3. Add 5 ml of Freunds incomplete adjuvant supplemented (IFA) with 5 mg/ml (25 mg total) Mycobacterium Tuberculosis H37ra to the 20 ml syringe
4. Cover with a double layer of parafilm and vortex mixture for 1 minute.
5. Sonicate (15 min; Decon FS Minor sonicating water bath)
6. Emulsify by repeated passing between two 20 ml syringes (20 passes; syringes connected with PVC tubing, secured with cable ties).
7. Check emulsion—place drop of emulsion onto water. Drop should stay as entity, if drop dissipates quickly repeat step 5.
8. Dispense 10 ml aliquots into 10 ml syringes and maintain either frozen (−80° C.) or on ice until used.

Induction Protocol

1. At day 0 mice were injected sc. in two sites on the lower flanks with 0.1 ml of MOG (35-55) adjuvant. Mice also receive 30 ng pertussis toxin in 100 µl of PBS iv or ip.
2. At day 2 mice received 30 ng of pertussis toxin in 100 µl of PBS iv or ip.
3. At day 7 mice were injected sc. in two sites on the medial flanks with 0.1 mL of MOG (35-55) adjuvant.
4. Mice were observed daily for clinical symptoms.

Points to Note

Sites of adjuvant injection should not be areas that are involved in scruffing of animals. Manipulation of sc. sites leads to reduced induction and peak scores.

Pertussis toxin, MTB, MOG and IFA should all be batch tested as some batches reduce induction and peak scores.

Animals must be more than 20 g on induction of disease, otherwise, there is a mortality rate of about 20% (normally less than 5%).

Chronic Mouse EAE Scoring

Animals receive two scores. One gives an accurate assessment of the animals' disability (cumulative score). The second reflects the overall severity of the animal (peak score).

Peak score=maximum score reached

Cumulative score=Sum of scores from each section e.g. if mouse has FT, IRR, HLP, peak score is 4, cumulative score is 7.

| | | |
|---|---|---|
| Slightly Floppy Tail (half tail paralysis)/Slight Tail Spasticity | SFT/STSp | 0.5 |
| Floppy Tail/Tail Spasticity | FT/TSp | 1 |
| Slightly Impaired Righting Reflex | SIRR | 1.5 |
| Impaired Righting Reflex | IRR | 2 |
| Slight Hind Limb Weakness/Hind Limb Weakness in one leg | SHLW/HLWx1 | 2.5 |
| Slight Hind Limb Spasticity/Hind Limb | SHLSp/ | 2.5 |

| | | |
|---|---|---|
| Spasticity in one leg | HLSpx1 | |
| Hind Limb Weakness/Hind Limb Spasticity | HLW/HLSp | 3 |
| Hind Limb Weakness in one leg and Paralysis in the other/'Very' Hind Limb Weakness in both legs/Hind Limb Spasticity Causing Immobility of One Limb/Very Hind Limb Spasticity | HLW/P/ VHLW/ HLW/SP/ VHLSp | 3.5 |
| Hind Limb Paralysis/Hind Limb Spasticity Causing Immobility of Both Hind Limbs | HLP/HLP(Sp) | 4 |
| Slight Fore Limb Weakness/Fore Limb Weakness in one leg/Slight Fore Limb Spasticity | SFLW/FLWx1/ SFLSp | 4.5 |
| Fore Limb Weakness/Fore Limb Spasticity | FLW/FLSp | 5 |
| Fore Limb Weakness in one leg and Paralysis in the other/'Very' Fore Limb Weakness/ Fore Limb Spasticity Causing Immobility of One Fore Limb/Very Fore Limb Spasticity | FLW/P/VFLW/ FLW/Sp/ VFLSp | 5.5 |
| Fore Limb Paralysis/Fore Limb Spasticity Causing Immobility of Both Fore Limbs | FLP/FLP (Sp) | 6 |
| Moribund | Mori | 7 |

Short Description of Scores

Tail
Slightly Floppy Tail—Up to 50% of tail without tone.
Floppy Tail—More than 50% of tail without tone.
Hind Limb Weakness
Slight Hind Limb Weakness—Impaired gate but legs still load bearing.
Hind Limb Weakness—Impaired gate and loss of load bearing in hind limbs.
Very Hind Limb Weakness—Inability to move hind limb through more than 50% of stride and non load bearing.
Hind Limb Paralysis—Complete loss of movement of hind limbs
Fore Limb Weakness
Slights Forelimb Weakness—Reduced grip in forelimbs.
Forelimb Weakness—Reduced grip in forelimbs leading to problems with forward movement.
Very Forelimb Weakness—Limbs still moving but inability to move.
Forelimb Paralysis—Complete loss of movement in forelimbs.
Spasticity
Spasticity scores are comparable in disability with weakness scores but due to rigidity rather than loss of muscle tone.

REFERENCES

Nicole Heijmans et al. Journal of Neuroimmunology, 167, (2005) 23-33
Dusanka S. Skundric et al. Journal of Neuroimmunology, 136 (2003) 34-45
S Amor et al, Journal of Immunology, 150, (1993) 5666-5672
Baker et al. Journal of Neuroimmunology, 28, (1990) 261-271

Results

Figure 2:
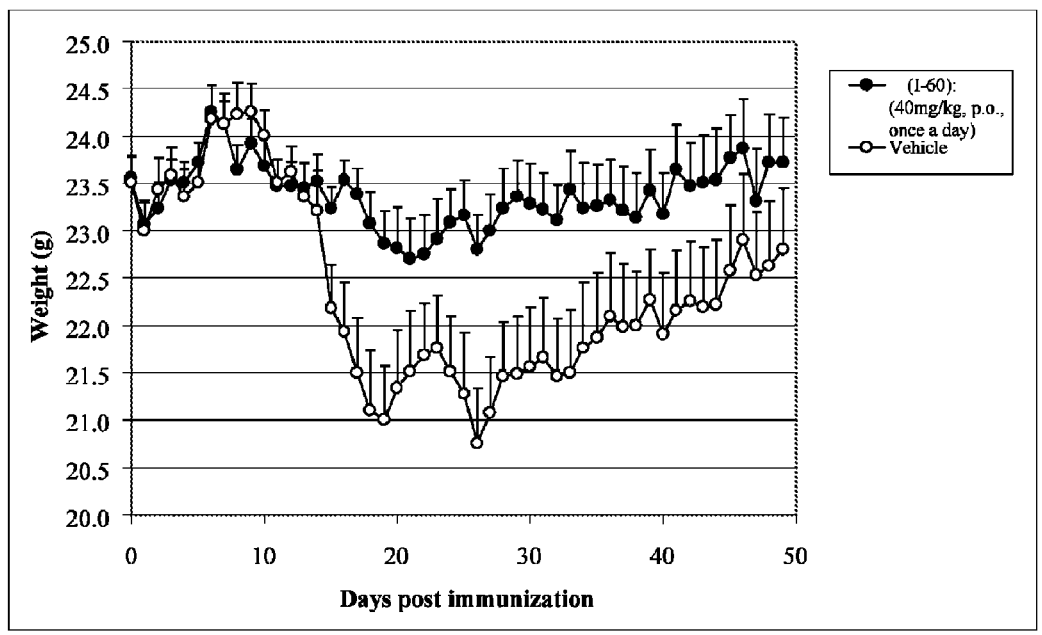
FIG. 2 shows the effect of (I-60) (40 mg/kg, p.o., once daily) on animals' weight in the EAE experiment in mice.
Figure 3:
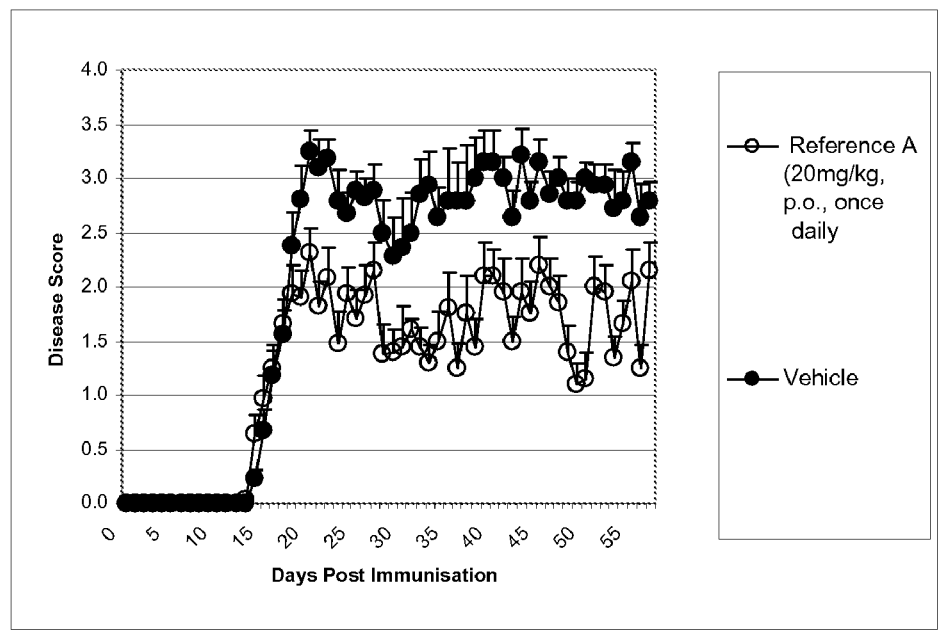
FIG. 3 shows the effect of reference compound A (20 mg/kg, p.o., once daily) on peak disease score in the EAE experiment in mice.
Figure 4:
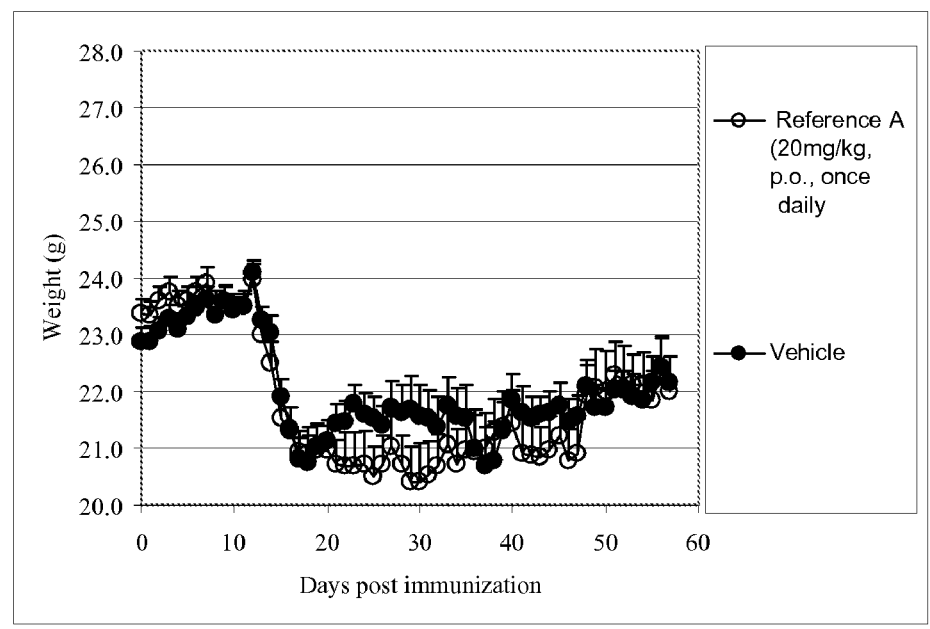
FIG. 4 shows the effect of reference compound A (20 mg/kg, p.o., once daily) on animals' weight in the EAE experiment in mice.

The results of EAE experiments for (I-60) and reference aromatic compound A are shown in FIGS. 1-4. The drug was administered at the appearance of symptoms (score 1; floppy tail).
FIG. 1 shows the effect of (I-60) (40 mg/kg, p.o., once daily) on peak disease score in the EAE experiment in mice;
FIG. 2 shows the effect of (I-60) (40 mg/kg, p.o., once daily) on animals' weight in the EAE experiment in mice;
FIG. 3 shows the effect of reference compound A (20 mg/kg, p.o., once daily) on peak disease score in the EAE experiment in mice; and
FIG. 4 shows the effect of reference compound A (20 mg/kg, p.o., once daily) on animals' weight in the EAE experiment in mice.

The invention claimed is:
1. A compound of formula (I);
or a pharmaceutically acceptable salt thereof,

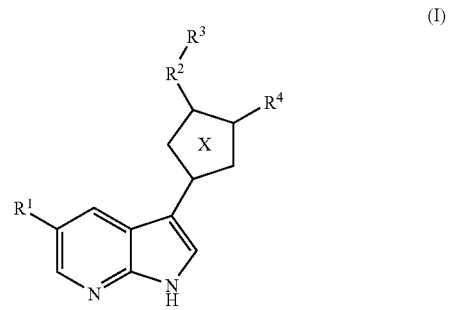
(I)

wherein Ring X represents a thiazole ring;
$R^1$ represents a 5-7 membered non-aromatic hydrocarbon cyclic group optionally and independently substituted with 1-4 substituent(s) selected from the group consisting of a halogen atom, an oxo group, an ethylenedioxy group, a $C_{1-6}$ alkyl group, a $C_{1-6}$ alkoxy group, a $C_{1-6}$ hydroxyalkyl group, —C(O)OH, a ($C_{1-6}$ alkyl)amino group, a di($C_{1-6}$ alkyl)amino group and -Ra-Rb;
wherein $R^a$ represents a single bond or —$CH_2$—;
wherein $R^b$ represents a 4-7 membered non-aromatic heterocyclic group, a $C_{6-10}$ aryl group or a 5-6 membered heteroaryl group, optionally and independently substituted with 1-4 substituent(s) selected from the group consisting of a halogen atom and a $C_{1-6}$ alkyl group;
wherein $R^2$ represents a single bond or a carbonyl group;
wherein $R^3$ represents hydrogen, a hydroxyl group, a $C_{1-6}$ alkyl group, a $C_{1-6}$ alkoxy group, a $C_{1-6}$ haloalkyl group, a di($C_{1-6}$ alkyl)amino group or a 4-7 membered non-aromatic heterocyclic group wherein at least one ring heteroatom is a nitrogen atom, optionally and independently substituted with 1-4 $C_{1-6}$ alkyl group(s); and
wherein $R^4$ represents hydrogen or a $C_{1-6}$ alkyl group.
2. The compound or a pharmaceutically acceptable salt thereof according to claim 1 wherein the compound is of formula (Ia),

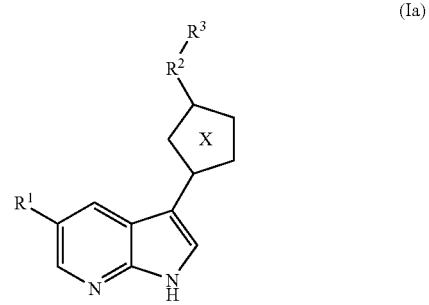
(Ia)

wherein Ring X, $R^1$, $R^a$ and $R^b$ are as claimed in claim 1, wherein $R^2$ represents a single bond or a carbonyl group;

and wherein R³ represents a hydroxyl group, a di(C₁₋₆ alkyl)amino group or a 4-7 membered non-aromatic heterocyclic group wherein at least one ring heteroatom is a nitrogen atom, optionally and independently substituted with 1-4 C₁₋₆ alkyl group(s).

3. The compound or a pharmaceutically acceptable salt thereof according to claim 2 wherein
R¹ represents a 5-7 membered non-aromatic hydrocarbon cyclic group optionally and independently substituted with 1-4 substituent(s) selected from the group consisting of a halogen atom, an oxo group, an ethylenedioxy group, a C₁₋₆ alkyl group, a C₁₋₆ alkoxy group, a C₁₋₆ hydroxyalkyl group, —C(O)OH, and -Ra-Rb;
and wherein Ring X, Rᵃ, Rᵇ, R² and R³ are as claimed in claim 2.

4. The compound or a pharmaceutically acceptable salt thereof according to claim 1 wherein R¹ represents a cyclopentyl group, a cyclohexyl group, a cyclopentenyl group, a cyclohexenyl group or a cyclohexadienyl group, optionally and independently substituted with 1-4 substituent(s) selected from the group consisting of a halogen atom, an oxo group, an ethylenedioxy group, a C₁₋₆ alkyl group, a C₁₋₆ alkoxy group, a C₁₋₆ hydroxyalkyl group, —C(O)OH, a (C₁₋₆ alkyl)amino group, a di(C₁₋₆ alkyl)amino group and —Rᵃ—Rᵇ;

wherein Rᵃ represents a single bond or —CH₂—;
wherein Rᵇ represents a 4-7 membered non-aromatic heterocyclic group, a C₆₋₁₀ aryl group or a 5-6 membered heteroaryl group, optionally and independently substituted with 1-4 substituent(s) selected from the group consisting of halogen atom and C₁₋₆ alkyl group.

5. The compound or a pharmaceutical acceptable salt thereof according to claim 1
wherein R¹ represents a cyclopentyl group, a cyclohexyl group, a cyclopentenyl group, a cyclohexenyl group or a cyclohexadienyl group, optionally and independently substituted with 1-4 substituent(s) selected from the group consisting of an ethylenedioxy group, a C₁₋₆ alkyl group and a morpholino group.

6. The compound or a pharmaceutically acceptable salt thereof according to claim 1 wherein R² represents a single bond.

7. The compound or a pharmaceutically acceptable salt thereof according to claim 1 wherein R² represents a carbonyl group.

8. The compound or the pharmaceutically acceptable salt thereof according to claim 1
wherein R³ represents hydrogen, a methyl group, a methyoxy group, an ethoxy group, a trifluoromethyl group, a dimethylamino group, a piperidyl group, a piperazinyl group or a morpholino group optionally and independently substituted with a C₁₋₆ alkyl group.

9. The compound or a pharmaceutically acceptable salt thereof according to claim 1 wherein R⁴ is hydrogen or methyl.

10. A compound selected from the following group or a pharmaceutically acceptable salt thereof;

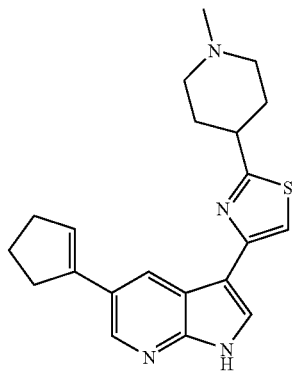

(I-1)

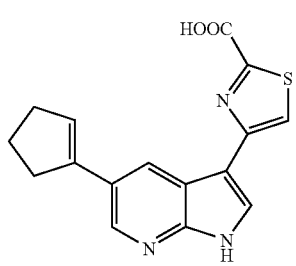

(I-2)

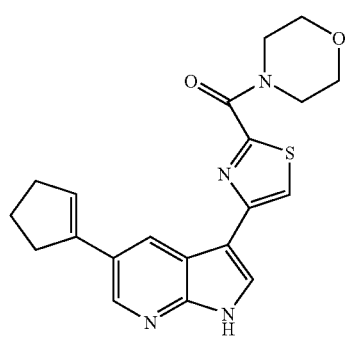

(I-3)

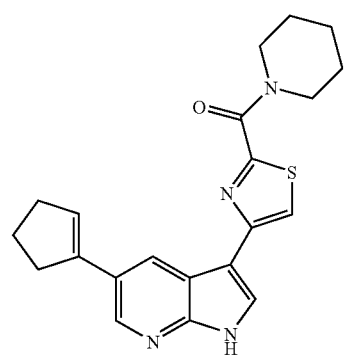

(I-4)

(I-5)
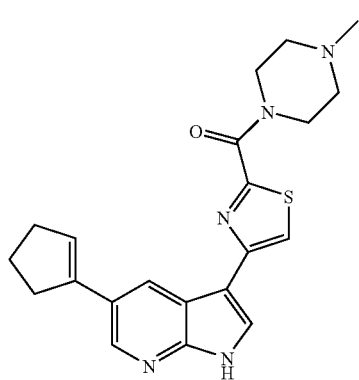
(I-6)
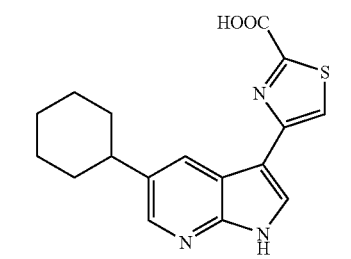
(I-7)
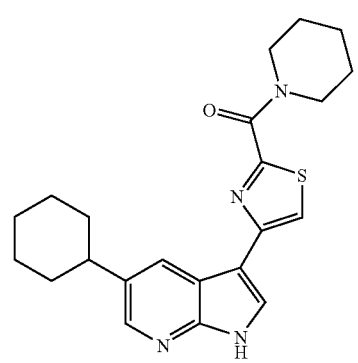
(I-8)
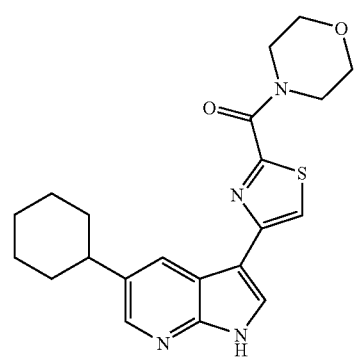
(I-9)
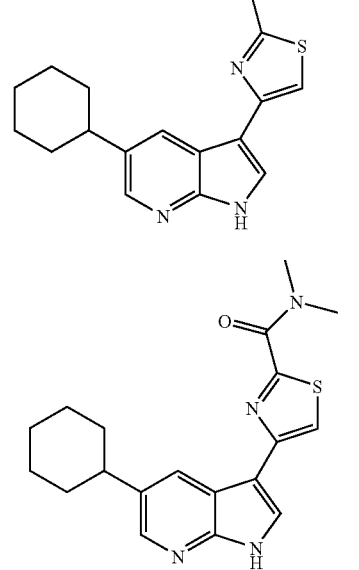
(I-10)
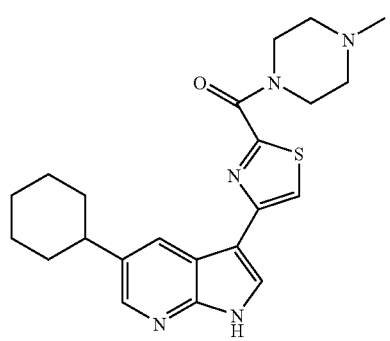
(I-11)
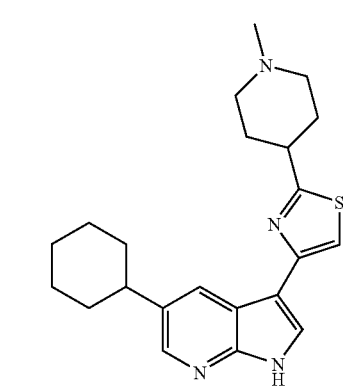
(I-12)
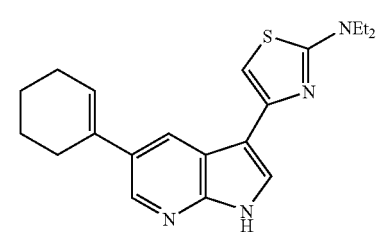
(I-13)
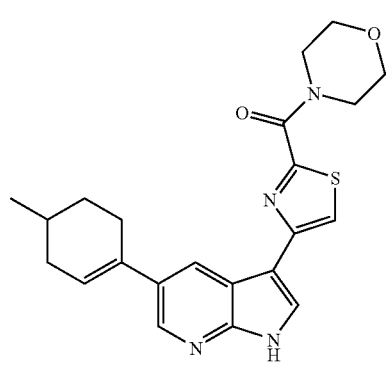
(I-14)
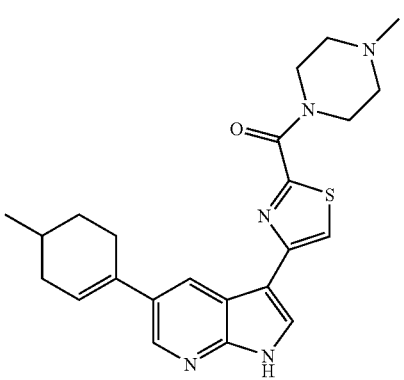

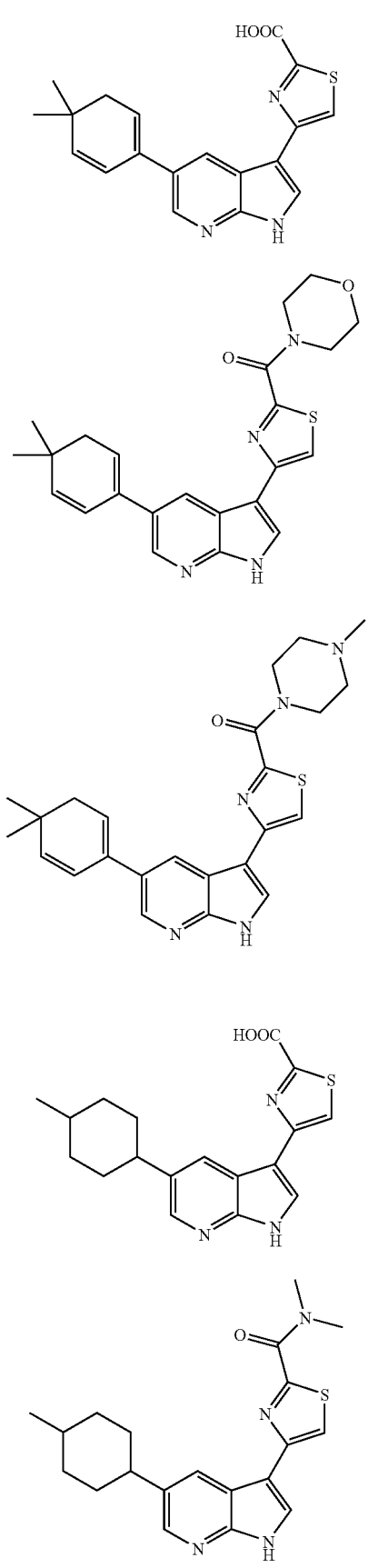
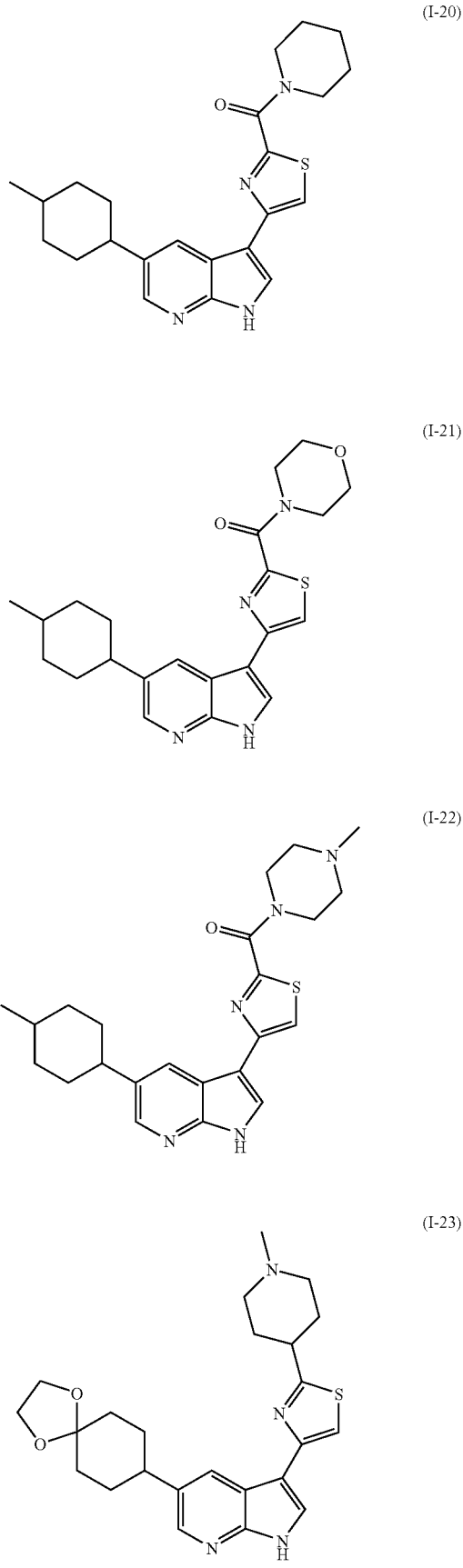

(I-24)
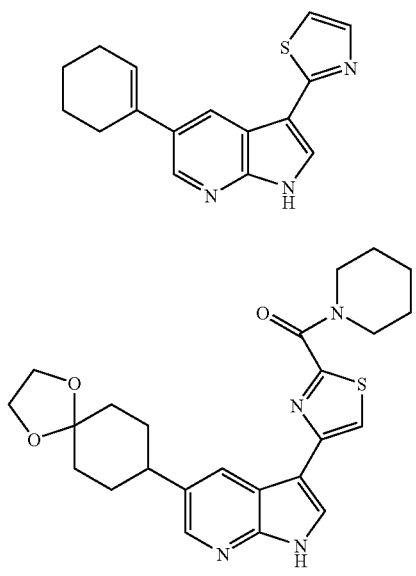
(I-25)
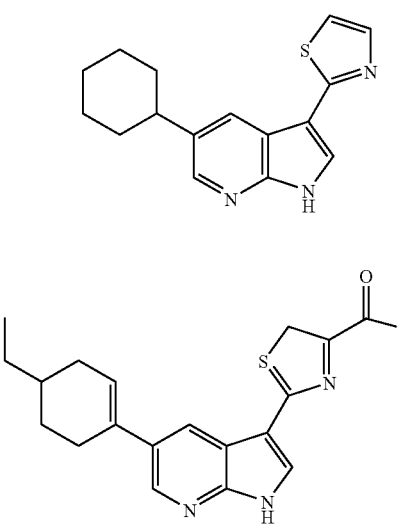
(I-26)
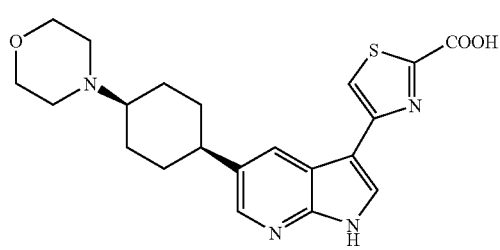
(I-27)
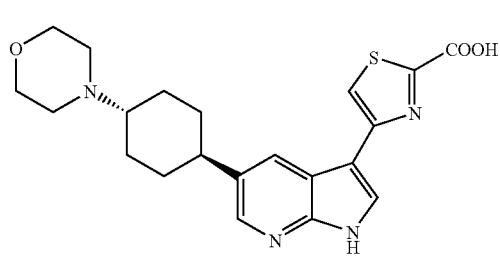
(I-28)
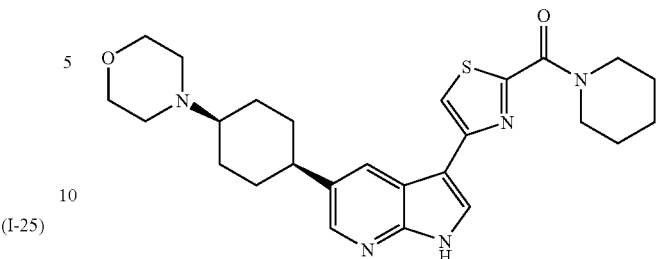
(I-29)
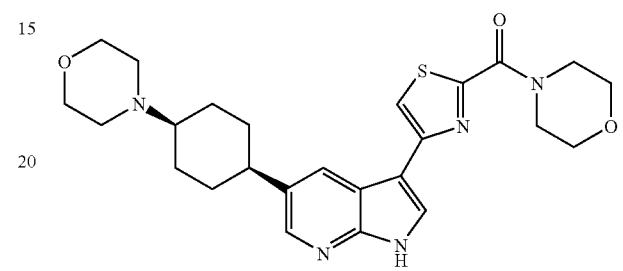
(I-30)
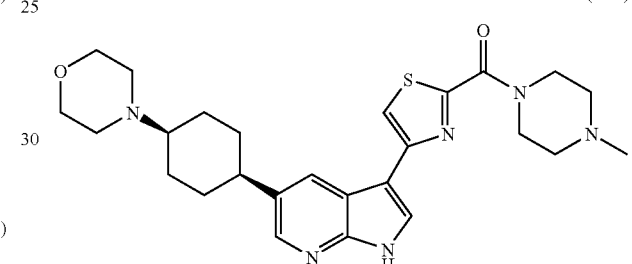
(I-31)
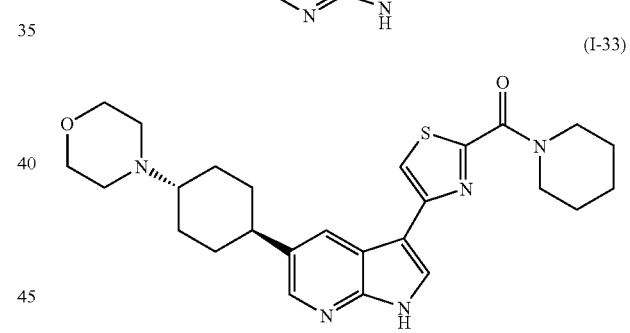
(I-32)
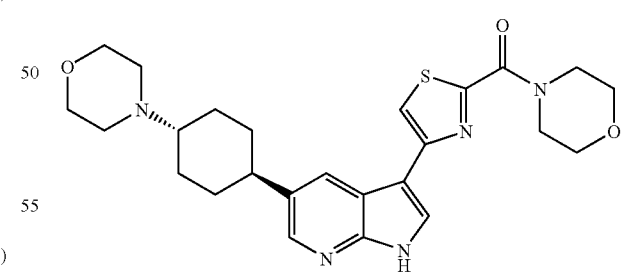
(I-33)
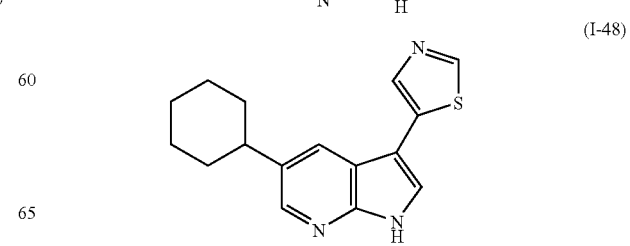
(I-34)
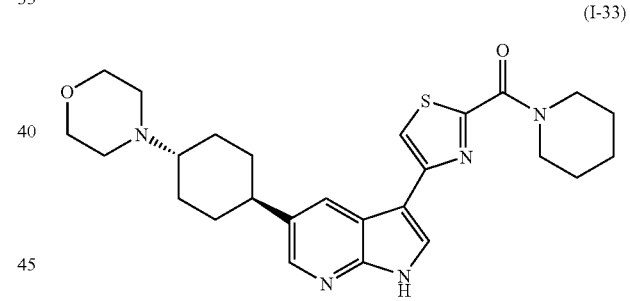
(I-48)
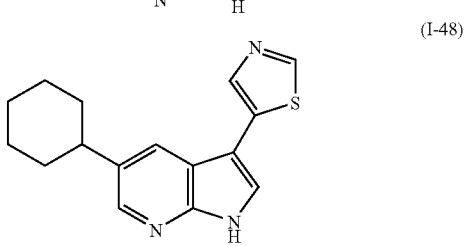

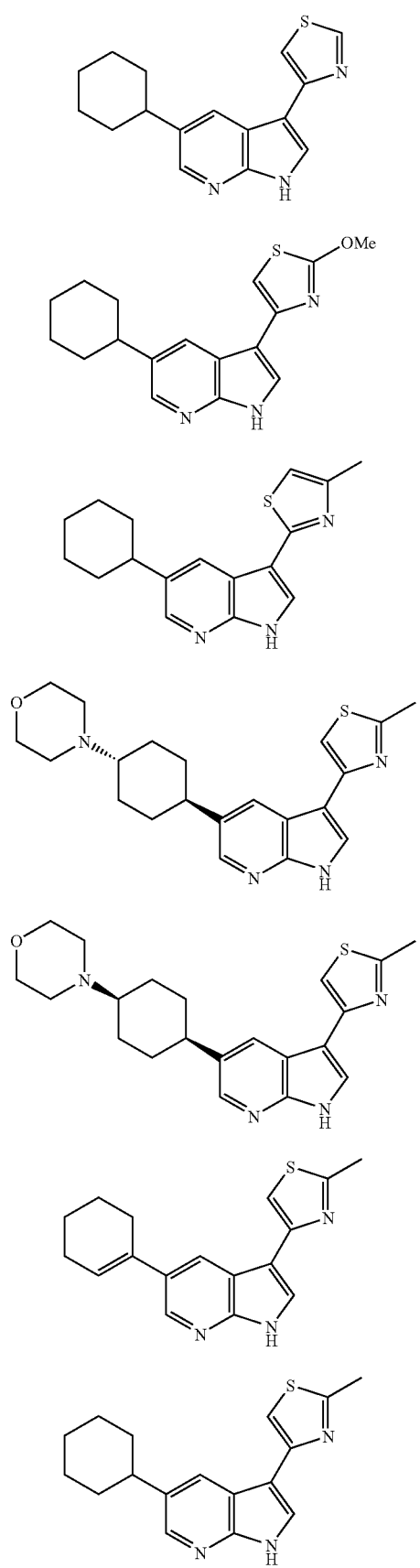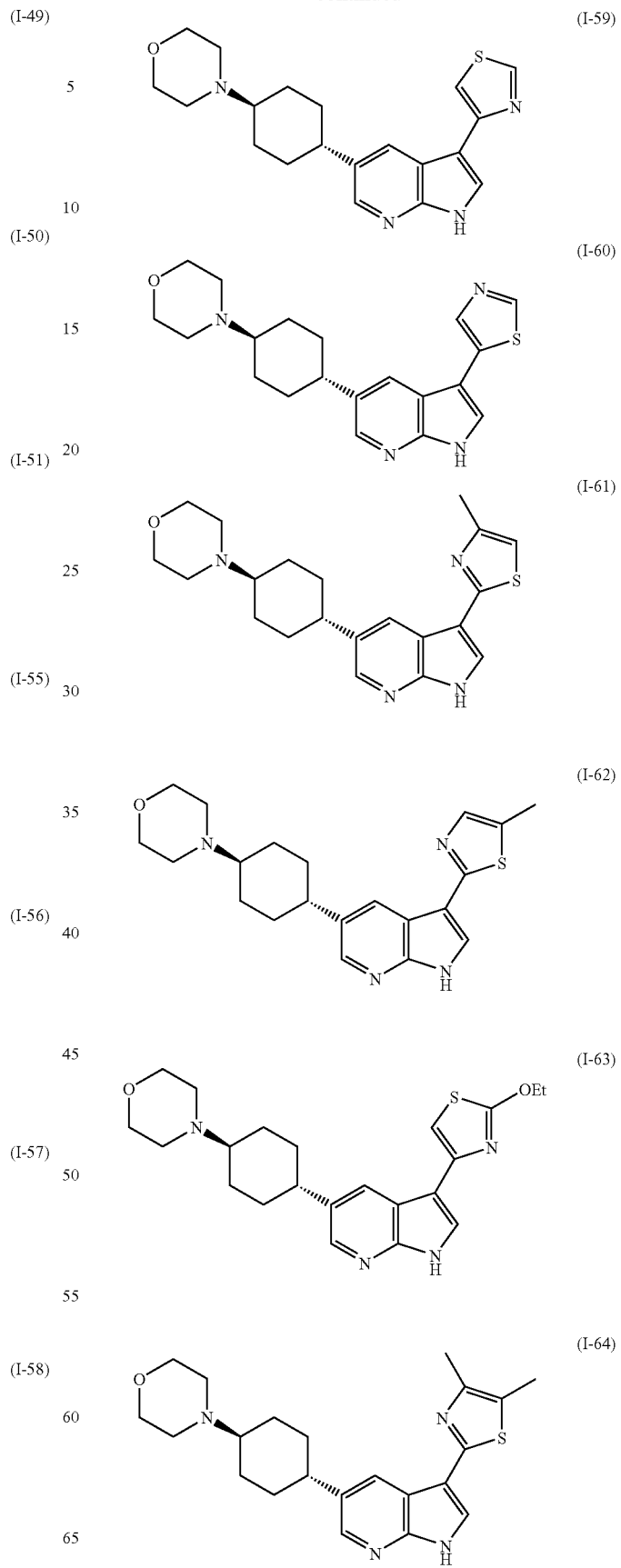

-continued
(I-69)
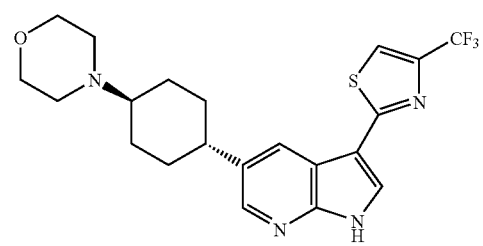
(I-70)
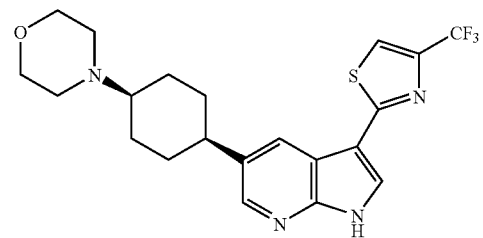
(I-74)
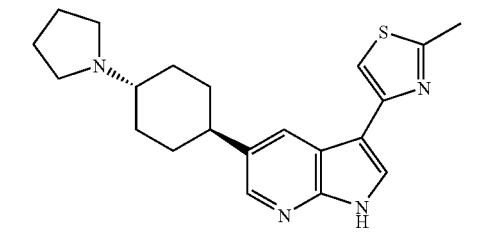
(I-75)
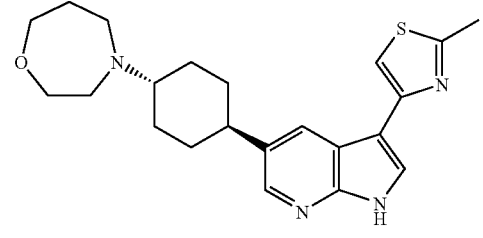
(I-76)
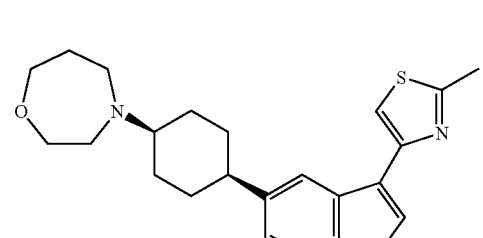
(I-78)
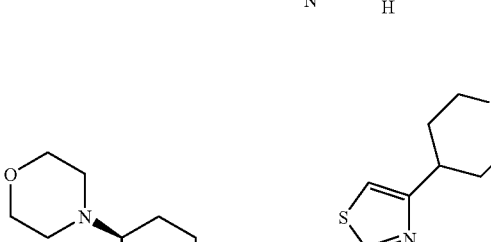
-continued
(I-79)
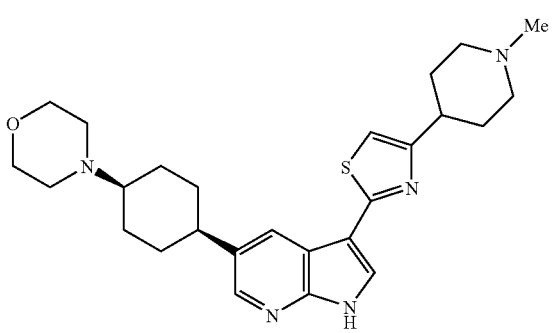
(I-80)
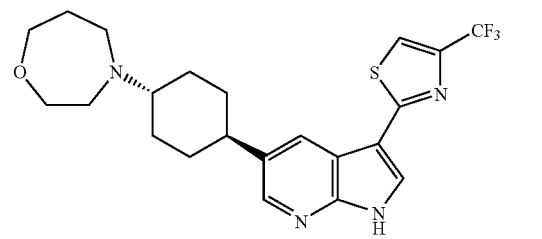
(I-81)
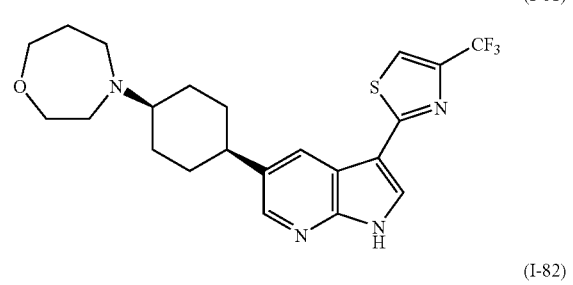
(I-82)
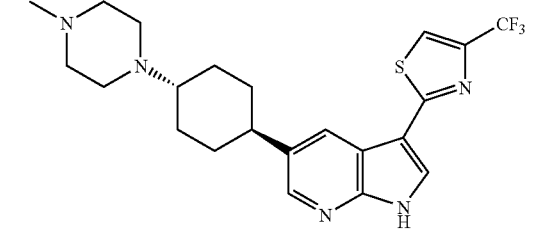
(I-83)
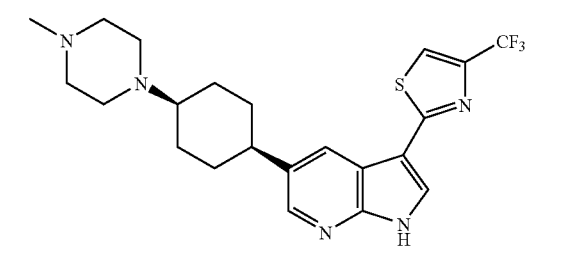
(I-84)

-continued
(I-85)
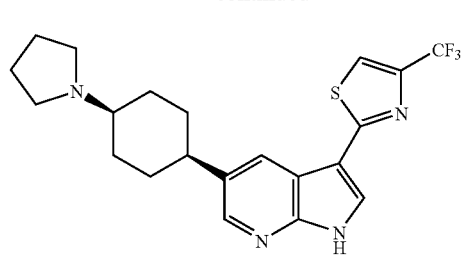
(I-89)
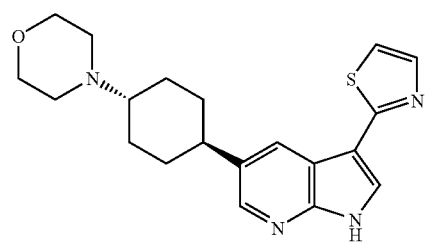
(I-90)
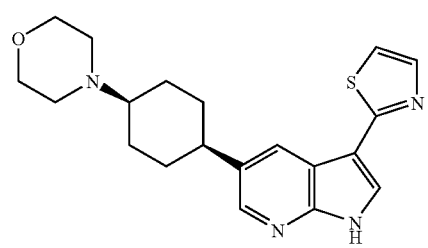
(I-91)
(I-92)
(I-94)
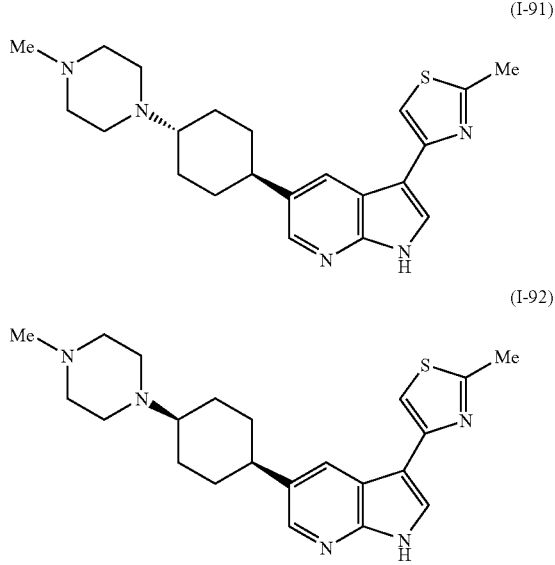
-continued
(I-96)
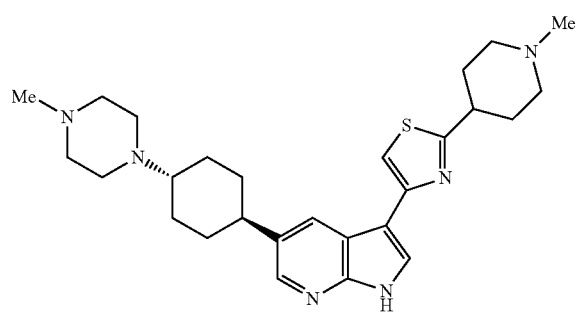
(I-98)
(I-100)
(I-101)
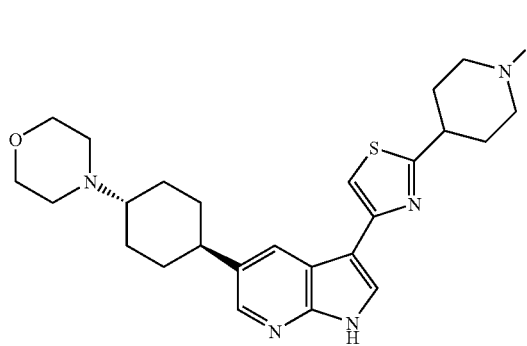

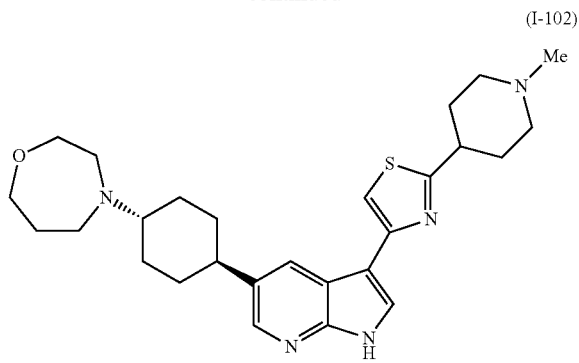
(I-102)
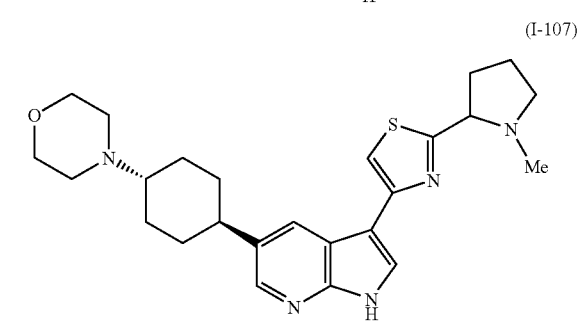
(I-107)
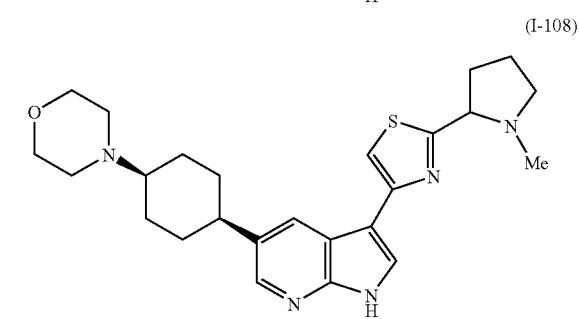
(I-108)
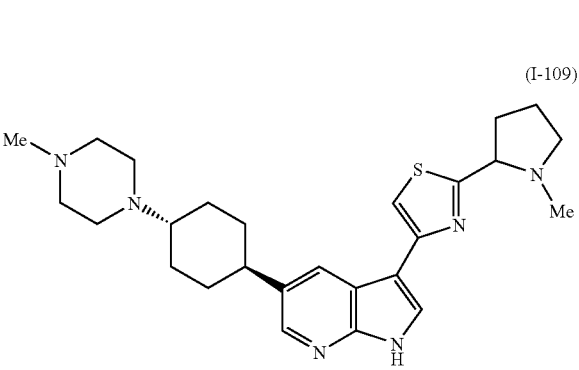
(I-109)
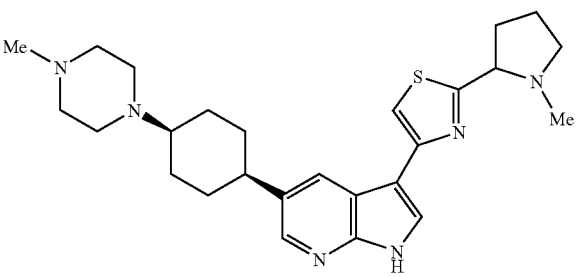
(I-110)
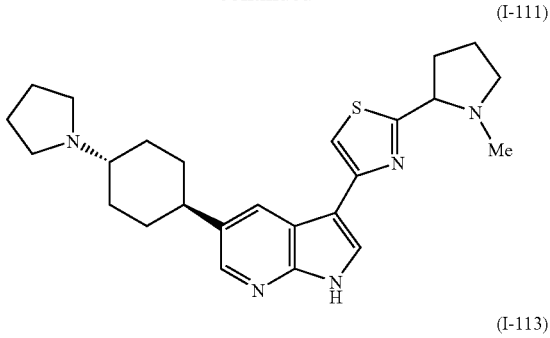
(I-111)
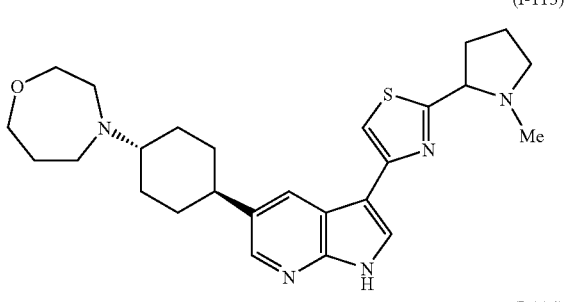
(I-113)
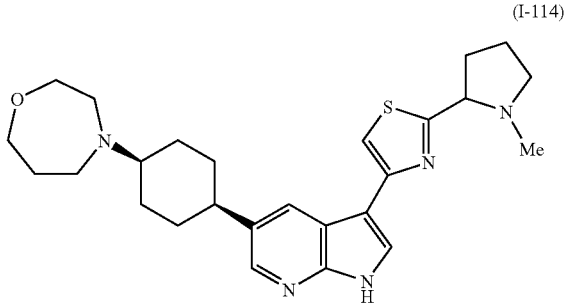
(I-114)
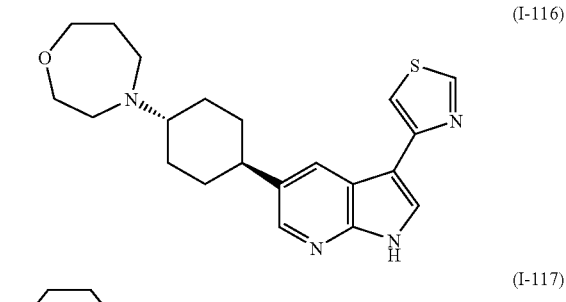
(I-116)
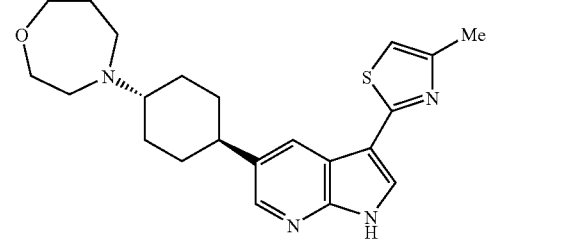
(I-117)
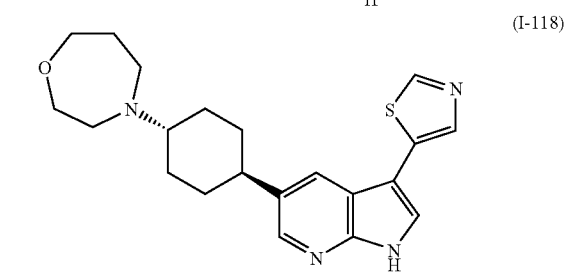
(I-118)

(I-119)
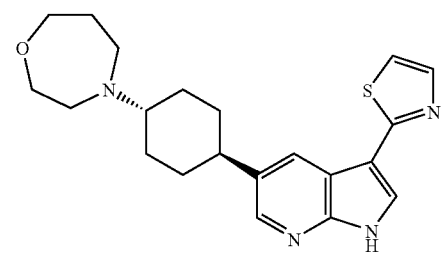
(I-120)
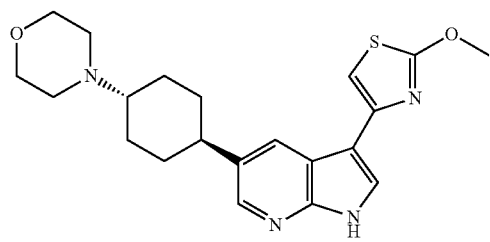
(I-121)
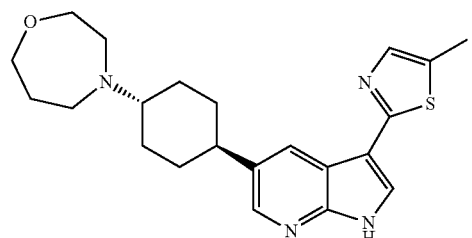
(I-122)
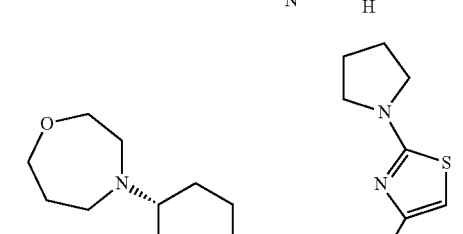
(I-123)
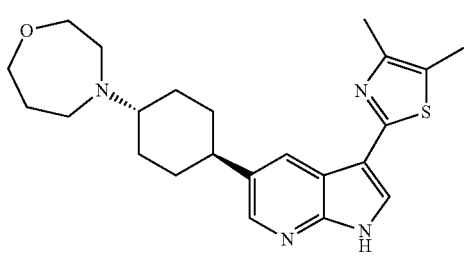
(I-124)
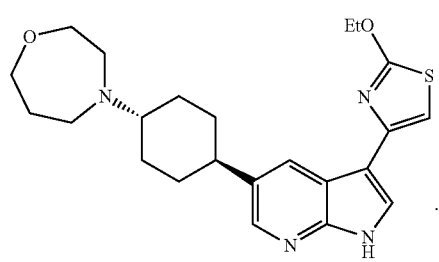
and
(I-125)
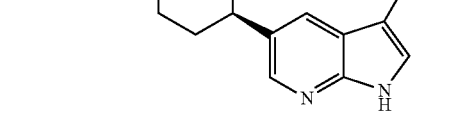
11. A pharmaceutical composition comprising a compound according to claim 1.
* * * * *